United States Patent
Denker et al.

(10) Patent No.: US 12,083,112 B2
(45) Date of Patent: *Sep. 10, 2024

(54) COMBINATION OF A PD-1 ANTAGONIST AND A VEGFR/FGFR/RET TYROSINE KINASE INHIBITOR FOR TREATING CANCER

(71) Applicants: MERCK SHARP & DOHME LLC, Rahway, NJ (US); EISAI R&D MANAGEMENT CO., LTD., Tokyo (JP)

(72) Inventors: Andrew Evan Denker, Ardmore, PA (US); Yu Kato, Tokyo (JP); Kimiyo Tabata, Tokyo (JP); Yusaku Hori, Tokyo (JP)

(73) Assignees: EISAI R&D MANAGEMENT CO., LTD., Tokyo (JP); Merck Sharp & Dohme LLC, Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/502,962

(22) Filed: Oct. 15, 2021

(65) Prior Publication Data

US 2022/0023285 A1 Jan. 27, 2022

Related U.S. Application Data

(63) Continuation of application No. 15/554,577, filed as application No. PCT/US2016/020747 on Mar. 3, 2016, now Pat. No. 11,547,705.

(60) Provisional application No. 62/171,615, filed on Jun. 5, 2015, provisional application No. 62/128,232, filed on Mar. 4, 2015.

(30) Foreign Application Priority Data

Mar. 4, 2015 (JP) .................. 2015-042683
Jun. 5, 2015 (JP) .................. 2015-114890

(51) Int. Cl.
| | | |
|---|---|---|
| A61K 39/00 | (2006.01) | |
| A61K 31/47 | (2006.01) | |
| A61K 39/395 | (2006.01) | |
| A61K 45/06 | (2006.01) | |
| C07K 16/28 | (2006.01) | |

(52) U.S. Cl.
CPC ........ *A61K 31/47* (2013.01); *A61K 39/39558* (2013.01); *A61K 45/06* (2013.01); *C07K 16/2818* (2013.01); *C07K 16/2827* (2013.01); *A61K 2039/505* (2013.01); *A61K 2300/00* (2013.01); *C07K 2317/76* (2013.01)

(58) Field of Classification Search
CPC .. A61K 31/47; A61K 39/39558; A61K 45/06; A61K 2039/505; A61K 2300/00; A61P 35/00
See application file for complete search history.

(56) References Cited

U.S. PATENT DOCUMENTS

| | | |
|---|---|---|
| 4,000,278 A | 12/1976 | Curran |
| 4,526,988 A | 7/1985 | Hertel |
| 4,563,417 A | 1/1986 | Albarella et al. |
| 4,582,789 A | 4/1986 | Sheldon, III et al. |
| 4,742,003 A | 5/1988 | Derynck et al. |

(Continued)

FOREIGN PATENT DOCUMENTS

| | | |
|---|---|---|
| AU | 2012246490 B2 | 8/2016 |
| CA | 2 361 057 A1 | 7/2000 |

(Continued)

OTHER PUBLICATIONS

Paul, Fundamental Immunology, 3rd Edition, 1993, pp. 292-295 (Year: 1993).*
Almagro & Fransson, Frontiers in Bioscience 2008; 13:1619-33 (Year: 2008).*
Rudikoff et al (Proc. Natl. Acad. Sci. USA 1982 vol. 79: p. 1979) (Year: 1982).*

(Continued)

*Primary Examiner* — Sheela J. Huff
(74) *Attorney, Agent, or Firm* — MARSHALL, GERSTEIN & BORUN LLP

(57) ABSTRACT

The present disclosure describes combination therapies comprising an antagonist of Programmed Death 1 receptor (PD-1) and a multi-RTK inhibitor, and the use of the combination therapies for the treatment of cancer. The multi-RTK inhibitor may be represented by Formula (I):

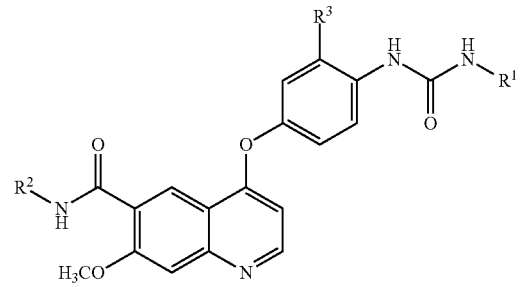

(I)

wherein $R^1$ is $C_{1-6}$ alkyl or $C_{3-8}$ cycloalkyl, $R^2$ is a hydrogen atom or $C_{1-6}$ alkoxy, and $R^3$ is a hydrogen atom or a halogen atom. A tumor therapeutic agent is disclosed that combines a compound or pharmaceutically acceptable salt thereof represented by Formula I and an anti-PD-1 antibody.

21 Claims, 11 Drawing Sheets

Specification includes a Sequence Listing.

(56) References Cited

U.S. PATENT DOCUMENTS

| | | |
|---|---|---|
| 4,743,450 A | 5/1988 | Harris et al. |
| 4,764,454 A | 8/1988 | Ichijima et al. |
| 4,816,567 A | 3/1989 | Cabilly et al. |
| 5,009,894 A | 4/1991 | Hsiao |
| 5,120,548 A | 6/1992 | McClelland et al. |
| 5,180,818 A | 1/1993 | Cech et al. |
| 5,211,951 A | 5/1993 | Sparer et al. |
| 5,445,934 A | 8/1995 | Fodor et al. |
| 5,464,826 A | 11/1995 | Grindey et al. |
| 5,487,889 A | 1/1996 | Eckert et al. |
| 5,553,037 A | 9/1996 | Tachibana |
| 5,624,937 A | 4/1997 | Reel et al. |
| 5,633,006 A | 5/1997 | Catania et al. |
| 5,650,376 A | 7/1997 | Badaye et al. |
| 5,656,454 A | 8/1997 | Lee et al. |
| 5,658,374 A | 8/1997 | Glover |
| 5,686,104 A | 11/1997 | Mills et al. |
| 5,733,913 A | 3/1998 | Blankley et al. |
| 5,747,651 A | 5/1998 | Lemischka |
| 5,750,376 A | 5/1998 | Weiss et al. |
| 5,770,599 A | 6/1998 | Gibson |
| 5,792,783 A | 8/1998 | Tang et al. |
| 5,891,996 A | 4/1999 | Mateo de Acosta del Rio et al. |
| 5,948,438 A | 9/1999 | Staniforth et al. |
| 6,027,880 A | 2/2000 | Cronin et al. |
| 6,057,100 A | 5/2000 | Heyneker |
| 6,143,764 A | 11/2000 | Kubo et al. |
| 6,156,501 A | 12/2000 | McGall et al. |
| 6,156,522 A | 12/2000 | Keay et al. |
| 6,214,865 B1 | 4/2001 | Littlefield et al. |
| 6,217,866 B1 | 4/2001 | Schlessinger et al. |
| 6,242,002 B1 | 6/2001 | Trittthart et al. |
| 6,261,776 B1 | 7/2001 | Pirrung et al. |
| 6,329,511 B1 | 12/2001 | Vasquez et al. |
| 6,346,398 B1 | 2/2002 | Pavco et al. |
| 6,351,255 B1 | 2/2002 | Ishizuka et al. |
| 6,475,525 B1 | 11/2002 | Komuro et al. |
| 6,476,040 B1 | 11/2002 | Norris et al. |
| 6,524,583 B1 | 2/2003 | Thorpe et al. |
| 6,534,535 B1 | 3/2003 | Zhu et al. |
| 6,544,552 B2 | 4/2003 | Sparks et al. |
| 6,576,424 B2 | 6/2003 | Fodor et al. |
| 6,596,311 B1 | 7/2003 | Dobetti et al. |
| 6,676,941 B2 | 1/2004 | Thorpe et al. |
| 6,762,180 B1 | 7/2004 | Roth et al. |
| 6,797,823 B1 | 9/2004 | Kubo et al. |
| 6,811,779 B2 | 11/2004 | Rockwell et al. |
| 6,812,341 B1 | 11/2004 | Conrad |
| 6,821,987 B2 | 11/2004 | Kubo et al. |
| 7,005,430 B2 | 2/2006 | Ueno et al. |
| 7,074,880 B2 | 7/2006 | Rhine et al. |
| 7,101,663 B2 | 9/2006 | Godfrey et al. |
| 7,135,466 B2 | 11/2006 | Sakai et al. |
| 7,169,789 B2 | 1/2007 | Kubo et al. |
| 7,175,856 B2 | 2/2007 | Ullah et al. |
| 7,211,587 B2 | 5/2007 | Kubo et al. |
| 7,253,286 B2 | 8/2007 | Funahashi et al. |
| 7,312,243 B1 * | 12/2007 | Pravda .................. A61K 31/12 424/653 |
| 7,321,241 B1 | 1/2008 | Marak et al. |
| 7,435,590 B2 | 10/2008 | Komurasaki |
| 7,485,658 B2 | 2/2009 | Bolger et al. |
| 7,488,802 B2 | 2/2009 | Collins et al. |
| 7,495,104 B2 | 2/2009 | Miwa et al. |
| 7,521,051 B2 | 4/2009 | Collins et al. |
| 7,547,703 B2 | 6/2009 | Roth et al. |
| 7,550,483 B2 | 6/2009 | Sakaguchi et al. |
| 7,612,092 B2 | 11/2009 | Funahashi et al. |
| 7,612,208 B2 | 11/2009 | Matsushima et al. |
| 7,683,172 B2 | 3/2010 | Naito et al. |
| 7,725,303 B2 | 5/2010 | Tramontana |
| 7,759,518 B2 | 7/2010 | Maderna et al. |
| 7,790,885 B2 | 9/2010 | Nagai et al. |
| 7,820,664 B2 | 10/2010 | Vernier et al. |
| 7,846,941 B2 | 12/2010 | Zhang et al. |
| 7,855,290 B2 | 12/2010 | Matsushima et al. |
| 7,863,288 B2 | 1/2011 | Ibrahim et al. |
| 7,973,160 B2 | 7/2011 | Funahashi et al. |
| 7,982,060 B2 | 7/2011 | Austad et al. |
| 7,994,159 B2 | 8/2011 | Yamamoto et al. |
| 7,998,948 B2 | 8/2011 | Obaishi et al. |
| 8,008,449 B2 | 8/2011 | Korman et al. |
| 8,044,240 B2 | 10/2011 | Dimock |
| 8,063,049 B2 | 11/2011 | Koh et al. |
| 8,093,410 B2 | 1/2012 | Chase et al. |
| 8,101,799 B2 | 1/2012 | Maderna et al. |
| 8,143,271 B2 | 3/2012 | Ibrahim et al. |
| 8,168,757 B2 | 5/2012 | Finnefrock et al. |
| 8,252,842 B2 | 8/2012 | Dimock |
| 8,288,538 B2 | 10/2012 | Matsushima et al. |
| 8,350,067 B2 | 1/2013 | Endo et al. |
| 8,354,509 B2 | 1/2013 | Carven et al. |
| 8,372,981 B2 | 2/2013 | Funahashi et al. |
| 8,377,938 B2 | 2/2013 | Matsushima et al. |
| 8,383,796 B2 | 2/2013 | Korman et al. |
| 8,415,469 B2 | 4/2013 | Ibrahim et al. |
| 8,466,316 B2 | 6/2013 | Dimock |
| 8,470,818 B2 | 6/2013 | Ibrahim et al. |
| 8,492,560 B2 | 7/2013 | Stokes et al. |
| 8,580,254 B2 | 11/2013 | Adam et al. |
| 8,648,116 B2 | 2/2014 | Vernier et al. |
| 8,759,577 B2 | 6/2014 | Dimock |
| 8,808,742 B2 | 8/2014 | Quart et al. |
| 8,815,241 B2 | 8/2014 | Yamamoto |
| 8,871,450 B2 | 10/2014 | Hacker |
| 8,962,650 B2 | 2/2015 | Narita et al. |
| 8,969,379 B2 * | 3/2015 | Furitsu ................. C07D 215/48 514/312 |
| 8,992,915 B2 | 3/2015 | Heider et al. |
| 9,006,256 B2 * | 4/2015 | Matsui .................... A61P 35/00 514/312 |
| 9,174,998 B2 | 11/2015 | Inoue et al. |
| 9,334,239 B2 * | 5/2016 | Gotoda .................... A61P 35/02 |
| 9,948,862 B2 | 4/2018 | Hagiwara |
| 10,259,791 B2 | 4/2019 | Nakamura et al. |
| 10,259,817 B2 | 4/2019 | Kushida et al. |
| 10,407,393 B2 | 9/2019 | Nakamura et al. |
| 10,517,861 B2 * | 12/2019 | Funahashi ........ G01N 33/57484 |
| 10,583,133 B2 | 3/2020 | Math et al. |
| 10,822,307 B2 | 11/2020 | Nakamura et al. |
| 11,547,705 B2 * | 1/2023 | Denker .............. C07K 16/2827 |
| 2002/0010203 A1 | 1/2002 | Lipson et al. |
| 2002/0032217 A1 | 3/2002 | Fanara et al. |
| 2002/0040127 A1 | 4/2002 | Jiang et al. |
| 2003/0013208 A1 | 1/2003 | Jendoubi |
| 2003/0087907 A1 | 5/2003 | Kubo et al. |
| 2003/0113713 A1 | 6/2003 | Glezer et al. |
| 2003/0124129 A1 | 7/2003 | Oliner |
| 2003/0187019 A1 | 10/2003 | Ullah et al. |
| 2003/0215523 A1 | 11/2003 | Ozawa et al. |
| 2004/0002505 A1 | 1/2004 | Ozawa et al. |
| 2004/0009965 A1 | 1/2004 | Collins et al. |
| 2004/0034026 A1 | 2/2004 | Wood et al. |
| 2004/0053908 A1 | 3/2004 | Funahashi et al. |
| 2004/0086915 A1 | 5/2004 | Lin et al. |
| 2004/0132727 A1 | 7/2004 | Sakai et al. |
| 2004/0132772 A1 | 7/2004 | Awad et al. |
| 2004/0152759 A1 | 8/2004 | Abrams et al. |
| 2004/0162333 A1 | 8/2004 | Mezaache et al. |
| 2004/0167134 A1 | 8/2004 | Bruns et al. |
| 2004/0171068 A1 | 9/2004 | Wehland et al. |
| 2004/0191254 A1 | 9/2004 | Fagin |
| 2004/0198806 A1 | 10/2004 | Littlefield et al. |
| 2004/0224972 A1 | 11/2004 | Ozawa et al. |
| 2004/0229876 A1 | 11/2004 | Kubo et al. |
| 2004/0242506 A1 | 12/2004 | Barges Causeret et al. |
| 2004/0243205 A1 | 12/2004 | Keravel et al. |
| 2004/0253205 A1 | 12/2004 | Yamamoto et al. |
| 2004/0259834 A1 | 12/2004 | Kasprzyk et al. |
| 2005/0014727 A1 | 1/2005 | Muller et al. |
| 2005/0049264 A1 | 3/2005 | Miwa et al. |
| 2005/0119303 A1 | 6/2005 | Wakabayashi et al. |
| 2005/0176802 A1 | 8/2005 | Tang et al. |
| 2005/0187236 A1 | 8/2005 | Tsuruoka et al. |

(56) References Cited

U.S. PATENT DOCUMENTS

| | | |
|---|---|---|
| 2005/0209452 A1 | 9/2005 | Bornsen et al. |
| 2005/0261337 A1 | 11/2005 | Wang et al. |
| 2005/0272688 A1 | 12/2005 | Higgins et al. |
| 2005/0277652 A1 | 12/2005 | Matsushima et al. |
| 2005/0288521 A1 | 12/2005 | Naidu et al. |
| 2006/0004017 A1 | 1/2006 | Stokes et al. |
| 2006/0004029 A1 | 1/2006 | Tsuruoka et al. |
| 2006/0018909 A1 | 1/2006 | Oliner et al. |
| 2006/0057195 A1 | 3/2006 | Nonomura et al. |
| 2006/0079494 A1 | 4/2006 | Santi et al. |
| 2006/0104984 A1 | 5/2006 | Littlefield et al. |
| 2006/0135486 A1 | 6/2006 | Owa et al. |
| 2006/0160832 A1 | 7/2006 | Funahashi et al. |
| 2006/0178399 A1 | 8/2006 | Nishizawa et al. |
| 2006/0189629 A1 | 8/2006 | Bolger et al. |
| 2006/0246071 A1 | 11/2006 | Green et al. |
| 2006/0247259 A1 | 11/2006 | Funahashi et al. |
| 2006/0252777 A1 | 11/2006 | Kim et al. |
| 2006/0292192 A1 | 12/2006 | Hasenzahl et al. |
| 2007/0004773 A1 | 1/2007 | Sakaguchi et al. |
| 2007/0014856 A1 | 1/2007 | Takagi et al. |
| 2007/0027318 A1 | 2/2007 | Kubo et al. |
| 2007/0032521 A1 | 2/2007 | Moussy et al. |
| 2007/0037849 A1 | 2/2007 | Naito et al. |
| 2007/0078159 A1 | 4/2007 | Matsushima |
| 2007/0117842 A1 | 5/2007 | Arimoto et al. |
| 2007/0214604 A1 | 9/2007 | Yi |
| 2007/0254930 A1 | 11/2007 | Ryu et al. |
| 2007/0298111 A1 | 12/2007 | Ueki |
| 2008/0207617 A1 | 8/2008 | Miwa et al. |
| 2008/0214557 A1 | 9/2008 | Ueki et al. |
| 2008/0214604 A1 | 9/2008 | Furitsu et al. |
| 2008/0214606 A1 | 9/2008 | Szakacs et al. |
| 2008/0241835 A1 | 10/2008 | Mehraban et al. |
| 2008/0246404 A1 | 10/2008 | Shelton et al. |
| 2008/0267971 A1 | 10/2008 | Green et al. |
| 2008/0280302 A1 | 11/2008 | Kebebew |
| 2008/0286282 A1 | 11/2008 | Semba et al. |
| 2009/0028858 A1 | 1/2009 | Wang et al. |
| 2009/0042213 A1 | 2/2009 | Hoofnagle et al. |
| 2009/0047278 A1 | 2/2009 | Owa et al. |
| 2009/0047365 A1 | 2/2009 | Owa et al. |
| 2009/0053236 A1 | 2/2009 | Yamamoto |
| 2009/0104285 A1 | 4/2009 | Littlefield et al. |
| 2009/0171112 A1 | 7/2009 | Naito et al. |
| 2009/0191212 A1 | 7/2009 | Oliner et al. |
| 2009/0202541 A1 | 8/2009 | Bruns et al. |
| 2009/0209580 A1 | 8/2009 | Matsui |
| 2009/0217401 A1 | 8/2009 | Korman et al. |
| 2009/0247576 A1 | 10/2009 | Kamata |
| 2009/0264464 A1 | 10/2009 | Yamamoto et al. |
| 2009/0304694 A1 | 12/2009 | Oliner et al. |
| 2009/0311175 A1 | 12/2009 | Brose |
| 2010/0048503 A1 | 2/2010 | Yamamoto |
| 2010/0048620 A1 | 2/2010 | Yamamoto |
| 2010/0092490 A1 | 4/2010 | Uenaka et al. |
| 2010/0105031 A1 | 4/2010 | Matsui et al. |
| 2010/0197911 A1 | 8/2010 | Funahashi et al. |
| 2010/0239688 A1 | 9/2010 | Yamamoto |
| 2010/0324087 A1 | 12/2010 | Yamamoto |
| 2011/0020410 A1 | 1/2011 | Nonomura et al. |
| 2011/0028498 A1 | 2/2011 | Ryan et al. |
| 2011/0060049 A1 | 3/2011 | Vernier et al. |
| 2011/0104161 A1 | 5/2011 | Burgess et al. |
| 2011/0118470 A1 | 5/2011 | Funahashi et al. |
| 2011/0158983 A1 | 6/2011 | Bascomb et al. |
| 2011/0166174 A1 | 7/2011 | Zhang et al. |
| 2011/0172446 A1 | 7/2011 | Littlefield et al. |
| 2011/0207756 A1 | 8/2011 | Matsui |
| 2011/0271358 A1 | 11/2011 | Freeman et al. |
| 2011/0293615 A1 | 12/2011 | Yamamoto |
| 2011/0311546 A1 | 12/2011 | Oliner et al. |
| 2012/0022076 A1 | 1/2012 | Maderna et al. |
| 2012/0052073 A1 | 3/2012 | Green et al. |
| 2012/0053177 A1 | 3/2012 | Ibrahim et al. |
| 2012/0077837 A1 | 3/2012 | Okamoto et al. |
| 2012/0077842 A1 | 3/2012 | Bando |
| 2012/0184452 A1 | 7/2012 | Pastoriza |
| 2012/0207753 A1* | 8/2012 | Yu .................... G01N 33/57484 |
| | | 424/134.1 |
| 2012/0219522 A1 | 8/2012 | Xi |
| 2012/0244209 A1 | 9/2012 | Roth et al. |
| 2012/0263677 A1 | 10/2012 | Eagle et al. |
| 2012/0283206 A1 | 11/2012 | Bruns et al. |
| 2013/0071403 A1* | 3/2013 | Rolland ................ A61P 35/04 |
| | | 424/142.1 |
| 2013/0085152 A1 | 4/2013 | Matsui et al. |
| 2013/0108626 A1 | 5/2013 | Delmar et al. |
| 2013/0121999 A1 | 5/2013 | De Haas et al. |
| 2013/0123274 A1 | 5/2013 | Nakagawa et al. |
| 2013/0133091 A1 | 5/2013 | Korman et al. |
| 2013/0142799 A1 | 6/2013 | Oliner et al. |
| 2013/0171135 A1 | 7/2013 | Andres et al. |
| 2013/0171160 A1 | 7/2013 | Green et al. |
| 2013/0183300 A1 | 7/2013 | Andres et al. |
| 2013/0183301 A1 | 7/2013 | Delmar et al. |
| 2013/0183302 A1 | 7/2013 | De Haas et al. |
| 2013/0183303 A1 | 7/2013 | De Haas et al. |
| 2013/0195857 A1 | 8/2013 | Delmar et al. |
| 2013/0225581 A1 | 8/2013 | Furuta et al. |
| 2013/0237565 A1 | 9/2013 | Furitsu et al. |
| 2013/0243758 A1 | 9/2013 | Andres et al. |
| 2013/0296365 A1 | 11/2013 | Bando |
| 2013/0309250 A1* | 11/2013 | Cogswell ............ A61K 39/3955 |
| | | 530/388.2 |
| 2013/0336959 A1 | 12/2013 | Andres et al. |
| 2013/0336960 A1 | 12/2013 | Andres et al. |
| 2013/0344059 A1 | 12/2013 | Andres et al. |
| 2013/0344060 A1 | 12/2013 | Andres et al. |
| 2014/0017231 A1 | 1/2014 | Andres et al. |
| 2014/0017232 A1 | 1/2014 | Andres et al. |
| 2014/0023639 A1 | 1/2014 | Andres et al. |
| 2014/0023640 A1 | 1/2014 | Andres et al. |
| 2014/0031384 A1 | 1/2014 | Narita et al. |
| 2014/0056874 A1 | 2/2014 | Andres et al. |
| 2014/0056875 A1 | 2/2014 | Andres et al. |
| 2014/0056876 A1 | 2/2014 | Andres et al. |
| 2014/0079706 A1 | 3/2014 | Cannarile et al. |
| 2014/0148483 A1 | 5/2014 | Semba et al. |
| 2014/0193397 A1 | 7/2014 | Andres et al. |
| 2014/0212422 A1 | 7/2014 | Korman et al. |
| 2014/0234296 A1† | 8/2014 | Sharma |
| 2014/0243316 A1 | 8/2014 | Takaishi et al. |
| 2014/0294852 A1 | 10/2014 | Korman et al. |
| 2014/0302019 A1 | 10/2014 | Delmar et al. |
| 2014/0328833 A1 | 11/2014 | Korman et al. |
| 2014/0348743 A1 | 11/2014 | Korman et al. |
| 2015/0005343 A1 | 1/2015 | Nomoto et al. |
| 2015/0125455 A1 | 5/2015 | Green et al. |
| 2015/0165025 A1 | 6/2015 | Korman et al. |
| 2015/0175615 A1 | 6/2015 | Inoue et al. |
| 2015/0210769 A1* | 7/2015 | Freeman .......... G01N 33/57484 |
| | | 435/254.2 |
| 2015/0366866 A1 | 12/2015 | Ali et al. |
| 2016/0222118 A1 | 8/2016 | Chen et al. |
| 2017/0088615 A1 | 3/2017 | Korman et al. |
| 2017/0191137 A1 | 7/2017 | Semba et al. |
| 2017/0233344 A1 | 8/2017 | Nakamura et al. |
| 2018/0092901 A1 | 4/2018 | Denker et al. |
| 2022/0023285 A1 | 1/2022 | Denker et al. |

FOREIGN PATENT DOCUMENTS

| | | |
|---|---|---|
| CA | 2606719 A1 | 12/2006 |
| CA | 3 044 658 A1 | 8/2018 |
| CH | 656535 A5 | 7/1986 |
| CN | 1083728 A | 3/1994 |
| CN | 1293041 A | 5/2001 |
| CN | 1473041 A | 2/2004 |
| CN | 1478078 A | 2/2004 |
| CN | 1634043 A | 7/2005 |
| CN | 1642415 A | 7/2005 |
| CN | 1744881 A | 3/2006 |

(56) References Cited

FOREIGN PATENT DOCUMENTS

| | | |
|---|---|---|
| CN | 1772052 A | 5/2006 |
| CN | 1878751 A | 12/2006 |
| CN | 1890220 A | 1/2007 |
| CN | 101001629 A | 7/2007 |
| CN | 101029022 A | 9/2007 |
| CN | 101198590 A | 6/2008 |
| CN | 101316590 A | 12/2008 |
| CN | 101337931 A | 1/2009 |
| CN | 101443009 A | 5/2009 |
| CN | 101454286 A | 6/2009 |
| CN | 101454311 A | 6/2009 |
| CN | 101616671 A | 12/2009 |
| CN | 101848895 A | 9/2010 |
| CN | 102036962 A | 4/2011 |
| CN | 102470133 A | 5/2012 |
| CN | 102958523 A | 3/2013 |
| CN | 103003262 A | 3/2013 |
| CN | 103402519 A | 11/2013 |
| CN | 105338977 A | 2/2016 |
| CN | 107305202 A | 10/2017 |
| CN | 107305202 B | 4/2020 |
| EP | 0 203 126 A1 | 12/1986 |
| EP | 0 297 580 A1 | 1/1989 |
| EP | 0 405 425 A2 | 1/1991 |
| EP | 0 408 496 A2 | 1/1991 |
| EP | 0 427 519 A2 | 5/1991 |
| EP | 0 543 942 A1 | 6/1993 |
| EP | 0 602 851 A1 | 6/1994 |
| EP | 0 684 637 A2 | 11/1995 |
| EP | 0 684 820 A1 | 12/1995 |
| EP | 0 712 863 A1 | 5/1996 |
| EP | 0 795 556 A1 | 9/1997 |
| EP | 0 837 063 A1 | 4/1998 |
| EP | 0 860 433 A1 | 8/1998 |
| EP | 0 870 842 A2 | 10/1998 |
| EP | 0 930 305 A1 | 7/1999 |
| EP | 0 930 310 A1 | 7/1999 |
| EP | 1 029 853 A1 | 8/2000 |
| EP | 1 044 969 A2 | 10/2000 |
| EP | 1 153 920 A1 | 11/2001 |
| EP | 1 331 005 A1 | 7/2003 |
| EP | 1 382 604 A1 | 1/2004 |
| EP | 1 411 046 A1 | 4/2004 |
| EP | 1 415 987 A1 | 5/2004 |
| EP | 1 447 045 A1 | 8/2004 |
| EP | 1 447 405 A1 | 8/2004 |
| EP | 1 473 043 A1 | 11/2004 |
| EP | 1 506 962 A2 | 2/2005 |
| EP | 1 522 540 A1 | 4/2005 |
| EP | 1 535 910 A1 | 6/2005 |
| EP | 1 552 833 A1 | 7/2005 |
| EP | 1 566 379 A1 | 8/2005 |
| EP | 1 604 665 A1 | 12/2005 |
| EP | 1 683 785 A1 | 7/2006 |
| EP | 1 698 623 A1 | 9/2006 |
| EP | 1 719 763 A1 | 11/2006 |
| EP | 1 777 218 A1 | 4/2007 |
| EP | 1 797 877 A1 | 6/2007 |
| EP | 1 797 881 A1 | 6/2007 |
| EP | 1 859 793 A1 | 11/2007 |
| EP | 1 859 797 A1 | 11/2007 |
| EP | 1 889 836 A1 | 2/2008 |
| EP | 1 894 918 A1 | 3/2008 |
| EP | 1 925 676 A1 | 5/2008 |
| EP | 1 925 941 A1 | 5/2008 |
| EP | 1 949 902 A1 | 7/2008 |
| EP | 1 964 837 A1 | 9/2008 |
| EP | 2 058 302 A1 | 5/2009 |
| EP | 2 062 886 A1 | 5/2009 |
| EP | 2 116 246 A1 | 11/2009 |
| EP | 2 119 707 A1 | 11/2009 |
| EP | 2 133 094 A1 | 12/2009 |
| EP | 2 133 095 A1 | 12/2009 |
| EP | 2 218 712 A1 | 8/2010 |
| EP | 2 293 071 A1 | 3/2011 |
| EP | 2 711 433 A1 | 3/2014 |
| EP | 2 700 403 B1 | 11/2015 |
| EP | 3384901 A1 | 10/2018 |
| EP | 3524595 A1 | 8/2019 |
| EP | 3524595 B1 | 8/2022 |
| EP | 4147689 A1 | 3/2023 |
| GB | 2253848 A | 9/1992 |
| GB | 2456907 A | 8/2009 |
| IL | 148756 A | 10/2007 |
| IN | 236500 | 11/2009 |
| JP | S61-148115 A | 7/1986 |
| JP | S63-028427 A | 2/1988 |
| JP | S64-22874 A | 1/1989 |
| JP | H02-291295 A | 12/1990 |
| JP | H05194259 A | 8/1993 |
| JP | H07-176103 A | 7/1995 |
| JP | H08-045927 A | 2/1996 |
| JP | H08-048078 A | 2/1996 |
| JP | H09-023885 A | 1/1997 |
| JP | H09-234074 | 9/1997 |
| JP | H10-114655 A | 5/1998 |
| JP | H10-147524 A | 6/1998 |
| JP | H10-316576 A | 12/1998 |
| JP | H11-501343 A | 2/1999 |
| JP | H11-143429 A | 5/1999 |
| JP | H11-158149 A | 6/1999 |
| JP | H11-322596 A | 11/1999 |
| JP | 3040486 B2 | 5/2000 |
| JP | 3088018 B2 | 9/2000 |
| JP | 2000-325080 A | 11/2000 |
| JP | 2001-047890 A | 2/2001 |
| JP | 2001-131071 A | 5/2001 |
| JP | 2002-003365 A | 1/2002 |
| JP | 2002-505269 A | 2/2002 |
| JP | 2002-114710 A | 4/2002 |
| JP | 2002-509872 A | 4/2002 |
| JP | 2002-518384 A | 6/2002 |
| JP | 2002-536056 A | 10/2002 |
| JP | 2002-536414 A | 10/2002 |
| JP | 2003-012668 A | 1/2003 |
| JP | 2003-026576 A | 1/2003 |
| JP | 2003-033472 A | 2/2003 |
| JP | 3420549 B2 | 6/2003 |
| JP | 2003-252737 A | 9/2003 |
| JP | 2003-525595 A | 9/2003 |
| JP | 2004-513964 A | 5/2004 |
| JP | 2004-155773 A | 6/2004 |
| JP | 2004-517859 A | 6/2004 |
| JP | 2004-531549 A | 10/2004 |
| JP | 2005-501074 A | 1/2005 |
| JP | 2005-504111 A | 2/2005 |
| JP | 2005-124034 A | 5/2005 |
| JP | 2005-520834 A | 7/2005 |
| JP | 2005-272474 A | 10/2005 |
| JP | 3712393 B2 | 11/2005 |
| JP | 2006-508981 A | 3/2006 |
| JP | 2006-515884 A | 6/2006 |
| JP | 2006-230816 A | 9/2006 |
| JP | 2006-340714 A | 12/2006 |
| JP | 2007-153894 A | 6/2007 |
| JP | 2008-546797 A | 12/2008 |
| JP | 2009-132660 A | 6/2009 |
| JP | 4-341454 B2 | 10/2009 |
| JP | 2010-502209 A | 1/2010 |
| JP | 2010-535233 A | 11/2010 |
| JP | 2014-521308 A | 8/2014 |
| JP | 2016-528162 A | 9/2016 |
| JP | 6-153952 B2 | 6/2017 |
| JP | 6-287148 B2 | 3/2018 |
| JP | 6788600 B2 | 11/2020 |
| KR | 2003-0040552 A | 5/2003 |
| KR | 200340552 Y1 | 2/2004 |
| KR | 100589032 B1 | 6/2006 |
| KR | 10-2006-0113759 A | 11/2006 |
| KR | 20070053205 A | 5/2007 |
| KR | 20070116217 A | 12/2007 |
| KR | 20080008374 A | 1/2008 |
| KR | 20160023816 A | 3/2016 |
| KR | 20160094980 A | 8/2016 |

(56) References Cited

FOREIGN PATENT DOCUMENTS

| | | |
|---|---|---|
| RU | 2192863 C2 | 11/2002 |
| RU | 2264389 C2 | 11/2005 |
| RU | 2328489 C2 | 7/2008 |
| RU | 2362771 C1 | 7/2009 |
| RU | 2385867 C2 | 4/2010 |
| RU | 2404992 C2 | 11/2010 |
| RU | 2448708 C2 | 4/2012 |
| RU | 2582964 C2 | 4/2016 |
| TW | I304061 B | 12/2008 |
| WO | WO-1986/003222 | 6/1986 |
| WO | WO-1992/020642 | 11/1992 |
| WO | WO-1993/011748 | 6/1993 |
| WO | WO-1994/009010 | 4/1994 |
| WO | WO-1995/015758 | 6/1995 |
| WO | WO-1995/017181 | 6/1995 |
| WO | WO-1995/019774 | 7/1995 |
| WO | WO-1996/009294 | 3/1996 |
| WO | WO-1996/026997 | 9/1996 |
| WO | WO-1996/030347 | 10/1996 |
| WO | WO-1996/033980 | 10/1996 |
| WO | WO-1996/039145 | 12/1996 |
| WO | WO-1996/040080 | 12/1996 |
| WO | WO-1996/040142 | 12/1996 |
| WO | WO-1997/003069 | 1/1997 |
| WO | WO-1997/013760 | 4/1997 |
| WO | WO-1997/013771 | 4/1997 |
| WO | WO-1997/017329 | 5/1997 |
| WO | WO-1997/021437 | 6/1997 |
| WO | WO-1997/038984 | 10/1997 |
| WO | WO-1997/048693 | 12/1997 |
| WO | WO-1998/000134 | 1/1998 |
| WO | WO-1998/002434 | 1/1998 |
| WO | WO-1998/002437 | 1/1998 |
| WO | WO-1998/002438 | 1/1998 |
| WO | WO-1998/013350 | 4/1998 |
| WO | WO-1998/014437 | 4/1998 |
| WO | WO-1998/023613 | 6/1998 |
| WO | WO-1998/029137 | 7/1998 |
| WO | WO-1998/032436 | 7/1998 |
| WO | WO-1998/035958 | 8/1998 |
| WO | WO-1998/037079 | 8/1998 |
| WO | WO-1998/050346 | 11/1998 |
| WO | WO-1998/052558 | 11/1998 |
| WO | WO-99/003854 A1 | 1/1999 |
| WO | WO-1999/000357 | 1/1999 |
| WO | WO-1999/032106 | 7/1999 |
| WO | WO-1999/032110 | 7/1999 |
| WO | WO-1999/032111 | 7/1999 |
| WO | WO-1999/032436 | 7/1999 |
| WO | WO-1999/035132 | 7/1999 |
| WO | WO-1999/035146 | 7/1999 |
| WO | WO-1999/043654 | 9/1999 |
| WO | WO-1999/062890 | 12/1999 |
| WO | WO-2000/019985 A2 | 4/2000 |
| WO | WO-00/35460 A2 | 6/2000 |
| WO | WO-2000/031048 A1 | 6/2000 |
| WO | WO-2000/042012 A1 | 7/2000 |
| WO | WO-2000/043366 A1 | 7/2000 |
| WO | WO-2000/043384 A1 | 7/2000 |
| WO | WO-2000/044728 A1 | 8/2000 |
| WO | WO-2000/047212 A1 | 8/2000 |
| WO | WO-2000/050405 A1 | 8/2000 |
| WO | WO-2000/071097 A1 | 11/2000 |
| WO | WO-2001/002369 A2 | 1/2001 |
| WO | WO-2001/023375 A2 | 4/2001 |
| WO | WO-2001/027081 A1 | 4/2001 |
| WO | WO-2001/032926 A2 | 5/2001 |
| WO | WO-2001/036403 A1 | 5/2001 |
| WO | WO-2001/040217 A1 | 6/2001 |
| WO | WO-2001/045689 A2 | 6/2001 |
| WO | WO-2001/047890 A1 | 7/2001 |
| WO | WO-2001/047931 A1 | 7/2001 |
| WO | WO-2001/060814 A2 | 8/2001 |
| WO | WO-2002/016348 A1 | 2/2002 |
| WO | WO-2002/032872 A1 | 4/2002 |
| WO | WO-2002/036117 A1 | 5/2002 |
| WO | WO-2002/041882 A2 | 5/2002 |
| WO | WO-2002/044156 A2 | 6/2002 |
| WO | WO-2002/072578 A2 | 9/2002 |
| WO | WO-2002/080975 A1 | 10/2002 |
| WO | WO-2002/088110 A1 | 11/2002 |
| WO | WO-2002/092091 A1 | 11/2002 |
| WO | WO-2002/096361 A2 | 12/2002 |
| WO | WO-2003/000660 A1 | 1/2003 |
| WO | WO-2003/006462 A1 | 1/2003 |
| WO | WO-2003/013529 A1 | 2/2003 |
| WO | WO-2003/024386 A2 | 3/2003 |
| WO | WO-2003/027102 A1 | 4/2003 |
| WO | WO-2003/028711 A2 | 4/2003 |
| WO | WO-2003/033472 A1 | 4/2003 |
| WO | WO-2003/050090 A1 | 6/2003 |
| WO | WO-2003/074045 A1 | 9/2003 |
| WO | WO-2003/075840 A2 | 9/2003 |
| WO | WO-2003/079020 A2 | 9/2003 |
| WO | WO-2003/087026 A1 | 10/2003 |
| WO | WO-2003/099771 A2 | 12/2003 |
| WO | WO-2004/004771 A1 | 1/2004 |
| WO | WO-2004/006862 A2 | 1/2004 |
| WO | WO-2004/020434 A1 | 3/2004 |
| WO | WO-2004/032872 A2 | 4/2004 |
| WO | WO-2004/032937 A1 | 4/2004 |
| WO | WO-2004/035052 A1 | 4/2004 |
| WO | WO-2004/039782 A1 | 5/2004 |
| WO | WO-2004/041308 A1 | 5/2004 |
| WO | WO-2004/043472 A1 | 5/2004 |
| WO | WO-2004/045523 A2 | 6/2004 |
| WO | WO-2004/056875 A1 | 7/2004 |
| WO | WO-2004/064730 A2 | 8/2004 |
| WO | WO-2004/072286 A1 | 8/2004 |
| WO | WO-2004/076412 A2 | 9/2004 |
| WO | WO-2004/078144 A2 | 9/2004 |
| WO | WO-2004/080462 A1 | 9/2004 |
| WO | WO-2004/080966 A1 | 9/2004 |
| WO | WO-2004/087096 A1 | 10/2004 |
| WO | WO-2004/089286 A2 | 10/2004 |
| WO | WO-2004/101526 A1 | 11/2004 |
| WO | WO-2005/004870 A1 | 1/2005 |
| WO | WO-2005/021537 A1 | 3/2005 |
| WO | WO-2005/027972 A2 | 3/2005 |
| WO | WO-2005/030140 A2 | 4/2005 |
| WO | WO-2005/044788 A1 | 5/2005 |
| WO | WO-2005/051366 A2 | 6/2005 |
| WO | WO-2005/056764 A2 | 6/2005 |
| WO | WO-2005/063713 A1 | 7/2005 |
| WO | WO-2005/070891 A2 | 8/2005 |
| WO | WO-2005/082854 A1 | 9/2005 |
| WO | WO-2005/082855 A1 | 9/2005 |
| WO | WO-2005/092896 A1 | 10/2005 |
| WO | WO-2005/117867 A2 | 12/2005 |
| WO | WO-2005/117887 A1 | 12/2005 |
| WO | WO-2006/004636 A2 | 1/2006 |
| WO | WO-2006/014325 A2 | 2/2006 |
| WO | WO-2006/030826 A1 | 3/2006 |
| WO | WO-2006/030941 A1 | 3/2006 |
| WO | WO-2006/030947 A1 | 3/2006 |
| WO | WO-2006/036941 A2 | 4/2006 |
| WO | WO-2006/038552 A1 | 4/2006 |
| WO | WO-2006/062984 A2 | 6/2006 |
| WO | WO-2006/090930 A1 | 8/2006 |
| WO | WO-2006/090931 A1 | 8/2006 |
| WO | WO-2006/105798 A2 | 10/2006 |
| WO | WO-2006/137474 A1 | 12/2006 |
| WO | WO-2007/000347 A2 | 1/2007 |
| WO | WO-2007/002325 A1 | 1/2007 |
| WO | WO-2007/014335 A2 | 2/2007 |
| WO | WO-2007/015569 A1 | 2/2007 |
| WO | WO-2007/015578 A1 | 2/2007 |
| WO | WO-2007/023768 A1 | 3/2007 |
| WO | WO-2007/040565 A2 | 4/2007 |
| WO | WO-2007/052849 A1 | 5/2007 |
| WO | WO-2007/052850 A1 | 5/2007 |
| WO | WO-2007/061127 A1 | 5/2007 |
| WO | WO-2007/061130 A1 | 5/2007 |
| WO | WO-2007/061874 A2 | 5/2007 |

(56) References Cited

FOREIGN PATENT DOCUMENTS

| | | |
|---|---|---|
| WO | WO-2007/136103 A1 | 11/2007 |
| WO | WO-2008/023698 A1 | 2/2008 |
| WO | WO-2008/026577 A1 | 3/2008 |
| WO | WO-2008/026748 A1 | 3/2008 |
| WO | WO-2008029123 A1 | 3/2008 |
| WO | WO-2008/053602 A1 | 5/2008 |
| WO | WO-2008/088088 A1 | 7/2008 |
| WO | WO-2008/093855 A1 | 8/2008 |
| WO | WO-2008/102870 A1 | 8/2008 |
| WO | WO-2008/155387 A2 | 12/2008 |
| WO | WO-2008/156712 A1 | 12/2008 |
| WO | WO-2009/018238 A1 | 2/2009 |
| WO | WO-2009/060945 A1 | 5/2009 |
| WO | WO-2009/077874 A2 | 6/2009 |
| WO | WO-2009/096377 A1 | 8/2009 |
| WO | WO-2009/114335 A2 | 9/2009 |
| WO | WO-2009/140549 A1 | 11/2009 |
| WO | WO-2009/150256 A1 | 12/2009 |
| WO | WO-2010/006225 A1 | 1/2010 |
| WO | WO-2010/027827 | 3/2010 |
| WO | WO-2010/048304 A2 | 4/2010 |
| WO | WO-2010/077634 A1 | 7/2010 |
| WO | WO-2010/086964 A1 | 8/2010 |
| WO | WO-2011/017583 A1 | 2/2011 |
| WO | WO-2011/021597 A1 | 2/2011 |
| WO | WO-2011/022335 A1 | 2/2011 |
| WO | WO-2011/066342 A2 | 6/2011 |
| WO | WO-2011/162343 A1 | 12/2011 |
| WO | WO-2012/019300 A1 | 2/2012 |
| WO | WO-2012/144463 A1 | 10/2012 |
| WO | WO-2012/154935 A1 | 11/2012 |
| WO | WO-2012/157672 A1 | 11/2012 |
| WO | WO-2012/166899 A2 | 12/2012 |
| WO | WO-2013/132044 A1 | 9/2013 |
| WO | WO-2013/019906 A9 | 3/2014 |
| WO | WO 2014/055648 * | 4/2014 |
| WO | WO2014055648 A1 † | 4/2014 |
| WO | WO-2014100079 A1 | 6/2014 |
| WO | WO-2014/113729 A2 | 7/2014 |
| WO | WO-2014/133022 A1 | 9/2014 |
| WO | WO2014151006 A2 † | 9/2014 |
| WO | WO-2014/185540 A1 | 11/2014 |
| WO | WO-2014/208774 A1 | 12/2014 |
| WO | WO-2015/098853 A1 | 7/2015 |
| WO | WO 2015/119944 * | 8/2015 |
| WO | WO-2016/141218 A1 | 9/2016 |
| WO | WO-2016/0196389 A1 | 12/2016 |
| WO | WO-2016/204193 A1 | 12/2016 |
| WO | WO-2016/208576 A1 | 12/2016 |

OTHER PUBLICATIONS

Pascalis et al (The Journal of Immunology (2002) 169, 3076-3084) (Year: 2002).*
Casset et al. (2003) BBRC 307, 198-205, (Year: 2003).*
D'Angelo et al, Frontiers in Immunology vol. 9 p. 1 (2018) (Year: 2018).*
Eisai Product Information (Feb. 2015), (Year: 2015).*
Boss et al British Journal of Cancer vol. 106 p. 1598 (2012) (Year: 2012).*
Kimura et al, Cancer Science 109:3993 (2018), (Year: 2018).*
Japanese Submission Documents in Application No. P2020-182679, dated Oct. 8, 2021, 25 pages.
Official Letter mailed Nov. 18, 2021 in MX Patent Application No. MX/a/2019/013014 (w.English translation).
Official Letter mailed Nov. 19, 2021 in U.S. Appl. No. 17/228,025.
Official Letter mailed Nov. 3, 2021 in RU Patent Application No. 2017104496 (w.English translation).
Official Letter mailed Nov. 4, 2021 in U.S. Appl. No. 17/022,675.
Official Letter mailed Nov. 5, 2021 in PK Patent Application No. 548/2015.
Official Letter mailed Nov. 8, 2021 in MX Patent Application No. MX/a/2019/013014.
Official Letter mailed Sep. 21, 2021 in BR Patent Application No. BR112015009004-4 (w/English translation).
Official Letter mailed Sep. 21, 2021 in BR Patent Application No. BR1120170028271.
Official Letter mailed Sep. 21, 2021 in BR Patent Application No. BR1120170174286 (w.English Translation).
Official Letter mailed Sep. 21, 2021 in BR Patent Application No. BR1120170241960 (w.English translation).
Official Letter mailed Sep. 21, 2021 in BR Patent Application No. BR1120180027324 (w.English translation).
Submission Document filed Nov. 8, 2021 in Australian Patent Application No. 2015384801.
Submission Document filed Nov. 8, 2021 in European Patent Application No. 20207489.4.
Submission Document filed Oct. 25, 2021 in U.S. Appl. No. 17/022,675.
Submission Documents filed Nov. 12, 2021 in U.S. Appl. No. 15/573,197.
Ahmadzadeh, Mojgan et al., "Tumor antigen-specific CD8 T cells infiltrating the tumor express high levels of PD-1 and are functionally impaired," Blood, 2009(114), p. 1537-p. 1544.
Baj-Krzyworzeka, Monika et al., "Elevated level of some cytokines in plasma of gastric cancer patients," Central European Journal Immunology, vol. 41, No. 4, 2016, p. 358-p. 362.
Dong H et al., "Tumor-associated B7-H1 promotes T-cell apoptosis: a potential mechanism of immune evasion," Nat. Med., 2002 8(8), p. 793-p800.
E Ruiz-Garcia et al., "Gene expression profiling identifies Fibronectin 1 and CXCL9 as candidate biomarkers for breast cancer screening," British Journal of Cancer, vol. 102, No. 3, Jan. 12, 2010, p. 462-p. 468.
Gao, Qiang et al., "Overexpression of PD-L1 Significantly Associates with Tumor Aggressiveness and Postoperative Recurrence in Human Hepatocellular Carcinoma," Clinical Cancer Research, 2009(15), p. 971-p. 979.
Ghebeh, Hazem et al., "The B7-H1 (PD-L1) T lymphocyte-inhibitory molecule is expressed in breast cancer patients with infiltrating ductal carcinoma: correlation with important high-risk prognostic factors," Neoplasia, 2006(8), p. 190-p. 198.
Ghebeh, Hazem et al., "Foxp3$^+$ T$_{regs}$ and B7-H1$^+$/PD-1$^+$ T lymphocytes coinfiltrate the tumor tissues of high-risk breast cancer patients: Implication for immunotherapy", BMC Cancer., 2008(8):57, p. 1-p. 12.
Hamanishi, Junzo et al., "Programmed cell death 1 ligand 1 and tumorinfiltrating CD8+ T lymphocytes are prognostic factors of human ovarian cancer," Proceeding of the National Academy of Sciences USA, 2007(104), p. 3360-p. 3365.
Hino, Ryosuke et al., "Tumor Cell Expression of Programmed Cell Death-1 Is a Prognostic Factor for Malignant Melanoma," Cancer, 2010(116):7, p. 1757-p. 1766.
Inman, Brant A. et al., "PD-L1 (B7-H1) Expression by Urothelial Carcinoma of the Bladder and BCG-Induced Granulomata: Associations With Localized Stage Progression," Cancer, 2007(109), p. 1499-p. 1505.
Iwai, Yoshiko et al., "Involvement of PD-L1 on tumor cells in the escape from host immune system and tumor immunotherapy by PD-L1 blockade," PNAS, 2002(99):19, p. 12293-p. 12297.
Nakanishi, Juro et al., "Overexpression of B7-H1 (PD-L1) significantly associates with tumor grade and postoperative prognosis in human urothelial cancers," Cancer Immunol. Immunother., 2007(56), p. 1173-p. 1182.
Nomi, Takeo et al., "Clinical significance and therapeutic potential of the programmed death-1 ligand/programmed death-1 pathway in human pancreatic cancer," Clinical Cancer Research, 2007(13), p. 2151-p. 2157.
Ohigashi, Yuichiro et al., "Clinical Significance of Programmed Death-1 Ligand-1 and Programmed Death-1 Ligand 2 Expression in Human Esophageal Cancer," Clin. Cancer Research, 2005(11), p. 2947-p. 2953.
Sacher, Adrian G. et al., "Biomarkers for the Clinical Use of PD-1/PD-LI Inhibitors in Non- Small-Cell Lung Cancer: A Review," JAMA Oncology, vol. 2, No. 9, Sep. 1, 2016, p. 1217-p. 1222.

(56) References Cited

OTHER PUBLICATIONS

Ribas, Antoni et al., "Oncolytic Virotherapy Promotes Intratumoral T Cell Infiltration and Improves Anti-PD-1 Immunotherapy," Cell, Elsevier, vol. 170, No. 6, Sep. 7, 2017, p. 1109-p. 1119.
Sharpe, A.H, et al., "The function of programmed cell death 1 and its ligands in regulating autoimmunity and infection," Nature Immunology, 2007(8), p. 239-p. 245.
Shimauchi, Takatoshi et al., "Augmented expression of programmed death-1 in both neoplasmatic and non-neoplastic CD4+ T-cells in adult T-cell leukemia/lymphoma," Int. J. Cancer, 2007(121), p. 2585-p. 2590.
Tahara, Makoto et al., "Exploratory analysis of biomarkers associated with clinical outcomes from the study of lenvatinib in differentiated cancer of the thyroid," European Journal of Cancer, vol. 75, Feb. 24, 2017, p. 213-p. 221.
Taylor, M. et al., "A phase 1 trial of lenvatinib plus pembrolizumab in patients with selected solid tumors," Annals of Oncolog, vol. 27, 2016.
Thompson RH et al., "Significance of B7-H1 overexpression in kidney cancer," Clinical Genitourin Cancer, 2006(5), p. 206-p. 211.
Thompson, RH et al., "PD-1 Is Expressed by Tumor-Infiltrating Immune Cells and Is Associated with Poor Outcome for Patients with Renal Cell Carcinoma," Clinical Cancer Research, 2007, p. 1757-p. 1761.
Yang, Wanbua et al., "PD-L1: PD-1 Interaction Contributes to the Functional Suppression of T-Cell Responses to Human Uveal Melanoma Cells In Vitro," Invest. Ophthalmol. Vis. Sci., 2008 49(6), p. 2518-p. 2525.
Yamada, Kazuhiko et al., "Phase I Dose-Escalation Study and Biomarker Analysis of E7080 in Patients with Advanced Solid Tumors," Clinical Cancer Research, vol. 17, No. 8, Mar. 3, 2011, p. 2528-p. 2537.
Written Opinion of the International Searching Authority mailed Sep. 17, 2019 for PCT/US2019/031967.
Amin A., et al., "Nivolumab (anti-PD-1; BMS-936558, ONO-4538) in combination with sunitinib or pazopanib in patients (pts) with metastatic renal cell carcinoma (mRCC)," Journal of Clinical Oncology, 2014 ASCO Annual Meeting Abstracts, vol. 32, No. 15, (May 20 Supplement), 2014, 2 pages.
Krepler C., et al., "Highlights of melanoma research presented at the 49th annual meeting of the American Society of Clinical Oncology in Chicago, 2013," Pigment Cell Melanoma Research, 27; E1-E5, Jan. 1, 2014.
"Current Protocols in Molecular Biology", John Wiley & Sons Section 11.4-11.13 (1987), 62, pages.
"FDA-AACR Oncology Dose Finding Workshop—Session 3 Transcript [URL:https://www.aacr.org/AdvocacyPolicy/GovernmentAffairs/Documents/6.13.16%20FDA-AACR%20Oncology%20Dose%20Finding%20Workshop%20Session%203%20Transcript.pdf]", Jun. 13, 2016, 27 pages.
"FMC BioPolymer; http://www.fmcbiopolymer.com/portals/pharm/content/docs/fmc_alubra_brochurefinal.pdf," Mar. 16, 2015, 6 pages.
"In 1571/CHENP/2007", Aug. 31, 2007, 50 pages (English Translation).
"In 383/CHENP/2008", Sep. 19, 2008, 26 pages (English Translation).
"Mix: Merriam-Webster Dictionary (Year: 2018), " 2018.
"Molecular Targets and Cancer Therapeutics," Poster Session A, A92, Kato et al., Nov. 6, 2015, p. 64.
"Pharmaceuticals Interview Form—LENVIMA®," Pharmaceuticals and Medical Devices Agency (PMDA), Mar. 2015, Ver. 1. [Full Translation].
"Pharmaceuticals Interview Form—LENVIMA®," Pharmaceuticals and Medical Devices Agency (PMDA), Mar. 2018, Ver. 5. [Full Translation].
Suttle et al., "Pharmacokinetics (PK) and tolerability of GW786034, a VEGFR tyrosine kinase inhibitor, after daily oral administration to patients with solid tumors," Proc. Am. Soc. Clin. Oncology, (Abstract 3054), 2004.
"Prescribing Information of AFINITOR (everolimus) tables for oral administration, AFINITOR Disperz (everolimus tablets for oral suspension) [Retrieved on Jun. 12, 2017 URL:https://www.accessdata.fda.gov/drugsatfda_docs/label/2016/022334s036lbl.pdf,2.2,]," Novartis Pharmaceuticals Corporation, Feb. 2016, 42 pages.
"Prescribing Information of LENVIMA (lenvatinib) capsules, for oral use, Eisai Inc." [URL:https://www.accessdata.fda.gov/drugsatfda_docs/label/2015/206947s000lbl.pdf,2.1,2.2,8.6,8.7,Tablesl-3], Feb. 2015, 25 pages.
Tyagi, Preeta., "Recent Results and Ongoing Trials with Panitumumab (ABX-EGF), a Fully Human Anti-Epidermal Growth Factor Receptor Antibody, in Metastatic Colorectal Cancer," Clinical Colorectal Cancer. 2005; 5(1): 21-3.
Gaspar et al. "Single-agent expansion cohort of lenvatinib (LEN) and combination dose-finding cohort of LEN + etoposide (ETP) + ifosfamide (IFM) in patients (pts) aged 2 to ≤ 25 years with relapsed/refractory osteosarcoma (Os)," DOI: 10.1200/JCO.2018.36.15_suppl.11527 Journal of Clinical Oncology 36, No. 15_suppl (May 20, 2018) 11527-11527.
"Single-agent Expansion Cohort of Lenvatinib (LEN) and Combination Dose-finding Cohort of LEN + Etoposide (ETP) + Ifosfamide (IFM) in Patients (pts) Aged 2 to ≤ 25 Years With Relapsed/Refractory Osteosarcoma (OS)", American Society of Clinical Oncology (ASCO) Annual Meeting; Jun. 1-5, 2018; Chicago, IL, 2018.
"Single-agent Expansion Cohort of Lenvatinib (LEN) and Combination Dose-finding Cohort of LEN + Etoposide (ETP) + Ifosfamide (IFM) in Patients (pts) Aged 2 to ≤ 25 Years With Relapsed/Refractory Osteosarcoma (OS)", International Society for Pediatric Oncology (SIOP); Nov. 16-19, 2018; Kyoto, Japan, 2018.
Abrams et al., "SU11248 inhibits KIT and platelet-derived growth factor receptor beta in preclinical models of human small cell lung cancer." Molecular cancer therapeutics vol. 2,5 (2003): 471-8 .
Additional Response in IL Application No. 188670, dated Oct. 25, 2011, 4 pages (with English translation).
Advisory Action for U.S. Appl. No. 12/092,539 issued on Jun. 28, 2011.
Advisory Action in U.S. Appl. No. 12/315,291, dated Mar. 24, 2011, 10 pages.
Agarwal et al., "Binding of discoidin domain receptor 2 to collagen I: an atomic force microscopy investigation," Biochemistry, 41(37):11091-11098 (2002).
Agnieszka et al., "Emergence of potential biomarkers of response to anti-angiogenic anti-tumor agents," Int J Cancer, Sep. 2010, 127(6):1251-1258.
Altschul et al., "Basic Local Alignment Search Tool", J. Mol. Biol. 215:403-410 (1990).
Amended Claims filed in European Application No. 11798224.9, filed Aug. 2, 2013, 15 pages.
Amended Claims filed in Korean Application No. 10-2010-7011023, filed Jul. 17, 2013, 15 pages, with English translation.
Amended claims in European Application No. 04807580.8, dated Jun. 16, 2014, 7 pages.
Amended description filed after receipt of search report in European Patent App. No. 10809938.3, filed Dec. 8, 2011.
Amended description filed after receipt of search report in European Patent App. No. 10809938.3, filed Sep. 14, 2010.
Amended Drawing in Filipino Application No. 1-2011-502441, dated Oct. 17, 2014, 2 pages.
Amended Drawing in Israeli Application No. 217197, dated Oct. 22, 2014, 4 pages, with English translation.
Amended set of Claims in European Application No. 11798224.9, dated Sep. 19, 2014, 53 pages.
Amendment after Allowance dated Jan. 4, 2011 in CA Application No. 2426461.
Amendment and Reply to Restriction Requirement filed Jan. 22, 2020, in U.S. Appl. No. 16/092,245.
Amendment and Response filed in U.S. Appl. No. 11/997,543, dated Dec. 19, 2013.
Amendment and Response to Final Office Action in U.S. Appl. No. 12/864,817, dated Dec. 5, 2011.
Amendment and Response to Non-Final Office Action in U.S. Appl. No. 11/997,543, dated Aug. 19, 2011.

(56) References Cited

OTHER PUBLICATIONS

Amendment and Response to Office Action dated Apr. 2, 2013 in U.S. Appl. No. 13/083,338.
Amendment and Response to Office Action in U.S. Appl. No. 11/997,543, dated Jan. 9, 2012.
Amendment and Response to Office Action in U.S. Appl. No. 12/439,339, dated Aug. 22, 2013.
Amendment and Response to Office Action in U.S. Appl. No. 12/439,339, dated Feb. 7, 2012.
Amendment and Response to Office Action in U.S. Appl. No. 12/524,754, dated Feb. 17, 2012.
Amendment and Response to Office Action in U.S. Appl. No. 12/741,682, dated Jul. 30, 2012.
Amendment and Response to Office Action in U.S. Appl. No. 12/864,817, dated Aug. 9, 2011.
Amendment and Response to Office Action in U.S. Appl. No. 13/205,328, dated Apr. 11, 2012.
Amendment dated Apr. 11, 2006 in Chinese Application No. 01819710.8, with English translation.
Amendment dated Apr. 19, 2005 in Japanese Application No. 2002-536056, with English translation.
Amendment dated Aug. 13, 2013 in Japanese Application No. P2009-540099, 10 pages, with English translation.
Amendment dated Aug. 17, 2004 in South African Application No. 2003/3567.
Amendment dated Aug. 4, 2004 in South African Application No. 2003/3567.
Amendment dated Aug. 6, 2013, in Japanese Application No. 2009-551518, 18 pages, with English translation.
Amendment dated Dec. 12, 2011 in Jordan (JO) Patent App. No. 55/2011, with English translation.
Amendment dated Dec. 15, 2011 in Vietnam Application No. 1-2011-03484, with English translation.
Amendment dated Dec. 22, 2011 in South African Application No. 2011/08697.
Amendment dated Feb. 9, 2011 in Taiwanese Application No. 100104281.
Amendment dated Jan. 11, 2010 in Chinese Application No. 200580026468.7, with English translation.
Amendment dated Jan. 26, 2010 in Chinese Application No. 200710007097.9, with English translation.
Amendment dated Jul. 2, 2009 in Chinese Application No. 200710007097.9, with English translation.
Amendment dated Mar. 23, 2009 in Japanese Application No. 2005-124034, with English translation.
Amendment dated Mar. 7, 2005 in Japanese Application No. 2002-536056, with English translation.
Amendment dated Mar. 8, 2006 in Korean Application No. 10-2005-7020292, with English translation.
Amendment dated May 21, 2009 in Japanese Application No. 2005-124034, with English translation.
Amendment dated May 28, 2003 in Chinese Application No. 01819710.8, with English translation.
Amendment dated Nov. 24, 2011 in Korean Application No. 10-2007-7001347, with English translation.
Amendment dated Oct. 1, 2013 in Indian Application No. 10502/CHENP/2012, 10 pages.
Amendment dated Oct. 25, 2005 in Korean Application No. 10-2003-7005506, with English translation.
Amendment dated Oct. 9, 2006 in Chinese Application No. 01819710.8, with English translation.
Amendment dated Sep. 13, 2005 in Chinese Application No. 01819710.8, with English translation.
Amendment filed in Brazilian Application No. BR112012032462-4, dated Nov. 4, 2013, 21 pages, with English translation.
Amendment filed in European Application No. 12774278.1, filed Aug. 13, 2013, 12 pages.
Amendment filed in European Application No. 12793322.4, dated Nov. 28, 2013, 6 pages.
Amendment filed in Korean Application No. 10-2008-7027527, dated Jan. 27, 2014, 12 pages, with English translation.
Amendment filed in Korean Application No. 10-2008-7029472, dated May 1, 2014, 14 pages, with English translation.
Amendment filed in Korean Application No. 10-2008-7029472, dated Nov. 20, 2013, 81 pages, with English translation.
Amendment filed in Korean Application No. 10-2009-7005657, dated May 7, 2014, 15 pages, with English translation.
Amendment filed in Korean Application No. 10-2009-7017694, dated Feb. 28, 2014, 7 pages.
Amendment filed in Korean Application No. 10-2013-7020616, dated Nov. 22, 2013, 22 pages, with English translation.
Amendment filed in U.S. Appl. No. 13/805,826, dated Sep. 9, 2013, 14 pages.
Amendment in Australian Application No. 2005217325, dated Aug. 9, 2006, 11 pages.
Amendment in Australian Application No. 2005217328, dated Aug. 9, 2006, 10 pages.
Amendment in Australian Application No. 2006282456, dated Apr. 26, 2012, 6 pages.
Amendment in Australian Application No. 2006282456, dated Jan. 25, 2008, 26 pages.
Amendment in Bangladesh Application No. 184/2006, dated Sep. 26, 2007, 4 pages.
Amendment in Brazilian Application No. PI0616799/3, dated May 29, 2012, 6 pages.
Amendment in Canadian Application No. 2828946, dated Aug. 30, 2013, 14 pages.
Amendment in Chinese Application No. 200680021939.X, dated Dec. 18, 2007, 23 pages, with English translation.
Amendment in Chinese Application No. 200780019520.5, dated Nov. 27, 2008, 10 pages, with English translation.
Amendment in Chinese Application No. 2008800045113, dated Aug. 7, 2009, 36 pages, with English translation.
Amendment in European Application No. 06796594.7, dated Apr. 19, 2012, 3 pages.
Amendment in European Application No. 06796594.7, dated Jan. 11, 2008, 3 pages.
Amendment in European Application No. 06796594.7, dated Nov. 16, 2007, 3 pages.
Amendment in European Application No. 07793075.8, dated Jan. 26, 2011, 12 pages.
Amendment in European Application No. 07793075.8, dated Mar. 3, 2009, 5 pages.
Amendment in European Application No. 08711837.8, dated Sep. 8, 2009, 23 pages.
Amendment in European Application No. 09713617.0, dated Sep. 1, 2010, 3 pages.
Amendment in European Patent Application No. 12793322.4, dated Sep. 15, 2017, 20 pages.
Amendment in Filipino Application No. 1-2007-502319, dated May 14, 2012, 3 pages.
Amendment in Indian Application No. 1424/CHENP/2008, dated Apr. 27, 2012, 4 pages.
Amendment in Indian Application No. 2371/CHENP/2012, dated Oct. 30, 2014, 2 pages.
Amendment in Indian Application No. 7026/CHENP/2013, dated Sep. 5, 2013, 8 pages.
Amendment in Israeli Application No. 188670, dated May 2, 2012, 7 pages, with English translation.
Amendment in Israeli Application No. 197002, dated Feb. 11, 2009, 4 pages.
Amendment in Israeli Application No. 200090, dated Oct. 2, 2013, 10 pages, with English translation.
Amendment in Israeli Application No. 200466, dated Aug. 18, 2009, 28 pages.
Amendment in Israeli Application No. 217197, dated Dec. 24, 2015, 5 pages, with English translation.
Amendment in Japanese Application No. 2007-532099, dated Dec. 25, 2007, 6 pages, with English translation.
Amendment in Japanese Application No. 2007-532099, dated Sep. 25, 2007, 28 pages, with English translation.

(56) References Cited

OTHER PUBLICATIONS

Amendment in Japanese Application No. 2008-530917, dated Dec. 13, 2012, 6 pages, with English translation.
Amendment in JO Application No. 280/2006, dated Oct. 19, 2007, 3 pages, with English translation.
Amendment in Korean Application No. 10-2006-7013940, dated Oct. 1, 2007, 43 pages, with English translation.
Amendment in Korean Application No. 10-2007-7026886, dated Dec. 27, 2007, 4 pages, with English translation.
Amendment in Korean Application No. 10-2007-7026886, dated Nov. 21, 2007, 9 pages, with English translation.
Amendment in Korean Application No. 10-2007-7026886, dated Oct. 27, 2009, 4 pages, with English translation.
Amendment in Korean Application No. 10-2008-7029577, dated Apr. 1, 2009, 6 pages, with English translation.
Amendment in Korean Application No. 10-2009-7013723, dated Aug. 10, 2009, 17 pages, with English translation.
Amendment in Korean Application No. 10-2010-7011023, dated Oct. 21, 2014, 31 pages.
Amendment in Korean Application No. 10-2010-7018835, dated Dec. 1, 2014, 18 pages, with English translation.
Amendment in Korean Application No. 10-2012-7003846, dated Nov. 26, 2014, 20 pages, with English translation.
Amendment in Korean Application No. 10-2012-7033886, dated Sep. 27, 2013, 34 pages, with English translation.
Amendment in Mexican Application No. MX/a/2012/014776, dated Oct. 21, 2013, 5 pages.
Amendment in Norwegian Application No. 20080460, dated May 14, 2012, 4 pages, with English translation.
Amendment in Russian Application No. 2012158142, dated Oct. 17, 2013, 48 pages, with English translation.
Amendment in Saudi Arabian Application No. 06270287, dated Oct. 22, 2007, 12 pages.
Amendment in Singapore Application No. 200718614/1, dated Aug. 24, 2010, 13 pages.
Amendment in Taiwanese Application No. 100104281, dated Oct. 22, 2014, 8 pages.
Amendment in TH Application No. 0601004017, dated Sep. 25, 2007, 6 pages, with English translation.
Amendment in U.S. Appl. No. 11/065,631, dated May 28, 2008, 16 pages.
Amendment in U.S. Appl. No. 11/662,425, dated Sep. 2, 2014, 6 pages.
Amendment in U.S. Appl. No. 11/892,785, dated Dec. 17, 2008, 17 pages.
Amendment submitted Jan. 6, 2020, in Singaporean Patent Application No. 11201801083U.
Amendment submitted Jul. 30, 2019, in Japanese Patent Application No. 2018-567437.
Amendment submitted Oct. 10, 2019, in LK Patent Application No. 16523.
Amendment submitted Oct. 30, 2019, in Taiwanese Patent Application No. 104127982.
Amendment, Response to Office Action under 37 C.F.R. § 1.111 and Information Disclosure Statement for U.S. Appl. No. 13/624,278, filed Jun. 28, 2013, 23 pages.
Amendments received before examination for EP Application No. 01976786.2, dated Sep. 10, 2004.
Amendments to the specification filed on Mar. 26, 2012 for AU Patent Appl. No. 2010285740.
Amino et al., "YM-231146, a Novel Orally Sioavailable Inhibitor of Vascular Endothelial Growth Factor Receptor-2, Is Effective against Paclitaxel Resistant Tumors," Biological and Pharmaceutical Bulletin. 28: 2096-2101, 2005.
Anderson et al, "Clinical, Safety, and Economic Evidence in Radioactive Iodine-Refractory Differentiated Thyroid Cancer: A Systematic Literature Review", Thyroid, 23(4):392-407, 2013.

Anderson et al., 1996, "Preparation of Water-soluble Compounds through Salt Formation. The Practice of Medicinal Chemistry," Technomics, 347-349 and 355-356 (Japanese Language Version published Sep. 25, 1999),.
Anonymous, "Scientific Discussion," EMEA, URL: http://www.ema.europa.eu/docs/en_GB/document_library/EPARScientific_Discussion/human/000406/WC500022203.pdf, 1-61 (2004) (XP007918143).
Appeal for Reversal in CO Application No. 12-022608, dated Jan. 28, 2014, 17 pages (with English translation).
Appeal in SA Application No. 06270287, dated Jun. 23, 2010, 4 pages (with English translation).
Applicant Interview Summary Under 37 C.F.R. § 1.133(b) for U.S. Appl. No. 12/439,339, dated May 31, 2013, 7 pages.
Applicant Observation for CN Application No. 200780017371.9, filed May 29, 2013, 6 pages (with English translation).
Application for Patent Term Adjustment in U.S. Appl. No. 12/439,339, dated Dec. 18, 2014, 8 pages.
Approval of request for amendments for EP Application No. 04025700.8, dated Mar. 13, 2008.
Araujo et al., "Polimorfismo na produção de medicamentos," Rev Ciênc Farm Básica Apl., 2012, 33(1): 27-36. (with English translation).
Argument and Amendment for JP Application No. 2008-556208, filed Mar. 21, 2013, 15 pages (with English translation).
Argument and Amendment for CN 200880002425.9 filed on Jul. 18, 2011, 8 pages with English translation.
Argument and Amendment for JP Application No. 2008-532141, filed Nov. 29, 2012, 12 pages (with English translation).
Argument and Amendment for JP. Application No. 2008-516724, filed Nov. 28, 2012, 22 pages (with English translation).
Argument and Amendment for JP. Application No. 2009-123432, dated Jun. 12, 2012, 12 pages (with English translation).
Argument and Amendment for JP. Application No. 2009-529019, dated Jul. 3, 2012, 14 pages (with English translation).
Argument Brief filed in KR Application No. 10-2008-7029577, dated Feb. 27, 2014, 30 pages (with English translation).
Argument Brief filed on Mar. 8, 2006 for KR Application No. 10-2005-7020292 (with English translation).
Argument Brief filed on Nov. 24, 2011 for KR Application No. 10-2007-7001347 (with English translation).
Argument filed in KR Application No. 10-2009-7017694, dated Feb. 28, 2014, 48 pages.
Argument filed on Aug. 6, 2013 for JP Patent Application No. 2009-551518, 18 pages (with English translation).
Argument filed on Mar. 23, 2009 for JP Application No. 2005-124034 (with English translation).
Argument submitted Apr. 3, 2020, in Japanese Patent Application No. 2017-502388.
Argument submitted Aug. 12, 2020, in Japanese Patent Application No. 2017-535551.
Argument submitted Dec. 19, 2019, in Japanese Patent Application No. 2016-545564.
Argument submitted Jul. 17, 2020, in Japanese Patent Application No. 2017-502388.
Asai et al., "Mechanism of Ret Activation by a Mutation of Aspartic Acid 631 Identified in Sporadic Pheochromocytoma", Biochemical and Biophysical Research Communications, 255, 587-590 (1999).
Asano et al., "Broad-spectrum preclinical combination activity of eribulin combined with various anticancer agents in human breast cancer, lung cancer, ovarian cancer, and melanoma xenograft models," European J Cancer, 50 (Suppl 6): 20, Nov. 19, 2014. (Poster Session).
Asano et al., "Inhibition of Tumor Growth and Metastasis by an Immunoneutralizing Monoclonal Antibody to Human Vascular Endothelial Growth Factor/Vascular Permeability Factor121", Cancer Research, 55, 5296-5301, 1995.
Asu no Shinyaku ("The New Drugs of Tomorrow"), editing/printing by Technomics, Inc., 81-83 (Dec. 2006) (English translation), 14 pages.
Auburn University, "Thyroid Cancer," (as of Feb. 25, 2006, using Wayback machine), Feb. 25, 2006, 8 pages.

(56) References Cited

OTHER PUBLICATIONS

Australian ("AU") Office Action issued on Oct. 29, 2009 for corresponding AU Application No.; 2006285673.
Australian Amendment—Request Voluntary Amendment (Specification) in Application No. 2010285740, dated Nov. 20, 2015, 11 pages.
Australian Notice of Allowance in Application No. 2011270165, dated Dec. 14, 2015, 3 pages.
Australian Office Action directed at Appl. No. 2007252506 issued on Jan. 13, 2012, 2 pages.
Australian Office Action directed at Appl. No. 2007252506 issued on Nov. 7, 2011, 5 pages.
Australian Office Action for Application No. 2008205847, issued on Apr. 11, 2012.
Australian Office Action for Application No. 2008211952, issued on Apr. 3, 2012.
Australian Office Action for Application No. AU2006309551 issued on Apr. 28, 2011.
Australian Office Action in Application No. 2011271065, dated Nov. 6, 2015, 3 pages.
Australian Response to Office Action directed at Appl. No. 2007252506 filed on Jan. 4, 2012, 74 pages.
Australian Response to Office Action directed at Appl. No. 2007252506 filed on Mar. 2, 2012, 4 pages.
Australian Response to Office Action for Application No. 2006309551 filed on Jan. 27, 2012.
Bainbridge et al., "A peptide encoded by exon 6 of VEGF (EG3306) inhibits VEGF-induced angiogenesis in vitro and ischaemic retinal neovascularisation in vivo", Biochem Biophys Res Commun., 302, 793-799, 2003.
Baj-Krzyworzeka, M., et al., "Elevated level of some chemokines in plasma of gastric cancer patients," Cent. Eur. J. Immunol., 2016, 41(4): 358-362.
Bajwa et al., "Antimalarials. 1. Heterocyclic Analogs of N-Substituted Naphthalenebisoxazines," J Med Chem., 16(2):134-138, Aug. 9, 1972.
Bastin et al., "Salt Selection and Optimisation Procedures for Pharmaceutical New Chemical Entities," Organic Process Research & Development, 4(5):427-435 (2000) (XP002228592).
Beebe et al., "Pharmacological Characterization of CP-547,632, a Novel Vascular Endothelial Growth Factor Receptor-2 Tyrosine Kinase Inhibitor for Cancer Therapy1", Cancer Research. 63:7301-9, 2003.
Behr et al., Improved Treatment of Medullary Thyroid Cancer in a Nude Mouse Model by Combined Radioimmunochemotherapy: Doxorubicin Potentiates the Therapeutic Efficacy of Radiolabeled Antibodies in a Radioresistant Tumor Type, 57 Cancer Res. 5309-5319 (Dec. 1, 1997).
Bellone, G et al., "Growth stimulation of colorectal carcinoma cells via the c-kit receptor is inhibited by TGF-beta 1," Journal of cellular physiology vol. 172, 1 (1997): 1-11.
Benjamin et al., "Selective ablation of immature blood vessels in established human tumors follows vascular endothelial growth factor withdrawal," J. Clin. Invest., 103(2):159-165 (1999).
Bennett, J. C., & Plum, F. (Eds.). (1996). Cecil Textbook of Medicine, 20th ed., vol. 1, pp. 1004-1010.
Berge et al., "Pharmaceutical Salts," Journal of Pharmaceutical Sciences, 66(1):1-19 (Jan. 1977) (XP002550655).
Bergers et al., "Benefits of targeting both pericytes and endothelial cells in the tumor vasculature with kinase inhibitors," J. Clin. Invest., 111(9):1287-1295 (2003).
Berndt et al., "A New Hot Spot for Mutations in the ret Protooncogene Causing Familial Medually Thyroid Carcinoma and Multiple Endocrine Neoplasia Type 2A", Journal of Clinical Endocrinology and Metabolism, 83, 770-774 (1998).
Bernex et al., "Spatial and temporal patterns of c-kit-expressing cells in WlacZ/+ and WlacZ/WlacZ mouse embryos", Development 122:3023-3033 (1996).
Besson et al., "PTEN/MMAC1/TEP1 in signal transduction and tumorigenesis," EP J Biochem., 1999, 263:605-611.

Blume-Jensen et al., "Activation of the Human c-kit Product by Ligand-Induced Dimerization Mediates Circular Actin Reorganization and Chemotaxis," The EMBO Journal, 10(13):4121-4128 (1991).
Board of Appeal of the European Patent Office, "Decision—T1212/01 3.3.2," dated Feb. 3, 2015, 55 pages.
Boissan et al., "c-Kit and c-kit mutations in mastocytosis and other hematological diseases," J. Leukocyte Biol., 67:135-148 (2000).
Bold et al., "New anilinophthalazines as potent and orally well absorbed inhibitors of the VEGF receptor tyrosine kinases useful as antagonists of tumor-driven angiogenesis", Journal of Medicinal Chemistry., 43:2310-2323 (2000).
Bonferoni et al., "Influence of medium on dissolution-erosion behavior of Na carboxymethylcellulose and on viscoelastic properties of gels," International journal of pharmaceutics, 1995, vol. 117, No. 1, pp. 41-48.
Boss et al., "A Phase I study of E7080, a multitargeted tyrosine kinase inhibitor, in patients with advanced solid tumours," British Journal of Cancer, 106:1598-1604 (2012).
Bramhall, S., "The Matrix Metalloproteinases and Their Inhibitors in Pancreatic Cancer", International J. Pancreatol., 21, 1-12, 1997.
Brazilian Office Action in Application No. PI0418200-6, dated Jun. 16, 2015, 1 page.
Brief communication to applicant for EP Application No. 01976786.2, dated Sep. 9, 2005.
Brose et al, "Sorafenib in radioactive iodine-refractory, locally advanced or metastatic differentiated thyroid cancer: a randomised, double-blind, phase 3 trial", The Lancet, 384:319-328, Jul. 26, 2014.
Brueggen et al., "Preclinical profile of ABP309, a potent 2nd generation VEGF receptor tyrosine kinase inhibitor belonging to the class of aminonicotinamides," EORTC-NCI-AACR Symp Mol Targets Cancer Ther., 2, (Abstract 172), 2004, 2 pages.
Bruheim et al., "Antitumour activity of oral E7080, a novel inhibitor of multiple tyrosine kinases, in human sarcoma xenografts", International Journal of Cancer, vol. 129, No. 3, 2011, p. 742-p. 750.
Bruns et al., "Effect of the vascular endothelial growth factor receptor-2 antibody DC101 plus gemcitabine on growth, metastasis and angiogenesis of human pancreatic cancer growing orthotopically in nude mice," J. Cancer, 102:101-108 (2002).
Burwell, Jr, "The Cleavage of Ethers," Chem Rev., 54(4):615-685, Feb. 26, 1954.
Bussolino et al., "Role of Soluble Mediators in Angiogenesis," Eur. J. Cancer, 32A(14):2401-2412 (1996).
Cainap, C., et al., "Linifanib Versus Sorafenib in Patients With Advanced Hepatocellular Carcinoma: Results of a Randomized Phase III Trial," J. Clin. Oncol., 2015, 33(2): 172-179.
Cairns et al., "New antiallergic pyrano[3,2g]quinoline-2,8-dicarboxylic acids with potential for the topical treatment of asthma," J. Med. Chem., 28(12):1832-1842 (1985).
Canadian ("CA") Office Action issued on Jan. 6, 2011 for Application No. 2,620,594.
Canadian Notice of Allowance in Application No. 2676796, dated Oct. 8, 2015, 1 page.
Canadian Office Action for Application No. 2426461, dated Dec. 6, 2007.
Canadian Office Action for Application No. 2426461, dated Feb. 10, 2010.
Canadian Office Action for Application No. 2426461, dated May 8, 2009.
Canadian Office Action for Application No. 2426461, dated Nov. 20, 2008.
Canadian Office Action in Application No. 2828946, dated Nov. 30, 2015, 4 pages.
Canadian Office Action in Application No. 2704000, dated Jan. 14, 2016, 3 pages.
Canadian Office Action in Application No. 2704000, dated Jul. 14, 2015, 3 pages.
Canadian Office Action in Application No. 2713930, dated Sep. 15, 2015, 3 pages.
Canadian Office Action in Application No. 2802644, dated Oct. 23, 2015, 6 pages.
Canadian Response to Office Action in Application No. 2802644, dated Apr. 18, 2016, 9 pages.

(56) References Cited

OTHER PUBLICATIONS

Canadian Submission Documents in Application No. 2713930, dated Jun. 22, 2015, 8 pages.
Cancercare, "Types of Lung Cancer," Cancer Care, Inc. [online] [retrieved on Nov. 12, 2009]. Retrieved from the Internet: www.lungcancer.org/reading/types.php?printable=true (2009).
Cappellen et al., "Frequent activating mutations of FGFR3 in human bladder and cervix carcinomas," Nat. Genet., 23:18-20 (1999).
Carey, "Organic Chemistry 4e: Chapter 24: Phenols," McGraw Hill, http://www.mhhe.com/physsci/chemistry/carey/student/olc/ch24reactionsarylethers.html. Accessed Oct. 3, 2014.
Carlomagno et al., "BAY 43-9006 inhibition of oncogenic RET mutants," J. Natl. Cancer Inst., 98(5):326-34 (2006).
Carlomagno et al., "Point Mutation of the RET Proto-Oncogene in the TT Human Medullary Thyroid Carcinoma cell Line," Biochemical and Biophysical Research Communications, 207,1022-1028 (1995).
Carlomagno et al., "ZD6474, an orally available inhibitor of KDR tyrosine kinase activity, efficiently blocks oncogenic RET kinases," Cancer Res., 62:7284-7290 (2002).
Carniti et al., "The RetC620R Mutation Affects Renal and Enteric Development in a mouse Model of Hirschprung's Disease", American Journal of Pathology, 168, 1262-1275, (2006).
Carter et al., "Inhibition of drug-resistant mutants of ABL, KIT and EGF receptor kinases", Proceedings of the National Academy of Sciences of the United States of America., 102, 11011-11016, 2005.
Chaki et al., "mGlu2/3 and mGlu5 receptors: Potential targets for novel antidepressants," Neuropharmacology, 2013, 66:40-52.
Chemical & Engineering News, "The Top Pharmaceuticals That Changed the World," 83, [cited: Mar. 29, 2016], Jun. 20, 2005, 3 pages.
Chen et al., "FGFR3 as a therapeutic target of the small molecule inhibitor PKC412 in hematopoietic malignancies," Oncogene, 24:8259-8267 (2005).
Cheng, A., et al., "Sunitinib Versus Sorafenib in Advanced Hepatocellular Cancer: Results of a Randomized Phase III Trial," J. Clin. Oncol., 2013, 31(32): 4067-4075.
Chesi et al., "Activated fibroblast growth factor receptor 3 is an oncogene that contributes to tumor progression in multiple myeloma," Blood, 97:729-736 (2001).
Chesi et al., "Frequent translocation t(4;14)(p16.3;q32.3) in multiple myeloma is associated with increased expression and activating mutations of fibroblast growth factor receptor 3," Nat. Genet., 16:260-264 (1997).
Cheung et al., "Discovery of indazolylpyrimidines as potent inhibitors of VEGFR2 tyrosine kinase," Proceedings of the American Association for Cancer Research, 44, 9, (Abstract 40), 2003, 2 pages.
Chikahisa et al., "TSU-68 KDR/flk-1 inhibitor, can modulate the anti-tumor activity of paclitaxel by the induction of endothelial cell and tumor cell apoptosis," 61st Annual Meeting of the Japanese Cancer Association, 2002, 61(1374):443, 5 total pages (with English translation).
Chilean Response to Examiner's Report in Application No. 2012-00412, dated Mar. 30, 2015, 16 pages, with English translation.
Chinese ("CN") Office Action issued on Dec. 4, 2009 for corresponding CN Application No. 200680036592.6, with English translation.
Chinese Notice of Allowance in Application No. 201280010898.X, dated Sep. 2, 2015, 4 pages.
Chinese Office Action directed at Appl. No. 200780017371.9 mailed on Oct. 20, 2010, 13 pages with English translation.
Chinese Office Action for Application No. 200710007097.9, issued on Mar. 6, 2009.
Chinese Office Action for Application No. 200780017371.9, issued on Mar. 7, 2012, with English translation.
Chinese Office Action for Application No. 200880002425.9, issued on Mar. 7, 2012, with English translation.
Chinese Office Action for Application No. 200880003336.6, issued on May 24, 2011, with English translation.
Chinese Office Action for Application No. 200880115011.7, issued on Feb. 20, 2012, with English translation.
Chinese Office Action for Application No. 201080030508.6, issued on Nov. 30, 2012.
Chinese Office Action for Application No. 200680041355.9 issued on Aug. 24, 2010 with English translation.
Chinese Office Action for Application No. 200680041355.9 issued on Mar. 5, 2010 with English translation.
Chinese Office Action in Application No. 201280010898.X, dated Mar. 30, 2015, 13 pages, with English translation.
Chinese Office Action with the English translation dated, Feb. 29, 2012, for Application No. 200680036592.6.
Chinese Response in Reexamination and Invalidation Procedure in Application No. 200780017371.9, dated Jan. 19, 2015, 8 pages, with English translation.
Chinese Response to Office Action directed at Application No. 200780017371.9 filed on Feb. 24, 2011, 10 pages with English translation.
Chinese Response to Office Action for Application No. 200680041355.9 filed on Jul. 19, 2010 with English translation.
Chinese Response to Office Action for Application No. 200680041355.9 filed on Nov. 8, 2010 with English translation.
Chinese Response to the Chinese Decision of Rejection, filed on Feb. 7, 2013, for corresponding Chinese Application No. 200680036592.6.
Chinese Submission Documents in Application No. 201280010898.X, dated Jun. 15, 2015, 12 pages.
Ciardiello et al., "ZD1839 (IRESSA), an EGFR-selective tyrosine kinase inhibitor, enhances taxane activity in bcl-2 overexpressing, multidrug-resistant MCF-7 ADR human breast cancer cells," Int. J. Cancer, 98:463-469 (2002).
CIPO Notice of Allowance for Appl. No. 2,620,594 dated May 3, 2012.
Clark et al., "Safety and Pharmacokinetics of the Dual Action Raf Kinase and Vascular Endothelial Growth Factor Receptor Inhibitor, BAY43-9006, in Patients with Advanced Refractory Solid Tumors ," Clin. Cancer Res., 11:5472-5480 (2005).
Clinicaltrials.gov, "A Study of E7080 Alone, and in Combination With Everolimus in Subjects With Unresectable Advanced or Metastatic Renal Cell Carcinoma Following One Prior Vascular Endothelial Growth Factor (VEGF)-Targeted Treatment," National Institutes of Health, Food and Drug Administration, National Library of Medicine, [online] [retrieved on Sep. 27, 2010]. Retrieved from the Internet: http://clinicaltrials.gov/ct2/show/NCT01136733, (May 26, 2010).
CN200780032071.8 Office Action issued on Oct. 13, 2010 with English translation.
CN200780032071.8 Response to Office Action filed on Feb. 16, 2011 with English translation.
CN200880003336.6 Response to Office Action filed on Oct. 8, 2011, 10 pages.
Cohen et al., "Expression of Stem Cell Factor and c-kit in Human Neuroblastoma," Blood, 84(10):3465-3472 (1994).
Colombian Office Action for Application No. 12-022608, dated Oct. 7, 2013, 10 pages (with English translation).
Colombian Official Notification in Application No. 12-022608, dated Jan. 6, 2015, 8 pages, with English translation.
Comments re Board of Appeal in EP Application No. 04807580.8, dated Jul. 7, 2014, 3 pages.
Communication about intention to grant a European patent for EP Application No. 01976786.2, dated Sep. 4, 2006.
Communication about intention to grant a European patent for EP Application No. 04025700.8, dated Oct. 15, 2007.
Communication about intention to grant a European patent for EP Application No. 05783232.1, dated Nov. 20, 2008.
Communication about intention to grant a European patent for EP Application No. 06023078.6, dated Jul. 18, 2008.
Communication from the Examining Division for EP Application No. 01976786.2, dated Aug. 17, 2005.
Communication from the Examining Division for EP Application No. 01976786.2, dated Mar. 21, 2006.

(56) References Cited

OTHER PUBLICATIONS

Communication from the Examining Division for EP Application No. 01976786.2, dated Sep. 19, 2005.
Communication from the Examining Division for EP Application No. 04025700.8, dated Apr. 10, 2006.
Communication from the Examining Division for EP Application No. 04025700.8, dated Oct. 23, 2006.
Communication from the Examining Division for EP Application No. 05783232.1, dated Feb. 7, 2008.
Communication from the Examining Division for EP Application No. 06023078.6, dated Aug. 2, 2007.
Communication from the Examining Division for EP Application No. 06023078.6, dated Sep. 26, 2007.
Communication re Intention to Grant Patent in EP Application No. 07793075.8, dated Nov. 9, 2012, 97 pages.
Communication re Intention to Grant Patent in EP Application No. 07805959.9, dated Jun. 21, 2011, 70 pages.
Communication regarding the expiry of opposition period for EP Application No. 01976786.2, dated Jan. 4, 2008.
Communication regarding the expiry of opposition period for EP Application No. 04025700.8, dated May 7, 2009.
Communication regarding the expiry of opposition period for EP Application No. 05783232.1, dated Feb. 19, 2010.
Communication regarding the expiry of opposition period for EP Application No. 06023078.6, dated Nov. 4, 2009.
Continuation Patent Application, Preliminary Amendment and Information Disclosure Statement for U.S. Appl. No. 13/923,858, filed Jun. 21, 2013, 97 pages.
Corbin et al., "Sensitivity of oncogenic KIT mutants to the kinase inhibitors MLN518 and PD180970", Blood., 104, 3754-3757, 2004.
Corrected Notice of Allowability in U.S. Appl. No. 15/503,108, dated Feb. 7, 2019, 4 pages.
Correction Request in CO Application No. 12-022608, dated Dec. 24, 2014, 3 pages (with English translation).
Corvi et al., "RET IPCM-1: a novel fusion gene in papillary thyroid carcinoma", Oncogene, 19:4236-4242 (2000).
Coupling Reagents, "Advanced Automated Peptide Protein Technologies," Published Aug. 3, 2007, 4 pages.
Croom et al., "Imatinib mesylate," Drugs, 63(5):513-522 (2003).
Da Silva et al., "A novel germ-line point mutation in RET exon 8 (Gly(533)Cys) in a large kindred with familial medullary thyroid carcinoma," J. Clin. Endocrinol. Metab., 88:5438-5443 (2003).
Dankort et al., "Braf V660E cooperates with Pten loss to induce metastic melanoma," Nature Genetics, 2009, 41(5):544-552.
David et al., "A Phase I Trial of the Epidermal Growth Factor Receptor (EGFR)-Directed Bispecific Antibody (BsAB) MDX-447 in Patients with Solid Tumors. (Meeting abstract).", ASCO 18: 433, Abstract 1999.
Davies et al., "Mutations of the BRAF gene in human cancer," Nature, Jun. 27, 2002, 417:949- 954.
De Lange et al., "Phase II trial of cisplatin and gemcitabine in patients with advanced gastric cancer," Annals of Oncology, 15:484-488 (2004).
Decision of Grant in RU Application No. 2008110932, dated Feb. 6, 2009, 29 pages (with English translation).
Decision of Reexamination dispatched May 27, 2019, in Chinese Patent Application No. 201510031628.2.
Decision of Rejection mailed on Oct. 30, 2012 issued for corresponding Chinese Application No. 200680036592.6 with full English language translation.
Decision to grant a European patent for EP Application No. 01976786.2, dated Feb. 1, 2007.
Decision to grant a European patent for EP Application No. 04025700.8, dated Jun. 5, 2008.
Decision to grant a European patent for EP Application No. 05783232.1, dated Mar. 19, 2009.
Decision to grant a European patent for EP Application No. 06023078.6, dated Dec. 4, 2008.
Decision to Grant a Patent dispatched Aug. 27, 2019, in Japanese Patent Application No. 2018-567437.
Decision to Grant a Patent dispatched Aug. 4, 2020, in Japanese Patent Application No. 2017-560343.
Decision to Grant a Patent dispatched Feb. 4, 2020, in Japanese Patent Application No. 2016-545564.
Decision to Grant a Patent dispatched Jul. 2, 2019, in Japanese Patent Application No. 2017-535558.
Decision to Grant a Patent dispatched Nov. 4, 2020, in Japanese Patent Application No. 2017-502388.
Decision to Grant a Patent dispatched Oct. 6, 2020, in Japanese Patent Application No. 2017-546133.
Decision to Grant dispatched Feb. 3, 2020, in Russian Patent Application No. 2018104697.
Decision to Grant issued May 22, 2020, in Russian Patent Application No. 2018103737.
Decision to Grant Patent in EP Application No. 05719973.9, dated Jun. 1, 2012, 1 page.
Decision to Grant Patent in EP Application No. 07805959.9, dated Nov. 4, 2011, 2 pages.
Decision to Grant Patent in JP Application No. 2007-532099, dated Jan. 8, 2008, 5 pages (with English translation).
Decision to Grant Patent in JP Application No. 2008-530917, dated Jan. 15, 2013, 6 pages (with English translation).
Decision to Grant Patent in JP Application No. 2008-532065, dated Nov. 13, 2012, 6 pages (with English translation).
Decision to Grant Patent in JP Application No. P2009-510543, dated Feb. 2, 2010, 6 pages (with English translation).
Deficiencies in sequence listing for EP Application No. 06023078.6, dated Dec. 5, 2006.
Delay-Approval dated Feb. 10, 2019 in Israel Appl. No. 253946.
Demand for Appeal Trial filed in JP Application No. 2008-532141, filed Jul. 5, 2013, 10 pages (with English translation).
Deplanque et al., "Anti-Angiogenic Agents: Clinical Trial Design and Therapies in Development," European Journal of Cancer, 36:1713-1724 (2000).
Dermer, G., "Another Anniversary for the War on Cancer," Bio/Technology, 1994, 12: 320.
Dezso et al., Systems biology analysis to identify biomarkers for lenvatinib in the preclinical cancer cell line panels. Abstract of the presentation #6 (abstract 1371), AACR Annual Meeting, 2015, 2 pages.
Di Raimondo et al., "Antiogenic Factors in multiple myeloma: higher levels in bone than in peripheral blood," Haematologica, 85:800-805 (2000).
Dias et al., "IL-12 Regulates VEGF and MMPs in a Murine Breast Cancer Model", International J. Cancer., 78, 361-5, 1998.
Dietrich, "BRAF Inhibition in Refractory Hairy-Cell Leukemia," N Eng J Med, 366 (21): 2038-2040, May 24, 2012.
Dilorenzo et al., "Targeted Therapy in the Treatment of Metastatic Renal Cell Cancer," Oncology, 77(suppl 1):122-131 (2009).
Dourisboure et al., "Penetrance and Clinical Manifestations of Non-Hotspot Germ line RET Mutation, C630R, in a Family with Medullary Thyroid Carcinoma", Thyroid, 15, 668-671, 2005.
Dupont et al., "Phase 1 study of VEGF Trap in patients with solid tumors and lymphoma," Proc. Am. Soc. Clin. Oncology, (Abstract 776), 2003, 2 pages.
Dvorakova et al., "Exon 5 of the RET proto-oncogene: A newly detected risk exon for familial medullary thyroid carcinoma, a novel germ-line mutation Gly321Arg", Journal of Endocrinological Investigation, 28, 905-909, 2005.
Egyptian Submission Documents in Application No. PCT 283/2012, dated Jan. 18, 2015, 26 pages, with English translation.
Eisai Co., Ltd. (Jun. 1, 2015). *The combination of lenvatinib with everolimus demonstrates extension in PFS in renal cell carcinoma* [Press release]. Retrieved from https://tass.ru/press-relizy/2010118.
Eisai Co., Ltd., "Phase II Study Results Showed Eisai's Lenvatinib (E7080) Demonstrated an Objective Response Rate of 59% in Advance Radioiodine-Refractory Differentiated Thyroid Cancer", News Release: 2011 PR Department, Eisai Co., Ltd., No. 11-44, https://www.eisai.co.jp/news/news201144.html, Jun. 2, 2011, p11-p44.
Election of Species issued Apr. 30, 2020, in U.S. Appl. No. 16/092,245.

(56) References Cited

OTHER PUBLICATIONS

Electronic Medicines Compendium (eMC), "LENVIMA 4mg hard capsules", 2015-06-08.
Elisei et al., "Identification of a novel point mutation in the RET gene (Ala883Thr), which is associated with medullary thyroid carcinoma phenotype only in homozygous condition," J. Clin. Endocrinol. Metab., 89:5823-5827 (2004).
Elisei et al., "Subgroup Analyses of a Phase 3 Multicenter, Double-Blind, Placebo-Controlled Trial of Lenvatinib (E7080) in Patients with 131I-Refractory Differentiated Thyroid Cancer," Poster, No. 1033P, presented at European Society for Medical Oncology 2014 Congress, Sep. 26-30, 2014, 1 page.
Emanuel et al., "A Vascular Endothelial Growth Factor Receptor-2 Kinase Inhibitor Potentiates the Activity of the Conventional Chemotherapeutic Agents Paclitaxel and Doxorubicin in Tumor Xenograft Models", Molecular Pharmacology., 66, 635-647, 2004.
Emoto et al., "Localization of the VEGF and angiopoietin genes in uterine carcinosarcome," Gynecologic Oncology, 95:474-482 (2004).
EP Communication under Rule 71(3) EPC for Application No. 06832529.9 issued on Nov. 25, 2011.
EP07806561.2 Office Action issued on Dec. 9, 2011.
EP07806561.2 Office Action issued on Feb. 7, 2011, 1 page.
EP07806561.2 Office Actions issued on Jan. 19, 2011.
EP07806561.2 Response to Office Action filed on Aug. 9, 2011.
Erber et al., "Combined inhibition of VEGF and PDGF signaling enforces tumor vessel regression by interfering with pericyte-mediated endothelial cell survival mechanisms," FASEB J., 18(2):338-340 (2004).
Erdem et al., "Correlation of E-cadherin, VEGF, COX-2 expression to prognostic parameters in papillary thyroid carcinoma," Experimental Mole Pathol., 90: 312-317 (2011).
European Notice of Allowance in Application No. 07743994.1, dated May 8, 2015, 51 pages.
European Notice of Allowance in Application No. 10809938.3, dated Jan. 8, 2016, 2 pages.
European Notice of Allowance in Application No. 10809938.3, dated Sep. 3, 2015, 30 pages.
European Notice of Allowance in Application No. 11798224.9, dated Sep. 29, 2015, 37 pages.
European Office Action in Application No. 04719054.1, dated Oct. 30, 2009.
European Office Action in Application No. 04807580.8, dated Apr. 18, 2011.
European Office Action in Application No. 04807580.8, dated Dec. 3, 2010.
European Office Action in Application No. 04807580.8, dated Oct. 25, 2011.
European Office Action in Application No. 04818213.3, dated Feb. 2, 2012.
European Office Action in Application No. 06832529.9, dated Oct. 15, 2009.
European Office Action in Application No. 06832529.9, dated Sep. 12, 2011.
European Office Action in Application No. 07743994.1, dated Oct. 10, 2012.
European Office Action in Application No. 12786619.2, dated Dec. 8, 2015, 4 pages.
European Patent Office, International Search Report for International Application No. PCT/US2015/063796, mailed Feb. 29, 2016.
European Patent Office, Written Opinion for International Application No. PCT/US2015/063796, mailed Feb. 29, 2016.
European Response to Communication Pursuant to Article 94(3) EPC in Application No. 10809938.3, dated Apr. 13, 2015, 12 pages.
European Response to Office Action in Application No. 06832529.9, dated Oct. 4, 2011.
European Response to Office Action in Application No. 12786619.2, dated May 12, 2015, 99 pages.
European Search Report in Application No. 03791389.4, dated Jul. 7, 2011.
European Search Report in Application No. 04025700.8, dated Jan. 13, 2005.
European Search Report in Application No. 04719054.1, dated Apr. 17, 2009.
European Search Report in Application No. 04818213.3, dated Jul. 30, 2007.
European Search Report in Application No. 05783232.1, dated Sep. 7, 2007.
European Search Report in Application No. 06023078.6, dated Mar. 16, 2007.
European Search Report in Application No. 06767145.3, dated May 23, 2011.
European Search Report in Application No. 06768437.3, dated Oct. 11, 2010.
European Search Report in Application No. 06782407.8, dated Jul. 23, 2010.
European Search Report in Application No. 06832529.9, dated Jul. 29, 2009.
European Search Report in Application No. 06833681.7, dated Nov. 24, 2010.
European Search Report in Application No. 07743994.1, dated May 4, 2010.
European Search Report in Application No. 07806561.2, dated Jan. 19, 2011.
European Search Report in Application No. 10015141.4, dated Sep. 9, 2011.
European Search Report in Application No. 10809938.3, dated Jan. 2, 2013.
European Search Report in Application No. 12793322.4, dated May 26, 2015, 9 pages.
European Search Report in Application No. 12793322.4, dated Sep. 10, 2015, 13 pages.
European Search Report in Application No. 13865671.5, dated May 23, 2016, 7 pages.
European Search Report in EP 08704376.6 dated Jun. 14, 2012, 12 pages.
European Submission Document in Application No. 09705712.9, dated Feb. 24, 2015, 196 pages.
Examination Report dispatched Feb. 20, 2020, in Indian Patent Application No. 201747028834.
Examination Report dispatched Jan. 30, 2020, in Indian Patent Application No. 201847004787.
Examination Report dispatched Jul. 4, 2019, in GCC Patent Application No. GC2015-29939.
Examination Report dispatched Jun. 14, 2019, in Australian Patent Application No. 2014266223.
Examination Report dispatched Mar. 3, 2020, in Indian Patent Application No. 201847003846.
Examination Report dispatched Sep. 13, 2019, in Indian Patent Application No. 6971/CHENP/2015.
Examination Report dispatched Sep. 9, 2020, in Indian Patent Application No. 201847037747.
Examination Report in Australian Application No. 2001295986, dated May 4, 2006.
Examination Report in Australian Application No. 2001295986, dated Sep. 20, 2005.
Examination Report in Australian Application No. 2005217325, dated Aug. 1, 2007, 2 pages.
Examination Report in Australian Application No. 2005217328, dated Aug. 1, 2007, 2 pages.
Examination Report in Australian Application No. 2006203099, dated Feb. 27, 2007.
Examination Report in Australian Application No. 2006236039, dated Mar. 26, 2008.
Examination Report in Australian Application No. 2007288793, dated Dec. 22, 2011, 2 pages.
Examination Report in Australian Application No. 2007289787, dated Nov. 25, 2011, 2 pages.
Examination Report in Australian Application No. 2008217931, dated Jun. 28, 2012, 3 pages.
Examination Report in Australian Application No. 2008325608, dated Nov. 24, 2012.

(56) References Cited

OTHER PUBLICATIONS

Examination Report in Australian Application No. 2009210098, dated Jan. 30, 2013, 10 pages.
Examination Report in New Zealand Application No. 525324, dated Feb. 18, 2005.
Examination Report in New Zealand Application No. 525324, dated Oct. 13, 2003.
Examination Report in New Zealand Application No. 525324, dated Sep. 2, 2004.
Examination Report in Pakistan Application No. 155/2005, dated Mar. 11, 2009, 2 pages.
Examination Report issued Jun. 30, 2020, in Australian Patent Application No. 2016224583.
Examiner report No. 1 issued Apr. 2, 2019 in Australian Patent Application No. 2015309862.
Experimental Medicine, Supplementary Volume, "A New Handbook of Genetic Engineering", Section 4, Yodosha, 2003 (Japanese with English Translation).
Explanation of Circumstances Concerning Accelerated Examination filed May 10, 2012 for JP Patent Application No. 2011-527665, 21 pages (with English Translation).
Extended European Search Report dated Jun. 3, 2019, in European Patent Application No. 19151846.3.
Extended European Search Report dated Nov. 12, 2019, in European Patent Application No. 17782552.8.
Extended European Search Report in Application No. 06796594.7, dated Sep. 7, 2011, 5 pages.
Extended European Search Report in Application No. 06797249.7, dated Dec. 7, 2012.
Extended European Search Report in Application No. 07793075.8, dated Sep. 8, 2010, 6 pages.
Extended European Search Report in Application No. 07805959.9, dated Nov. 16, 2010, 6 pages.
Extended European Search Report in Application No. 08711837.8, dated Mar. 28, 2011, 5 pages.
Extended European Search Report in Application No. 09713617.0, dated Apr. 28, 2011, 5 pages.
Extended European Search Report in Application No. 12195436.6, dated Feb. 21, 2013 8 pages.
Extended European Search Report in Application No. 12786619.2, dated Nov. 25, 2014, 6 pages.
Extended European Search Report in Application No. 16755489.8, dated Jul. 30, 2018, 8 pages.
Extended European Search Report issued Mar. 18, 2019 in European Patent Application No. 16837135.9.
Extended European Search Report issued Mar. 22, 2019 in European Patent Application No. 16837150.
Ezzat et al., "Dual Inhibition of RET and FGFR4 Retains Medullary Thyroid Cancer Cell Growth," Clinical Cancer Research, Feb. 2005, 11:1336-1341.
Fala, L., "Lenvima (Lenvatinib), a Multireceptor Tyrosine Kinase Inhibitor, Approved by the FDA for the Treatment of Patients with Differentiated Thyroid Cancer", American Health & Drug Benefits Mar. 2015, vol. 8, No. Spec Feature, 176-179 (2015).
Fargnoli et al., "Preclinical studies of BMS-582664, an alanine prodrug of BMS-540215, a potent, dual inhibitor of VEGFR-2 and FGFR-1 kinases," AACR American Association Cancer Research, 96th Annual Meeting, 46 (Abstract 3033), Anaheim, Orange County CA USA Apr. 16-20, 2005, 2 pages.
Ferrara, "Vascular Endothelial Growth Factor: Basic Science and Clinical Progress," Endocrine Reviews, 25 (4): 581-611, Aug. 2004. Important note.
Filipino Office Action in Application No. 1-2011-502441, dated May 8, 2015, 2 pages.
Finn et al., "A multicenter, open-label, phase 3 trial to compare the efficacy and safety of lenvatinib (E7080) versus sorafenib in first-line treatment of subjects with unresectable hepatocellular carinoma," Am Soc Clin Oncol Annual Meeting Abstract, May 31, 2014, 5 pages.

First Examination Report issued May 21, 2019, in New Zealand Patent Application No. 714049.
First Office Action issued on Mar. 6, 2012 for the corresponding JP application, JP2007-542863, 17 pages and English translation.
First Statement of Voluntary Amendments submitted Jul. 3, 2020, in Australian Patent Application No. 2015309862.
Folkman et al., "Angiogenesis," The Journal of Biological Chemistry, 267(16):10931-10934 (1992).
Folkman et al., "Seminars in Medicine of the Beth Israel Hospital, Boston: Clinical Applications of Research on Angiogenesis," The New England Journal of Medicine, 333(26):1757-1763 (1995).
Folkman et al., "What is the Evidence That Tumors are Angiogenesis Dependent?," Journal of the National Cancer Institute, 82(1):4-6 (1990).
Folkman, "New Perspective in Clinical Oncology From Angiogenesis Research," J. Eur. J. Cancer, 32A(4):2534-2539 (1996).
Fong et al., "SU5416 Is a Potent and Selective Inhibitor of the Vascular Endothelial Growth Factor Receptor (Flk-1/KDR) That Inhibits Tyrosine Kinase Catalysis, Tumor Vascularization, and Growth of Multiple Tumor Types", Cancer Research., 59, 99-106, 1999.
Forbes et al., "Dissolution kinetics and solubilities of p-aminosalicylic acid and its salts," International Journal of Pharmaceutics, 126: 199-208 (1995).
Form 2: Complete Specification entitled "Antitumor Agent for Thyroid Cancer," submitted Nov. 24, 2008, in Indian Patent Application No. 6415/CHENP/2008.
Form 2: Complete Specification entitled "Biomarkers for a Combination Therapy Comprising Lenvatinib and Everolimus," dated Nov. 13, 2017, for Indian Patent Application No. 201747040368.
Freshney, R. I. (1983). *Culture of Animal Cells: A Manual of Basic Technique*. Alan R. Liss, Inc., p. 4.
Freshney, R. Ian, "Culture of Animal Cells, A Manual of Basic Technique," Alan R. Liss, New York, 29-32 (1983).
Frings, "New Molecular Targeted Therapeutic Drugs Clinical Results of Bevacizumab in Non-Small Cell Lung Cancer (NSCLC)", Jap. J. Lung Cancer, Jun. 2006, 46(3):277-281 (with English Translation).
Fugazzola et al., "Molecular and biochemical analysis of RET/PTC4, a novel oncogenic rearrangement between RET and ELE1 genes, in a post-Chernobyl papillary thyroid cancer", Oncogene, 13, 1093-1097, 1996.
Fujii et al., "Angiogenesis Inhibitor/Kekkan Shinsei Sogaiyaku," Clin Gastroenterol., May 25, 2004, 19:220-227.
Fujii et al., "MP-412, a dual EGFR/HER2 tyrosine kinase inhibitor: 2. In vivo antitumor effects," Am. Assoc. Cancer Research, A3394, 2005, 2 pages.
Funahashi et al., "ASCO Annual Meeting Abstracts," Jounral of Clinical Oncology, 1(29):8566, 2011.
Funahashi et al., "P-2123, Lenvatinib treatment of differentiated thyroid cancer (DTC): Analysis to identify biomarkers associated with response," The 71st Annual Meeting of the Japanese Cancer Association, Sep. 19-21, 2012, p. 339.
Furitsu et al., "Identification of Mutations in the Coding Sequence of the Proto-Oncogene c-kit in a Human Mast Cell Leukemia Cell Line Causing Ligand-Independent Activation of c-kit Product," J. Clin. Invest., 92:1736-1744 (1993).
Furitsu et al., "Stable medicinal compositions of quinolinecarboxamide derivative," Database Caplus Chemical Abstracts Service, Columbus, OH, US (2006) (XP002520305).
Further Examination Report issued Dec. 23, 2019, in New Zealand Patent Application No. 714049.
Furuta et al., "Synthesis and Biological Evaluation of Selective Inhibitors of PDGF Receptor Auto Phosphorylation," #64, American Chemical Society, 226th ACS National Meeting, New York, NY (Sep. 7-11, 2003).
Gall-Istok et al., "Notes on the Synthesis of 4-Amino-6,7-Di-Sec-Butoxyquinoline, -6,7-Methylene-Dioxyquinoline and its N-Alkylaminoacetyl Derivatives," Acta Chimica Hungarica, 112(2):241-247 (1983).
Gardner et al., "In Vitro Activity Sorghum-Selective Fluorophenyl Urea Herbicides," Pesticide Biochemistry and Physiology, 24(3):285-297 (1985).

(56) References Cited

OTHER PUBLICATIONS

Gaspar et al., "Single-agent Dose-finding Cohort of a Phase 1/2 Study of Lenvatinib in Children and Adolescents With Refractory or Relapsed Solid Tumors," ASCO 2017 Poster 301, ITCC-50 Study, Jun. 26, 2017.
Gatzemeier et al., "Phase III comparative study of high-dose cisplatin versus a combination of paclitaxel and cisplatin in patients with advanced non-small-cell lung cancer," J. Clin. Oncol., 18(19):3390-3399 (2000).
Gayed et al., "Prospective evaluation of plasma levels of ANGPT2, TuM2PK, and VEGF in patients with renal cell carcinoma." BMC urology vol. 15 24. Apr. 3, 2015, doi:10.1186/s12894-015-0019-4.
Genitourinary Cancers, Prostate Cancer Genitourinary, http://www.merkmanuals.com/professional/print/sec17/ch241/ch241e.html Mar. 16, 2011.
Gentet et al., "Ifosfamide and etoposide in childhood osteosarcoma. A phase II study of the French Society of Paediatric Oncology," European Journal of Cancer, vol. 33, 1997, 232-237.
Gild et al, "Multikinase inhibitors: a new option for the treatment of thyroid cancer", Nature Reviews Endocrinol., 7:617-624, Oct. 2011.
Giles, "The vascular endothelial growth factor (VEGF) signaling pathway: a therapeutic target in patients with hematologic malignancies," Oncologist, 6(suppl 5):32-39 (2001).
Gingrich et al., "A new class of potent vascular endothelial growth factor receptor tyrosine kinase inhibitors: structure-activity relationships for a series of 9-alkoxymethyl-12-(3-hydroxypropyl)indeno[2,1-a]pyrrolo[3,4-c]carbazole-5-ones and the identification of CEP-5214 and its dimethylglycine ester prodrug clinical candidate CEP-7055." Journal of medicinal chemistry vol. 46, 25 (2003): 5375-88. doi:10.1021/jm0301641.
Glen et al., "Correlative analyses of serum biomarkers and clinical outcomes in the phase 2 study of lenvatinib, everolimus, and the combination, in patients with metastatic renal cell carcinoma following 1 VEGF-targeted therapy", European Journal of Cancer, vol. 51, Sep. 1, 2015, p. S89, XP055510094.
Glen, "Pre-clinical investigation and clinical development of E7080, a multi-targeted tyrosine kinase inhibitor: implications for melanoma," Ph.D. thesis submitted to the Faculty of Medicine, Division of Cancer Sciences and Molecular Pathology, University of Glasgow, Aug. 11, 2010, 2 pages.
Goede, "Identification of serum angiopoietin-2 as a biomarker-for clinical outcome of colorectal cancer patients treated with bevacizumab-containing therapy," Br J Cancer, 103(9):1407-1414, Oct. 2010.
Golkar et al., "Mastocytosis," Lancet, 349:1379-1385 (1997).
Goorin et al., "Phase II/III trial of etoposide and high-dose ifosfamide in newly diagnosed metastatic osteosarcoma: a pediatric oncology group trial", Journal of Clinical Oncology: Official Journal of the American Society of Clinical Oncology, vol. 20, No. 2, Jan. 15, 2002, p. 426-p. 433.
Grieco et al., "PTC is a Novel Rearranged Form of the ret Proto-Oncogene and Is Frequentrly; Detected in Vivo in Human Thyroid Papillary Carcinomas", Cell, 60: 557-563 (1990);.
Grier et al., "Addition of Ifosfamide and Etoposide to Standard Chemotherapy for Ewing's Sarcoma and Primitive Neuroectodermal Tumor of Bone", The New England Journal of Medicine, vol. 348, 2003, p. 694-p. 701.
Guo et al., "Expression of gastric cancer-associated MG7 antigen in gastric cancer, precancerous lesions and H. pylori-associated gastric diseases", Word J. Gastroenterol, 8(6):1009-1013 (2002).
Guo et al., "In Vitro Pharmacological Characterization of TKI-28, a Broad-Spectrum Tyrosine Kinase Inhibitor with Anti-Tumor and Anti-Angiogenic Effects," Cancer Biol Ther., 4, 1125-1132 (2005).
Guo, "Dose Optimization Study: E7080-G000-218 [URL:https://www.aacr.org/AdvocacyPolicy/GovernmentAffairs/Documents/6.13.16%20FDA-AACR%20Dose%20Finding%20for%20Online.pdf]", Presentation slides at FDA-AACR: Oncology Dose-finding Workshop, Jun. 13, 2016, 25 pages.
Gura, "Cancer Models Systems for Identifying new drugs are often faulty," Science, 278:1041-1042 (1997).

Gutheil et al., "Targeted antiangiogenic therapy for cancer using Vitaxin: a humanized monoclonal antibody to the integrin alphavbeta3." Clinical cancer research : an official journal of the American Association for Cancer Research vol. 6,8 (2000): 3056-61.
Haleblian, "Characterization of habits and crystalline modification of solids and their pharmaceutical applications," J. Pharm. Sci., 64(8):1269-1288 (1975).
Haller, "Chemotherapy for advanced pancreatic cancer," Int. J. Radiation Oncol. Biol. Phys., 56:16-23 (2003).
Hamby et al., "Structure-Activity Relationships for a Novel Series of Pyrido[2,3-d]pyrimidine Tyrosine Kinase Inhibitors", Journal of Medicinal Chemistry., 40, 2296-2303, 1997.
Hamel et al., "The Road Less Travelled: c-kit and Stem Cell Factor," Journal of Neuro-Oncology, 35:327-333 (1997).
Hara et al., "Amplification of c-myc, K-sam, and c-met in Gastric Cancers: Detection by Fluorescence In Situ Hybridization", Laboratory Investigation, 78, 1143-1153, 1998.
Hattori et al., "Immunohistochemical detection of K-sam protein in stomach cancer," Clin. Cancer Res., 2(8):1373-1381 (1996).
Havel et al., "E7080 (lenvatinib) in addition to best supportive care (BSC) versus (BSC) alone in third-line or greater nonsquamous, non-small cell lung cancer (NSCLC)," Am Soc Clin Oncol Annual Meeting Abstract, May 31, 2014, abstract 8043, 4 pages.
Hayamo et al., "Pericytes in experimental MDA-MB231 tumor angiogenesis," Histochemistry and Cell Biology, 117(6):527-534, Abstract (Jun. 2002).
Hayato, "In-silico trial to evaluate the utility of a postmarketing trial for dose optimization-Lenvatinib in Renal Cell Carcinoma— [URL:https://insp.memberclicks.net/mcdatafiles/receiptattach/insp/11395454/7966299/ACOP7_Session4a_SeiichiHayato_19Oct2016.pptx]", Presentation slides at the Seventh American Conference on; Pharmacometrics, Oct. 25, 2016, 17 pages.
Hayek et al., "An In Vivo Model for Study of the Angiogenic Effects of Basic Fibroblast Growth Factor," Biochemical and Biophysical Research Communications, 147(2):876-880 (1987).
Hearing Notice dated Jan. 10, 2020, in Indian Patent Application No. 2371/CHENP/2012.
Hearing Notice issued Jul. 10, 2020, in Indian Patent Application No. 201847004787.
Hearing Notice issued May 4, 2012, in India Patent Application No. 383/CHENP/2008.
Heinemann et al., "Comparison of the cellular pharmacokinetics and toxicity of 2',2'-difluorodeoxycytidine and 1-beta-D-arabinofuranosylcytosine." Cancer research vol. 48,14 (1988):4024-31.
Heinrich et al., "Inhibition of c-kit receptor tyrosine kinase activity by STI 571, a selective tyrosine kinase inhibitor," Blood, 96(3):925-932 (2000) (XP001097629).
Heinrich et al., "Inhibition of KIT tyrosine kinase activity: a novel molecular approach to the treatment of KIT-positive malignancies," J. Clin. Oncol., 20(6):1692-1703 (2002).
Heinrich et al., "Kinase Mutations and Imatinib Response in Patients with Metastatic; Gastrointestinal Stromal Tumor", Journal of Clinical Oncology, vol. 21, No. 23:4342-4349 (2003).
Helfrich et al., "Angiopoietin-2 Levels Are Associated with Disease Progression in Metastatic Malignant Melanoma," Clin Cancer Res 15(4):1384-1392, Feb. 15, 2009.
Hennequin et al., "Design and structure-activity relationship of a new class of potent VEGF receptor tyrosine kinase inhibitors." Journal of medicinal chemistry vol. 42,26 (1999): 5369-89. doi:10.1021/jm990345w.
Hennequin et al., "Novel 4-Anilinoquinazolines with C-7 Basic Side Chains: Design and Structure Activity Relationship of a Series of Potent, Orally Active, VEGF Receptor Tyrosine Kinase Inhibitors," J. Med. Chem., 45:1300-1312 (2002).
Herbst et al., "AMG 706 first in human, open-label, dose-finding study evaluating the safety and pharmacokinetics (PK) in subjects with advanced sold tumors," EORTC-NCI-AACR Symp Mol Targets Cancer Ther., 2, (Abstract 151), 2004, 1 page.
Hertel et al., "Evaluation of the Antitumor Activity of Gemcitabine (2',2' -Difluoro-2'-deoxycytidine)", Cancer Research, 50, 4417-4422, 1990.

(56) References Cited

OTHER PUBLICATIONS

Hibi et al., "Coexpression of the Stem Cell Factor and the c-kit Genes in Small-Cell Lung Cancer," Oncogene, 6:2291-2296 (1991).
Highlights of Prescribing Information: GLEEVEC® (imatinib mesylate) Tablets for Oral Use (Initial U.S. Approval 2001; Label Revised Jan. 2012).
Highlights of Prescribing Information: LENVIMA® (lenvatinib) capsules, for oral use (Initial U.S. Approval: 2015; Label Revised Feb. 2017).
Hines et al., "Coexpression of the c-kit and Stem Cell Factor Genes in Breast Carcinomas," Cell Growth & Differentiation, 6:769-779 (1995).
Hori et al., "Suppression of Solid Tumor Growth by Immunoneutralizing Monoclonal Antibody against Human Basic Fibroblast Growth Factor", Cancer Research., 51, 6180-4, 1991.
Hu-Lowe et al., "SU014813 is a novel multireceptor tyrosine kinase inhibitor with potent antiangiogenic and antitumor activity," AACR American Association Cancer Research., 96th Annual Meeting, 46, (Abstract 2031), Anaheim, Orange County, CA, USA Apr. 2005, 2 pages.
Hungarian Amendment to the Specification in Application No. P0302603, dated Jul. 7, 2015, 45 pages, with English translation.
Hungarian Notice of Allowance in Application No. P0302603, dated Aug. 19, 2015, 4 pages, with English translation.
Hungarian Office Action in Application No. P0302603, dated Apr. 7, 2015, 5 pages, with English translation.
Hungarian Office Action in Application No. P0302603, dated Nov. 26, 2015, 4 pages.
Hurwitz et al., "Bevacizumab plus irinotecan, fluorouracil, and leucovorin for metastatic colorectal cancer," N. Engl. J. Med., 350(23):2335-2342 (2004).
Huston et al., "Protein engineering of antibody binding sites: Recovery of specific activity in an anti-digoxin single-chain Fv analogue produced in *Escherichia coli*", Proc. Natl. Acad. Sci. USA 85: 5879-83, 1988.
Ikeda et al, "A Phase 2 Study of Lenvatinib Monotherapy as Second-line Treatment in Unresectable Biliary Tract Cancer: Primary Analysis Results", ESMO 2017 Congress, Sep. 8-12, 2017.
Ikeda et al., "Changes in Phenotype and Proliferative Potential of Human Acute Myeloblastic Leukemia Cells in Culture with Stem Cell Factor," Experimental Hematology, 21:1686-1694 (1993).
Ikeda et al., "Expression and Functional Role of the Proto-Oncogene c-kit in Acute Myeloblastic Leukemia Cells," Blood, 78(11):2962-2968 (1991).
Ikeda, K., et al., "Phase 2 study of lenvatinib in patients with advanced hepatocellular carcinoma," *J. Gastroenterol.*, 2016, 52: 512-519.
Ikeda, M., et al., "Safety and Pharmacokinetics of Lenvatinib in Patients with Advanced Hepatocellular Carcinoma," *Clin. Cancer Res.*, 2015, 22(6): 1385-1394.
Ikuta et al., "E7080, a Multi-Tyrosine Kinase Inhibitor, Suppresses the Progression of Malignant Pleural Mesothelioma with Different Proangiogenic Cytokine Production Profiles," Clin Cancer Res., Nov. 24, 2009, 15(23):7229-7237.
Inai et al., "Inhibition of vascular endothelial growth factor (VEGF) signaling in cancer causes loss of endothelial fenestrations, regression of tumor vessels, and appearance of basement membrane ghosts," American Journal of Pathology, 165:35-52 (2004).
Indian Office Action for Application No. 1571/CHENP/2007, issued on Oct. 30, 2012.
Indian Office Action in Application No. 6415/CHENP/2008, dated Oct. 3, 2013, 2 pages.
Information about decision on request for EP Application No. 06023078.6, dated Mar. 21, 2007.
Inoue et al., "Molecular Target Therapy Targeting Angiogenesis Pathways," The Nishinihon Journal of Urology, 66:425-432 (2004).
International Adjuvant Lung Cancer Trial Collaborative Group, "Cisplatin-Based Adjuvant Chemotherapy in Patients with Completely Resecected Non-Small Cell Lung Cancer," The New England Journal of Medicine, 350 (4): 351-360 (2004).
International Preliminary Report in International Application No. PCT/IB2008/003880, dated Aug. 11, 2009, 4 pages.
International Preliminary Report in International Application No. PCT/JP2007/066185, dated Mar. 5, 2009, 6 pages.
International Preliminary Report in International Application No. PCT/JP2007/066635, dated Mar. 12, 2009, 9 page.
International Preliminary Report in International Application No. PCT/JP2008/053066, dated Sep. 11, 2009, 12 pages.
International Preliminary Report in International Application No. PCT/JP2008/071881, dated Jul. 14, 2011, 7 pages.
International Preliminary Report in International Application No. PCT/JP2009/0524001, dated Oct. 14, 2010, 5 pages.
International Preliminary Report in Patentability in International Application No. PCT/JP2006/316331, dated Feb. 26, 2008, 5 pages.
International Preliminary Report on Patentability and Written Opinion of the International Searching Authroity for Application No. PCT/JP2006/312487, issued on Dec. 24, 2007.
International Preliminary Report on Patentability for Application No. PCT/JP01/09221, dated Jan. 8, 2003.
International Preliminary Report on Patentability for Application No. PCT/JP2004/003087, issued on Feb. 13, 2006.
International Preliminary Report on Patentability for Application No. PCT/JP2005/016941, dated on Mar. 20, 2007.
International Preliminary Report on Patentability for Application No. PCT/JP2010/063804, issued on Mar. 13, 2012.
International Preliminary Report on Patentability for Application No. PCT/JP2011/064430, dated Jan. 24, 2013, 6 pages.
International Preliminary Report on Patentability for Application No. PCT/JP2018/018810, dated Aug. 7, 2018, 10 pages.
International Preliminary Report on Patentability for International Application No. PCT/JP2003/010964 dated Aug. 10, 2004, 7 pages.
International Preliminary Report on Patentability for International Application No. PCT/JP2007/060560 on Nov. 18, 2008, 6 pages with English translation.
International Preliminary Report on Patentability for International Application No. PCT/JP2007/060560, dated Dec. 10, 2008, 7 pages.
International Preliminary Report on Patentability for International Application No. PCT/JP2007/067088 dated Mar. 3, 2009, 16 pages with English translation.
International Preliminary Report on Patentability for International Application No. PCT/JP2008/051024 dated Jul. 21, 2009, 15 pages with English translation.
International Preliminary Report on Patentability for International Application No. PCT/JP2008/051697, issued on Aug. 4, 2009, 18 pages.
International Preliminary Report on Patentability for International Application No. PCT/JP2008/070321, issued May 11, 2010, 15 pages with English translation.
International Preliminary Report on Patentability for International Application No. PCT/JP2009/051244 issued on Aug. 31, 2010, 12 pages (with English translation).
International Preliminary Report on Patentability in Application No. PCT/JP2013/084052, dated Jul. 2, 2015, 7 pages.
International Preliminary Report on Patentability in International Application No. PCT/JP2005/003701, dated Sep. 19, 2006, 7 pages.
International Preliminary Report on Patentability in International Application No. PCT/JP2005/003704, dated Sep. 19, 2006, 7 pages.
International Preliminary Report on Patentability in International Application No. PCT/JP2006/315563 dated Feb. 5, 2008, 5 pages.
International Preliminary Report on Patentability in International Application No. PCT/JP2006/315698 dated Feb. 5, 2008, 7 pages English translation.
International Preliminary Report on Patentability in International Application No. PCT/JP2006/322514 issued on May 7, 2008, 8 pages.
International Preliminary Report on Patentability in International Application No. PCT/JP2006/322516 issued on May 7, 2008, 8 pages.
International Preliminary Report on Patentability in International Application No. PCT/JP2012/060279, dated Oct. 23, 2013, 11 pages.

(56) References Cited

OTHER PUBLICATIONS

International Preliminary Report on Patentability in International Application No. PCT/JP2012/062509, dated Nov. 19, 2013, 10 pages.
International Preliminary Report on Patentability in International Application No. PCT/JP2016/055268, dated Sep. 8, 2017, 9 pages.
International Preliminary Report on Patentability in International Patent Application No. PCT/JP2016/074017, dated Mar. 1, 2018, 8 pages (English Translation).
International Preliminary Report on Patentability mailed Aug. 22, 2019, in International Patent Application No. PCT/JP2018/004007.
International Search Report and Written Opinion in Application No. PCT/JP2014/063134, dated Sep. 9, 2014, 8 pages.
International Search Report and Written Opinion in International Application No. PCT/JP2008/071881, dated Jan. 27, 2009, 12 pages.
International Search Report and Written Opinion in International Application No. PCT/JP2009/0524001, dated Mar. 10, 2009, 9 pages.
International Search Report and Written Opinion in International Application No. PCT/JP2017/015461, dated Jun. 27, 2017, 8 pages.
International Search Report and Written Opinion mailed Jan. 2, 2018 in PCT/US2017/056552.
International Search Report and Written Opinion mailed Sep. 17, 2019, in International Patent Application No. PCT/US2019/031967.
International Search Report for Application No. PCT/JP01/09221, issued on Jan. 15, 2002.
International Search Report for Application No. PCT/JP2005/016941, dated on Nov. 15, 2005.
International Search Report for Application No. PCT/JP2006/315563, issued on Sep. 5, 2006.
International Search Report for Application No. PCT/JP2006/315698, issued on Oct. 17, 2006.
International Search Report for Application No. PCT/JP2006/322514, issued on Jan. 23, 2007.
International Search Report for Application No. PCT/JP2006/323881, issued on Jan. 23, 2007.
International Search Report for Application No. PCT/JP2007/060560, issued on Sep. 11, 2007.
International Search Report for Application No. PCT/JP2007/063525, issued on Sep. 4, 2007.
International Search Report for Application No. PCT/JP2007/067088, issued on Nov. 20, 2007.
International Search Report for Application No. PCT/JP2008/051024, issued on Apr. 1, 2008.
International Search Report for Application No. PCT/JP2008/051697, issued on Mar. 4, 2008.
International Search Report for Application No. PCT/JP2008/070321, issued on Jan. 20, 2009.
International Search Report for Application No. PCT/JP2009/051244, issued on Mar. 24, 2009.
International Search Report for Application No. PCT/JP2010/063804, issued on Sep. 14, 2010.
International Search Report for International Application No. PCT/JP2006/317307, issued on Dec. 12, 2006, 3 pages.
International Search Report for PCT/JP2012/060279, May 29, 2012.
International Search Report in International Application No. PCT/IB2008/003880, dated Aug. 11, 2009, 7 pages.
International Search Report in International Application No. PCT/JP2005/003701, dated May 31, 2005, 6 pages (with English translation).
International Search Report in International Application No. PCT/JP2005/003704, dated May 31, 2005, 6 pages (with English translation).
International Search Report in International Application No. PCT/JP2006/316331, dated Oct. 17, 2006, 5 pages (with English translation).
International Search Report in International Application No. PCT/JP2006/322516 issued on Jan. 23, 2007, 5 pages.
International Search Report in International Application No. PCT/JP2007/066185, dated Sep. 25, 2007, 4 pages.
International Search Report in International Application No. PCT/JP2007/066635, dated Oct. 16, 2007, 5 pages.
International Search Report in International Application No. PCT/JP2008/053066, dated May 20, 2008, 8 pages.
International Search Report in International Patent Application No. PCT/JP2016/055268, dated May 17, 2016, 2 pages (English Translation).
International Search Report in International Patent Application No. PCT/JP2016/074017, dated Nov. 8, 2016, 2 pages (English Translation).
International Search Report mailed Aug. 7, 2018, in International Patent Application No. PCT/JP2018/018810.
Interview Summary filed Jan. 30, 2020, in U.S. Appl. No. 16/038,710.
Interview Summary in U.S. Appl. No. 12/558,982, dated Oct. 20, 2011, 3 pages.
Interview Summary issued Dec. 30, 2019, in U.S. Appl. No. 16/038,710.
Interview Summary issued Jun. 23, 2020, in U.S. Appl. No. 15/748,980.
Invitation to declare maintenance of the application for EP Application No. 01976786.2, dated Jul. 12, 2004.
Invitation to declare maintenance of the application for EP Application No. 05783232.1, dated Sep. 25, 2007.
Invitation to declare maintenance of the application for EP Application No. 06023078.6, dated May 2, 2007.
Invitation to Respond to Written Opinion issued Nov. 5, 2019, in Singaporean Patent Application No. 11201706630U.
Israel 200090 Office Actions issued on Jun. 22, 2010, 3 pages (with English translation).
Israel 200090 Response to Office Action filed on Oct. 12, 2010, 3 pages.
Israel Office Action directed at Appl. No. 195282 issued on Jan. 26, 2010, 4 pages with English translation.
Israel Response (IDS List) to Office Action directed at Appl. No. 195282 filed on May 3, 2010, 6 pages with English translation.
Israeli Notice of Allowance in Application No. 205512, dated Feb. 15, 2015, 5 pages, with English translation.
Israeli Office Action dated Mar. 27. 2012 for Israeli Application No. 189589 with English translation.
Israeli Office Action for Application No. 155447, issued on Oct. 16, 2007 (with English translation).
Israeli Office Action for Application No. 189677, issued on Feb. 18, 2009 (with English translation).
Israeli Office Action for Application No. 195282, issued on Feb. 5, 2012 (with English translation).
Israeli Office Action for Application No. 199907, issued on Apr. 22, 2012 (with English translation).
Israeli Office Action in Application No. 217197, dated Oct. 25, 2015, 4 pages.
Israeli Office Action in Application No. 223695, dated Aug. 25, 2015, 6 pages, with English translation.
Israeli Office Action in Application No. 223695, dated Feb. 16, 2015, 5 pages, with English translation.
Israeli Office Action in Application No. 227558, dated Aug. 2, 2015, 5 pages, with English translation.
Israeli Office Action in Application No. 238463, dated Oct. 28, 2015, 5 pages, with English translation.
Israeli Office Action issued on May 16, 2010 for corresponding Israeli Application No. 189589, with English translation.
Israeli Submission Documents in Application No. 223695, dated May 4, 2015, 4 pages, with English translation.
Issue Notification in U.S. Appl. No. 11/508,322, dated Dec. 1, 2010, 1 page.
Issue Notification in U.S. Appl. No. 12/031,568, dated Jan. 30, 2013, 4 pages (with English translation).
Issue Notification in U.S. Appl. No. 12/315,291, dated Jul. 27, 2011, 1 page.
Issue Notification in U.S. Appl. No. 12/558,982, dated Sep. 26, 2012, 1 page.
Issued Notification in U.S. Appl. No. 11/892,785, dated Aug. 18, 2010, 1 page.

(56) References Cited

OTHER PUBLICATIONS

Itoh et al., "Preferential alternative splicing in cancer generates a K-sam messenger RNA with higher transforming activity," Cancer Res., 54:3237-3241 (1994).
Jain, "Normalizing tumor vasculature with anti-angiogenic therapy: A new paradigm for combination therapy," Nature Medicine 7(9): 987-989 (2001).
Jakeman et al., "Developmental Expression of Binding Sites and Messenger Ribonucleic Acid for Vascular Endothelial Growth Factor Suggests a Role for This Protein in Vasculogenesis and Angiogenesis," Endocrinology, 133(2):848-859 (1993).
Jang et al., "Mutations in Fibroblast Growth Factor Receptor 2 and Fibroblast Growth Factor Receptor 3 Genes Associated with Human Gastric and Colorectal Cancers", Cancer Research,; 61:3541-3543 (2001).
Japanese Allowance for Application No. P2005-516605, issued on Dec. 7, 2010.
Japanese Classification of Gastric Carcinoma "Igan-Toriatsukai Kiyaku" (Jun. 1999, 13th ed.) and an English translation, 10 pages.
Japanese Decision to Grant a Patent dated Jan. 30, 2013 for Japanese Application No. 2007-533350, with English translation.
Japanese Notice of Allowance in Application No. P2011-206481, dated Aug. 4, 2015, 7 pages, with English translation.
Japanese Notice of Reasons for Rejection dated May 15, 2012 for Japanese Application No. 2007-533350 with English translation.
Japanese Office Action dated Apr. 11, 2005 for Application No. 2002-536056 (with English translation).
Japanese Office Action for Application No. 2007-522356, issued on Feb. 8, 2011.
Japanese Office Action for Application No. P2005-516605, issued on Nov. 4, 2009.
Japanese Office Action for Application No. P2008-516724, issued on Oct. 9, 2012 (with English translation).
Japanese Office Action in Application No. P2011-206481, dated Jun. 2, 2015, 7 pages, with English translation.
Japanese Office Action in Application No. P2012-521531, dated Mar. 3, 2015, 6 pages, with English translation.
Japanese Office Action in Application No. P2012-521531, dated Sep. 29, 2015, 4 pages, with English translation.
Japanese Office Action in Application No. P2013-510994, dated Jul. 28, 2015, 5 pages, with English translation.
Japanese Office Action in Application No. P2013-510994, dated Jun. 9, 2015, 6 pages, with English translation.
Jhiang, "The RET proto-oncogene inn human cancers," Oncogene, 19:5590-5597 (2000).
Jiang, "ZD6474: an Agent That Selectively Targets Both VEGFR Tyrosine Kinase and EGFR Tyrosine Kinase", Jap. J. Lung Cancer, Jun. 2006, 46(3):283-288 (with English translation).
Jimenez et al., "Pheochromocytoma and medullary thyroid carcinoma: a new genotype-phenotype correlation of the RET protooncogene 891 germline mutation," J. Clin. Endocrinol. Metab., 89:4142-4145 (2004).
Bugalho al. "Somatic trinucleotide change encompassing codons 882 and 883 of the RET proto-oncogene in a patient with sporadic medullary thyroid carcinoma." European journal of endocrinology vol. 142,6 (2000): 573-5. doi:10.1530/eje.0.1420573.
Johnson et al., "Influence of ionic strength on matrix integrity and drug release from hydroxypropyl cellulose compacts," International journal of pharmaceutics, 1993, vol. 90, No. 2, pp. 151-159.
Johnson et al., "Paclitaxel plus carboplatin in advanced non-small-cell lung cancer: a phase II trial," J. Clin. Oncol., 14(7):2054-2060 (1996).
Johnson et al., "Randomized phase II trial comparing bevacizumab plus carboplatin and paclitaxel with carboplatin and paclitaxel alone in previously untreated locally advanced or metastatic non-small-cell lung cancer," J Clin Oncol 22 (11): 2184-2191 (2004).
Johnson et al., "Brivanib Versus Sorafenib as First-Line Therapy in Patients With Unresectable, Advanced Hepatocellular Carcinoma: Results From the Randomized Phase III Brisk-FL Study," J. Clin. Oncol., 2013, 31 (28): 3517-3524.

Joly et al., "In vitro and in vivo characterization of exel-7647, a novel spectrum selective receptor tyrosine kinase inhibitor that modulates angiogenesis and tumor cell proliferation," EORTC-NCI-AACR Symp Mol Targets Cancer Ther., (Abstract 134), 2004, 1 page.
Jung et al., "Effects of combination anti-vascular endothelial growth factor receptor and anti-epidermal growth factor receptor therapies on the growth of gastric cancer in a nude mouse model," Eur. J. Cancer, 38:1133-1140 (2002).
Juurikivi et al., "Inhibition of c-kit tyrosine kinase by imatinib mesylate induces apoptosis in mast cells in rheumatoid synovia: a potential approach to the treatment of arthritis," Ann Rheum. Dis., 64:1126-1131 (2005).
Kanai et al., "Current status and future perspective of molecular targeted therapy for hepatocellular carcinoma," Journal of the Japanese Society of Gastroenterology, 106: 1727-1735 (2009) ( with English translation).
Kanakura et al., "Expression, Function and Activation of the Proto-Oncogene c-kit Product in Human Leukemia Cells," Leukemia and Lymphorma, 10:35-41 (1993).
Kashuk et al., "Phenotype-genotype correlation in Hirschsprung disease is illuminated by comparative analysis of the RET protein sequence," PNAS, 102(25):8949-8954 (2005).
Kawano et al., "Presentation Abstract, Abstract Number; 1619, Combination of VEGFR inhibitor lenvatinib (E7080) and Met/EphB4inhibitor golvatinib (E7050) overcomes VEGFR inhibitor-resistant tumor vascular", Annual Meeting 2013, Walter E. Washington Convention Center, Washington, D.C., Apr. 6-10, 2013, 1 page.
Kay et al., "Eosinophils and Eosinophil-Associated Cytokines in Allergic Inflammation," Int. Arch. Allergy Immunol., 113:196-199 (1997).
Kelly et al., "Randomized phase III trial of paclitaxel plus carboplatin versus vinorelbine plus cisplatin in the treatment of patients with advanced non-small-cell lung cancer: a Southwest Oncology Group trial," J. Clin. Oncol., 19(13):3210-3218 (2001).
Kharkyevitch, "Farmakologiya," Third addition, and revised supplemented, Moscow, "Meditsina," 1987, partial translation, 5 pages.
Kibbe, Handbook of Pharmaceutical Excipients. Third Edition, 2000, pp. 6-1 through 6-6.
Kim et al., "A phase II study of irinotecan plus cisplatin for patients with advanced stage IIIB or IV NSCLC previously treated with nonplatinum-based chemotherapy," Cancer, 107(4):799-805 (2006).
Kim et al., "An orally administered multitarget tyrosine kinase inhibitor, SU11248, is a novel potent inhibitor of thyroid oncogenic RET/papillary thyroid cancer kinases," J. Clin. Endocrinol. Metlab., 91(10):4070-4076 (2006).
Kim, "Technology evaluation: Matuzumab, Merck KGaA," Curr Opin Mol Ther. 2004; 6(1):96-103.
Kinlaw et al., "Multiple endocrine neoplasia 2A due to a unique C6095 Ret mutation presents with pheochromocytoma and reduced penetrance of medullary thyroid carcinoma", Clin Endocrinol, 69, 676-682, 2005.
Kitamura et al., "Regulation of Development, Survival and Neoplastic Growth of Mast Cells through the c-kit Receptor," Int. Arch Allergy Immunol., 107:54-56 (1995).
Kitteringham et al., "A Simple Method for the Synthesis of Unsymmetrical Ureas," Synthetic Communications, 30(11):1937-1943 (2000).
Kleespies et al., "Tyrosine kinase inhibitors and gemcitabine: New treatment options in pancreatic cancer," Drug Resistance Updates, 9:1-18 (2006).
Klein et al. "Vascular endothelial growth factor gene and protein: strong expression in thyroiditis and thyroid carcinoma," The Journal of endocrinology vol. 161, 1 (1999): 41-9.
Klugbauer and Rabes, "The transcription coactivator HT1 F1 and a related protein are fused to the RET receptor tyrosine kinase in childhood papillary thyroid carcinomas", Oncogene, 18: 4388-4393 (1999).
Klugbauer et al., "A Novel Type of RET Rearrangement (PTC8) in Childhood Papillary Thyroid Carcinomas and Characterization of the Involved Gene (RFG8)", Cancer Research, 60: 7028-7032 (2000).

(56) References Cited

OTHER PUBLICATIONS

Klugbauer et al., "Detection of a Novel Type of RET Rearrangement (PTC5) in Thyroid Carcinomas after Chernobyl and Analysis of the Involved RET-fused Gene RFG5", Cancer Research, 58:198-203 (1998).
Knollman et al., "Muscle-invasive urothelial bladder cancer: an update on systemic therapy", Therapeutic Advances in Urology, vol. 7, No. 6, pp. 312-330 (2015).
Ko, "Stomach Cancer," Cancer Supportive Care.com [published online Feb. 2003], [retrieved on Dec. 28, 2011]. Retrieved from the Internet: http://web.archive.org/web/20030224212825/http://www.cancersupportivecare.com/stomach.html.
Kolibaba et al., "Protein Tyrosine Kinases and Cancer," Biochimica et Biophysica Acta, 1333:F217-F248 (1997).
Konno, "Physical and Chemical Changes of Medicinals in Mixtures with Adsorbents in the Solid State IV," Study on Reduced-Pressure Mixing for Practical Use of Amorphous Mixtures of Flufenamic Acid, Chem. Pharm Bull, 1990, p. 2003.
Korean ("KR") Notice of Allowance issued on Aug. 25, 2010 corresponding KR Application No. 10-2008-7005195, with English translation.
Korean ("KR") Office Action issued on Dec. 24, 2009 for corresponding KR Application No. 10-2008-7005195, with English translation.
Korean ("KR") Office Action issued on May 29, 2010 for corresponding KR Application No. 10- 2008-7005195, with English translation.
Korean Notice of Allowance in Application No. 10-2010-7011023, dated Mar. 24, 2015, 3 pages, with English translation.
Korean Office Action for Application No. 10-2003-7005506, issued on Jan. 5, 2006 (with English translation).
Korean Office Action for Application No. 10-2005-7020292, issued on Dec. 8, 2005 (with English translation).
Korean Office Action for Application No. 10-2006-7013993, issued on Jul. 31, 2007 (with English translation).
Korean Office Action for Application No. 10-2007-7001347, issued on Apr. 27, 2012 (with English translation).
Korean Office Action for Application No. 10-2007-7001347, issued on Sep. 28, 2011 (with English translation).
Korean Office Action in KR Application No. 10-2008-7029472, dated Sep. 30, 2013, 27 pages (with English translation).
Korean Request for Examination in Application No. 10-2012-7033886, dated Aug. 26, 2015, 12 pages, with English translation.
Kotva et al., "Substances with antineoplastic activity. LIII. N-{?-(4-pyrrolo[2,3-d]pyrimidinylthio)valeryl}amino acids and analogous derivatives of di- and triglycine," Collection Czechoslov. Chem. Commun., 38:1438-1444 (1973).
Koyama et al, "Anti-tumor effect of E7080, a novel angiogenesis inhibitor," Folia Pharmacol. Japan., 2008, 132: 100-104 (with English translation).
Kremer, "Lenvatinib Advisory Board", The presentation document, American Society of Clinical Oncology, Annual meeting 2014, May 31, 2014, 138 pages.
Kruckeberg et al., "Pyrosequencing Technology as a Method for the Diagnosis of Multiple Endocrine Neoplasia Type 2", Clinical Chemistry, 50, 522-529, 2004.
Krystal et al., "Indolinone Tyrosine Kinase Inhibitors Block Kit Activation and Growth of Small Cell Lung Cancer Cells", Cancer Research., 61, 3660-3668, 2001.
Kubo et al., "a novel series of 4-phenoxyquinolines: potent and highly selective inhibitors of pdgf receptor autophosphorylation", Bioorganic and Medicinal Chemistry Letters, 7, 2935-2940, 1997.
Kubo et al. "Novel potent orally active selective VEGFR-2 tyrosine kinase inhibitors: synthesis, structure-activity relationships, and antitumor activities of N-phenyl-N'-{4-(4-quinolyloxy)phenyl}ureas," Journal of medicinal chemistry vol. 48,5 (2005): 1359-66.
Kudo, M., et al., "Lenvatinib versus sorafenib in first-line treatment of patients with unresectable hepatocellular carcinoma: a randomised phase 3 non-inferiority trial," *Lancet*, 2018, 391: 1163-1173.
Kumar et al., "Discovery and biological evaluation of GW654652: A pan inhibitor of VEGF receptors," Proceedings of the American Association for Cancer Research, 44, 9, (Abstract 39), 2003, 2 pages.
Kumar et al., "Survival and failure outcomes in primary thyroid lymphomas: A single centre experience of combined modality approach," Journal of Thyroid Research, vol. 2013, Jun. 18, 2013, 6 pages.
Laird et al., "SU6668 Is a Potent Antiangiogenic and Antitumor Agent That Induces Regression of Established Tumors1", Cancer Research., 60, 4152-4160, 2000.
Lam et al., "Extemporaneous Compounding of Oral Liquid Dosage Formulations and Alternative Drug Delivery Methods for Anticancer Drugs," Reviews of Therapeutics, Pharmacotherapy, 2011, 31(2):164-192.
Lam et al., "High prevalence of RET proto-oncogene activation (RET/PTe) in papillary thyroid carcinomas", Eur J Endocrinology, 147: 741-745 (2002).
Lasota et al., "Mutations in Exons 9 and 13 of KIT Gene Are Rare Events in Gastrointestinal Stromal Tumors," American Journal of Pathology, 157(4):1091-1095 (2000).
LeDoussal et al. "bispecific-antibody-mediated targeting of radiolabeled bivalent haptens: theoretical, experimental and clinical results", Int. J. Cancer Suppl. 7: 58-62, 1992.
Lee et al., "In vivo target modulation and biological activity of CHIR-258, a multitargeted growth factor receptor kinase inhibitor, in colon cancer models," Clinical cancer research : an official journal of the American Association for Cancer Research vol. 11,10 (2005): 3633-41.
Lennartsson et al., The Stem Cell Factor Receptor/c-Kit as a Drug Target in Cancer, Current Cancer Drug Targets, 6: 65-75 (2006).
Lenvatinib in Wikipedia: the Free Encyclopedia, http://en/wikipeida/org/wiki/Lenvatinib (accessed Dec. 18, 2013), 2 pages.
Leow et al. "MEDI3617, a human anti-angiopoietin 2 monoclonal antibody, inhibits angiogenesis and tumor growth in human tumor xenograft models", International Journal of Oncology, Demetrios A. Spandidos ED. & PUB, GR, vol. 40, No. 5, May 1, 2012, p. 1321-p. 1330, XP002721374.
Lesueur et al., "Polymorphisms in RET and its coreceptors and ligands as genetic modifiers of multiple endocrine neoplasia type 2A," Cancer Res., 66:1177-1180 (2006).
Lev et al., "A Specific Combination of Substrates is Involved in Signal Transduction by the Kit-Encoded Receptor," The EMBO Journal, 10(3):647-654 (1991).
Li et al., "Abrogation of c-kit/Steel factor-dependent tumorigenesis by kinase defective mutants of the c-kit receptor: c-kit kinase defective mutants as candidate tools for cancer gene therapy," Cancer Res., 56:4343-4346 (1996) (XP002522473).
Li et al., "ABT-869 a novel multi-targeted receptor tyrosine kinase inhibitor: characterization of FLT3 phosphorylation in a model of acute myelogenous leukemia," AACR American Association Cancer Research, 96th Annual Meeting, 46:1407, (Abstract 5981), Anaheim, Orange County CA USA Apr. 16-20, 2005, 2 pages.
Lin et al., "The vascular endothelial growth factor receptor tyrosine kinase inhibitor PTK787/ZK222584 inhibits growth and migration of multiple myeloma cells in the bone marrow microenvironment," Cancer Res., 62(17):5019-5026 (2002).
List of Corresponding Applications / List of Citations dated Feb. 5, 2019 in Israel Appl. No. 253946.
Liu et al., "Dose Adjustment Integrated Exposure Response Analysis (DAIER) for Dose Optimization Lenvatinib Renal Call Carcinoma [URL:https://www.aacr.org/AdvocacyPolicy/GovernmentAffairs/Documents/6.13.I6%20FDA-AACR%; 20Dose%20Finding%20for%20Online.pdf]", Presentation slides at FDA-AACR: Oncology Dose-finding Workshop, Jun. 13, 2016, 19 pages.
Liu et al., "Structure of Human Methionine Aminopeptidase-2 Complexed with Fumagillin", Science., 282, 1324-1327, 1998.
Llovet et al., "Plasma biomarkers as predictors of outcome in patients with advanced hepatocellular carcinoma," Clinical Cancer Res, 2012, 18(8):2290-2300.
Llovet et al., ""Sorafenib in Advanced Hepatocellular Carcinoma,"" N. Engl. J. Med., 2008, 359 (4): 378-390.

(56) References Cited

OTHER PUBLICATIONS

Logie et al., "Activating mutations of the tyrosine kinase receptor FGFR3 are associated with benign skin tumors in mice and humans," Human Mol. Genet., 14:1153-1160 (2005).
Longley et al., "Classes of c-KIT activating mutations: proposed mechanisms of action and implications for disease classification and therapy," Leuk. Res., 25:571-576 (2001).
Longley et al., "Somatic c-KIT Activating Mutation in Urticaria Pigmentosa and Aggressive Mastocytosis: Establishment of Clonality in a Human Mast Cell Neoplasm," Nature Genetics, 12:312-314 (1996).
Lu et al., "Tailoring in Vitro Selection for a Picomolar Affinity Human Antibody Directed Against Vascular Endothelial Growth Factor Receptor 2 for Enhanced Neutralizing Activity," J Biol Chem., 2003, 278(44):43496-43507.
Lukacs et al., "Stem Cell Factor (c-kit Ligand) Influences Eosinophil Recruitment and Histamine Levels in Allergic Airway Inflammation," J. Immunol., 156:3945-3951 (1996).
Macedonian Notice of Allowance in Application No. P/2015/231, dated Oct. 13, 2015, 2 pages, with English translation.
Machens et al., "Genotype-Phenotype Correlations in Hereditary Medullary Thyroid Carcinoma:; Oncological Features and Biochemical Properties", Journal of Clinical Endocrinology and; Metabolism, 86(3):1104-1109 (2001).
Response to EP Search Report in EP Application No. 06796594.7, dated Dec. 21, 2011, 43 pages.
Maintenance of the application for EP Application No. 01976786.2, dated Sep. 6, 2004.
Maintenance of the application for EP Application No. 05783232.1, dated Nov. 9, 2007.
Maintenance of the application for EP Application No. 06023078.6, dated Jun. 19, 2007.
Makker, V., et al., "Lenvatinib plus pembrolizumab in patients with advanced endometrial cancer: an interim analysis of a multicentre open-label, single-arm, phase 2 trial," *Lancet Oncol.*, 2019, 20: 711-718.
Marchetti et al., "Clinical Features and Outcome of Patients with Non-Small-Cell Lung Cancer Harboring BRAF Mutations," J Clin Oncol, 29 (26): 3574-3579 (2011).
Marzioni et al., "Clinical Implications of novel aspects of biliary pathophysiology", 20th National Congress of Digestive Diseases/Digestive and Liver Disease, W.B. Saunders, GB, vol. 42, No. 4, Apr. 1, 2010, p. 238-p. 244.
Masferrer et al., "COX-2 Inhibitors A New Class of Antiangiogenic Agents", Annals of N.Y. Acad. Science., 889:84-6, 1999.
Matsui et al., "E7080,a novel multi-targeted tyrosine kinase inhibitor, exhibits anti-angiogenic activity via inhibition of KIT signaling in a small cell lung cancer xenograft model," European Journal of Cancer, Sep. 29, 2004, p. 47.
Matsui et al., "E7080 (ER-203492-00), a Novel VEGF Receptor Tyrosine Kinase Inhibitor-I. Characterization as an Angiogenesis Inhibitor," Abstract # 51, AACR, Washington, USA (Jul. 11-14, 2003).
Matsui et al., "E7080 (ER-203492-00), a Novel VEGF Receptor Tyrosine Kinase Inhibitor-I. Characterization as an Angiogenesis Inhibitor," Abstract # 51, AACR, Toronto, Canada (Apr. 5-9, 2003).
Matsui et al., "E7080, a novel inhibitor that targets multiple kinases, has potent antitumor activities against stem cell factor producing human small cell lung cancer H146, based on angionenesis inhibition," Int. J. Cancer, 122:664-671 (2008).
Matsui et al., "E7080, a novel multi-receptor Tyrosine Kinase Inhibitor, inhibited in vitro / in vivo VEGF- and SCF-driven angiogenesis SCLC cell line," Abstract #146, EORTC-NCI-AACR, Geneva, Switzerland (Sep. 28-Oct. 1, 2004).
Matsui et al., "Mechanism of antitumor activity of E7080, a selective VEGFR and FGFR tyrosine kinase inhibitor (TKI), in combination with selective mutant BRAF inhibition," J Clin Oncol., May 20, 2011, 29(15), Suppl., Asco Meeting Abstracts, Part 1, Abstract No. 8567, 2 pages.
Matsui et al., "Multi-Kinase Inhibitor E7080 Suppresses Lymph Node and Lung Metastases of Human Mammary Breast Tumor MDA-MB-231 via Inhibition of Vascular Endothelial Growth Factor-Receptor (VEGF-R) 2 and VEGF-R3 Kinase," Clin Cancer Res., 2008, 14:5459-5465.
Matsui et al., "Quantitative analysis of the profile of tumor vessels may be useful as predictive biomarkers for E7080," Abstract #4631, 98th AACR annual meeting, Los Angeles, CA, (Apr. 14-18, 2007).
Matsui et al., "VEGFRs inhibitor E7080 inhibits lymph node metastasis of human breast carcinoma, by preventing murine lymphatic endothelial cells from lymphangiogenesis," Abstract #PD12-8, 18th EORTC-NCI-AACR Symposium on "Molecular Targets and Cancer Therapeutics," Prague, Czech Republic (Nov. 7-10, 2006).
Matsui, "Extracellular matrix of linitis plastica as a possible new therapeutic target," Surgical Treatment, Sep. 2003, 89(3):301-306 (with English translation).
Matsuki et al., "Antitumor activity of a combination of lenvatinib mesilate, ifosfamide, and etoposide against human pediatric osteosarcoma cell lines", Abstract 3233, Cancer Research; 107TH Annual Meeting of the American-Association-Of-Cancer-Research (AACR), American Association for Cancer Research, US; New Orleans, LA, USA, vol. 76, No. Suppl. 14, Jun. 30, 2016, p. 3266.
Matsushima et al., "Preparation of pyridine and pyrimidine derivatives as inhibitors of hepatocyte growth factor receptor (HGFR)," Hcaplus, 2005, 977021.
McCarty et al., "ZD6474, a vascular endothelial growth factor receptor tyrosine kinase inhibitor with additional activity against epidermal growth factor receptor tyrosine kinase, inhibits orthotopic growth and angiogenesis of gastric cancer," Mol. Cancer Ther., 3(9):1041-1048 (2004).
McCulloch et al., "Astragalus-based Chinese herbs and platinum-based chemotherapy for advanced non-small-cell lung cancer: meta-analysis of randomized trials," J. Clin. Oncol., 24(3):419-430 (2006).
Meltzer, "The Pharmacological Basis for the Treatment of Perennial Allergic Rhinitis and Non-Allergic Rhinitis with Topical Corticosteroids," Allergy, 52:33-40 (1997).
Mendel et al., "In vivo antitumor activity of SU11248, a novel tyrosine kinase inhibitor targeting vascular endothelial growth factor and platelet-derived growth factor receptors: determination of a pharmacokinetic/pharmacodynamic relationship," Clin. Cancer Res., 9:327-337 (2003).
Metcalfe et al., "Lineage Commitment in the Progeny of Murine Hematopoietic Preprogenitor Cells: Influence of Thrombopoietin and Interleukin 5," Proc. Nat'l Acad. Sci. USA, 95:6408-6412 (1998).
Metcalfe et al., "Mast cells," Physiol. Rev., 77(4):1033-1079 (1997).
Metcalfe, "Classification and Diagnosis of Mastocytosis: Current Status," J. Invest. Dermatol., 96:2S-4S (1991).
Mexican Notice of Allowance in Application No. MX/a/2012/014776, dated Mar. 18, 2015, 3 pages, with English translation.
Mexican Notice of Allowance in Application No. MX/a/2013/009931, dated Jun. 29, 2015, 3 pages, with English translation.
Mexican Office Action in Application No. MX/a/2010/008187, dated Aug. 21, 2013, 6 pages (with English translation).
Mexican Office Action in Application No. MX/a/2013/009931, dated Apr. 9, 2015, 3 pages, with English translation.
Mexican Submission Documents in Application No. MX/a/2014/010594, dated Oct. 8, 2015, 10 pages, with English translation.
Mexican Submission Documents in Application No. MX/a/2014/010594, dated Sep. 24, 2015, 2 pages, with English translation.
Michael et al., "Emergence of potential biomarkers of response to anti-angiogenic anti-tumor agents," Int J Cancer, 127(6):1251-1258, Sep. 1, 2010.
Micke et al., "Characterization of c-kit expression in small cell lung cancer: prognostic and therapeutic implications," Clin. Cancer Res., 9:188-194 (2003).
Miknis et al., "AARY-334543, A potent, orally active small molecule inhibitor of EGFR and ErbB-2," Am. Assoc. Cancer Res. Abstract 3399, 2005, 2 pages.
Miller et al., "Genomic amplification of MET with boundaries within fragile site FRA7G and upregulation of MET pathways in esophageal adenocarcinoma," Oncogene, 2005, 25(3):409-418.

(56) References Cited

OTHER PUBLICATIONS

Miller et al., "Paclitaxel plus bevacizumab versus paclitaxel alone for metastatic breast cancer," N. Engl. J. Med., 357(26):2666-2676 (2007).
Millstein and Cuello, "Hybrid hybridomas and their use in immunohistochemistry", Nature 305:537-9, 1983.
Ministry of Health, Labor and Welfare of Japan, "Strong Mutagenic Chemical Substances," Report No. 166, Dec. 11, 2012. [Partial translation].
Mitchell et al., "The influence of additives on the cloud point, disintegration and dissolution of hydroxypropylmethylcellulose gels and matrix tablets," International journal of pharmaceutics, 1990, vol. 66, No. 1/3, pp. 233-242.
Miyauchi et al., "Two germline missense mutations at codons 804 and 806 of the RET proto-oncogene in the same allele in a patient with multiple endocrine neoplasia type 2B without codon 918 mutation," Japanese journal of cancer research : Gann vol. 90,1 (1999): 1-5.
Miyazaki et al., "Synthesis, Structure and Biological Activity Relationship of E7080 and its Derivatives as Novel and Potent Antiangiogenic Protein Tyrosine Kinase Inhibitors Including the VEGF Receptors, FGFR1 Receptor and PDGF Receptor," AIMECS03, Kyoto, Japan (Oct. 14-17, 2003).
Mizushima, T., "Drug-repositioning," *Bio Industry*, 2014, 31(11): 4-10. [Full Translation].
Mohammadi et al., "Crystal structure of an angiogenesis inhibitor bound to the FGF receptor tyrosine kinase domain", EMBO J., 17, 5896-5904, 1998.
Molina et al., "A phase 1b clinical trial of the multitargeted tyrosine kinase inhibitor lenvatinib (E7080) in combination with everolimus for treatment of metastatic renal cell carcinoma; (RCC)", Cancer Chemotherapy and Pharmacology, 2014.01, vol. 73, No. 1, p. 181-p. 189.
Mologni et al., "Inhibition of RET tyrosine kinase by SU5416," J. Mol. Endocrinol., 37(2):199-212 (2006).
Montalbetti and Falque, "Tetrahedron report No. 740: Amide bond formation and peptide coupling," Tetrahedron, 2005, 61:10827-10852.
Morgan et al., "Dynamic contrast-enhanced magnetic resonance imaging as a biomarker for the pharmacological response of PTK787/ZK 222584, an inhibitor of the vascular endothelial growth factor receptor tyrosine kinases, in patients with advanced colorectal cancer and liver metastases: results from two phase I studies," J. Clin. Oncol., 21(21):3955-3964 (2003).
Morikawa et al., "Angiogenesis and Pericytes," The Cell, 37(4):164-168 (2005) (English translation).
Morris et al., "An Integrated Approach to the Selection of optimal Salt Form for a New Drug Candidate," International Journal of Pharmaceutics, 105:209-217 (1994) (XP023724810).
Mototsugu, "mTOR inhibitors," Nippohn Rinsho, Jun. 2010, 68(6):1067-1072 (with English abstract).
Motzer et al., "Lenvatinib, everolimus, and the combination in patients with metastatic renal cell carcinoma: a randomised, phase 2, open-label, multicentre trial," Lancet Oncol, (2015), 11(16):1473-1482.
Motzer, R., et al., "Independent assessment of lenvatinib plus everolimus in patients with metastatic renal cell carcinoma," *Lancet Oncol.*, 2016, 17(1): e4-e5.
Myers et al., "The Preparation and SAR of 4-(Anilino), 4-(Phenoxy), and 4-(Thiophenoxy)-Quinazolines: Inhibitors of p56lck and EGF-R Tyrosine Kinase Activity," Bioorgan. & Med. Chem. Letters, 7:417-420 (1997).
Naclerio et al., "Rhinitis and Inhalant Allergens," JAMA, 278(22):1842-1848 (1997).
Nagata et al., "Elevated Expression of the Proto-Oncogene c-kit in Patients with Mastocytosis," Leukemia, 12:175-181 (1998).
Nakagawa et al., "E7050: A dual c-Met and VEGFR-2 tyrosine kinase inhibitor promotes tumor regression and prolongs survival in mouse xengraft models," Cancer Sci., 101(1):210-215 (2010).
Nakagawa et al., "Lenvatinib in combination with golvatinib overcomes hepatocyte growth factor pathway-induced resistance to vascular endothelial growth factor receptor inhibitor", Cancer Science, vol. 105, No. 6, p. 723-p. 730 (2014).
Nakamura et al., "E7080 (ER-203492-00), a Novel VEGF Receptor Tyrosine Kinase Inhibitor-II. Effects on Growth of Human Tumor Xenografts and Life Span of Mice in Colon 38 Orthotopic Transplantation Model," Abstract #52, AACR, Toronto, Canada (Apr. 5-9, 2003).
Nakamura et al., "In Vitro selectivity and potency of KRN951, a novel inhibitor of VEGF receptor tyrosine kinases", Cancer Research, cited Jul. 13, 2016, 2 pages.
Nakamura et al., "In vitro selectivity and potency of KRN951, a novel inhibitor of VEGF receptor tyrosine kinases," Proceedings of the American Association for Cancer Research, 45, 594, (Abstract 2571), 2004, 1 page.
Nakamura et al., "KRN633: A Selective inhibitor of vascular endothelial growth factor receptor-2; tyrosine kinase that suppresses tumor angiogenesis and growth", Molecular Cancer Therapeutics., 2004, 3:1639-49.
Nakanishi et al., "Overexpression of B7-H1 (PD-L1) significantly associates with tumor grade and ostoperative prognosis in human urothelial cancers," Cancer Immunol. Immunother. (2007) 56: 1173-1182.
Nakanishi, "Molecular diversity of glutamate receptors and implications for brain function," Science, 1992, pp. 597-603.
Nakata et al., "Fusion of a Novel Gene, ELKS, to RET Due to Translocation t(1 0; 12) (q11; p13) in; a Papillary Thyroid Carcinoma", Genes Chromosomes Cancer, 25: 97-103 (1999).
Nakazawa et al., "Maximizing the efficacy of anti-angiogenesis cancer therapy: A multi-targeting strategy by tyrosine kinase inhibitors," AACR Annual Meeting 2014, Presentation Abstract and Poster, Apr. 5-9, 2014, 2 pages.
Nakazawa et al., "Multitargeting strategy using lenvatinib and golvatinib: Maximizing anti-angiogenesis activity in a preclinical cancer model", Cancer Science, 2015.02, vol. 106, No. 2, p. 201-p. 207.
Nakazawa, "Combination strategy of lenvatinib: Maximizing its anti-angiogenesis efficacy," Tsukuba Res Laboratory, Eisai Co., Ltd., Ibaraki, Japan, Jun. 27, 2014, 10 pages.
Naran eta l., "Inhibition of HGF/MET as therapy for malignancy," Expert Opin. Ther. Targets, 2009, p. 569-581.
Naruse et al., "Antitumor activity of the selective epidermal growth factor receptor-tyrosine kinase inhibitor (EGFR-TKI) Iressa (ZD1839) in an EGFR-expressing multidrug-resistant cell line in vitro and in vivo," Int. J. Cancer, 98:310-315 (2002).
Naski et al., "Graded activation of fibroblast growth factor receptor 3 by mutations causing achondroplasia and thanatophoric dysplasia," Nat. Genet., 13:233-237 (1996).
Natali et al., "Breast Cancer is Associated with Loss of the c-kit Oncogene Product," Int. J. Cancer, 52:713-717 (1992).
NCBI GenBank Accession No. NM_000222, Coffey et al. (Feb. 11, 2008).
Neidle, "Cancer Drug Design and Discovery" Elsevier/Academic Press, 2008, pp. 427-431.
Nicolaus, "Symbiotic Approach to Drug Design," Decision Making Drug Res., Jan. 1983, 173-186.
Nishikawa et al., "Cys611Ser mutation in RET proto-oncogene in a kindred with medullary thryroid; carcinoma and Hirschsprung's disease", European Journal of Human Genetics, 11, 364-368 (2003).
Nishio et al., "Phase 1 study of lenvatinib combined with carboplatin and paclitaxel in patients with non-small-cell lung cancer", British Journal of Cancer, 2013, 109:538-544.
Nocka et al., "Expression of c-kit gene products in known cellular targets of W mutations in normal and W mutant mice—evidence for an impaired c-kit kinase in mutant mice," Cold Spring Harbor Laboratory Press, 3:816-826 (1989) (XP002522472).
Nomi et al., "Clinical significance and therapeutic potential of the programmed death-1 ligand/programmed death-1 pathway in human pancreatic cancer," *Clinical Cancer Research* (2007): 13: 2151-2157.
Noriyuki et al., "Anti-tumor effect of E7080, a novel angiogenesis inhibitor," Database BIOSIS [Online] Biosciences Information Ser-

(56) References Cited

OTHER PUBLICATIONS vice, Philadelphia, PA, US: Database accession No. PREV200800475929, Aug. 2008, XP002677323.
Notice of Acceptance dated Aug. 10, 2004 for South African Patent App. No. 2003/3567.
Notice of Acceptance dated Aug. 3, 2006 for Australian Application No. 2001295986.
Notice of Acceptance dated Jun. 10, 2020, in Australian Patent Application No. 2014266223.
Notice of Acceptance dated May 13, 2008 for Australian Application No. 2006236039.
Notice of Acceptance for Australian Application No. 2009210098, dated Jun. 4, 2013, 3 pages.
Notice of Acceptance in Australian Application No. 2005217325, dated Nov. 20, 2007, 3 pages.
Notice of Acceptance in Australian Application No. 2005217328, dated Sep. 24, 2007, 3 pages.
Notice of Acceptance in Australian Application No. 2006282456, dated Aug. 17, 2009, 1 page.
Notice of Acceptance in Australian Application No. 2007288793, dated Apr. 10, 2012, 3 pages.
Notice of Acceptance in Australian Application No. 2007289787, dated Mar. 16, 2012, 3 pages.
Notice of Acceptance in DB Application No. 60/2005, dated Nov. 16, 2006, 1 page.
Notice of Acceptance in New Zealand Application No. 547517, dated Mar. 6, 2009, 1 page.
Notice of Acceptance in New Zealand Application No. 566793, dated Feb. 12, 2010, 2 pages.
Notice of Acceptance issued Mar. 31, 2020, in Australian Patent Application No. 2015309862.
Notice of Acceptance issued May 21, 2020, in New Zealand Patent Application No. 714049.
Notice of Acceptance of Complete Specification dated Mar. 4, 2005 for NZ Application No. 525324.
Notice of Allowability dated Nov. 28, 2007 for Philippines Application No. 1-2003-500266.
Notice of Allowability in Philippines Application No. 1-2007-502319, dated Feb. 29, 2012, 1 page.
Notice of Allowance dated Oct. 18, 2018 in Chilean Appl. No. CL2012-00412.
Notice of Allowance dated Apr. 1, 2019 in U.S. Appl. No. 15/750,712.
Notice of Allowance dated Apr. 19, 2005 for Russian Application No. 2003114740 (with English translation).
Notice of Allowance dated Apr. 19, 2011 for Japanese Application No. 2007-522356.
Notice of Allowance dated Apr. 24, 2012 for U.S. Appl. No. 12/524,754.
Notice of Allowance dated Apr. 29, 2010 for Australia Application No. 2005283422.
Notice of Allowance dated Aug. 2, 2005 for Japanese Application No. 2002-536056 (with English translation).
Notice of Allowance dated Aug. 7, 2012 for Japanese Application No. P2007-529565 (with English translation).
Notice of Allowance dated Dec. 15, 2006 for Chinese Application No. 01819710.8.
Notice of Allowance dated Dec. 26, 2007 for Israeli Application No. 155447 (with English translation).
Notice of Allowance dated Feb. 15, 2013 for New Zealand Application No. 598291, 1 page.
Notice of Allowance dated Feb. 27, 2009 for U.S. Appl. No. 11/293,785.
Notice of Allowance dated Feb. 5, 2010 for Chinese Application No. 200580026468.7 (with English translation).
Notice of Allowance dated Jul. 17, 2012 for Japanese Application No. P2011-527665 (with English translation).
Notice of Allowance dated Jul. 21, 2009 for Japanese Application No. 2005-124034 (with English translation).
Notice of Allowance dated Jul. 24, 2019, in Mexican Patent Application No. MX/a/2015/015605.
Notice of Allowance dated Jun. 20, 2012 for European Application No. 06782407.8.
Notice of Allowance dated Jun. 25, 2012 for European Application No. 07806561.2.
Notice of Allowance dated Jun. 3, 2008 for U.S. Appl. No. 11/293,785.
Notice of Allowance dated Mar. 14, 2010 for Israeli Application No. 189677 (with English translation).
Notice of Allowance dated Mar. 16, 2007 for U.S. Appl. No. 10/420,466.
Notice of Allowance dated Mar. 21, 2013 for European Application No. 07793075.8, 2 pages.
Notice of Allowance dated Mar. 22, 2012 for U.S. Appl. No. 12/986,638.
Notice of Allowance dated Mar. 8, 2013 for Canadian Application No. 2627598, 1 page.
Notice of Allowance dated May 16, 2013 for European Application No. 06796594.7, 2 pages.
Notice of Allowance dated May 18, 2009 for U.S. Appl. No. 11/293,785.
Notice of Allowance dated May 6, 2013 for European Application No. 04818213.3, 22 pages.
Notice of Allowance dated Nov. 14, 2011 for Israeli Application No. 181697 (with English translation).
Notice of Allowance dated Nov. 19, 2008 for U.S. Appl. No. 11/293,785.
Notice of Allowance dated Nov. 2, 2012 for European Application No. 06782407.8.
Notice of Allowance dated Nov. 2, 2012 for European Application No. 07806561.2.
Notice of Allowance dated Oct. 14, 2010 for Canadian Application No. 2426461.
Notice of Allowance dated Oct. 17, 2011 for Canadian Application No. 2579810.
Notice of Allowance dated Oct. 18, 2006 for Mexican Application No. PA/a/2003/003362 (with English translation).
Notice of Allowance dated Oct. 20, 2008 for Taiwanese Application No. 90125928 (with English translation).
Notice of Allowance dated Oct. 21, 2019, in Pakistan Patent Application No. 94/2011.
Notice of Allowance dated Oct. 21, 2020, in U.S. Appl. No. 16/465,277.
Notice of Allowance dated Oct. 31, 2008 for Norwegian Application No. 20031731 (with English translation).
Notice of Allowance dated Oct. 9, 2010 for Chinese Application No. 200710007097.9 (with English translation).
Notice of Allowance dated Oct. 9, 2012 for U.S. Appl. No. 12/524,754.
Notice of Allowance dated Jun. 13, 2006 for U.S. Appl. No. 10/420,466.
Notice of Allowance dated Sep. 20, 2011 for Japanese Application No. 2006-535174.
Notice of Allowance dated Sep. 25, 2012 for U.S. Appl. No. 12/986,638.
Notice of Allowance dated Sep. 4, 2012 in Japanese Application No. P2009-123432 (with English translation).
Notice of Allowance dispatched Jun. 9, 2020, in Brazilian Patent Application No. BR112012003592-4.
Notice of Allowance for Chinese Application No. 200980103218.7, dated May 27, 2013, 4 pages (with English translation).
Notice of Allowance for Japanese Application No. 2008-516724, dated Jan. 22, 2013, 4 pages, with English translation.
Notice of Allowance for U.S. Appl. No. 12/524,754, dated Jan. 18, 2013, 9 pages.
Notice of Allowance for U.S. Appl. No. 12/741,682, dated Feb. 19, 2013, 24 pages.
Notice of Allowance for U.S. Appl. No. 12/741,682, dated Jun. 19, 2013, 10 pages.
Notice of Allowance for U.S. Appl. No. 11/997,719, dated Sep. 13, 2013, 20 pages.
Notice of Allowance for U.S. Appl. No. 13/083,338, dated Sep. 26, 2013, 15 pages.
Notice of Allowance for U.S. Appl. No. 13/205,328, dated Oct. 3, 2013, 11 pages.

(56) References Cited

OTHER PUBLICATIONS

Notice of Allowance in Australian Application No. 2010285740, dated Nov. 19, 2014, 1 page.
Notice of Allowance in Australian Patent Application No. 2012246490, dated Jul. 25, 2016, 3 pages.
Notice of Allowance in Canadian Application No. 2605854, dated Apr. 7, 2010, 1 page.
Notice of Allowance in Canadian Application No. 2652442, dated Apr. 16, 2014, 1 page.
Notice of Allowance in Canadian Application No. 2661333, dated Dec. 19, 2013, 1 page.
Notice of Allowance in Canadian Application No. 2661702, dated Sep. 26, 2013, 1 page.
Notice of Allowance in Canadian Application No. 2771403, dated Oct. 22, 2014, 1 page.
Notice of Allowance in Canadian Patent Application No. 2704000, dated Jul. 7, 2016, 1 page.
Notice of Allowance in Canadian Patent Application No. 2802644, dated Aug. 5, 2016, 1 page.
Notice of Allowance in Canadian Patent Application No. 2828946, dated Feb. 22, 2016, 1 page.
Notice of Allowance in Chinese Patent Application No. 201480026871.9, dated Jun. 28, 2017, 8 pages (English Translation).
Notice of Allowance in Chinese Application No. 200680021939.X, dated Jan. 11, 2012, 4 pages (with English translation).
Notice of Allowance in Chinese Application No. 200780019200.X, dated Jan. 15, 2013, 4 pages (with English translation).
Notice of Allowance in Chinese Application No. 200780019520.5, dated Apr. 27, 2011, 4 pages (with English translation).
Notice of Allowance in Chinese Application No. 201180030568.2, dated Sep. 9, 2014, 4 pages (with English translation).
Notice of Allowance in European Application No. 04807580.8, dated Dec. 15, 2014, 103 pages.
Notice of Allowance in European Application No. 04818213.3, dated Sep. 19, 2013, 2 pages.
Notice of Allowance in European Application No. 07743994.1, dated May 8, 2015, 51 pages.
Notice of Allowance in European Application No. 08704376.6, dated Aug. 19, 2014, 62 pages.
Notice of Allowance in European Application No. 08846814.5, dated Jan. 8, 2015, 36 pages.
Notice of Allowance in European Patent Application No. 12786619.2, dated Sep. 30, 2016, 155 pages.
Notice of Allowance in European Patent Application No. 12793322.4, dated Feb. 14, 2018, 82 pages.
Notice of Allowance in European Patent Application No. 12793322.4, dated Jun. 4, 2018, 7 pages.
Notice of Allowance in European Patent Application No. 14727633.1, dated Feb. 9, 2018, 72 pages.
Notice of Allowance in Indonesian App. Ser No. W-00 2008 00601, dated Oct. 17, 2012, 12 pages (with English translation).
Notice of Allowance in Israeli Application No. 195282, dated Aug. 11, 2014, 5 pages (with English translation).
Notice of Allowance in Israeli Application No. 197141, dated Oct. 27, 2013, 2 pages (with English translation).
Notice of Allowance in Israeli Application No. 200090, dated Nov. 18, 2013, 5 pages (with English translation).
Notice of Allowance in Israeli Application No. 207089, dated Nov. 10, 2014, 5 pages (with English translation).
Notice of Allowance in Indonesian Patent Application No. W-00201201031, dated Dec. 28, 2016, 5 pages (English Translation).
Notice of Allowance in Israeli Patent Application No. 217197, dated Jun. 26, 2016, 3 pages, (English translation).
Notice of Allowance in Israeli Patent Application No. 223695, dated Apr. 4, 2017, 3 pages (English Translation).
Notice of Allowance in Israeli Patent Application No. 227558, dated May 8, 2017, 6 pages (English Translation).
Notice of Allowance in Israeli Patent Application No. 242519, dated Dec. 13, 2017, 6 pages (English Translation).

Notice of Allowance in Japanese Patent Application No. P2012-521531, dated Mar. 1, 2016, 6 pages (English Translation).
Notice of Allowance in Japanese Patent Application No. P2013-515178, dated May 17, 2016, 6 pages (English Translation).
Notice of Allowance in Japanese Patent Application No. P2014-513691, dated Oct. 4, 2016, 6 pages (English Translation).
Notice of Allowance in Japanese Patent Application No. P2015-555882, dated Sep. 4, 2018, 6 pages (English Translation).
Notice of Allowance in Japanese Patent Application No. P2016-214593, dated Sep. 4, 2018, 6 pages (English Translation).
Notice of Allowance in Jordan Patent Application No. 55/2011, dated Apr. 16, 2017, 2 pages (English Translation).
Notice of Allowance in Japanese Application No. P2009-540099, dated Oct. 21, 2014, 6 pages (with English translation).
Notice of Allowance in Japanese Application No. P2009-551518, dated Oct. 22, 2013, 5 pages (with English translation).
Notice of Allowance in Korean Patent Application No. 10-2012-7033886, dated Oct. 18, 2016, 3 pages (English Translation).
Notice of Allowance in Korean Patent Application No. 10-2013-7020616, dated Jun. 29, 2017, 3 pages (English Translation).
Notice of Allowance in Korean Application No. 10-2006-7013907, dated Jan. 14, 2008, 3 pages (with English translation).
Notice of Allowance in Korean Application No. 10-2006-7013940, dated Jan. 14, 2008, 3 pages (with English translation).
Notice of Allowance in Korean Application No. 10-2008-7013685, dated Nov. 29, 2013, 3 pages (with English translation).
Notice of Allowance in Korean Application No. 10-2008-7027527, dated Mar. 3, 2014, 4 pages (with English translation).
Notice of Allowance in Korean Application No. 10-2008-7029472, dated Sep. 16, 2014, 3 pages (with English translation).
Notice of Allowance in Korean Application No. 10-2009-7005657, dated Sep. 19, 2014, 3 pages (with English translation).
Notice of Allowance in Korean Application No. 10-2009-7017694, dated Jul. 28, 2014, 3 pages (with English translation).
Notice of Allowance in Korean Application No. 10-2010-7018835, dated Jan. 20, 2015, 3 pages (with English translation).
Notice of Allowance in Korean Application No. 10-2012-7003846, dated Feb. 3, 2015, 3 pages.
Notice of Allowance in Mexican Patent Application No. MX/a/2014/010594, dated Nov. 17, 2016, 3 pages (English Translation).
Notice of Allowance in Mexican Application No. MX/a/2008/002156, dated Oct. 15, 2010, 3 pages (with English translation).
Notice of Allowance in Mexican Application No. MX/a/2010/008187, dated Jul. 17, 2014, 3 pages (with English translation).
Notice of Allowance in Malaysian Application No. PI20071922, dated Jan. 15, 2010, 3 pages.
Notice of Allowance in Pakistan Application No. 1024/2006, dated Nov. 2, 2010, 1 page.
Notice of Allowance in Pakistan Application No. 375/2008, dated Nov. 2, 2010, 1 page.
Notice of Allowance in Russian Application No. 2006134254, dated Jan. 14, 2008, 30 pages (with English translation).
Notice of Allowance in Russian Application No. 2012103471, dated Dec. 19, 2014, 12 pages (with English translation).
Notice of Allowance in Russian Patent Application No. 2015148193, dated Apr. 23, 2018, 15 pages (English Translation).
Notice of Allowance in Singapore Patent Application No. 11201509278X, dated Nov. 22, 2017, 5 pages (English Translation).
Notice of Allowance in Taiwanese Application No. 095130665, dated Sep. 7, 2012, 4 pages (with English translation).
Notice of Allowance in U.S. Appl. No. 10/797,903, dated Mar. 10, 2011, 22 pages.
Notice of Allowance in U.S. Appl. No. 13/870,507, dated Jul. 26, 2016, 13 pages.
Notice of Allowance in UA Application No. a201203132, dated Mar. 21, 2014, 6 pages.
Notice of Allowance in U.S. Appl. No. 11/997,719, dated Dec. 2, 2014, 21 pages.
Notice of Allowance in U.S. Appl. No. 11/997,719, dated Jun. 5, 2014, 14 pages.
Notice of Allowance in U.S. Appl. No. 12/031,568, dated Jun. 1, 2012, 23 pages.

(56) References Cited

OTHER PUBLICATIONS

Notice of Allowance in U.S. Appl. No. 12/031,568, dated Oct. 19, 2011, 11 pages.
Notice of Allowance in U.S. Appl. No. 12/031,568, dated Sep. 18, 2012, 6 pages.
Notice of Allowance in U.S. Appl. No. 12/315,291, dated Apr. 26, 2011, 6 pages.
Notice of Allowance in U.S. Appl. No. 12/439,339, dated Apr. 1, 2014, 16 pages.
Notice of Allowance in U.S. Appl. No. 12/439,339, dated Nov. 7, 2013, 64 pages.
Notice of Allowance in U.S. Appl. No. 12/524,754, dated Feb. 13, 2014, 18 pages.
Notice of Allowance in U.S. Appl. No. 12/524,754, dated Nov. 22, 2013, 12 pages.
Notice of Allowance in U.S. Appl. No. 12/524,754, dated Sep. 18, 2014, 34 pages.
Notice of Allowance in U.S. Appl. No. 12/558,982, dated Apr. 3, 2012, 11 pages.
Notice of Allowance in U.S. Appl. No. 12/558,982, dated May 25, 2012, 20 pages.
Notice of Allowance in U.S. Appl. No. 12/741,682, dated Feb. 7, 2014, 11 pages.
Notice of Allowance in U.S. Appl. No. 12/741,682, dated May 15, 2014, 11 pages.
Notice of Allowance in U.S. Appl. No. 12/741,682, dated Oct. 21, 2013, 12 pages.
Notice of Allowance in U.S. Appl. No. 12/741,682, dated Oct. 6, 2014, 11 pages.
Notice of Allowance in U.S. Appl. No. 13/083,338, dated Dec. 5, 2014, 19 pages.
Notice of Allowance in U.S. Appl. No. 13/083,338, dated Feb. 6, 2014, 15 pages.
Notice of Allowance in U.S. Appl. No. 13/083,338, dated Jul. 10, 2014, 22 pages.
Notice of Allowance in U.S. Appl. No. 13/205,328, dated Jan. 30, 2014, 11 pages.
Notice of Allowance in U.S. Appl. No. 13/205,328, dated May 8, 2014, 10 pages.
Notice of Allowance in U.S. Appl. No. 13/624,278, dated Jun. 25, 2014, 57 pages.
Notice of Allowance in U.S. Appl. No. 13/624,278, dated Oct. 31, 2014, 14 pages.
Notice of Allowance in U.S. Appl. No. 13/624,278, dated Sep. 16, 2013, 20 pages.
Notice of Allowance in U.S. Appl. No. 13/805,826, dated Dec. 17, 2014, 5 pages.
Notice of Allowance in U.S. Appl. No. 13/983,891, dated Mar. 20, 2014, 9 pages.
Notice of Allowance in U.S. Appl. No. 14/002,018, dated Oct. 24, 2014, 70 pages.
Notice of Allowance in U.S. Appl. No. 14/122,339, dated Dec. 21, 2017, 8 pages.
Notice of Allowance in Vietnamese Application No. 1-2008-00723, dated Aug. 19, 2010, 2 pages (with English translation).
Notice of Allowance in Vietnamese Application No. 1-2011-03484, dated Apr. 28, 2014, 2 pages.
Notice of Allowance in South African Application No. 2007/09572, dated Mar. 12, 2009, 1 page.
Notice of Allowance issued in Chinese Application No. 201080030508.6, dated Jul. 4, 2013, 4 pages (with English translation).
Notice of Allowance issued in European Application No. 10015141.4, dated Jul. 1, 2013, 41 pages.
Notice of Allowance issued in Israeli Application No. 175363, dated Aug. 13, 2013, 2 pages (with English translation).
Notice of Allowance issued in Japanese Application No. P2008-556208, dated Jul. 9, 2013, 4 pages (with English translation).
Notice of Allowance issued Jul. 21, 2020, in Israeli Patent Application No. 257433.
Notice of Allowance issued Jul. 22, 2020, in U.S. Appl. No. 15/750,712.
Notice of Allowance issued Jun. 16, 2020, in U.S. Appl. No. 16/559,293.
Notice of Allowance issued Jun. 25, 2020, in U.S. Appl. No. 16/465,277.
Notice of Allowance issued Jun. 30, 2020, in U.S. Appl. No. 16/038,710.
Notice of Allowance mailed Aug. 28, 2019, in U.S. Appl. No. 14/890,207.
Notice of Allowance mailed Jul. 8, 2019, in U.S. Appl. No. 15/750,712.
Notice of Allowance mailed Jun. 24, 2019, in U.S. Appl. No. 16/229,805.
Notice of Allowance mailed Oct. 22, 2019, in U.S. Appl. No. 15/750,712.
Notice of Appeal and Pre-Appeal Brief Request for Review filed Sep. 5, 2019, in U.S. Appl. No. 13/923,858.
Notice of Appeal filed Aug. 5, 2019, in U.S. Appl. No. 15/460,629.
Notice of Appeal in European Patent Application No. 08846814.5, dated Jul. 5, 2017, 3 pages.
Notice of Appeal in U.S. Appl. No. 11/662,425, dated Sep. 5, 2014, 11 pages.
Notice of Appeal in U.S. Appl. No. 12/039,381, dated Aug. 29, 2014, 9 pages.
Notice of decision for patent dated Jun. 12, 2006 for Korean Application No. 10-2003-7005506 (with English translation).
Notice of Final Rejection in Korean Application No. 10-2009-7013723, dated Jul. 29, 2011, 4 pages (with English translation).
Notice of Final Rejection mailed Dec. 26, 2019, in Korean Patent Application No. 10-2015- 7009430.
Notice of Grant in Korean Application No. 10-2007-7026886, dated Dec. 31, 2009, 5 pages (with English translation).
Notice of Non-Substantive Deficiencies Prior to Allowance in Israeli Application No. 197141, dated Feb. 3, 2013, 16 pages (with English translation).
Notice of Panel Decision from Pre-Appeal Brief Review issued Oct. 28, 2019, in U.S. Appl. No. 13/923,858.
Notice of Reasons for Rejection dispatched Aug. 20, 2019, in Japanese Patent Application No. 2016-545564.
Notice of Reasons for Rejection dispatched Dec. 17, 2019, in Japanese Patent Application No. 2017-502388.
Notice of Reasons for Rejection dispatched Jan. 7, 2020, in Japanese Patent Application No. 2017-546075.
Notice of Reasons for Rejection dispatched Jul. 21, 2020, in Japanese Patent Application No. 2017-546075.
Notice of Reasons for Rejection dispatched Jun. 16, 2020, in Japanese Patent Application No. 2017-535551.
Notice of Reasons for Rejection dispatched Jun. 2, 2020, in Japanese Patent Application No. 2017-502388.
Notice of Reasons for Rejection dispatched Mar. 10, 2020, in Japanese Patent Application No. 2017-546133.
Notice of Reasons for Rejection dispatched Mar. 10, 2020, in Japanese Patent Application No. 2017-560343.
Notice of Reasons for Rejection issued in Japanese Application No. P2009-540099, dated Jul. 2, 2013, 7 pages (with English translation).
Notice of Reasons for Rejection mailed on Nov. 13, 2012 issued for corresponding Japanese Application No. 2007-533350 with full English language translation.
Notice Prior to Allowance in Israeli Application No. 188670, dated Sep. 12, 2011, 2 pages (with English translation).
Notice Prior to Allowance in Israeli Application No. 197002, dated Oct. 28, 2012, 2 pages (with English translation).
Notice Prior to Examination dated Jun. 29, 2008 for Israeli Application No. 189677 (with English translation).
Notice Prior to Examination dated Mar. 9, 2009 for Israeli Application No. 181697 (with English translation).
Notice Prior to Examination in Israeli Application No. 188670, dated Aug. 13, 2009, 3 pages (with English translation).
Notice Prior to Examination in Israeli Application No. 197002, dated Mar. 23, 2010, 3 pages (with English translation).

(56) References Cited

OTHER PUBLICATIONS

Notice Prior to Examination in Israeli Application No. 197141, dated Mar. 23, 2010, 3 pages (with English translation).
Notice Prior to Examination in Israeli Application No. 200466, dated Jun. 22, 2010, 3 pages (with English translation).
Notice re Appeal dated Jul. 15, 2019, in Indian Patent Application No. 6415/CHENP/2008.
Notices of Opposition dated Jul. 31, 2019, in Indian Patent Application No. 1511/CHENP/2009.
Notification dated Apr. 25, 2008 for Philippines Application No. 1-2003-500266.
Notification of Consent dispatched May 26, 2020, in Brazilian Patent Application No. BR112013021941-6.
Notification of Defects for Israeli Application No. 195282, dated Apr. 10, 2013, 4 pages (with English Translation).
Notification of Non-Compliant Amendment filed on Jan. 13, 2005 for U.S. Appl. No. 10/420,466.
Notification of the First Office Action issued Apr. 17, 2020, in Chinese Patent Application No. 201780020786.5.
Notification of the First Office Action issued Dec. 18, 2019, in Chinese Patent Application No. 201680009824.2.
Notification of the First Office Action issued Mar. 12, 2020, in Chinese Patent Application No. 201680044979.X.
Notification of the First Office Action issued Mar. 23, 2020, in Chinese Patent Application No. 201680046598.5.
Notification of the Fourth Office Action issued Sep. 27, 2020, in Chinese Patent Application No. 201680027234.2.
Notification of the Second Office Action dispatched Jun. 19, 2019, in Chinese Patent Application No. 201680027234.2.
Notification of the Second Office Action dispatched Jun. 3, 2020, in Chinese Patent Application No. 201680009824.2.
Notification of the Second Office Action issued Aug. 14, 2020, in Chinese Patent Application No. 201680046598.5.
Notification of the Second Office Action issued Feb. 21, 2020, in Chinese Patent Application No. 201580042365.3.
Notification of the Second Office Action issued Oct. 13, 2020, in Chinese Patent Application No. 201680044979.X.
Notification of the Third Office Action issued Feb. 19, 2020, in Chinese Patent Application No. 201680027234.2.
Notification of the Third Office Action issued Sep. 27, 2020, in Chinese Patent Application No. 201680009824.2.
Noy et al., "Tumor-Associated Macrophages: From Mechanisms to Therapy," Immunity 41: 49-61 (2014).
Nugiel et al., "Synthesis and evaluation of indenopyrazoles as cyclin-dependent kinase inhibitors. 2. Probing the indeno ring substituent pattern," J. Med. Chem., 45(24):5224-5232 (2002).
Nyati et al., "Radiosensitization by Pan ErbB Inhibitor CI-1033 in Vitro and in Vivo", Clinical Cancer Research., 10:691-700, 2004.
Observation for Chinese Application No. 200880115011.7, dated Apr. 11, 2013, 10 pages (with English translation).
Observation in the Reexamination and Invalidation Procedures issued Apr. 30, 2019 in Chinese Patent Application No. 2015100316282.
Observations for Chinese Application No. 201080030508.6, dated May 27, 2013, 7 pages (with English translation).
Ocqueteau et al., Expression of the CD117 antigen (C-Kit) on normal and myelomatous plasma cells, Br. J. Haematol., 95:489-493 (1996).
Office Action dated Mar. 5, 2019 in Chinese Appl. No. 201580042365.3.
Office Action dated Apr. 16, 2019 in Indian Appl. No. 10502/CHENP/P2012.
Office Action dated May 13, 2005 for Chinese Application No. 01819710.8 (with English translation).
Office Action dated May 16, 2008 for Norwegian Application No. 20031731 (with English translation).
Office Action dated May 3, 2013 for Canadian Application No. 2661702, 2 pages.
Office Action dated Nov. 13, 2012 for Japanese Application No. P2008-532141 (with English translation).
Office Action dated Nov. 20, 2009 for Chinese Application No. 200580026468.7 (with English translation).
Office Action dated Nov. 26, 2007 for Mexican Application No. PA/a/2005/013764 (with English translation).
Office Action dated Oct. 11, 2007 for Taiwanese Application No. 90125928 (with English translation).
Office Action dated Oct. 15, 2012 for Israeli Application No. 200090 (with English translation).
Office Action dated Oct. 15, 2012 for New Zealand Application No. 598291.
Office Action dated Oct. 4, 2005 for Mexican Application No. PA/a/2003/003362 (with English translation).
Office Action dated Oct. 4, 2007 for Norwegian Application No. 20031731 (with English translation).
Office Action dated Sep. 11, 2009 for Chinese Application No. 200710007097.9 (with English translation).
Office Action dated Sep. 19, 2012 for Canadian Application No. 2627598.
Office Action dated Sep. 28, 2011 for Korean Application No. 10-2007-7001347 (with English translation).
Office Action dated Sep. 28, 2012 for Chinese Application No. 200780017371.9 (with English translation).
Office Action dated Sep. 29, 2012 for Chinese Application No. 200980103218.7 (with English translation).
Office Action dated Sep. 5, 2008 for Norwegian Application No. 20031731 (with English translation).
Office Action dated Sep. 5, 2012 for Chinese Application No. 200880003336.6 (with English translation).
Office Action dated Sep. 5, 2012 for Chinese Application No. 200880115011.7 (with English translation).
Office Action dated Sep. 7, 2007 for Filipino Application No. 1-2003-500266.
Office Action dispatched Aug. 11, 2020, in Mexican Patent Application No. MX/a/2017/010474.
Office Action dispatched Jul. 23, 2020, in Mexican Patent Application No. MX/a/2018/001439.
Office Action dispatched Oct. 23, 2019, in Egyptian Patent Application No. 2012020283.
Office Action dispatched Sep. 3, 2020, in Mexican Patent Application No. MX/a/2019/006504.
Office Action for Canadian Application No. 2,620,594, dated Aug. 15, 2011.
Office Action for Canadian Application No. 2579810 dated Jul. 15, 2011.
Office Action for Canadian Application No. 2652442, dated Apr. 16, 2013 2 pages.
Office Action for Chinese Application No. 01819710.8 dated Feb. 10, 2006 (with English translation).
Office Action for Chinese Application No. 01819710.8, dated Aug. 11, 2006 (with English translation).
Office Action for Chinese Application No. 200580026468.7 dated Jun. 26, 2009 (with English translation).
Office Action for Chinese Application No. 200680020317.5, dated Aug. 3, 2012 (with English translation).
Office Action for Chinese Application No. 200710007096.4 dated Jul. 24, 2009 (with English translation).
Office Action for Chinese Application No. 200710007097.9 dated Apr. 27, 2010 (with English translation).
Office Action for Chinese Application No. 200710007097.9 dated Dec. 25, 2009 (with English translation).
Office Action for Chinese Application No. 200710007097.9 dated Mar. 6, 2009 (with English translation).
Office Action for Chinese Application No. 200780017371.9, dated Mar. 14, 2013 9 pages (with English translation).
Office Action for Chinese Application No. 201080030508.6, dated Apr. 9, 2013, 6 pages (with English translation).
Office Action for European Application No. 08846814.5, dated Apr. 16, 2013, 5 pages.
Office Action for Filipino Application No. 1-2003-500266 dated Aug. 8, 2003.
Office Action for Filipino Application No. 1-2003-500266 dated Jul. 21, 2006.

(56) References Cited

OTHER PUBLICATIONS

Office Action for Filipino Application No. 1-2003-500266 dated Jun. 27, 2007.
Office Action for Filipino Application No. 1-2003-500266 dated Mar. 21, 2007.
Office Action for IL 199907 issued on Jun. 17, 2010, 3 pages with English translation.
Office Action for Israeli Application No. 181697 dated Dec. 20, 2010 (with English translation).
Office Action for Israeli Application No. 217197, dated Apr. 11, 2013 4 pages (with English translation).
Office Action for Japanese Application No. 2005-124034 dated Apr. 28, 2009 (with English translation).
Office Action for Japanese Application No. 2005-124034 dated Jan. 27, 2009 (with English translation).
Office Action for Japanese Application No. 2009-123432 dated Jun. 5, 2012 (with English translation).
Office Action for Korean Application No. 10-2003-7005506 dated Jul. 27, 2005 (with English translation).
Office Action for Mexican Application No. PA/a/2003/003362 dated Jun. 7, 2006 (with English translation).
Office Action for Norwegian Application No. 20031731 dated Mar. 7, 2007 (with English translation).
Office Action for U.S. Appl. No. 11/997,719, dated Apr. 8, 2013 55 pages.
Office Action for U.S. Appl. No. 13/624,278, dated Mar. 29, 2013 8 pages.
Office Action in Algerian Patent Application No. 120036, dated Dec. 31, 2017, 2 pages (English Translation).
Office Action in Australian Application No. 2006282456, dated Jun. 12, 2009, 1 page.
Office Action in Australian Application No. 2010285740, dated Aug. 22, 2014, 3 pages.
Office Action in Australian Patent Application No. 2012246490, dated Apr. 20, 2016, 3 pages.
Office Action in Australian Patent Application No. 2012246490, dated Feb. 5, 2016, 3 pages.
Office Action in Australian Patent Application No. 2013364953, dated Apr. 19, 2017, 3 pages.
Office Action in Australian Patent Application No. 2013364953, dated Feb. 16, 2017, 3 pages.
Office Action in Canadian Application No. 2543859, dated Aug. 19, 2008, 5 pages.
Office Action in Canadian Application No. 2543861, dated Aug. 19, 2008, 4 pages.
Office Action in Canadian Application No. 2605854, dated Jul. 29, 2009, 2 pages.
Office Action in Canadian Application No. 2652442, dated Oct. 4, 2013, 2 pages.
Office Action in Canadian Application No. 2676796, dated Dec. 30, 2013, 5 pages.
Office Action in Canadian Application No. 2676796, dated Jan. 29, 2015, 5 pages.
Office Action in Canadian Application No. 2713930, dated Jan. 30, 2015, 5 pages.
Office Action in Canadian Application No. 2771403, dated Jul. 16, 2014, 3 pages.
Office Action in Canadian Patent Application No. 2704000, dated Mar. 27, 2015, 3 pages.
Office Action in Canadian Patent Application No. 2713930, dated Mar. 7, 2016, 5 pages.
Office Action in Chilean Patent Applciation No. 2012-00412, dated Jan. 23, 2017, 4 pages (English Translation).
Office Action in Chilean Patent Application No. 2012-00412, dated Jan. 28, 2015, 17 pages, with English translation.
Office Action in Chinese Application No. 200680020317.5, dated Mar. 4, 2014, 13 pages.
Office Action in Chinese Application No. 200680021939.X, dated May 27, 2010, 9 pages (with English translation).
Office Action in Chinese Application No. 200680021939.X, dated Sep. 2, 2010, 10 pages (with English translation).
Office Action in Chinese Application No. 200780017371.9, dated Dec. 11, 2014, 9 pages (with English translation).
Office Action in Chinese Application No. 200780017371.9, dated May 15, 2015, 17 pages (with English translation).
Office Action in Chinese Application No. 200780019200.X, dated Apr. 6, 2012, 9 pages (with English translation).
Office Action in Chinese Application No. 200780019520.5, dated Dec. 21, 2010, 7 pages (with English translation).
Office Action in Chinese Application No. 200780019520.5, dated Sep. 27, 2010, 8 pages (with English translation).
Office Action in Chinese Application No. 2008800045113, dated Jul. 5, 2011, 10 pages (with English translation).
Office Action in Chinese Application No. 201180030568.2, dated Mar. 24, 2014, 8 pages (with English translation).
Office Action in Chinese Application No. 201180030568.2, dated Oct. 12, 2013, 11 pages (with English translation.
Office Action in Chinese Application No. 201280010898.X, dated Aug. 11, 2014, 14 pages (with English translation).
Office Action in Chinese Patent Application No. 201380054667.3 dated Aug. 9, 2017, 11 pages (English Translation).
Office Action in Chinese Patent Application No. 201380054667.3, dated Feb. 14, 2017, 9 pages (English Translation).
Office Action in Chinese Patent Application No. 201380054667.3, dated Jul. 18, 2016, 18 pages (English Translation).
Office Action in Chinese Patent Application No. 201480026871.9, dated Feb. 21, 2017, 10 pages (English Translation).
Office Action in Chinese Patent Application No. 201510031628.2, dated Dec. 12, 2017, 11 pages (English Translation).
Office Action in Chinese Patent Application No. 201510031628.2, dated Jul. 19, 2018, 11 pages (English Translation).
Office Action in Chinese Patent Application No. 201510031628.2, dated Jun. 2, 2016, 11 pages (English Translation).
Office Action in Chinese Patent Application No. 201680022734.2, dated Oct. 22, 2018, 12 pages (English Translation).
Office Action in Colombian Application No. 12-022608, dated Dec. 17, 2013, 12 pages (with English translation).
Office Action in DB Application No. 60/2005, dated Jul. 25, 2006, 2 pages.
Office Action in Egyptian Patent Application No. PCT 283/2012, dated Feb. 19, 2018, 10 pages (English Translation).
Office Action in European Application No. 03791389.4, dated Dec. 2, 2014, 5 pages.
Office Action in European Application No. 03791389.4, dated Jun. 10, 2014, 4 pages.
Office Action in European Application No. 04807580.8, dated Mar. 18, 2014, 12 pages.
Office Action in European Application No. 05719973.9, dated Feb. 11, 2011, 7 pages.
Office Action in European Application No. 05719973.9, dated Nov. 2, 2011, 4 pages.
Office Action in European Application No. 07743994.1, dated Sep. 9, 2014, 8 pages.
Office Action in European Application No. 07793075.8, dated Mar. 1, 2011, 3 pages.
Office Action in European Application No. 08704376.6, dated Feb. 24, 2014, 4 pages.
Office Action in European Application No. 08846814.5, dated Jun. 4, 2014, 4 pages.
Office Action in European Application No. 10809938.3, dated Feb. 10, 2015, 4 pages.
Office Action in European Application No. 10809938.3, dated Oct. 16, 2014, 5 pages.
Office Action in European Patent Application No. 07743994.1, dated Apr. 18, 2017, 5 pages.
Office Action in European Patent Application No. 07743994.1, dated Mar. 8, 2017, 5 pages.
Office Action in European Patent Application No. 08846814.5, dated Apr. 29, 2016, 28 pages.
Office Action in European Patent Application No. 08846814.5, dated Sep. 13, 2017, 19 pages.

(56) References Cited

OTHER PUBLICATIONS

Office Action in European Patent Application No. 08846814.5, dated Sep. 28, 2016, 14 pages.
Office Action in European Patent Application No. 09705712.9, dated Apr. 11, 2018, 5 pages.
Office Action in European Patent Application No. 12793322.4, dated May 19, 2017, 4 pages.
Office Action in European Patent Application No. 13865671.5, dated Mar. 7, 2017, 4 pages.
Office Action in European Patent Application No. 14727633.1, dated Oct. 13, 2016, 4 pages.
Office Action in European Patent Application No. 15836577.5, dated Mar. 23, 2018, 9 pages.
Office Action in Gulf Cooperation Council Patent Application No. GC2011-17812, dated Aug. 2, 2018, 8 pages (English Translation).
Office Action in Gulf Cooperation Council Patent Application No. GC2015-29939, dated Feb. 22, 2018, 16 pages (English Translation).
Office Action in Indian Application No. 1571/CHENP/2007, dated Oct. 23, 2013, 2 pages.
Office Action in Indian Application No. 1571/CHENP/2007, Dec. 9, 2013, 2 pages.
Office Action in Indian Patent Application No. 10502/CHENP/2012, dated Dec. 29, 2017, 5 pages (English Translation).
Office Action in Indian Patent Application No. 1511/CHENP/2009, dated Feb. 27, 2017, 7 pages (English Translation).
Office Action in Indian Patent Application No. 2371/CHENP/2012, dated Jul. 27, 2017, 5 pages (English Translation).
Office Action in Indian Patent Application No. 2371/CHENP/2012, dated Jun. 15, 2018, 3 pages (English Translation).
Office Action in Indian Patent Application No. 2371/CHENP/2012, dated Oct. 29, 2018, 1 page (English Translation).
Office Action in Indian Patent Application No. 2371/CHENP/2012, dated Sep. 17, 2018, 3 pages (English Translation).
Office Action in Indian Patent Application No. 2793/CHENP/2013, dated Feb. 28, 2018, 2 pages (English Translation).
Office Action in Indian Patent Application No. 2793/CHENP/2013, dated Sep. 13, 2017, 12 pages (English Translation).
Office Action in Indian Patent Application No. 3334/CHENP/2010, dated Feb. 6, 2017, 13 pages (English Translation).
Office Action in Indian Patent Application No. 5022/CHENP/2009, dated Jun. 28, 2016, 7 pages.
Office Action in Indian Patent Application No. 5022/CHENP/2009, dated Jun. 29, 2017, 3 pages (English Translation).
Office Action in Indian Patent Application No. 5287/CHENP/2010, dated Mar. 15, 2017, 8 pages (English Translation).
Office Action in Indian Patent Application No. 5287/CHENP/2010, Dated Mar. 22, 2018, 2 pages (English Translation).
Office Action in Indian Patent Application No. 6415/CHENP/2008, dated Jan. 19, 2017, 5 pages (English Translation).
Office Action in Indian Patent Application No. 7026/CHENP/2013, dated Mar. 8, 2018, 7 pages (English Translation).
Office Action in Indonesian Patent Application No. W-00201201031, dated Mar. 14, 2016, 4 pages (English translation).
Office Action in Israeli Application No. 175363, dated Jan. 2, 2013, 2 pages, with English translation.
Office Action in Israeli Application No. 188670, dated Jul. 3, 2011, 2 pages (with English translation).
Office Action in Israeli Application No. 197002, dated Feb. 8, 2012, 2 pages (with English translation).
Office Action in Israeli Application No. 197141, dated Feb. 22, 2012, 18 pages (with English translation).
Office Action in Israeli Application No. 200090, dated Jul. 24, 2013, 5 pages (with English translation).
Office Action in Israeli Application No. 205512, dated Dec. 20, 2012, 8 pages, with English translation.
Office Action in Israeli Application No. 205512, dated Oct. 28, 2013, 5 pages (with English translation).
Office Action in Israeli Application No. 205512, dated Sep. 22, 2014, 5 pages (with English translation).
Office Action in Israeli Application No. 207089, dated Jan. 6, 2013, 5 pages (with English translation).
Office Action in Israeli Application No. 207089, dated Nov. 25, 2013, 6 pages (with English translation).
Office Action in Israeli Application No. 217197, dated Oct. 22, 2014, 4 pages (with English translation).
Office Action in Israeli Application No. 255564, dated Aug. 15, 2018, 5 pages (English Translation).
Office Action in Israeli Patent Application No. 227558, dated Mar. 13, 2016, 5 pages (English Translation).
Office Action in Israeli Patent Application No. 238463, dated Feb. 1, 2018, 6 pages (English Translation).
Office Action in Israeli Patent Application No. 242519, dated Aug. 9, 2017, 7 pages (English Translation).
Office Action in Israeli Patent Application No. 253946, dated Oct. 17, 2018, 5 pages (with English Translation).
Office Action in Japanese Application No. 2008-530917, dated Oct. 23, 2012, 4 pages (with English translation).
Office Action in Japanese Application No. 2008-556208, dated Jan. 22, 2013, 8 pages, with English translation.
Office Action in Japanese Application No. P2005-516605 mailed Jun. 1, 2010, 3 pages.
Office Action in Japanese Application No. P2008-532141, dated May 21, 2013, 4 pages (with English translation).
Office Action in Japanese Application No. P2009-510543, dated Sep. 29, 2009, 7 pages (with English translation).
Office Action in Japanese Application No. P2009-540099, dated Mar. 25, 2014, 6 pages (with English translation).
Office Action in Japanese Application No. P2014-553200, dated Jun. 6, 2017, 6 pages (with English tranlsation).
Office Action in Japanese Patent Application No. P2014-513691, dated Jun. 21, 2016, 4 pages, (English Translation).
Office Action in Japanese Patent Application No. P2014-513691, dated Mar. 8, 2016, 6 pages (English Translation).
Office Action in Japanese Patent Application No. P2015-555882, dated Mar. 27, 2018, 4 pages (English Translation).
Office Action in Japanese Patent Application No. P2016-214593, dated Jun. 19, 2018, 7 pages (English Translation).
Office Action in Japanese Patent Application No. P2016-214593, dated Oct. 17, 2017, 9 pages (English Translation).
Office Action in Jordan Patent Application No. 55/2011, dated Feb. 16, 2017, 2 pages (English Translation).
Office Action in Japanese 2007-542863 dated May 29, 2012, 8 pages with English translation.
Office Action in Korean Application No. 10-2006-7013907, dated Jul. 28, 2007, 7 pages (with English translation).
Office Action in Korean Application No. 10-2006-7013940, dated Jul. 31, 2007, 19 pages (with English translation).
Response to Office Action dated Aug. 27, 2009 in Korean Application No. 10-2007-7026886, 7 pages (with English translation).
Office Action in Korean Application No. 10-2008-7013685, dated May 20, 2013, 10 pages (with English translation).
Office Action in Korean Application No. 10-2008-7027527, dated Dec. 9, 2013, 6 pages (with English translation).
Office Action in Korean Application No. 10-2008-7029472, dated Mar. 28, 2014, 6 pages (with English translation).
Office Action in Korean Application No. 10-2008-7029577, dated Dec. 30, 2013, 7 pages (with English translation).
Office Action in Korean Application No. 10-2009-7005657, dated Mar. 28, 2014, 6 pages (with English translation).
Office Action in Korean Application No. 10-2009-7013723, dated May 19, 2011, 10 pages (with English translation).
Office Action in Korean Application No. 10-2009-7017694, dated Jan. 29, 2014, 26 pages (with English translation).
Office Action in Korean Application No. 10-2010-7011023, dated Sep. 3, 2014, 14 pages (with English translation).
Office Action in Korean Application No. 10-2010-7018835, dated Sep. 30, 2014, 6 pages (with English translation).
Office Action in Korean Application No. 10-2012-7003846, dated Oct. 7, 2014, 7 pages.
Office Action in Korean Patent Application No. 10-2013-7020616, dated Dec. 19, 2016, 12 pages (English Translation).

(56) References Cited

OTHER PUBLICATIONS

Office Action in Mexican Application No. MX/a/2010/008187, dated Apr. 28, 2014, 4 pages (with English translation).
Office Action in Mexican Application No. MX/a/2010/008187, dated Dec. 5, 2013, 8 pages (with English translation).
Office Action in Mexican Application No. MX/a/2012/002011, dated Apr. 28, 2014, 10 pages (with English translation).
Office Action in Mexican Application No. MX/a/2012/002011, dated Nov. 21, 2013, 8 pages (with English translation).
Office Action in Mexican Patent Application No. MX/a/2014/010594, dated Aug. 17, 2016, 10 pages (English Translation).
Office Action in Norwegian Patent Office Application No. 20063383, dated Mar. 15, 2016, 6 pages (English Translation).
Office Action in U.S. Appl. No. 12/558,982, dated Apr. 5, 2011, 31 pages.
Office Action in U.S. Appl. No. 12/558,982, dated Aug. 29, 2011, 13 pages.
Office Action in U.S. Appl. No. 12/864,817, dated Aug. 15, 2014, 79 pages.
Office Action in U.S. Appl. No. 12/867,646, dated Oct. 26, 2011, 37 pages.
Office Action in U.S. Appl. No. 13/083,338, dated Jan. 3, 2013, 9 pages.
Office Action in U.S. Appl. No. 13/238,085, dated Nov. 12, 2013, 74 pages.
Office Action in U.S. Appl. No. 13/238,085, dated Sep. 6, 2013, 10 pages.
Office Action in U.S. Appl. No. 13/805,826, dated Apr. 2, 2014, 8 pages.
Office Action in U.S. Appl. No. 13/805,826, dated Jul. 1, 2014, 88 pages.
Office Action in U.S. Appl. No. 13/805,826, dated Sep. 23, 2014, 25 pages.
Office Action in U.S. Appl. No. 13/870,507, dated Dec. 12, 2014, 10 pages.
Office Action in U.S. Appl. No. 13/923,858, dated Apr. 18, 2014, 64 pages.
Office Action in U.S. Appl. No. 13/923,858, dated Dec. 5, 2014, 67 pages.
Office Action in U.S. Appl. No. 13/983,891, dated Jan. 22, 2014, 11 pages.
Office Action in U.S. Appl. No. 14/002,018, dated Apr. 14, 2014, 28 pages.
Office Action in U.S. Appl. No. 14/002,018, dated Jul. 25, 2014, 14 pages.
Office Action in U.S. Appl. No. 14/002,018, dated Jun. 9, 2014, 19 pages.
Office Action in U.S. Appl. No. 14/862,349, dated Mar. 10, 2016, 11 pages.
Office Action in U.S. Appl. No. 13/870,507, dated Feb. 17, 2016, 28 pages.
Office Action in U.S. Appl. No. 13/923,858, dated Feb. 22, 2018, 16 pages.
Office Action in U.S. Appl. No. 13/923,858, dated May 4, 2017, 31 pages.
Office Action in U.S. Appl. No. 13/923,858, dated Oct. 4, 2018, 16 pages.
Office Action in U.S. Appl. No. 14/117,276, dated May 20, 2016, 11 pages.
Office Action in U.S. Appl. No. 14/122,339, dated Aug. 10, 2017, 10 pages.
Office Action in U.S. Appl. No. 14/122,339, dated Jan. 2, 2018, 3 pages.
Office Action in U.S. Appl. No. 14/122,339, dated Jul. 8, 2016, 12 pages.
Office Action in U.S. Appl. No. 14/890,207, dated Mar. 22, 2018, 19 pages.
Office Action in U.S. Appl. No. 15/460,629, dated Sep. 28, 2018, 10 pages.
Office Action in U.S. Appl. No. 15/503,108, dated Nov. 14, 2017, 12 pages.
Office Action in U.S. Appl. No. 15/503,108, dated Sep. 5, 2018, 8 pages.
Office Action in U.S. Appl. No. 15/550,124, dated May 3, 2018, 124 pages.
Office Action in U.S. Appl. No. 16/038,710, dated Nov. 20, 2018, 124 pages.
Office Action in Vietnamese Application No. 1-2011-03484, dated Dec. 31, 2013, 2 pages (with English translation).
Office Action in Yemen Patent Application No. 592/2011, dated Jan. 16, 2017, 2 pages (English Translation).
Office Action Israel Application No. 207089 issued on Nov. 13, 2011, 4 pages (with English translation).
Office Action issued Apr. 1, 2020, in European Patent Application No. 16802790.2.
Office Action issued Apr. 1, 2020, in Israeli Patent Application No. 257433.
Office Action issued Apr. 11, 2019 in Israeli Patent Application No. 255564 with English translation.
Office Action issued Apr. 15, 2019 in Mexican Patent Application No. MX/a/2015/015605 with English translation.
Office Action issued Apr. 2, 2020, in Russian Patent Application No. 2017139090 with English translation.
Office Action issued Apr. 23, 2020, in New Zealand Patent Application No. 714049.
Office Action issued Apr. 28, 2019, in Egyptian Patent Application No. 2012020283 with English translation.
Office Action issued Apr. 29, 2020, in Egyptian Patent Application No. 2012020283 with English translation.
Office Action issued Apr. 30, 2019 in Taiwanese Patent Application No. 104127982 with English translation.
Office Action issued Apr. 30, 2020, in Russian Patent Application No. 2017128583 with English translation.
Office Action issued Apr. 8, 2019 in U.S. Appl. No. 15/573,197.
Office Action issued Apr. 8, 2020, in European Patent Application No. 16837150.8.
Office Action issued Apr. 8, 2020, in GCC Patent Application No. GC 2015-29939 with English translation.
Office Action issued Aug. 22, 2019, in U.S. Appl. No. 16/092,245.
Office Action issued Aug. 23, 2020, in Israeli Patent Application No. 270317 with English translation.
Office Action issued Aug. 27, 2020, in U.S. Appl. No. 13/923,858.
Office Action issued Aug. 31, 2020, in Canadian Patent Application No. 2,912,219.
Office Action issued Aug. 6, 2020, in U.S. Appl. No. 15/748,980.
Office Action issued Dec. 12, 2019, in U.S. Appl. No. 16/559,293.
Office Action issued Dec. 18, 2019, in Taiwanese Patent Application No. 104127982 with English translation.
Office Action issued Dec. 3, 2019, in Mexican Patent Application No. MX/a/2018/001439 with English translation.
Office Action issued Dec. 6, 2019, in Mexican Patent Application No. MX/a/2018/001658 with English translation.
Office Action issued Feb. 14, 2020, in U.S. Appl. No. 15/573,197.
Office Action issued Feb. 21, 2020, in U.S. Appl. No. 13/923,858.
Office Action issued Feb. 5, 2020, in Israeli Patent Application No. 267159 with English translation.
Office Action issued for Chinese application No. 200880002425.9 on Mar. 2, 2011, 10 pages with English translation.
Office Action issued for European 06768437.3 (EPO Form1224) issued on Oct. 28, 2010, 47 pages.
European Search Report issued for European U.S. Appl. No. 06/782,407 on Sep. 29, 2011, 6 pages.
Office Action issued for Japanese Application No. 2007-529565 issued on Dec. 13, 2011, 7 pages with English full translation.
Office Action issued for Japanese Appl. No. 2007-529565 issued on May 8, 2012, 6 pages with English translation.
Office Action issued in Mexican Application No. MX/a/2012/002011, dated Jul. 17, 2013, 6 pages (with English translation).
Office Action issued Jan. 28, 2020, in Brazilian Patent Application No. BR112012003592-4.
Office Action issued Jan. 28, 2020, in Russian Patent Application No. 2018103737.

(56) References Cited

OTHER PUBLICATIONS

Office Action issued Jan. 7, 2011, in U.S. Appl. No. 12/092,539.
Office Action issued Jul. 13, 2020, in Mexican Patent Application No. MX/a/2018/001658.
Office Action issued Jul. 15, 2020, in Mexican Patent Application No. MX/a/2018/012193.
Office Action issued Jul. 22, 2020, in European Patent Application No. 19151846.3.
Office Action issued Jul. 26, 2020, in Jordan Patent Application No. 203/2015.
Office Action issued Jul. 28, 2020, in Brazilian Patent Application No. PI0418200-6.
Office Action issued Jun. 10, 2020, in Argentine Patent Application No. 20150102731.
Office Action issued Jun. 15, 2020, in U.S. Appl. No. 15/934,242.
Office Action issued Jun. 23, 2020, in Russian Patent Application No. 2017104496.
Office Action issued Jun. 3, 2019, in U.S. Appl. No. 15/748,980.
Office Action issued Mar. 10, 2020, in Korean Patent Application No. 10-2015-7032202.
Office Action issued Mar. 17, 2020, in Brazilian Patent Application No. PI0906576-8.
Office Action issued Mar. 19, 2020, in European Patent Application No. 16755489.8.
Office Action issued Mar. 20, 2020, in U.S. Appl. No. 16/465,277.
Office Action issued Mar. 29, 2019 in U.S. Appl. No. 16/229,805.
Office Action issued Mar. 3, 2020, in Australian Patent Application No. 2016273230.
Office Action issued Mar. 5, 2020, in Jordan Patent Application No. 203/2015.
Office Action issued May 14, 2020, in Israeli Patent Application No. 257292.
Office Action issued May 16, 2019 in U.S. Appl. No. 13/923,858.
Office Action issued May 2, 2019 in U.S. Appl. No. 16/038,710.
Office Action issued May 26, 2020, in Russian Patent Application No. 2018134943.
Office Action issued May 4, 2020, in Egyptian Patent Application No. PCT 283/2012.
Office Action issued Nov. 11, 2019, in Argentine Patent Application No. P110100513.
Office Action issued Nov. 12, 2019, in Russian Patent Application No. 2017139090.
Office Action issued Nov. 24, 2019, in Israeli Patent Application No. 262076.
Office Action issued Nov. 29, 2019, in U.S. Appl. No. 15/748,980.
Office Action issued Oct. 11, 2019, in Russian Patent Application No. 2018103737.
Office Action issued Oct. 15, 2020, in Canadian Patent Application No. 2,957,005.
Office Action issued Oct. 16, 2019, in GCC Patent Application No. GC2011-17812.
Office Action issued Oct. 24, 2019, in Russian Patent Application No. 2018104697.
Office Action issued Oct. 27, 2020, in Brazilian Patent Application No. PI0906576-8. [Partial translation].
Office Action issued Oct. 7, 2020, in U.S. Appl. No. 16/092,245.
Office Action issued Sep. 1, 2020, in Russian Patent Application No. 2017139090.
Office Action issued Sep. 10, 2019, in Brazilian Patent Application No. PI0906576-8.
Office Action issued Sep. 18, 2020, in Indian Patent Application No. 7026/CHENP/2013.
Office Action issued Sep. 19, 2019, in European Patent Application No. 16802790.2.
Office Action issued Sep. 25, 2019, in Canadian Patent Application No. 2,889,866.
Office Action issued Sep. 28, 2020, in European Patent Application No. 16837135.9.
Office Communication dated Sep. 13, 2004 for U.S. Appl. No. 10/420,466.
Office Letter Confirmation of Amendment After Allowance dated Jan. 11, 2011 for CA Application No. 2426461.
Official Action issued Feb. 28, 2019 in Russian Patent Application No. 2017128583 with English translation.
Official Action issued Mar. 11, 2019 in Argentinian Patent Application No. P110100513.
Official Communication dated Oct. 30, 2019, in European Patent Application No. 16755489.8.
Official Communication Regarding Intention to Grant dated Aug. 14, 2020, in European Patent Application No. 16802790.2.
Official Communication Regarding Intention to Grant dated Jun. 25, 2020, in European Patent Application No. 18197141.7.
Official Letter and Notice of Allowance for Australian Application No. 2008211952, dated Jul. 10, 2012.
Official Letter and Notice of Allowance for Australian Application No. 2008325608, dated Feb. 27, 2013, 7 pages.
Official Letter in Australian Application No. 2006282456, dated May 15, 2012, 1 page.
Official Letter in Australian Application No. 2006282456, dated Sep. 24, 2012, 259 pages.
Official Letter in Bangladeshes Application No. 184/2006, dated Feb. 2, 2012, 1 page.
Official Letter re Deficiencies in sequence listing in European Application No. 06796594.7, dated Mar. 10, 2008, 3 pages.
Official Letter re Grant of Request for Correction of Specification for Singapore Application No. 201108602-2, dated Aug. 8, 2012.
Official Letter re Intention to Grant Patent in European Application No. 05719973.9, dated Feb. 6, 2012, 553 pages.
Official Letter re invitation to declare maintenance in European Application No. 06796594.7, dated Sep. 26, 2011, 1 page.
Official Letter re invitation to declare maintenance in European Application No. 07793075.8, dated Sep. 27, 2010, 1 page.
Official Notification in Australian Patent Application No. 2005283422, dated Jul. 14, 2016, 8 pages.
Official Notification in Australian Patent Application No. 2005283422, dated Oct. 20, 2016, 1 pages.
Official Notification in Canadian Application No. 2771403, dated Dec. 16, 2014, 1 page.
Official Notification in European Application No. 04807580.8, dated Jun. 16, 2014, 1 page.
Official Notification in European Application No. 04807580.8, dated Jun. 27, 2014, 17 pages.
Official Notification in European Patent Application No. 07743994.1, dated Jul. 22, 2016, 1 page.
Official Notification in European Patent Application No. 14727633.1, dated Jun. 21, 2018, 2 pages.
Official Notification in Indian Patent Application No. 2371/CHENP/2012, dated Jan. 25, 2018, 3 pages (English Translation).
Official Notification in Indian Patent Application No. 5287/CHENP/2010, dated Apr. 6, 2018, 2 pages (English Translation).
Official Notification in Indian Patent Application No. 6415/CHENP/2008, dated Apr. 28, 2017, 5 pages (English Translation).
Official Notification in Israeli Patent Application No. 223695, dated May 29, 2017, 1 page (English Translation).
Official Notification in U.S. Appl. No. 13/923,858, dated Jul. 23, 2018, 15 pages.
Official Notification mailed Apr. 15, 2019 in Brazilian Patent Application No. BR112012003592-4.
Official Notification mailed Apr. 26, 2019 in Indian Patent Application No. 10502/CHENP/2012.
Official Notification re Decision on Petition in U.S. Appl. No. 11/997,719, dated Sep. 23, 2014, 1 page.
Official Notification re Interview Summary in U.S. Appl. No. 14/002,018, dated Oct. 6, 2014, 2 pages.
Ohe et al., "Randomized phase III study of cisplatin plus irinotecan versus carboplatin plus paclitaxel, cisplatin plus gemcitabine, and cisplatin plus vinorelbine for advanced non-small-cell lung cancer: Four-Arm Cooperative Study in Japan," Annals of Oncology 18 (2): 317-323 (2006).
Ohigashi et al., "Clinical Significance of Programmed Death-1 Ligand-1 and Programmed Death-1 Ligand-2 Expression in Human Esophageal Cancer," Clin. Cancer Research (2005): 11: 2947-2953.

(56) References Cited

OTHER PUBLICATIONS

Oikonomopoulos, G., et al., "Lenvatinib: a potential breakthrough in advanced hepatocellular carcinoma?," *Future Oncology*, 2016, 12(4): 465-476.
Okayama et al., "Activation of Eosinophils with Cytokines Produced by Lung Mast Cells," Int Arch Allergy Immunol., 114(suppl 1):75-77 (1997).
Okayama et al., "Human Lung Mast Cells are Enriched in the Capacity to Produce Granulocyte-Macrophage Colony-Stimulating Factor in Response to IgE-Dependent Stimulation," Eur. J. Immunol., 28:708-715 (1998).
Okura et al., "Effects of monoclonal anti-c-kit antibody (ACK2) on melanocytes in newborn mice," J. Invest. Dermatol., 105(3):322-328 (1995).
Okusaka et al., "Chemotherapy for biliary tract cancer", biliary tract, 2013, vol. 27, No. 1, p. 124-p. 134 (Machine Translation).
Olaso et al., "DDR2 receptor promotes MMP-2-mediated proliferation and invasion by hepatic stellate cells," J. Clin. Invest., 108(9):1369-1378 (2001).
Opposition submitted Dec. 3, 2019, in Indian Patent Application No. 201847037747.
Opposition submitted Jan. 3, 2020, in Indian Patent Application No. 201747040368.
O'Reilly et al., "Hydrolysis of tert-Butyl Methyl Ether (MTBE) in Dilute Aqueous Acid," Environ. Sci. Technol., 2001, 35:3954-3961.
Ozawa, Y., et al., "Abstract 5176: E7386, an orally active CBP/beta-catenin modulator, effects tumor microenvironment, resulting to the enhancement of antitumor activity of lenvatinib," AACR Annual Meeting 2017; Apr. 1-5, 2017; Washington, DC.
Ozols et al., "Phase III trial of carboplatin and paclitaxel compared with cisplatin and paclitaxel in patients with optimally resected stage III ovarian cancer: a Gynecologic Oncology Group study," J. Clin. Oncol., 21(17):3194-3200 (2003).
Pacini, "38th Annual Meeting of the European Thyroid Association", European Thyroid Association, Santiago de Compostela, Spain, Aug. 15, 2014, p. 73-p. 226.
Pakistani Office Action for Application No. 94/2011, issued on May 9, 2012.
Pal et al., "A Phase 2 Trial of Lenvatinib 18 mg vs 14 mg Once Daily (QD) in Combination With Everolimus (5 mg QD) in Renal Cell Carcinoma", A poster presentation at 16th International Kidney Cancer Symposium, Miami, FL, USA, 3-4, Nov. 2017, 1 page.
Pandey et al., "Identification of Orally Active, Potent, and Selective 4-Piperazinylquinazolines as Antagonists of the Platelet-Derived Growth Factor Receptor Tyrosine Kinase Family", *Journal of Medicinal Chemistry.*, 45, 3772-3793, 2002.
Papai et al., "The efficacy of a combination of etoposide, ifosfamide, and cisplatin in the treatment of patients with soft tissue sarcoma," Cancer, vol. 89, No. 1, p. 177-p. 180 (2000).
Park et al., "Serum Angiopoietin-2 as a Clinical Marker for Lung Cancer," Chest 132 (1): 200-206 (2007).
Partial European Search Report for Application No. 01976786.2, dated Apr. 6, 2004.
Patel et al., "The effect of excipients on the stability of levothyroxine sodium pentahydrate tablets," Int'l J Pharm., 2003, 264:35-43.
Paterson et al., "Preclinical studies of fibroblast growth factor receptor 3 as a therapeutic target in multiple myeloma," British Journal of Haematology, 124:595-603 (2004).
Paulus, "Preparation and Biomedical Applications of Bispecific Antibodies", Behring Inst. Mitt. 78 :; 118-132 (1985);.
Amendment after Allowance in CA Application No. 2771403, dated Nov. 24, 2014, 3 pages.
Paz et al., "Development of angiogenesis inhibitors to vascular endothelial growth factor receptor 2. Current status and future perspective," Frontiers in Bioscience, 10: 1415-1439 (2005).
Pearson, "Rapid and Sensitive Sequence Comparison with FASTP and FASTA", Methods in Enzymology 183 :63-98 (1990).
Peruvian Office Action in Application No. 2081-2011, dated Mar. 23, 2016, 12 pages, with English translation.
Petition in Japanese Application No. 2007-532099, dated Dec. 25, 2007, 3 pages (with English translation).
Petition in Japanese Application No. 2007-532099, dated Sep. 25, 2007, 3 pages (with English translation).
Petti et al., "Temporal quantitation of mutant Kit tyrosine kinase signaling attenuated by a novel thiophene kinase inhibitor OSI-930", Molecular Cancer Therapeutics., 4:1186-1197, 2005.
Pilaniya et al., "Recent trends in the impurity profile of pharmaceuticals," J Adv Pharm Technol Res, 1(3): 302-310 (2010).
Pisters et al., "Induction chemotherapy before surgery for early-stage lung cancer: A novel approach," J Thoracic Cardiovasc Surg 119 (3): 429-439 (2000).
Plowright et al., "Ectopic expression of fibroblast growth factor receptor 3 promotes myeloma cell proliferation and prevents apoptosis," Blood, 95:992-998 (2000).
Podar et al., "GW654652, the pan-inhibitor of VEGF receptors, blocks the growth and migration of multiple myeloma cells in the bone marrow microenvironment", Blood., 103, 3474-3479, 2004.
Polverino et al., "AMG 706, an Oral, Multikinase Inhibitor that Selectively Targets Vascular Endothelial Growth Factor, Platelet-Derived Growth Factor, and Kit Receptors, Potently inhibits Angiogenesis and Induces Regression in Tumor Xenografts," Cancer Research, 66(17):8715-8721 (2006).
Pre-Grant Hearing Notice dispatched Aug. 11, 2020, in Indian Patent Application No. 1511/CHENP/2009.
Pre-Grant Opposition Notice dated May 21, 2020, in Indian Patent Application No. 2371/CHENP/2012.
Pre-Grant Opposition Notice dated Nov. 21, 2019, in Indian Patent Application No. 1511/CHENP/2009.
Pre-Grant Opposition Notice dated Nov. 6, 2019, in Indian Patent Application No. 201747004829.
Pre-Grant Opposition Notice dated Sep. 9, 2020, in Indian Patent Application No. 201847037747.
Pre-Grant Opposition Notice dispatched Feb. 20, 2020, in Indian Patent Application No. 201747028834.
Pre-Grant Opposition Notice dispatched Mar. 2, 2020, in Indian Patent Application No. 201847003846.
Pre-Grant Opposition submitted Apr. 18, 2020, in Indian Patent Application No. 2371/CHENP/2012.
Preliminary Amendment and Response to Restriction Requirement in U.S. Appl. No. 12/439,339, filed Aug. 10, 2011.
Preliminary Amendment and Response to Restriction Requirement in U.S. Appl. No. 13/083,338, filed Apr. 30, 2012.
Preliminary Amendment dated Apr. 26, 2013 for U.S. Appl. No. 13/870,507, 10 pages.
Preliminary Amendment filed in European Application No. 12786619.2, dated Nov. 13, 2013, 7 pages.
Preliminary Amendment filed in U.S. Appl. No. 14/117,276, dated Nov. 12, 2013, 11 pages.
Preliminary Amendment filed in U.S. Appl. No. 14/122,339, dated Nov. 26, 2013, 10 pages.
Preliminary Amendment filed on Apr. 18, 2003 for U.S. Appl. No. 10/420,466.
Preliminary Amendment filed on Dec. 2, 2005 for U.S. Appl. No. 10/420,466.
Preliminary Amendment filed on Feb. 3, 2006 for U.S. Appl. No. 11/293,785.
Preliminary Amendment filed on May 23, 2003 for Korean Application No. 10-2003-7005506 (with English translation).
Preliminary Amendment filed on Oct. 27, 2003 for U.S. Appl. No. 10/420,517.
Preliminary Amendment for U.S. Appl. No. 13/624,278, filed Sep. 21, 2012, 7 pages.
Preliminary Amendment in U.S. Appl. No. 10/577,043, dated Apr. 24, 2006, 12 pages.
Preliminary Amendment in U.S. Appl. No. 10/577,065, dated Apr. 24, 2006, 11 pages.
Preliminary Amendment in U.S. Appl. No. 11/508,322, dated May 15, 2007, 4 pages.
Preliminary Amendment in U.S. Appl. No. 11/508,322, dated May 19, 2008, 15 pages.
Preliminary Amendment in U.S. Appl. No. 11/508,322, dated Nov. 5, 2007, 28 pages.

(56) References Cited

OTHER PUBLICATIONS

Preliminary Amendment in U.S. Appl. No. 11/892,785, dated Apr. 7, 2008, 16 pages.
Preliminary Amendment in U.S. Appl. No. 12/031,568, dated Jun. 6, 2008, 7 pages.
Preliminary Amendment in U.S. Appl. No. 12/315,291, dated Mar. 19, 2009, 17 pages.
Preliminary Amendment in U.S. Appl. No. 12/527,633, dated Apr. 14, 2010, 58 pages.
Preliminary Amendment in U.S. Appl. No. 12/527,633, dated Aug. 18, 2009, 62 page.
Preliminary Amendment in U.S. Appl. No. 12/867,646, dated Aug. 13, 2010, 5 pages.
Pritzker, "Cancer Biomarkers: Easier Said Than Done," Clinical Chemistry, 48(8):1147-1150 (2002).
Ramsden, "Angiogenesis in the thyroid gland," Journal of endocrinology, Apr. 11, 2000, 475-480.
Reasons for Reexamination dated Sep. 11, 2012 for Chinese Application No. 200680020317.5 (with English translation).
Reexamination filed on May 25, 2004 for Taiwanese Application No. 90125928 (with English translation).
Reexamination filed on Nov. 25, 2004 for Taiwanese Application No. 90125928 (with English translation).
Registered dated Feb. 24, 2009 for Philippines Application No. 1-2003-500266.
Registry's Letter in Malta Application No. 3723, dated Sep. 29, 2007, 1 page.
Rejection dated Apr. 26, 2004 for Taiwanese Application No. 90125928 (with English translation).
Remington, "The Science and Practice of Pharmacy," Remington, 20th Edition, 2000, pp. 1123-1124.
Ren "Advances in Medical Therapy of Melanoma," J of Practical Oncology, 25 (2): 137-140 (2010).
Replication of the Opponent to the Reply Statement of the Applicant submitted Jun. 5, 2019, in Indian Patent Application No. 2371/CHENP/2012.
Reply Statement submitted Aug. 19, 2020, in Indian Patent Application No. 2371/CHENP/2012.
Reply Statement submitted Feb. 20, 2020, in Indian Patent Application No. 1511/CHENP/2009.
Reply Statement submitted May 13, 2020, in Indian Patent Application No. 201747028834.
Reply Statement to Representation submitted Oct. 29, 2019, in Indian Patent Application No. 1511/CHENP/2009.
Reply to Action of Nov. 20, 2018 in U.S. Appl. No. 16/038,710 on Feb. 8, 2019.
Reply to communication from the Examining Division for European App. Ser. 06023078.6, dated Feb. 4, 2008.
Reply to communication from the Examining Division for European App. Ser. 06023078.6, dated Sep. 10, 2007.
Reply to communication from the Examining Division for European Application No. 01976786.2, dated Jan. 25, 2006.
Reply to communication from the Examining Division for European Application No. 01976786.2, dated Jul. 19, 2006.
Reply to communication from the Examining Division for European Application No. 04025700.8, dated Jan. 26, 2007.
Reply to communication from the Examining Division for European Application No. 04025700.8, dated Sep. 12, 2006.
Reply to Examination Report dated Feb. 8, 2013 for European Application No. 07743994.1, 4 pages.
Reply to final office action in U.S. Appl. No. 13/805,826, dated Nov. 26, 2014, 7 pages.
Reply to Final Office Action in U.S. Appl. No. 14/002,018, dated Oct. 1, 2014, 6 pages.
Reply to Non-Final Office Action filed Aug. 23, 2019, in U.S. Appl. No. 15/748,980.
Reply to Notice of Non-Compliant Amendment in U.S. Appl. No. 12/315,291, dated Nov. 12, 2010, 3 pages.
Reply to Office Action and Terminal Disclaimer filed May 30, 2019, in U.S. Appl. No. 16/229,805.
Reply to Office Action filed Jun. 11, 2020, in U.S. Appl. No. 16/465,277.
Reply to Office Action filed Jun. 2, 2020, in U.S. Appl. No. 16/559,293.
Reply to Office Action filed May 11, 2020, in U.S. Appl. No. 13/923,858.
Reply to Office Action submitted Apr. 13, 2020, in Brazilian Patent Application No. BR112012003592-4.
Reply to official communication for European Application No. 05783232.1, dated Apr. 30, 2008.
Reply to Opposition submitted Feb. 4, 2020, in Indian Patent Application No. 201747004829.
Reply to Replication submitted Aug. 21, 2019, in Indian Patent Application No. 2371/CHENP/2012.
Reply to Restriction Requirement filed Apr. 22, 2020, in U.S. Appl. No. 15/934,242.
Reply to Restriction Requirement filed Feb. 25, 2019 in U.S. Appl. No. 15/750,712.
Reply to Technical Opinion submitted May 28, 2020, in Brazilian Patent Application No. PI0906576-8.
Reply to the invitation to remedy deficiencies for European Application No. 06023078.6, dated Jan. 11, 2007.
Reply to the Unfavorable Opinion dated Jul. 10, 2019, in Brazilian Patent Application No. PI0418200-6.
Request according to Section 18 dated Apr. 16, 2019 in Israeli Patent Application No. 257292 with translation.
Request according to Section 18 dated Apr. 16, 2019 in Israeli Patent Application No. 257433 with translation.
Request for accelerated examination in Korean Application No. 10-2012-7003846, dated Jun. 18, 2014, 29 pages (with English translation).
Request for amendment of the text intended for grant and translation of claims for European Application No. 04025700.8, dated Feb. 1, 2008.
Request for amendment of the text intended for grant and translation of claims for European Application No. 06023078.6, dated Nov. 5, 2008.
Request for Certificate of Correction filed May 28, 2019, in U.S. Appl. No. 15/503,108.
Request for Continued Examination (RCE) in U.S. Appl. No. 13/624,278, dated Sep. 24, 2014, 1 page.
Request for Continued Examination (RCE) in U.S. Appl. No. 11/997,719, dated Aug. 29, 2014, 1 page.
Request for Continued Examination (RCE) transmittal for U.S. Appl. No. 12/864,817, filed Dec. 22, 2011.
Request for Continued Examination and Information Disclosure Statement filed Jan. 17, 2020, in U.S. Appl. No. 15/750,712.
Request for Continued Examination and Information Disclosure Statement filed Jun. 27, 2019, in U.S. Appl. No. 15/750,712.
Request for Continued Examination and Information Disclosure Statement filed Oct. 7, 2019, in U.S. Appl. No. 15/750,712.
Request for Continued Examination and Reply to Office Action filed Jun. 15, 2020, in U.S. Appl. No. 15/573,197.
Request for Continued Examination, Amendment, and Information Disclosure Statement filed Oct. 22, 2019, in U.S. Appl. No. 16/038,710.
Request for correction of errors in filed documents for European Application No. 06023078.6, dated Feb. 13, 2007.
Request for Delayed Examination submitted Sep. 22, 2020, in Israeli Patent Application No. 262076.
Request for Examination and Amendment submitted Oct. 20, 2020, in Korean Patent Application No. 10-2017-7027616. [Partial translation].
Request for Examination filed Mar. 13, 2019 in New Zealand Appl. No. 714049.
Request for Examination in Canadian Application No. 2713930, dated Oct. 21, 2013, 8 pages.
Request for Examination, Voluntary Amendment, and Submission of Information submitted Sep. 21, 2020, in Canadian Patent Application No. 2,978,226.
Request for RCE filed Feb. 14, 2019 in U.S. Appl. No. 14/890,207.
Request for Re-Examination in Chinese Patent Application 200701017371.9 dated Oct. 11, 2013, 9 pages (with English translation).

(56) References Cited

OTHER PUBLICATIONS

Request for Re-Examination submitted Feb. 10, 2020, in Taiwanese Patent Application No. 104127982.
Request for Substantive Examination for ID Application No. W-00201201031, filed Jun. 3, 2013, 6 pages (with English translation).
Request for Substantive Examination for UA Application No. a201203132, filed Apr. 15, 2013, 14 pages (with English translation).
Request for Supplementary Examination Report filed Sep. 19, 2019, in Singaporean Patent Application No. 11201709335X.
Request for Voluntary Amendments filed May 10, 2012, in Ukraine Patent Application No. a 2012 03132, with English Abstract.
Request to Amend Complete Specification dated Feb. 15, 2013 for Australian Application No. 2008325608, 23 pages.
Request to Amend Complete Specification dated May 9, 2013 for Australian Application No. 2009210098, 22 pages.
Response and Amended Claims filed in European Application No. 08846814.5, filed Aug. 1, 2013, 14 pages.
Response and Amended Claims filed in European Application No. 10809938.3, filed Jul. 19, 2013, 7 pages.
Response and Amendment for CA Application No. 2652442, dated Sep. 5, 2013, 17 pages.
Response filed in CA Application No. 2652442, dated Jan. 8, 2014, 5 pages.
Response filed in CO Application No. 12-022608, dated Nov. 13, 2013, 13 pages (with English translation).
Response filed in IL Application No. 195282, filed Jul. 11, 2013, 13 pages (with English translation).
Response filed in IN Application No. 1571/CHENP/2007, dated Oct. 30, 2013, 9 pages.
Response filed in MX Application No. MX/a/2010/008187, dated Nov. 4, 2013, 21 pages (with English translation).
Response filed in PH Application No. 1-2011-502441, dated Feb. 28, 2014, 4 pages.
Response filed in PH Application No. 1-2011-502441, dated Nov. 4, 2013, 28 pages.
Response filed in U.S. Appl. No. 10/797,903, dated Dec. 29, 2010, 13 pages.
Response filed in VN Application No. 1-2011-03484, dated Feb. 28, 2014, 40 pages (with English translation).
Response filed on Apr. 11, 2006 for CN Application No. 01819710.8 (with English translation).
Response filed on Apr. 17, 2007 for PH Application No. 1-2003-500266.
Response filed on Apr. 27, 2006 for AU Application No. 2001295986.
Response filed on Apr. 30, 2008 for PH Application No. 1-2003-500266.
Response filed on Aug. 13, 2009 for CA Application No. 2426461.
Response filed on Aug. 14, 2006 for PH Application No. 1-2003-500266.
Response filed on Aug. 18, 2008 for NO Application No. 20031731 (with English translation).
Response filed on Aug. 21, 2006 for MX Application No. PA/a/2003/003362 (with English translation).
Response filed on Aug. 26, 2004 for NZ Application No. 525324.
Response filed on Aug. 5, 2003 for PH Application No. 1-2003-500266.
Response filed on Dec. 11, 2007 for TW Application No. 90125928 (with English translation).
Response filed on Dec. 15, 2005 for MX Application No. PA/a/2003/003362 (with English translation).
Response filed on Feb. 23, 2009 for CA Application No. 2426461.
Response filed on Feb. 26, 2008 for U.S. Appl. No. 11/293,785.
Response filed on Jan. 11, 2010 for CN Application No. 200580026468.7 (with English translation).
Response filed on Jan. 21, 2005 for NZ Application No. 525324.
Response filed on Jan. 26, 2011 for IL Application No. 181697 (with English translation).
Response filed on Jul. 1, 2005 for U.S. Appl. No. 10/420,466.
Response filed on Jul. 26, 2006 for AU Application No. 2001295986.
Response filed on Jul. 31, 2007 for PH Application No. 1-2003-500266.
Response filed on Jun. 22, 2010 for CN Application No. 200710007097.9 (with English translation).
Response filed on Mar. 17, 2005 for RU Application No. 2003114740 (with English translation).
Response filed on May 13, 2009 for IL Application No. 189677 (with English translation).
Response filed on May 16, 2008 for CA Application No. 2426461.
Response filed on May 20, 2010 for CA Application No. 2426461.
Response filed on May 7, 2008 for No. U.S. Appl. No. 20/031,731 (with English translation).
Response filed on May 8, 2008 for AU Application No. 2006236039.
Response filed on Nov. 19, 2009 for CN Application No. 200710007097.9 (with English translation).
Response filed on Nov. 30, 2004 for RU Application No. 2003114740 (with English translation).
Response filed on Oct. 13, 2008 for NO Application No. 20031731 (with English translation).
Response filed on Oct. 15, 2007 for PH Application No. 1-2003-500266.
Response filed on Oct. 8, 2004 for U.S. Appl. No. 10/420,466.
Response filed on Oct. 9, 2006 for CN Application No. 01819710.8 (with English translation).
Response filed on Sep. 13, 2005 for CN Application No. 01819710.8 (with English translation).
Response filed on Sep. 15, 2003 for PH Application No. 1-2003-500266.
Response filed on Sep. 21, 2011 for CA Application No. 2579810.
Response filed on Sep. 23, 2009 for CN Application No. 200580026468.7 (with English translation).
Response filed on Sep. 8, 2003 for PH Application No. 1-2003-500266.
Response in Chinese Patent Application No. 201510031628.2, dated Aug. 11, 2017, 8 pages (English Translation).
Response in EP Application No. 06796594.7, dated Mar. 31, 2008, 3 pages.
Response in EP Application No. 12774278.1, dated Oct. 13, 2014, 4 pages.
Response in Indian Patent Applciation No. 5287/CHENP/2010, dated Sep. 12, 2017, 6 pages (English Translation).
Response submitted Apr. 16, 2020, in Indian Patent Application No. 201747004829.
Response submitted Apr. 29, 2020, in Chinese Patent Application No. 201680027234.2.
Response submitted Apr. 7, 2020, in Chinese Patent Application No. 201680009824.2.
Response submitted Aug. 13, 2019, in European Patent Application No. 18197141.7.
Response submitted Aug. 27, 2019, in European Patent Application No. 16837135.9.
Response submitted Aug. 28, 2019, in European Patent Application No. 16837150.8.
Response submitted Aug. 7, 2020, in European Patent Application No. 16837150.8.
Response submitted Dec. 16, 2019, in New Zealand Patent Application No. 714049.
Response submitted Dec. 26, 2019, in Russian Patent Application No. 2018103737.
Response submitted Dec. 4, 2019, in Brazilian Patent Application No. PI0906576-8.
Response submitted Dec. 9, 2019, in Israeli Patent Application No. 255564.
Response submitted Feb. 10, 2020, in European Patent Application No. 19151846.3.
Response submitted Feb. 4, 2020, in Mexican Patent Application No. MX/a/2018/001439.
Response submitted Feb. 6, 2020, in Russian Patent Application No. 2017139090.
Response submitted Jan. 21, 2020, in Egyptian Patent Application No. PCT 283/2012.

(56) References Cited

OTHER PUBLICATIONS

Response submitted Jan. 28, 2020, in European Patent Application No. 16802790.2.
Response submitted Jan. 8, 2020, in Mexican Patent Application No. MX/a/2018/001658.
Response submitted Jul. 16, 2020, in European Patent Application No. 16755489.8.
Response submitted Jul. 2, 2020, in Russian Patent Application No. 2017139090.
Response submitted Jul. 20, 2020, in Egyptian Patent Application No. PCT 283/2012.
Response submitted Jul. 3, 2020, in Chinese Patent Application No. 201680044979.X.
Response submitted Jul. 6, 2020, in Chinese Patent Application No. 201580042365.3.
Response submitted Jun. 4, 2020, in Chinese Patent Application No. 201880028701.2.
Response submitted Jun. 5, 2020, in European Patent Application No. 17782552.8.
Response submitted Mar. 18, 2020, in New Zealand Patent Application No. 714049.
Response submitted Mar. 20, 2020, in Australian Patent Application No. 2015309862.
Response submitted May 22, 2020, in Australian Patent Application No. 2014266223.
Response submitted May 28, 2020, in Israeli Patent Application No. 267159.
Response submitted May 29, 2020, in Indian Patent Application No. 201847003846.
Response submitted Oct. 21, 2019, in Chinese Patent Application No. 201680027234.2.
Response submitted Oct. 28, 2019, in GCC Patent Application No. GC2011-17812.
Response submitted Sep. 18, 2019, in Chinese Patent Application No. 201580042365.3.
Response submitted Sep. 22, 2020, in Israeli Patent Application No. 262076.
Response submitted Sep. 24, 2020, in Mexican Patent Application No. MX/a/2018/001439.
Response submitted Sep. 24, 2020, in Russian Patent Application No. 2018134943.
Response submitted Sep. 26, 2019, in GCC Patent Application No. GC2015-29939.
Response to Oct. 22, 2018 Office Action in Chinese Appl. No. 201680027234.2.
Response to Jan. 2, 2019 Restriction Requirement in U.S. Appl. No. 15/748,980.
Response to Action of Oct. 4, 2018 in U.S. Appl. No. 13/923,858, filed Jan. 2, 2019.
Response to Advisory Action in U.S. Appl. No. 12/315,291, dated Mar. 31, 2011, 6 pages.
Response to AU OA for AU 2008211952 filed on Jun. 28, 2012, 36 pages.
Response to Australian Office Action filed on Apr. 29, 2010 for corresponding AU Application No. 2006285673.
Response to Australian Office Action filed on Jul. 28, 2010 for corresponding AU Application No. 2006285673.
Response to Australian Office Action filed on Oct. 16, 2009 for corresponding AU Application No. 2006285673.
Response to Canadian Office Action filed Feb. 13, 2012, in Canadian Application No. 2,620,594.
Response to Canadian Office Action filed on Jun. 21, 2010 for corresponding CA Application No. 2,620,594.
Response to Chinese Office Action filed on Mar. 5, 2010 for corresponding CN Application No. 200680036592.6, with English translation.
Response to Chinese Office Action, filed Jul. 11, 2012 for Chinese Patent Application No. 200680036592.6, with English translation.
Response to CN Office Action for CN200880003336.6 filed on May 3, 2012, 15 pages.
Response to Communication in EP Application No. 07743994.1, dated Dec. 22, 2014, 60 pages.
Response to EESR in EP Application No. 09713617.0, dated Sep. 2, 2011, 12 pages.
Response to EP OA for EP 07806561.2 filed on Apr. 18, 2012, 8 pages.
Response to Examination Report in AU Application No. 2005217325, dated Oct. 26, 2007, 33 pages.
Response to Examination Report in AU Application No. 2005217328, dated Sep. 20, 2007, 6 pages.
Response to Examination Report in AU Application No. 2007288793, dated Mar. 30, 2012, 5 pages.
Response to Examination Report in Australian Patent Application No. 2012246490, dated Jul. 15, 2016, 30 pages.
Response to Extended European Search Report in EP Application No. 07793075.8, dated Nov. 8, 2010, 11 pages.
Response to Extended European Search Report in EP Application No. 07805959.9, dated Mar. 29, 2011, 2 pages.
Response to Hearing Notice in IN Application No. 1424/CHENP/2008, dated Sep. 11, 2012, 14 pages.
Response to Indian Office Action issued Feb. 2, 2012, dated Jun. 22, 2012, for Application No. 1908/DELNP/2008.
Response to Invitation to Correct Defects filed Jul. 8, 2019, in International Application No. PCT/US2019/031967.
Response to Israeli Office Action, filed Jul. 24, 2012 for corresponding Israeli Patent Application No. 189589.
Response to Japanese Office Action dated Jul. 17, 2012 for Japanese Application No. 2007-533350 with English translation.
Response to Korean Office Action filed on Feb. 24, 2010 for corresponding KR Application No. 10-2008-7005195, with English translation.
Response to Korean Office Action filed on Jul. 29, 2010 for corresponding KR Application No. 10-2008-7005195, with English translation.
Response to Notice of Allowability filed on Dec. 13, 2007 for PH Application No. 1-2003- 500266.
Response to Notice of Allowance in U.S. Appl. No. 13/205,328, dated Jul. 8, 2014, 7 pages.
Response to Notice of Incomplete Reply in U.S. Appl. No. 11/892,785, dated Apr. 17, 2008, 7 pages.
Response to Notice of Missing Parts and Preliminary Amendment in U.S. Appl. No. 11/892,785, dated Mar. 17, 2008, 4 pages.
Response to Notice Prior to Examination filed in IL Application No. 217197, filed Jul. 31, 2013, 9 pages (with English translation).
Response to Notice Prior to Examination filed on Apr. 22, 2009 for IL Application No. 181697 (with English translation).
Response to Notice Prior to Examination filed on Jan. 11, 2009 for IL Application No. 189677 (with English translation).
Response to Notice Prior to Examination in IL Application No. 188670, dated Nov. 22, 2009, 29 pages (with English translation).
Response to Notice Prior to Examination in IL Application No. 197002, dated Oct. 13, 2010, 18 pages (with English translation).
Response to Notice Prior to Examination in IL Application No. 197141, dated Jun. 1, 2010, 22 pages (with English translation).
Response to OA for EP 10015141 dated Mar. 5, 2012, 47 pages.
Response to Office Action dated Feb. 7, 2013 for CN Application No. 201080030508.6, 17 pages (with English translation).
Response to Office Action dated Jul. 5, 2012 for CN Application No. 200880115011.7 (with English translation).
Response to Office Action dated Nov. 30, 2012 for CN Application No. 200780017371.9, 4 pages (with English translation).
Response to Office Action filed in EP Application No. 04807580.8, dated May 16, 2014, 13 pages.
Response to Office Action filed on Jan. 25, 2013 for CA Application No. 2627598, 9 pages.
Response to Office Action filed on Jul. 11, 2012 for CN Application No. 200880003336.6 (with English translation).
Response to Office Action filed on May 29, 2012 for RU Application No. 2012103471 (with English translation).
Response to Office Action for Australian Application No. 2006309551, filed on Mar. 28, 2012.
Response to Office Action for IL 199907 filed on Oct. 11, 2010, 4 pages with English translation.

(56) References Cited

OTHER PUBLICATIONS

Response to Office Action for Israeli Application No. 205512, filed on Mar. 11, 2012 (with English translation).
Response to Office Action for Israeli Application No. 207089, filed on Mar. 11, 2012, with English translation.
Response to Office Action for MX Application No. MX/a/2012/002011, dated Aug. 29, 2013, 12 pages (with English translation).
Response to Office Action for U.S. Appl. No. 13/322,961, dated Jan. 25, 2013, 22 pages.
Response to Office Action for U.S. Appl. No. 10/420,466 dated Jun. 29, 2005.
Response to Office Action in AU Application No. 2006282456, dated Jul. 16, 2009, 2 pages.
Response to office action in AU Application No. 2007289787, dated Feb. 16, 2012, 27 pages.
Response to office action in AU Application No. 2010285740, dated Oct. 28, 2014, 14 pages.
Response to Office Action in BD Application No. 184/2006, dated Dec. 13, 2007, 2 pages.
Response to Office Action in CA Application No. 2605854, dated Oct. 8, 2009, 18 pages.
Response to Office Action in CA Application No. 2661333, dated Nov. 12, 2013, 18 pages.
Response to Office Action in CA Application No. 2676796, dated Jun. 27, 2014, 15 pages.
Response to Office Action in CA Application No. 2704000, dated Dec. 19, 2014, 13 pages.
Response to Office Action in CA Application No. 2704000, dated Dec. 24, 2015, 11 pages.
Response to Office Action in CA Application No. 2771403, dated Sep. 10, 2014, 11 pages.
Response to Office Action in Canadian Patent Application No. 2704000, dated May 19, 2016, 11 pages.
Response to Office Action in CN Application No. 200680020317.5 filed on Jan. 9, 2014, 7 pages (with English translation).
Response to Office Action in CN Application No. 200680021939.X, dated Jul. 27, 2010, 44 pages (with English translation).
Response to Office Action in CN Application No. 200680021939.X, dated May 20, 2011, 39 pages (with English translation).
Response to Office Action in CN Application No. 200680021939.X, dated Oct. 28, 2010, 40 pages (with English translation).
Response to office action in CN Application No. 200780019200.X, dated Jul. 24, 2012, 49 pages (with English translation).
Response to office action in CN Application No. 200780019520.5, dated Dec. 3, 2010, 28 pages (with English translation).
Response to office action in CN Application No. 200780019520.5, dated Feb. 21, 2011, 7 pages (with English translation).
Response to Office Action in CN Application No. 201180030568.2 filed on Jan. 13, 2014, 46 pages (with English translation).
Response to Office Action in CN Application No. 201180030568.2 filed on May 14, 2014, 10 pages (with English translation).
Response to Office Action in CN Application No. 201280010427.9, dated Jun. 12, 2014, 13 pages (with English translation).
Response to office action in CN Application No. 201280010898.X, dated Nov. 25, 2014, 7 pages (with English translation).
Response to Office Action in EP Application No. 03791389.4, dated Jul. 25, 2014, 75 pages.
Response to office action in EP Application No. 05719973.9, dated Dec. 21, 2011, 150 pages.
Response to office action in EP Application No. 05719973.9, dated May 24, 2011, 26 pages.
Response to office action in EP Application No. 07793075.8, dated May 27, 2011, 17 pages.
Response to Office Action in EP Application No. 08704376.6, dated Apr. 30, 2014, 73 pages.
Response to Office Action in EP Application No. 08846814.5, dated Jul. 24, 2014, 71 pages.
Response to Office Action in European Patent Application No. 12786619.2, dated Apr. 15, 2016, 41 pages.
Response to Office Action in European Patent Application No. 12793322.4, dated Apr. 8, 2016, 10 pages.
Response to office action in ID App. Ser No. W-00 2008 00601, dated Jun. 18, 2012, 3 pages (with English translation).
Response to office action in IL Application No. 188670, dated Aug. 15, 2011, 43 pages (with English translation).
Response to office action in IL Application No. 197141, dated Jun. 6, 2012, 10 pages (with English translation).
Response to office action in IL Application No. 217197, dated Nov. 26, 2014, 7 pages (with English translation).
Response to office action in JP Application No. 2008-530917, dated Dec. 13, 2012, 9 pages (with English translation).
Response to office action in JP Application No. P2009-510543, dated Nov. 9, 2009, 12 pages (with English translation).
Response to Office Action in JP Application No. P2009-540099, dated Apr. 28, 2014, 9 pages (with English Translation).
Response to office action in KR Application No. 10-2006-7013907, dated Sep. 28, 2007, 10 pages (with English translation).
Response to office action in KR Application No. 10-2006-7013940, dated Oct. 1, 2007, 20 pages (with English translation).
Response to Office Action in MX Application No. MX/a/2012/002011 filed on Jan. 16, 2014, 20 pages (with English translation).
Response to Office Action in MX Application No. MX/a/2012/014776, dated Jan. 7, 2015, 20 pages (with English translation).
Response to Office Action in MX Application No. MX/a/2012/014776, dated Jun. 20, 2014, 16 pages (with English translation).
Response to Office Action in MX Application No. MX/a/2013/009931, dated Dec. 9, 2014, 24 pages (with English translation).
Response to office action in NZ Application No. 566793, dated Jan. 17, 2010, 17 pages.
Response to office action in PH Application No. 1-2007-502319, dated Feb. 6, 2012, 19 pages.
Response to office action in PK Application No. 1024/2006, dated Apr. 20, 2009, 14 pages.
Response to office action in PK Application No. 1024/2006, dated Apr. 7, 2008, 17 pages.
Response to office action in PK Application No. 1024/2006, dated Jan. 29, 2009, 6 pages.
Response to office action in PK Application No. 155/2005, dated Jan. 4, 2008, 34 pages.
Response to office action in PK Application No. 375/2008, dated Apr. 8, 2009, 19 pages.
Response to office action in PK Application No. 375/2008, dated Dec. 20, 2008, 1 page.
Response to office action in PK Application No. 375/2008, dated Sep. 1, 2009, 20 pages.
Response to office action in RU Application No. 2006134254, dated Dec. 15, 2006, 23 pages (with English translation).
Response to office action in RU Application No. 2006134254, dated Nov. 20, 2007, 31 pages (with English translation).
Response to office action in RU Application No. 2008110932, dated Jan. 26, 2009, 29 pages (with English translation).
Response to Office Action in RU Application No. 2012103471, dated Jul. 21, 2014, 7 pages (with English translation).
Response to office action in RU Application No. 2012103471, dated Nov. 18, 2014, 17 pages (with English translation).
Response to Office Action in RU Application No. 2013139556, dated Dec. 25, 2013, 10 pages (with English translation).
Response to Office Action in SG Application No. 201108602-2, dated May 22, 2014, 37 pages.
Response to office action in TW Application No. 095130665, dated May 28, 2012, 379 pages (with English translation).
Response to Office Action in U.S. Appl. No. 13/870,507, dated May 17, 2016, 13 pages.
Response to office action in U.S. Appl. No. 11/508,322, dated Aug. 31, 2009, 11 pages.
Response to office action in U.S. Appl. No. 11/508,322, dated Mar. 18, 2009, 20 pages.
Response to Office Action in U.S. Appl. No. 11/662,425, filed May 20, 2014, 8 pages.
Response to office action in U.S. Appl. No. 12/031,568, dated Aug. 12, 2011, 12 pages.

(56) References Cited

OTHER PUBLICATIONS

Response to office action in U.S. Appl. No. 12/031,568, dated Jun. 2, 2010, 13 pages.
Response to Office Action in U.S. Appl. No. 12/039,381, dated Apr. 3, 2014, 7 pages.
Response to office action in U.S. Appl. No. 12/315,291, dated Aug. 18, 2010, 8 pages.
Response to office action in U.S. Appl. No. 12/315,291, dated Feb. 28, 2011, 8 pages.
Response to office action in U.S. Appl. No. 12/558,982, dated Jul. 5, 2011, 17 pages.
Response to Office Action in U.S. Appl. No. 13/805,826, dated Aug. 8, 2014, 9 pages.
Response to Office Action in U.S. Appl. No. 13/923,858, dated Aug. 8, 2014, 25 pages.
Response to Office Action in U.S. Appl. No. 13/983,891, dated Feb. 27, 2014, 6 pages.
Response to Office Action in U.S. Appl. No. 14/002,018, dated Jul. 18, 2014, 8 pages.
Response to Office Action in U.S. Appl. No. 14/002,018, filed May 28, 2014, 7 pages.
Response to office action in VN Application No. 1-2008-00723, dated May 10, 2010, 7 pages (with English translation).
Response to Office Action submitted Apr. 6, 2020, in Argentine Patent Application No. P110100513.
Response to Office Action submitted Jun. 25, 2019, in Mexican Patent Application No. MX/a/2015/015605.
Response to Office Action submitted Mar. 4, 2020, in Indian Patent Application No. 6971/CHENP/2015.
Response to Office Action submitted May 19, 2020, in Korean Patent Application No. 10-2015- 7032202.
Response to Office Action under 37 C.F.R. § 1.111 for U.S. Appl. No. 12/523,495, filed Dec. 7, 2011.
Response to Office Action under 37 C.F.R. § 1.111 for U.S. Appl. No. 13/083,338, filed Apr. 8, 2011, 23 pages.
Response to Office Action under 37 C.F.R. § 1.111 for U.S. Appl. No. 13/083,338, filed Sep. 6, 2012.
Response to Office Action under 37 C.F.R. § 1.111 and Information Disclosure Statement for U.S. Appl. No. 11/997,719, filed Jul. 3, 2013, 26 pages.
Response to Official Action submitted Apr. 24, 2020, in Russian Patent Application No. 2017104496.
Response to Official Action submitted Apr. 3, 2020, in Russian Patent Application No. 2018103737.
Response to Official Action submitted Jan. 20, 2020, in Russian Patent Application No. 2018104697.
Response to Official Action submitted Jul. 17, 2019, in Egyptian Patent Application No. PCT 283/2012.
Response to Official Action submitted Mar. 13, 2020, in Russian Patent Application No. 2017128583.
Response to Restriction Requirement for U.S. Appl. No. 11/997,543, filed Mar. 22, 2011.
Response to Restriction Requirement for U.S. Appl. No. 12/301,353, filed Nov. 23, 2010.
Response to Restriction Requirement for U.S. Appl. No. 12/524,754, filed Dec. 1, 2011.
Response to Restriction Requirement in U.S. Appl. No. 11/065,631, dated Nov. 26, 2007, 16 pages.
Response to Restriction Requirement in U.S. Appl. No. 13/238,085, dated Oct. 4, 2013, 3 pages.
Response to Restriction Response in U.S. Appl. No. 13/805,826, dated Jun. 2, 2014, 4 pages.
Response to the European Search Report for European Application No. 06782407, filed Nov. 8, 2010.
Response to the Office Action for European Application No. 06782407, filed Jan. 23, 2012, 19 pages.
Response to the Office Action issued for IN Application No. 6415/CHENP/2008 filed on Jan. 17, 2014, 16 pages.
Response to the Office Action issued for Japanese Application No. 2007-529565 filed on February; 3, 2012, 44 pages with English full translation;.
Response to Written Opinion submitted Feb. 17, 2020, in Singaporean Patent Application No. 11201706630U.
Restriction and Election of Species issued Jan. 3, 2020, in U.S. Appl. No. 15/934,242.
Restriction Requirement for U.S. Appl. No. 11/997,543, dated Feb. 23, 2011.
Restriction Requirement for U.S. Appl. No. 12/092,539, dated Oct. 29, 2010.
Restriction Requirement for U.S. Appl. No. 12/301,353, dated Oct. 29, 2010.
Restriction Requirement for U.S. Appl. No. 12/439,339, dated Jul. 29, 2011.
Restriction Requirement for U.S. Appl. No. 12/524,754, dated Nov. 3, 2011.
Restriction Requirement in U.S. Appl. No. 11/065,631, dated Oct. 25, 2007, 8 pages.
Restriction Requirement in U.S. Appl. No. 11/892,785, dated Oct. 7, 2009, 5 pages.
Restriction Requirement in U.S. Appl. No. 12/359,475, dated Mar. 7, 2011, 5 pages.
Restriction Requirement in U.S. Appl. No. 12/527,633, dated Aug. 13, 2012, 10 pages.
Ribas et al., "Oncolytic Virotherapy Promotes Intratumoral T Cell Infiltration and Improves Anti- PD-1 Immunotherapy," Cell, 2017, 170 (6): 1109-1119.
Roberts et al., "Antiangiogenic and Antitumor Activity of a Selective PDGFR Tyrosine Kinase Inhibitor, CP-673,451", Cancer Research., 65, 957-966, 2005.
Robinson et al., "Characterization of Tumor Size Changes Over Time From the Phase 3 Study of (E7080) Lenvatinib in Differentiated Cancer of the Thyroid (Select)", The Poster, No. 1031P, presented at European Society for Medical Oncology 2014 Congress, Sep. 26-30, 2014, 1 page.
Rosen and Goldberg, "Scatter Factor and Angiogenesis," *Advances in Cancer Research*, 1995, 67:257-279.
Ruggeri et al., "CEP-7055: A Novel, Orally Active Pan Inhibitor of Vascular Endothelial Growth Factor Receptor Tyrosine Kinases with Potent Antiangiogenic Activity and Antitumor Efficacy in Preclinical Models1", Cancer Research., 63, 5978-5991, 7542-7544, 2003.
Ruggeri et al., "CEP-7055: An orally-active VEGF-R kinase inhibitor with potent anti-angiogenic activity and anti-tumor efficacy against human tumor xenograft growth," AACR American Association Cancer Research., 93rd Annual Meeting, 43:1080, Apr. 6-10, 2002, San Francisco, CA, USA, abstract 5347, 2 pages.
Ruiz-Garcia et al., "Gene expression profiling identifies Fibronectin I and CXCL9 as candidate biomarkers for breast cancer screening," British Journal of Cancer, 2010, 102 (3): 462-468.
Ruling on Allowance of Patent issued Jan. 29, 2019 in Chilean Patent Application No. 2012-00412.
Russian Decision of Grant directed at Appl. No. 2008149948115(065561) received on Nov. 9, 2011, 16 pages with English translation.
Russian Notice of Allowance in Application No. 2012158142, dated May 5, 2015, 15 pages, with English translation.
Russian Office Action dated Apr. 11, 2012 for Application No. 2012103471, (with English translation).
Russian Office Action dated Jan. 19, 2005 for Application No. 2003114740 (with English translation).
Russian Office Action dated Jun. 29, 2004 for Application No. 2003114740 (with English translation).
Russian Submission Documents in Application No. 2015148193, dated Apr. 27, 2016, 10 pages, with English translation.
Sacher et al., "Biomarkers for the Clinical Use of PD-1/PD-L1 Inhibitors in Non-Small-Cell Lung Cancer: A Review," JAMA Oncol., 2016, 2 (9): 1217-1222.
Saeki et al., "Concurrent overexpression of Ets-1 and c-Met correlates with a phenotype of high cellular motility in human esophageal cancer," International J Cancer, 2002, 98(1):8-13.

(56) References Cited

OTHER PUBLICATIONS

Saito et al., "Angiogenic factors in normal endometrium and endometrial adenocarcinoma," Pathology International, 57: 140-147, 2007.
Salassidis et al., "Translocation t(10; 14) (q 11.2; q22.I) Fusing the Kinectin to the RET Gene; Creates a Novel Rearranged Form (PTC8) of the RET Proto-Oncogene in Radiation-induced; Childhood Papillary Thyroid Carcinoma", Cancer Research, 60: 2786-2789 (2000).
Salmon et al., "Anti-angiogenic treatment of gastrointestinal malignancies," Cancer Invest., 23(8):712-726 (2005).
Salvatore et al., "Molecular profile of hyalinizing trabecular tumours of the thyroid: High prevalence of RET/PTC rearrangements and absence of B-raf and N-raspoint mutations", European Journal of; Cancer, 41: 816-821 (2005);.
Sandler et al., "Paclitaxel-carboplatin alone or with bevacizumab for non-small-cell lung cancer," N Engl J Med, 355 (24): 2542-2550 (2006).
Sandler et al., "Phase III trial of gemcitabine plus cisplatin versus cisplatin alone in patients with locally advanced or metastatic non-small-cell lung cancer," J. Clin. Oncol., 18(1):122-130 (2000).
Sanger et al., "DNA sequencing with chain-terminating inhibitors", Proc. Natl. Acad. Sci. USA 74:5463 (1977).
Santoro et al., "Drug insight: Small-molecule inhibitors of protein kinases in the treatment of thyroid cancer," Nat. Clin. Pract. Endocrinol. Metab., 2(1):42-52 (2006).
Santoro et al., "Minireview: RET: normal and abnormal functions," Endocrinology, 145:5448-5451 (2004).
Santoro et al., "Molecular Mechanisms of RET Activation in Human Cancer," Ann. N.Y. Academy of Sciences, 963:116-121 (2002).
Sattler et al., "Targeting c-Kit mutations: basic science to novel therapies," Leukemia Research, 2004, 28S1:S11-S20.
Scheijen et al., "Tryosine Kinase Oncogenes in Normal Hematopoiesis and Hematological Disease," Oncogene, 21:3314-3333 (2002).
Schlumberger et al., "Lenvatinib versus Placebo in Radioiodine-Refractoly Thyroid Cancer (with supplementary material)," The New England Journal of Medicine 2015; 372, 621-630 (2005).
Schlumberger et al., "A Phase 2 Trial of the Multi-Targeted Kinase Inhibitor Lenvatinib (E7080) in Advanced Medullary Thyroid Cancer (MTC), " 2012 ASCO Annual Meeting, Poster Presentation, Jun. 1-5, 2012.
Schlumberger et al., "A phase 3, multicenter, double-blind, placebo-controlled trial of lenvatinib (E7080) in patients with 131I-refractory differentiated thyroid cancer (SELECT)," Am Soc Clin Oncol., Annual Meeting Abstract LBA6008, 2012, 4 pages.
Schoepp and Conn, "Metabotropic glutamate receptors in brain function and pathology," Trends in Pharmacological Sciences, 1993, pp. 13-20.
Search Report in EP Application No. 09705712.9, dated Aug. 7, 2014, 6 pages.
Search Report in EP Application No. 11798224.9, dated Mar. 21, 2014, 1 page.
Search Report in EP Application No. 11798224.9, dated Mar. 4, 2014, 6 pages.
Search Report in EP Application No. 12774278.1, dated Aug. 14, 2014, 8 pages.
Search Report in EP Application No. 12786619.2, dated Dec. 15, 2014, 6 pages.
Search Report in European Patent Application No. 15836577.5, dated Jun. 28, 2018, 9 pages.
Search Report issued Apr. 1, 2019, in Brazilian Patent Application No. PI0418200-6.
Second Preliminary Amendment and Response to Restriction Requirement for U.S. Appl. No. 12/092,539, filed Nov. 22, 2010.
Sekido et al., "Preferential Expression of c-kit Protooncogene Transcripts in Small Cell Lung Cancer," Cancer Res., 51:2416-2418 (1991).
Sennino and McDonald, "Controlling escape from angiogenesis inhibitors," Nature Rev Cancer, 12: 699-709 (2012).
Sharma et al., "Thyroid Cancer," Feb. 18, 2015, pp. 1-16.
Sharpe et al., "The function of programmed cell death 1 and its ligands in regulating autoimmunity and infection," Nature Immunology (2007); 8: 239-245.
Sherman et al., "A phase II trial of the multitargeted kinase inhibitor E7080in advanced radioiodine (RAI)-refractory differentiated thyroid cancer (DTC)," Journal of Clinical Oncology, 29 (15): 5503A (2011).
Shiang et al., "Mutations in the transmembrane domain of FGFR3 cause the most common genetic form of dwarfism, achondroplasia," Cell., 78:335-342 (1994).
Shibata et al., "Rapid Communication Association of Epstein-Barr Virus with Undifferentiated Gastric Carcinomas with Intense Lymphoid Infiltration", American Journal of Pahthology 139(3):469-473 (1991).
Shimauchi et al., "Augmented expression of programmed death-1 in both neoplastic and non-neoplastic CD4+ T-cells in adult T-cell Leukemia/ Lymphoma," Int. J. Cancer (2007): 121: 2585-2590.
Shimizu et al., "Orally active anti-proliferation agents: novel diphenylamine derivatives as FGF-R2 autophosphorylation inhibitors," Bioorganic and Medicinal Chemistry Letters, 14(4):875-879 (2004).
Shirai, Y., et al., "Role of low-substituted hydroxypropylcellulose in dissociation and bioavalability of novel fine granule system; for masking bitter taste," Biol. Pharm. Bull, 17(3): 427-431 (1994).
Shumaker et al., "Effect of lenvatinib (E7080) on the QTc interval: results from a thorough QT study in healthy volunteers," Cancer Chemother Pharmacol., published online Mar. 23, 2014, 9 pages (with English abstract).
Siegel et al., "Sorafenib: Where Do We Go from Here?," Hepatology, 52:360-369 (2010).
Siemeister et al., "ZK304709, the oral Multitarget Tumor Growth InhibitorTM, acts via inihibition of cell cycle progression and tumor-induced angiogenesis," Proceedings of the American Association for Cancer Research, 46, (Abstract 5842), 2005, 3 pages.
Sihto et al., "KIT and platelet-derived growth factor receptor alpha tyrosine kinase gene mutations and KIT amplifications in human solid tumors," Journal of Clinical Oncology, 23(1):49-57 (2005).
Singaporean Submission Documents in Application No. 11201706630U, dated Aug. 21, 2018, 9 pages.
Sondergaard et al., Differential sensitivity of melanoma cell lines with BRAFV600E mutation to the specific Raf inhibitor PLX4032, J Translational Med., 2010, 8: 39.
Spacey et al., "Indolocarbazoles, Potent and Selective Inhibitors of Platelet-Derived Growth Factor Receptor Autophosphorylation," Biochemical Pharmacology, 55:261-271 (1998).
St. Bernard et al., "Fibroblast Growth Factor Receptors as Molecular Targets in Thyroid Carcinoma," Endocrinology, 146 (3):1145-1153 (2005).
Stahl, et al., 2002, "Biological Effects of the Drug Salt Form" in ED. Stahl and Wermuth, Handbook of Pharmaceutical Salts: Properties, selection, and use, pp. 117-122.
Stinchcombe "Targeted therapy of advanced non-small cell lung cancer: the role of bevacizumab," Biologics: Targets & Therapy 1(3):185-194, 2007.
Stinchcombe and Scoinski, "Bevacizumab in the treatment of non-small-cell lung cancer," Oncogene 26: 3691-3698 (2007).
Stjepanovic and Capdevila, "Multikinase inhibitors in the treatment of thyroid cancer: specific role of lenvatinib," Biologics: Targets and Therapy, 8:129-139 (2014).
Strohmeyer et al., "Expression of the hst-1 and c-kit Protoonocogenes in Human Testicular Germ Cell Tumors," Cancer Res., 51:1811-1816 (1991).
Submission Document(s) Before the Patent Office for IL Application No. 200090, dated Dec. 23, 2012, 16 pages, with English translation.
Submission Document Before the Patent Office dated Apr. 22, 2013 for IL Application No. 207089, 7 pages (with English translation).
Submission Document Before the Patent Office dated Mar. 14, 2013 for IL Application No. 205512, 12 pages (with English translation).
Submission Document Before the Patent Office for CL Application No. 2012-00412, dated Aug. 31, 2012, 6 pages (with English translation).

(56) References Cited

OTHER PUBLICATIONS

Submission Document Before the Patent Office for EP Application No. 03791389.4, dated Dec. 20, 2012, 4 pages.
Submission Document Before the Patent Office for EP Application No. 08846814.5, dated Jan. 3, 2013, 102 pages.
Submission Document Before the Patent Office for EP Application No. 8704376.6, dated Jan. 2, 2013, 22 pages.
Submission Document Before the Patent Office re Observation dated Feb. 16, 2013 for CN Application No. 200980103218.7, 8 pages (with English translation).
Submission Document Before the Patent Office re RCE in U.S. Appl. No. 13/205,328, dated Sep. 10, 2013, 12 pages.
Submission Document in Australian Patent Application No. 2013364953, dated Apr. 13, 2017, 15 pages.
Submission Document in Chinese Patent Application No. 201380054667.3, dated Apr. 12, 2017, 9 pages.
Submission Document in Chilean Patent Application No. 2012-00412, dated Mar. 6, 2017, 9 pages (English Translation).
Submission Document in Chinese Patent Application No. 201480026871.9, dated May 8, 2017, 10 pages (English Translation).
Submission Document in CL Application No. 2012-00412, dated Aug. 12, 2014, 2 pages (with English translation).
Submission Document in Egyptian Patent Application No. PCT 283/2012, dated May 9, 2018, 13 pages (English Translation).
Submission Document in European Patent Application No. 08846814.5, dated Mar. 31, 2017, 45 pages.
Submission Document in European Patent Application No. 12793322.4, dated Apr. 19, 2018, 8 pages.
Submission Document in European Patent Application No. 16837135.9, dated Sep. 18, 2018, 2 pages.
Submission Document in Gulf Cooperation Council Patent Application No. GC2015-29939, dated May 21, 2018, 6 pages (English Translation).
Submission Document in Indian Patent Application No. 10502/CHENP/2012, dated May 3, 2018, 10 pages (English Translation).
Submission Document in Indian Patent Application No. 2371/CHENP/2012, dated Apr. 19, 2018, 21 pages (English Translation).
Submission Document in Indian Patent Application No. 2371/CHENP/2012, dated Aug. 21, 2018, 1 page (English Translation).
Submission Document in Indian Patent Application No. 2371/CHENP/2012, dated Jan. 8, 2018, 10 pages (English Translation).
Submission Document in Indian Patent Application No. 2371/CHENP/2012, dated Jun. 15, 2018, 15 pages (English Translation).
Submission Document in Indian Patent Application No. 2371/CHENP/2012, dated Oct. 22, 2018, 276 pages (English Translation).
Submission Document in Indian Patent Application No. 2371/CHENP/2012, dated Sep. 12, 2018, 18 pages (English Translation).
Submission Document in Indian Patent Application No. 2793/CHENP/2013, dated Apr. 20, 2018, 4 pages (English Translation).
Submission Document in Indian Patent Application No. 2793/CHENP/2013, dated Dec. 13, 2017, 10 pages (English Translation).
Submission Document in Indian Patent Application No. 3334/CHENP/2010, dated Jul. 26, 2017, 59 pages (English Translation).
Submission Document in Indian Patent Application No. 6415/CHENP/2008, dated Apr. 18, 2017, 317 pages (English Translation).
Submission Document in Indian Patent Application No. 7026/CHENP/2013, dated Jul. 9, 2018, 15 pages.
Submission Document in Israeli Patent Application No. 242519, dated Nov. 29, 2017, 13 pages (English Translation).
Submission Document in Jordan Patent Application No. 55/2011, dated Apr. 9, 2017, 7 pages (English Translation).
Submission Document in Jordan Patent Application No. 55/2011, dated Mar. 29, 2017, 5 pages (English Translation).
Submission Document in Korean Patent Application 10-2017-7032771, dated Jan. 8, 2018, 11 pages (English Translation).
Submission Document in MX Application No. MX/a/2014/010594, dated Sep. 4, 2014, 70 pages (with English translation).
Submission Document in PH App Ser. No. 1-2011-502441, dated May 22, 2015, 25 pages.
Submission Document in Russian Patent Application No. 2015148193, dated Mar. 23, 2018, 17 pages (English Translation).
Submission Document in Thailand Patent Application No. 1201000221, dated Mar. 12, 2018, 3 pages (English Translation).
Submission Document in U.S. Appl. No. 13/870,507, dated Apr. 11, 2017, 4 pages.
Submission Document in U.S. Appl. No. 14/122,339, date May 12, 2017, 5 pages.
Submission Document in U.S. Appl. No. 14/122,339, dated Mar. 1, 2018, 15 pages.
Submission Document in U.S. Appl. No. 14/122,339, dated Mar. 27, 2017, 14 pages.
Submission Document in U.S. Appl. No. 15/460,629, dated Nov. 28, 2018, 2 pages.
Submission Document in U.S. Appl. No. 15/503,108, dated Aug. 9, 2018, 15 pages.
Submission Document in U.S. Appl. No. 15/550,124, dated Mar. 14, 2018, 3 pages.
Submission Document in U.S. Appl. No. 15/573,197, dated Dec. 5, 2018, 4 pages.
Submission Document in U.S. Appl. No. 15/934,242, dated Mar. 26, 2018, 10 pages.
Submission Document re RCE and Amendment in U.S. Appl. No. 12/031,568, dated Oct. 26, 2010, 23 pages.
Submission Document re RCE and Information Disclosure Statement in U.S. Appl. No. 12/558,982, dated May 9, 2012, 27 pages.
Submission Document re RCE and Information Disclosure Statement on Oct. 18, 2013, in U.S. Appl. No. 12/524,754, 21 pages.
Submission Document re RCE and Information Disclosure Statement on Sep. 19, 2013 in U.S. Appl. No. 12/741,682, 11 pages.
Submission Document re RCE in U.S. Appl. No. 12/031,568, dated Aug. 30, 2012, 11 pages.
Submission Document re RCE in U.S. Appl. No. 12/031,568, dated Jan. 18, 2012, 11 pages.
Submission Document re RCE in U.S. Appl. No. 12/741,682, dated Aug. 14, 2014, 1 page.
Submission Documents Before the Patent Office for CN Application No. 201080030508.6, dated May 27, 2013, 7 pages (with English translation).
Submission Documents Before the Patent Office for GC Patent Application No. GC2011-17812, dated Oct. 24, 2018, 13 pages.
Submission Documents Before the Patent Office for KR Application No. 10-2009-7017694, dated Jan. 18, 2013, 22 pages, with English translation.
Submission documents dated Apr. 2, 2019 in JP Appl. No. P2017-546133.
Submission documents dated Mar. 21, 2019 in CL Appl. No. 2012-00412.
Submission Documents in Canadian Patent Application No. 2828946, dated Feb. 5, 2016, 6 pages.
Submission Documents in Chinese Patent Application No. 201380054667.3, dated Nov. 17, 2016, 8 pages (English Translation).
Submission Documents in Chinese Patent Application No. 201480026871.9, dated Nov. 14, 2016, 11 pages (English Translation).
Submission Documents in Chinese Patent Application No. 201510031628.2, dated Nov. 29, 2016, 8 pages (English Translation).
Submission Documents in European Patent Application No. 08846814.5, dated Mar. 2, 2017, 18 pages.
Submission Documents in European Patent Application No. 13865671.5, dated Jul. 7, 2016, 3 pages.
Submission Documents in European Patent Application No. 14727633.1, dated Feb. 2, 2017, 12 pages.
Submission Documents in European Patent Application No. 14727633.1, dated Jul. 18, 2016, 8 pages.
Submission Documents in Indian Patent Application No. 1511/CHENP/2009, dated Aug. 18, 2017, 55 pages (English Translation).
Submission Documents in Indian Patent Application No. 5022/CHENP/2009, dated Sep. 23, 2016, 9 pages (English Translation).

(56) References Cited

OTHER PUBLICATIONS

Submission Documents in Indonesia Patent Application No. W-00201201031, dated Aug. 11, 2016, 13 pages (English Translation).
Submission Documents in Indonesia Patent Application No. W-00201201031, dated Dec. 9, 2016, 4 pages (English Translation).
Submission Documents in Israel Patent Application No. 223695, dated Dec. 22, 2016, 5 pages (English Translation).
Submission Documents in Israel Patent Application No. 227558, dated Jul. 12, 2016, 6 pages (English Translation).
Submission Documents in Israeli Patent Application No. 227558, dated Jul. 12, 2016, 6 pages.
Submission Documents in Israeli Patent Application No. 242519, dated Apr. 13, 2016, 4 pages (English Translation).
Submission Documents in Korean Patent Application No. 10-2013-7020616, dated Feb. 13, 2017, 47 pages (English Translation).
Submission Documents in Mexican Patent Application No. MX/a/2014/010594, dated Oct. 20, 2016, 15 pages (English Translation).
Submission Documents in Norwegian Patent Application No. 20/063,383, dated Jun. 15, 2016, 181 pages.
Submission Documents in Russian Patent Application No. 2015148193, dated Aug. 5, 2016, 16 pages (English Translation).
Submission Documents in U.S. Appl. No. 14/117,276, dated Jul. 18, 2016, 3 pages.
Submission Documents in U.S. Appl. No. 14/890,207, dated Nov. 30, 2017, 15 pages.
Submission Documents re New Claim Set Before the Patent Office for AR Application No. P110100513, dated Aug. 27, 2013, 8 pages (with English translation).
Submission Documents re Preliminary Amendment Before the Patent Office for U.S. Appl. No. 14/002,018, dated Aug. 28, 2013, 9 pages.
Submission Documents re RCE Before the Patent Office for U.S. Appl. No. 13/083,338, dated Aug. 28, 2013, 20 pages.
Submission Documents re RCE Before the Patent Office for U.S. Appl. No. 12/524,754, dated Apr. 15, 2013, 17 pages.
Submission Documents re RCE filed in U.S. Appl. No. 12/524,754, dated May 13, 2014, 1 page.
Submission documents re RCE filed in U.S. Appl. No. 13/083,338, dated Dec. 2, 2013, 5 pages.
Submission documents re RCE filed in U.S. Appl. No. 13/205,328, dated Dec. 30, 2013, 1 page.
Submission documents re RCE filed in U.S. Appl. No. 13/624,278, dated Dec. 13, 2013, 15 pages.
Submission documents re RCE in U.S. Appl. No. 12/439,339, dated Jan. 27, 2014, 1 page.
Submission documents re RCE in U.S. Appl. No. 12/524,754, filed Feb. 3, 2014, 1 page.
Submission Documents re Request for Continued Examination filed in U.S. Appl. No. 12/741,682, dated May 6, 2014, 1 page.
Submission Documents re Request for Continued Examination filed in U.S. Appl. No. 13/083,338, dated May 6, 2014, 1 page.
Submission documents re Request for Continued Examination in U.S. Appl. No. 13/205,328, dated Apr. 28, 2014, 1 page.
Submission in EP Application No. 04807580.8, dated Jun. 13, 2014, 39 pages.
Submission of Amendments and Complete Specification dated Apr. 10, 2013 for IN Application No. 1571/CHENP/2007, 15 pages.
Submission of Claims in IL Application No. 223695, dated Jan. 17, 2015, 16 pages.
Submission of Document re Claims filed in Response to Second Office Action for CN Application No. 200880115011.7, filed on Nov. 20, 2012.
Submission of Document re Request for Examination in CO Application No. 12-022608, submitted on Jun. 12, 2012.
Submission of Documents before the Patent Office for CN Application No. 200980103218.7, dated Mar. 13, 2013, 6 pages (with English translation).
Submission of Documents Before the Patent Office for IL Application No. 175363, dated Feb. 27, 2013, 23 pages.
Submission of Documents dated Jun. 11, 2019 in Singapore Patent Application No. 11201700855X.
Submission of Documents re Amendment in UA Application No. a2012 03132, submitted on May 22, 2012.
Submission of Documents re Claim 3 and Figure 3 for KR Application No. 10-2009-7005657, filed on Jul. 13, 2012.
Submission of Documents submitted Apr. 26, 2019 in Indian Patent Application No. 10502/CHENP/2012.
Submission of Reference Materials in KR Application No. 10-2008-7013685, filed Jul. 5, 2013, 43 pages, (with English translation).
Sun et al., "Design, synthesis, and evaluations of substituted 3-[(3- or 4-carboxyethylpyrrol-2-yl)methylidenyl]indolin-2-ones as inhibitors of VEGF, FGF, and PDGF receptor tyrosine kinases", Journal of Medicinal Chemistry., 42:5120-5130 (1999).
Sun et al., "Synthesis and Biological Evaluations of 3-Substituted Indolin-2-ones: A novel class of Tyrosine kinase inhibitors that exhibit selectivity toward particular receptor tyrosine kinases", Journal of Medicinal Chemistry., 41:2588-2603 (1998).
Supplemental Notice of Allowance in U.S. Appl. No. 12/315,291, dated Jul. 21, 2011, 4 pages.
Supplemental Search Report in EP Application No. 05719973.9, dated Dec. 6, 2007, 3 pages.
Supplemental Search Report in EP Application No. 05719976.2, dated Dec. 6, 2007, 3 pages.
Supplementary European Search Report for Application No. 08846814.5, issued on Jun. 18, 2012.
Supplementary European Search Report issued Jul. 5, 2012, in European Patent Application No. 08846814.5.
Taguchi et al., "A novel orally active inhibitor of VEGF receptor tyrosine kinases KRN951: Anti- angiogenic and anti-tumor activity against human solid tumors," Proceedings of the AACR Annual Meeting, 45:595 (Mar. 2004) ( XP002536608).
Tahara et al., "Comprehensive Analysis of Serum Biomarkers and Tumor Gene Mutations Associated With Clinical Outcomes in the Phase 3 Study of (E7080) Lenvatinib in Differentiated Cancer of the Thyroid (SELECT)", The presentation document, presented at European Society for Medical Oncology 2014 Congress, Sep. 26-30, 2014, 24 pages.
Tahara, M., et al., "Exploratory analysis of biomarkers associated with clinical outcomes from the study of lenvatinib in differentiated cancer of the thyroid," *European Journal of Cancer*, 2017, 75: 213-221.
Taiwanese Notice of Allowance in Application No. 100104281, dated Jun. 9, 2015, 4 pages, with English translation.
Takahashi et al., "Phase II Study of Lenvatinib, A Multitargeted Tyrosine Kinase Inhibitor, In Patients With All Histologic Subtypes of Advanced Thyroid Cancer (Differentiated, Medullary, And Anaplastic)", The Poster, presented at the European Society for Medical Oncology 2014 Congress, Sep. 26-30, 2014, 1 page.
Takahashi et al., "A case of inoperable scirrhous gastric cancer that responded remarkably to a combination of TS-1+paclitaxel and showed complete loss of ascites," Japanese Journal of Cancer and Chemotherapy, 31 (7): 1093-1095 (2004). (English translation of the abstract).
Takahashi et al., "Preclinical Study of VEGFR and EGFR Inhibitor—Are They Potential Therapeutic Targets in Biliary Tract Carcinoma?," The Biliary Tract & Pancreas, vol. 36, No. 2, p. 153-p. 160 (2005) (Machine Translation).
Takeda et al., "AZD2171 shows potent anti-tumor activity against gastric cancer expressing variant K-SAM/FGFR2," Abstract #3785, Proceeding of the American Association for Cancer Research, 47:890 (2006).
Tamai et al., "Developmental strategy of Lenvatinib and developmental status in gastrointestinal cancer", BIO Clinica, 2014, vol. 29, No. 2, p. 61-p. 65 (Machine Translation).
Tamura et al., "Molecular Characterization of Undifferentiated-Type Gastric Carcinoma," Laboratory Investigation, 81 (4): 593-598, (2001).
Tan et al., "Randomized study of vinorelbine—gemcitabine versus vinorelbine—carboplatin in patients with advanced non-small cell lung cancer," Lung Cancer, 49(2):233-240 (2005).

(56) References Cited

OTHER PUBLICATIONS

Tanaka et al., "Biological Equivalence Test on Tandospirone Citrate 10 mg Tablet 'AMEL,'" Journal of New Remedies & Clinics, 57(6): 936-951 (2008) (Partial English Translation).
Taniguchi et al., "Effect of c-kit Mutation on Prognosis of Gastrointestinal Stromal Tumors," Cancer Res., 59:4297-4300 (1999).
Taylor et al., "A phase 1b trial of lenvatinib (LEN) plus pembrolizumab (PEM) in patients with selected solid tumors," Annals of Oncology, 2016, 27(6 Suppl).
Taylor et al., "Phase IB/II Trial of Lenvatinib Plus Pembrolizumab in Patients With Advanced Renal Cell Carcinoma, Endometrial Cancer, and Other Selected Advanced Solid Tumors," J. Clin. Oncol., 2020, 38 (11): 1154-1164.
Thailand Request for Examination in Application No. 0401005163, dated Aug. 21, 2015, 29 pages, with English translation.
The ESMO/European Sarcoma Network Working Group, "Bone sarcomas: ESMO Clinical Practice Guideline for diagnosis, treatment and follow-up", Annals of Oncology, vol. 23, supplement 7, 2012, pvii100-pvii109;.
The International Bureau of WIPO, International Preliminary Report on Patentability for International Application No. PCT/US2015/063796, dated Sep. 5, 2017.
The International Bureau of WIPO, International Preliminary Report on Patentability for International Application No. PCT/US2016/020747, dated Sep. 5, 2017.
Springer Verlag, "The Pharmacology of Monoclonal Antibody," vol. 113, Chapter 11, Rosenburg and Moore ed., (1994) pp. 269-315.
Third Office Action dated Feb. 25, 2013 for CN Application No. 200880115011.7, 6 pages (with English translation).
Thomas et al., "The Eosinophil and its Role in Asthma," Gen. Pharmac., 27(4)593-597 (1996).
Thompson et al., "PD-1 is Expressed by Tumor-Infiltrating Immune cells and Is Associated with Poor Outcome for Patients with Renal Cell Carcinoma," Clinical Cancer Research (2007) 13:1757-1761.
Thompson et al., "Significance of B7-H1 Overexpression in Kidney Cancer," Clinical Genitourinary Cancer (2006): 5: 206-211.
Thyroid Cancers, Endocrine and Metabolic Disorders, http://www.merkmanuals.com/professional/print/sec12/ch152/ch152j.html Mar. 16, 2011.
Tian et al., "Activating c-kit Gene Mutations in Human Germ Cell Tumors," American Journal of Pathology, 154(6):1643-1647 (1999).
To and Tsao, "The roles of hepatocyte growth factor/scatter factor and Met receptor in human cancers (Review)," *Oncology Reports*, 1998, 5:1013-1024.
Tohyama et al., "Antitumor Activity of Lenvatinib (E7080): An Angiogenesis Inhibitor That Targets Multiple Receptor Tyrosine Kinases in Preclinical Human Thyroid Cancer Models," J Thyroid Res, 2014:1-13, Sep. 10, 2014.
Tohyama et al., "P-3111, Preclinical effect of lenvatinib on human thyroid cancer targeting angiogenesis and receptor tyrosine kinase signaling," The 71st Annual Meeting of the Japanese Cancer Association, Sep. 19-21, 2012, p. 502.
Tonary et al., "Lack of expression of c-KIT in ovarian cancers is associated with poor prognosis," Int. J. Cancer, 89:242-250 (2000).
Tong et al., "Vascular normalization by vascular endothelial growth factor receptor 2 blockade induces a pressure gradient across the vasculature and improves drug penetration in tumors," Cancer Res., 64:3731-3736 (2004).
Toshiyuki et al., "Thermal recording materials with improved background stability," Database CA (Online) Chemical Abstracts Service, Columbus, OH, US (Feb. 20, 1996) (XP002443195).
Transmittal of Information Disclosure Statement, Terminal Disclaimer, Request for Continued Examination, and Response to Office Action under 37 C.F.R. §1.116 for U.S. Appl. No. 11/997,719, filed Jul. 6, 2011.
Traxler et al., "AEE788; A dual family epidermal growth factor receptor/ErbB2 and vascular endothelial growth factor receptor tyrosine kinase inhibitor with antitumor and antiangiogenic activity," Cancer Res., 64:4931-4941 (2004).

Trudel et al., "CHIR-258, a novel, multitargeted tyrosine kinase inhibitor for the potential treatment of t(4;14) multiple myeloma," Blood, 105:2941-2948 (2005).
Trudel et al., "Inhibition of fibroblast growth factor receptor 3 induces differentiation and apoptosis in t(4;14) myeloma," Blood, 103:3521-3528 (2004).
Tsao et al., "Genetic interaction between NRAS and BRAF mutations and PTEN/MMAC1 inactivation in melanoma," J Invest Dermatol., 122(2):337-41 (2004).
Tsou et al., "Optimization of 6,7-Disubstituted-4-(arylamino)quinoline-3-carbonitriles as Orally Active, Irreversible Inhibitors of Human Epidermal Growth Factor Receptor-2 Kinase Activity", Journal of Medicinal Chemistry., 48, 1107-1131, 2005.
Turner et al., "Fibroblast growth factor signalling: from development to cancer," Nature Reviews, Cancer, 10:116-129 (2010).
U.S. Certificate of Correction in U.S. Appl. No. 12/524,754, dated Aug. 11, 2015, 1 page.
U.S. Certificate of Correction in U.S. Appl. No. 12/741,682, dated Aug. 4, 2015, 2 pages.
U.S. Certificate of Correction in U.S. Appl. No. 13/624,278, dated Aug. 18, 2015, 1 page.
U.S. National Library of Medicine, "Phase 1/2 Study of Lenvatinib in Children and Adolescents With Refractory or Relapsed Solid Malignancies and Young Adults With Osteosarcoma," NLM identifier: NCT02432274, ClinicalTrials.gov, Aug. 10, 2020.
U.S. National Library of Medicine, "Study of Pembrolizumab (MK-3475) in Participants With Advanced Solid Tumors (MK-3475-012/KEYNOTE-012)," Nlm identifier: NCT01848834, ClinicalTrials.gov, May 8, 2013, available at https://clinicaltrials.gov/ct2/show/NCT01848834.
U.S. Notice of Allowance for U.S. Appl. No. 12/244,227, dated Oct. 22, 2010.
U.S. Notice of Panel Decision from Pre-Appeal Brief Review in U.S. Appl. No. 12/039,381, dated Mar. 4, 2016, 2 pages.
U.S. Office Action for U.S. Appl. No. 10/420,466, issued on Apr. 13, 2005.
U.S. Office Action for U.S. Appl. No. 10/577,531, issued on Sep. 23, 2008.
U.S. Office Action for U.S. Appl. No. 10/797,903, dated Jul. 23, 2008, 11 pages.
U.S. Office Action for U.S. Appl. No. 10/797,903, issued on Apr. 1, 2010.
U.S. Office Action for U.S. Appl. No. 10/797,903, issued on Aug. 20, 2009.
U.S. Office Action for U.S. Appl. No. 10/797,903, issued on Dec. 11, 2007.
U.S. Office Action for U.S. Appl. No. 10/797,903, issued on Sep. 1, 2010.
U.S. Office Action for U.S. Appl. No. 11/293,785, issued on Sep. 4, 2007.
U.S. Office Action for U.S. Appl. No. 11/347,749, issued on Feb. 9, 2009.
U.S. Office Action for U.S. Appl. No. 11/662,425, issued on May 3, 2010.
U.S. Office Action for U.S. Appl. No. 11/662,425, issued on Sep. 28, 2010.
U.S. Office Action for U.S. Appl. No. 11/997,543, issued on May 19, 2011.
U.S. Office Action for U.S. Appl. No. 11/997,543, issued on Nov. 9, 2011.
U.S. Office Action for U.S. Appl. No. 11/997,719, issued on Apr. 6, 2011.
U.S. Office Action for U.S. Appl. No. 11/997,719, issued on Sep. 3, 2010.
U.S. Office Action for U.S. Appl. No. 12/092,539, issued on May 9, 2011.
U.S. Office Action for U.S. Appl. No. 12/094,492, issued on Mar. 24, 2011.
U.S. Office Action for U.S. Appl. No. 12/301,353, issued on Jan. 24, 2011.
U.S. Office Action for U.S. Appl. No. 12/400,562, issued on Mar. 31, 2010.

(56) References Cited

OTHER PUBLICATIONS

U.S. Office Action for U.S. Appl. No. 12/439,339, issued on Mar. 30, 2012.
U.S. Office Action for U.S. Appl. No. 12/439,339, issued on Nov. 14, 2011.
U.S. Office Action for U.S. Appl. No. 12/523,495, issued on Dec. 27, 2011.
U.S. Office Action for U.S. Appl. No. 12/523,495, issued on Sep. 27, 2011.
U.S. Office Action for U.S. Appl. No. 12/741,682, issued on Apr. 30, 2012.
U.S. Office Action for U.S. Appl. No. 12/864,817, issued on Dec. 16, 2011.
U.S. Office Action for U.S. Appl. No. 12/864,817, issued on May 19, 2011.
U.S. Office Action for U.S. Appl. No. 12/864,817, issued on Nov. 3, 2011.
U.S. Office Action for U.S. Appl. No. 13/083,338, issued on Apr. 12, 2012.
U.S. Office Action for U.S. Appl. No. 13/083,338, issued on Jun. 8, 2012.
U.S. Office Action for U.S. Appl. No. 13/083,338, issued on Nov. 23, 2012.
U.S. Office Action for U.S. Appl. No. 13/205,328, issued on Jan. 12, 2012.
U.S. Office Action for U.S. Appl. No. 13/205,328, issued on May 1, 2012.
U.S. Office Action for U.S. Appl. No. 13/322,961, issued on Sep. 25, 2012.
U.S. Office Action in U.S. Appl. No. 12/039,381, dated Feb. 26, 2015, 13 pages.
U.S. Office Action in U.S. Appl. No. 13/870,507, dated Apr. 1, 2015, 82 pages.
U.S. Office Action in U.S. Appl. No. 13/923,858, dated Jan. 7, 2016, 2 pages.
U.S. Appl. No. 17/022,675, filed Sep. 16, 2020.
U.S. Response to Office Action in U.S. Appl. No. 12/039,381, dated Dec. 22, 2015, 10 pages.
U.S. Response to Restriction Requirement in U.S. Appl. No. 13/870,507, dated Jan. 27, 2015, 3 pages.
U.S. Submission Documents in U.S. Appl. No. 13/870,507, dated Jun. 18, 2015, 13 pages.
Ueda et al., "Deletion of the carboxyl-terminal exons of K-sam/FGFR2 by short homology-mediated recombination, generating preferential expression of specific messenger RNAs," Cancer Res., 59(24):6080-6086 (1999).
Ueda et al., "VGA1155, a Novel Binding Antagonist of VEGF, Inhibits Angiogenesis In Vitro and In Vivo", Anticancer Research., 24, 3009-3017, 2004.
US Office Action for U.S. Appl. No. 11/997,543, dated Sep. 30, 2013, 88 pages.
Valle et al., Cisplatin plus Gemcitabine versus Gemcitabine for Biliary Tract Cancer, The New England Journal of Medicine, Apr. 8, 2010, vol. 362, p. 1273-p. 1281.
Van Dijk et al. "Induction of Tumor-Cell Lysis by B-Specific Monoclonal Antibodies Recognizing Renal-Cell Carcinoma and CD3 Antigen", Int. J. Cancer 43: 344-9, 1989.
Van Oers et al., "A simple and fast method for the simultaneous detection of nine fibroblast growth factor receptor 3 mutations in bladder cancer and voided urine," Clin. Cancer Res., 11:7743-7748 (2005).
Varvoglis et al., "Chemical Transformations Induced by Hypervalent Iodine Reagents," Tetrahedron, 1997, 53(4):1179-1255.
Vergote et al., "A phase II trial of lenvatinib in patients with advanced or recurrent endometrial cancer: Angiopoietin-2 as a predictive marker for clinical outcomes", J. Clin. Oncol, vol. 31, No. 15 supplement, 5520, 2013, XP002728918.
Vergote et al., "Prognostic and prediction role of circulating angiopoietin-2 in multiple solid tumors: An analysis of approximately 500 patients treated with lenvatinib across tumor types," Am Soc Clin Oncol Annual Meeting Abstract, May 31, 2014, abstract 11061, 3 pages.
Vianna et al., "The histological rarity of thyroid cancer," Braz J Otorhinolaryngol 78 (4):48-51 ( 2012).
Vieira et al., "Expression of vascular endothelial growth factor (VEGF) and its receptors in thyroid carcinomas of follicular origin: a potential autocrine loop," European Journal of Endocrinology, 153: 701-709 (2005).
Vippagunta et al., "Crystalline solids," Advanced Drug Delivery Reviews, 48:3-26 (2001).
Vogel et al., "Sensing extracellular matrix: an update on discoidin domain receptor function," Cell Signaling, 18:1108-1116 (2006).
Voluntary Amendment filed Mar. 18, 2019 in Chinese Appl. No. 201780020786.5.
Voluntary Amendment filed in CA Application No. 2704000, filed Aug. 6, 2013, 6 pages.
Voluntary Amendment filed in CA Application No. 2802644, dated Nov. 22, 2013, 25 pages.
Voluntary Amendment filed on Aug. 11, 2010 for CN Application No. 200710007097.9 (with English translation).
Voluntary Amendment filed on Aug. 19, 2010 for CA Application No. 2426461.
Voluntary Amendment filed on Aug. 30, 2006 for AU Application No. 2006203099.
Voluntary Amendment filed on Feb. 27, 2007 for AU Application No. 2006236039.
Voluntary Amendment filed on Feb. 9, 2010 for AU Application No. 2005283422.
Voluntary Amendment filed on Jul. 6, 2010 for AU Application No. 2005283422.
Voluntary Amendment filed on Sep. 10, 2010 for HU Application No. P0302603 (with English translation).
Voluntary Amendment for Chinese counterpart of App. No. PCT/JP2010/063804, filed on Jan. 5, 2012 (with English translation).
Voluntary Amendment for counterpart Canadian patent application No. 2771403, filed on Feb. 16, 2012.
Voluntary Amendment for Russian Application No. 2012103471, filed on Feb. 1, 2012 (with English translation).
Voluntary Amendment for Thailand Application No. 1201000221, filed on Feb. 17, 2012.
Voluntary Amendment in ID Application No. W-00201201031, dated Nov. 5, 2014, 2 pages (with English translation).
Wakeling et al., "ZD1839 (Iressa): an orally active inhibitor of epidermal growth factor signaling with potential for cancer therapy," Cancer Res., 62(20)5749-5754 (2002).
Wakui, "Chemotherapy of scirrhous gastric cancer," Japanese Journal of Cancer and Chemotherapy, 21(14): 2398-2406 (1994) (with English translation).
Wang et al., "A Convenient Set of Bidentate Pyridine Ligands for Combinatorial Synthesis," Tetrahedron Lett., 40:4779-1478 (1999).
Wang et al., "Kras, Braf, PIK3CA mutations and Pten Expression in Human Colorectal Cancer- Relationship with Metastatic Colorectal Cancer," Ann Oncol., 2010, 21(Supp 6):V164.
Wang et al., "Phase II study of gemcitabine and carboplatin in patients with advanced non-small-cell lung cancer," Cancer Chemother Pharmacol., 60(4):601-607 (2007).
Wang et al., "The Expression of the Proto-Oncogene C-Kit in the Blast Cells of Acute Myeloblastic Leukemia," Leukemia, 3(10):699-702 (1989).
Wang et al., "The Role of Angiopoietins as Potential Therapeutic Targets in Renal Cell Carcinoma," Translational Oncology, vol. 7, No. 2, p. 188-p. 195 (2014), XP055218621.
Wang, Haiyi, et al., "Renal cell carcinoma: diffusion-weighted MR imaging for subtype differentiation at 3.0 T.", Radiology, 257.1: doi: 10.1148/radiol.10092396, 2010, p. 135-p. 143.
Waterman, M., "Computer Analysis of Nucleic Acid Sequences", Methods in Enzymology, 164:765-793 (1988).
Wedge et al., "AZD2171: a highly potent, orally bioavailable, vascular endothelial growth factor receptor-2 tyrosine kinase inhibitor for the treatment of cancer," Cancer Res., 65(10):4389-4400 (2005).

(56) References Cited

OTHER PUBLICATIONS

Wedge et al., "Pharmacological Efficacy of ZD6474, a VEGF Receptor Tyrosine Kinase Inhibitor, in Rat," AACR American Association Cancer Research, 92nd Annual Meeting, 42:583, Mar. 24-28, 2001, New Orleans, La, USA, abstract 3126, 2 pages.
Wedge et al., "ZD4190: An Orally Active Inhibitor of Vascular Endothelial Growth Factor Signaling with Broad-Spectrum Antitumor Efficacy", Cancer Research., 60, 970-975, 2000.
Wells et al., "Targeting the RET Pathway in Thyroid Cancer," Clin. Cancer Res., 15:7119-7123 (2009).
Wells Jr et al, "Vandetanib in Patients With Locally Advanced or Metastatic Medullary Thyroid Cancer: A Randomized, Double-Blind Phase III Trial," J Clinical Oncol., 30 (2): 134-141 ( 2012) corrections published Aug. 20, 2013.
Went et al, "Prevalence of KIT Expression in Human Tumor," Journal of Clinical Oncology, 4514- 4522 (2004).
Werner et al., "Gastric adenocarcinoma: pathomorphology and molecular pathology," J. Cancer Res. Clin. Oncology, 127:207-216 (2001) (English abstract).
WHO Drug Information, vol. 27, No. 1, pp. 68-69 (2013).
WHO Drug Information, vol. 27, No. 2, pp. 161-162 (2013).
Wickman et al., "Further characterization of the potent VEGF/PDGF receptor tyrosine kinase inhibitor AG-013736 in preclinical tumor models for its antiangiogenesis and antitumor activity," Proceedings of the American Association for Cancer Research, 44, 865, (Abstract 3780), 2003, 1 page.
Wilbur et al., "Rapid similarity searches of nucleic acid and protein data banks," ;. Natl. Acad. Sci, U.S.A. 80 (3): 726-730 (1983) .;.
Wilhelm et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis", Cancer Research., 64:7099-7109 (2004).
Willett et al., "Direct evidence that the VEGF-specific antibody bevacizumab has antivascular effects in human rectal cancer," Nat. Med., 10(2):145-1147 (2004).
Winkler et al., "Kinetics of vascular normalization by VEGFR2 blockade governs brain tumor response to radiation: Role of oxygenation, angiopoietin-1, and matrix metalloproteinases," Cancer Cell, 6: 553-563 (2004).
Wirth et al., "Treatment-Emergent Hypertension and Efficacy in the Phase 3 Study of (E7080) Lenvatinib in Differentiated Cancer of the Thyroid (Select)", The Poster, No. 1030P, presented at the European Society for Medical Oncology 2014 Congress, Sep. 26-30, 2014, 1 page.
Wisniewski et al., "Characterization of Potent Inhibitors of the Bcr-Abl and the c-Kit Receptor Tyrosine Kinases", Cancer Research., 62, 4244-4255, 2002.
Wood et al., "A Unique Structure for Epidermal Growth Factor Receptor Bound to GW572016 (Lapatinib): Relationships among Protein Conformation, Inhibitor Off-Rate, and Receptor Activity in Tumor Cells", Cancer Research., 64, 6652-6659. 2004.
Wood et al., "PTK787/ZK 222584, a Novel and Potent Inhibitor of Vascular Endothelial Growth Factor Receptor Tyrosine Kinases, Impairs Vascular Endothelial Growth Factor-Induced Responses and Tumor Growth after Oral Administration", Cancer Research., 60, 2178-2189, 2000.
Wozniak et al., "Randomized trial comparing cisplatin with cisplatin plus vinorelbine in the treatment of advanced non-small-cell lung cancer: a Southwest Oncology Group study," J. Clin. Oncol., 16(7):2459-2465 (1998).
Writ filed Aug. 2, 2019, in Argentine Patent Application No. P110100513.
Written Amendment filed on Jun. 16, 2009 for JP Application No. 2009-123432 (with English translation).
Written Amendment filed on Sep. 21, 2011 for JP Application No. 2011-527665 (with English translation).
Written Opinion mailed Aug. 7, 2018, in International Patent Application No. PCT/JP2018/018810.
Written Submission dated Jul. 17, 2019, in Indian Patent Application No. 10502/CHENP/2012.
Written Submission dated Mar. 24, 2020, in Indian Patent Application No. 2371/CHENP/2012.
Written Submission in Indian Patent Application No. 5022/CHENP/2009, dated Aug. 8, 2017, 16 pages (English Translation).
Written Submission regarding hearing in IN Application No. 1571/CHENP/2007 filed on Jan. 23, 2014, 8 pages.
Written Submission submitted Aug. 21, 2020, in Indian Patent Application No. 201847004787.
Wu et al., "A fully human monoclonal antibody against VEGFR-1 inhibits growth of human breast cancers," Proceedings of the American Association for Cancer Research, 45, 694, (Abstract 3005), 2004, 3 pages.
Wulff et al., "Luteal Angiogenesis: Prevention and Intervention by Treatment with Vascular Endothelial Growth Factor TrapA40", The Journal of Clinical Endocrinology & Metabolism. 86(7), 3377-3386, 2001.
Xu et al., "Research on Novelty Issue of Method Claims Including Use Feature," Paper of IP Forum of 5th Annual Conference of ACPAA, Part III, Apr. 1, 2014, pp. 1-5. [Full Translation].
Yamada et al., "Phase I Dose-Escalation Study and Biomarker Analysis of E7080 in Patients with Advanced Solid Tumors," Clin Cancer Res 17 (8):2528-2537 (2011).
Yamada et al., "New technique for staining," Monthly Medical Technology Supplementary Volume (Apr. 1999) (with English translation).
Yamada, K., et al., "Anti-tumor and anti-angiogenesis activities of E7386, an orally active CBP/b-catenin modulator, as a single agent and in combination with lenvatinib in human HCC xenograft models," Doi: 10.1158/1538-7445.AM2018-2927 Published Jul. 2018.
Yamamoto et al., "E7080 (ER-203492-00), a Novel VEGF Receptor Tyrosine Kinase Inhibitor-III. Significant prolongation of life span in mice transplanted with human ovarian carcinoma based on inhibition of VEGF signaling," Abstract #50, AACR, Toronto, Canada (Apr. 5-9, 2003).
Yamamoto et al., "E7080 a novel multitargeted tyrosine kinase inhibitor, has direct anti-tumor activity via inhibition of KIT signaling in small cell lung cancer," Abstract #4636, AACR, Orlando, FL, (Mar. 27-31, 2004).
Yamamoto et al., "E7080, an oral multi-targeted tyrosine kinase inhibitor, has direct anti-tumor efficacy via inhibition of KIT signaling in gastrointestinal stromal tumor (GIST)," Abstract #4038, 97th Annual Meeting AACR, Washington, DC. (Apr. 1-5, 2006).
Yamamoto et al., "E7080, an oral multi-targeted tyrosine kinase inhibitor, has direct anti-tumor efficacy via inhibition of KIT signaling in small cell lung cancer," Proceedings of the American Association for Cancer Research, 45:1070-1071 (Mar. 2004).
Yamamoto et al., "Lenvatinib, an angiogenesis inhibitor targeting VEGFR/FGFR, shows broad antitumor activity in human tumor xenograft models associated with microvessel density and pericyte coverage," Vascular Cell, 6(18):1-13, 2014.
Yamamoto et al., "Plasma biomarkers predictive for disease control duration in the phase I study of E7080, a multitarget kinase inhibitor," ASCO Annual Meeting Proceedings(Post Meeting Edition), Jonrnal of Clinical Oncology, 27:15S, 2009, 1 page.
Yamori et al., "Current Treatment of Solid Tumors New Approaches of Treatment, Drug Treatment, Kinase Inhibitors/Kokeigan no Saishin Chiryo Chiryo no Aratana Torikumi Yakubutsu Ryoho Kinase Inhibitors," JP J Clin Med., Jun. 1, 2010, 68(6):1059-1066 (was listed as vol. 38).
Yanagihara et al., "Development and biological analysis of peritoneal metastasis mouse models for human scirrhous stomach cancer," Cancer Sci., 96(6):323-332 (2005).
Yang et al., "PD-1 Interaction Contributes to the Functional Suppression of T-Cell Responses to Human Uveal Melanoma Cells in Vitro," Invest Ophthalmol. Vis. Sci. Jun. 2008; 49 (6): 49: 2518-2525 (2008).
Yang et al., "RG7204 (PLX4032), a Selective BRAF V600E Inhibitor, Displays Potent Antitumor Activity in Preclinical Melanoma Models," Cancer Res., 2010, 70(13):5518-5527.
Yang, C., et al., "Improvement of Sirolimus Oral Dosing Method," *Journal of Nursing Science*, 2009, 24(18): 82. [Partial translation].

(56) References Cited

OTHER PUBLICATIONS

Yigitbasi et al., "Tumor Cell and Endothelial Cell Therapy of Oral Cancer by Dual Tyrosine Kinase Receptor Blockade", Cancer Research, 64, 7977-7984, 2004.
Yokota, "Trends in Molecular Targeted Treatment, ASCO report: Gastrointestinal Cancer field/ASCO Hokoku Shokakigan Ryoiki," Gan Bunshi Hyoteki Chiryo, 2010, 8 (4): 271-283. [with English Translation].
Yoshikawa et al., "Clinicopathological and prognostic significance of EGFR, VEGF, and HER2 expression in cholangiocarcinoma," British Journal of Cancer 29, vol. 98, No. 2, 418-425 (2008).
Yu, "Amorphous Pharmaceutical Solids:Preparation Characterization and Stabilization," Advanced Drug Delivery Reviews, 48:27-42 (2001) (XP009065056).
Zhang et al., "Induction of apoptosis in EMT-6 breast cancer cell in line by a Sigma-2 selective ligand," Am. Assoc. Cancer Research, Abstract 5353, 2005, 2 pages.
Zhang et al., "Inhibition of both autocrine and paracrine growth and propagation of human myeloid leukemia with antibodies directed against VEGF receptor 2," Proceedings of the American Association for Cancer Research, 44, 1479, (Abstract 6454), 2003, 2 pages.
Zhang et al., "Overexpression of Platelet-Derived Growth Factor Receptor β in Endothelial Cells of Hepatocellular Carcinoma Associated with High Metastatic Potential," Clin. Cancer Res., 11(24):8557-8563 (2005).
Zhang et al., "Stage 1 in vivo evaluation of multi-receptor tyrosine-kinase inhibitor lenvatinib in osteosarcoma patient derived mouse xenograft models", AACR 2017, Abstract 697, Jul. 2017.
Zhang et al., "Synergic antiproliferative effect of DNA methyltransferase inhibitor in combination with anticancer drugs in gastric carcinoma," Cancer Sci., 97 (9):938-944 (2006).
Zhong et al., "Mechanisms underlying the synergistic effect of SU5416 and cisplatin on cytotoxicity in human ovarian tumor cells," Inter'l J Oncol., 25(2):445-451 (2004).
Zhou et al., "Correlation Research on VEGF Testing in Primary Gastric Cancer and Clinical Pathology Factor," Journal of Practical Oncology, 20 (2): 103-105 (2006) with English translation.
Zhu et al., "Fibroblast growth factor receptor 3 inhibition by short hairpin RNAs leads to apoptosis in multiple myeloma," Mol. Cancer Ther., 4(5):787-798 (2005).
Zhu et al., "Inhibition of human leukemia in an animal model with human antibodies directed against vascular endothelial growth factor receptor 2. Correlation between antibody affinity and biological activity," Leukemia, 17:604-611 (2003).
Zhu, A., et al., "Search: A Phase III, Randomized, Double-Blind, Placebo-Controlled Trial of Sorafenib Plus Erlotinib in Patients With Advanced Hepatocellular Carcinoma," J. Clin. Oncol., 2015, 33(6): 559-566.
Zieger et al., "Role of activating fibroblast growth factor receptor 3 mutations in the development of bladder tumors," Clin. Cancer Res., 11:7709-7719 (2005).
Zimmermann et al., "Potent and Selective Inhibitors of the Abl-Kinase:Phenylamino-Pyrimidine (PAP) Derivatives", Bioorganic and Medicinal Chemistry Letters., 7(2):187-192, 1997.
Zimmermann, "Electrical Breakdown, Electropermeabilization and Electrofusion", Rev. Physiol. Biochem. Pharmacol. 105:176-260 (1986).
Zurita et al., "A cytokine and angiogenic factor (CAF) analysis in plasma for selection of sorafenib therapy in patients with metastatic renal cell carcinoma," Annals of Oncology, 23 (1): 46-52 (2011).
Zurita et al., "Circulating biomarkers for vascular endothelial growth factor inhibitors in renal cell carcinoma," Cancer 115 (S10): 2346-2354 (2009).
Bartsch et al. "A Ret double mutation in the germline of a kindred with FMTC." Experimental and clinical endocrinology & diabetes : official journal, German Society of Endocrinology [and] German Diabetes Association vol. 108,2 (2000): 128-32. doi:10.1055/s-2000-5806.
Baker, Cheryl H et al. "Blockade of vascular endothelial growth factor receptor and epidermal growth factor receptor signaling for therapy of metastatic human pancreatic cancer." Cancer research vol. 62,7 (2002): 1996-2003.
"Afinitor/Afinitor Disperz, Highlights of Prescribing Information", https://www.pharma.us.novartis.com/sites/www.pharma.us.novartis.com/files/afinitor.pdf, 2009.
"Carboxymethyl Cellulose Sodium." Chemical Land 21. Retrieved Apr. 24, 2012. <http://www.chemicalland21.comlindustrialchem/perfonnancepolymer/CARBOXYMETHYL%20CELLULOSE%20S0DIUM%20SAL T.htm>.
"Carboxymethylcellulose Sodium." Merck Index: An Encyclopedia of Chemicals, Drugs, & Biologicals: 13th Ed. New Jersey: Merck & Co (2001), p. 308.
Rudolf Voigt Ed—Voigt R et al., "Chapter 2.2 Loslichkeit, Losungsgeschwindigkeit, Loslichkeitsverbesserung," Pharmazeutische Technologie fuer Studium und Beruf, DT. Apotheker-Verl, Stuttgart; DE, Jan. 1, 2000, p. 40-p. 52, XP008143620 (with English translation).
"Clinical Trial: AMG 706 20040273 Thyroid Cancer Study: Stage 4 Cancer Treatments, Chat w/a Cancer Info Expert About Stage 4 Cancer Treatment Options," accessed from www.CancerCenter.com, 4 pages (2005).
Amendment in Malaysian Application No. PI20071922, dated Jul. 17, 2008, 243 pages.
Ang C., "Role of the fibroblast growth factor receptor axis in cholangiocarcinoma. Journal of astroenterology and Hepatology." Jul. 2015; 30 (7):1116-1122. DOI: 10.1111/jgh. 12916.
European Response to EESR in Application No. 07743994.1-2123, dated Nov. 23, 2010, 22 pages.
European Response to Office Action in Application No. 06832529.9, dated Apr. 22, 2010.
Gong et al., "Expression of CC Chemokine Receptor 4 In Human Follicular Thyroid Carcinoma," Academic Journal of Military Medical University, 28: 701-703, 2007 English Translation.
Indian Office Action in Application No. 2365/CHENP/2015, dated Sep. 6, 2018, 6 pages (with English Translation).
International Preliminary Report on Patentability in International Patent Application No. PCT/JP2016/002562, dated Aug. 9, 2016, 4 pages (English Translation).
Office Action in Peruvian Patent Application No. 2081-2011, dated Jul. 15, 2016, 12 pages (English Translation).
Office Action in Philipines Application No. 1-2007-502319, dated Dec. 16, 2011, 1 page.
Office Action in Philipines Application No. 1-2011-502441 on Oct. 1, 2013, 1 page.
Office Action in Philipines Application No. 1-2011-502441, dated Feb. 19, 2014, 2 pages.
Office Action in Pakistan Application No. 1024/2006, dated Dec. 12, 2007, 3 pages.
Office Action in Pakistan Application No. 1024/2006, dated Feb. 24, 2009, 2 pages.
Office Action in Pakistan Application No. 1024/2006, dated Oct. 21, 2008, 2 pages.
Office Action in Pakistan Application No. 155/2005, dated Nov. 17, 2007, 2 pages.
Office Action in Pakistan Application No. 375/2008, dated Feb. 24, 2009, 1 page.
Office Action in Pakistan Application No. 375/2008, dated Jul. 20, 2009, 2 pages.
Office Action in Pakistan Application No. 375/2008, dated Nov. 6, 2008, 3 pages.
Office Action in Russian Application No. 2006134254, dated Oct. 13, 2006, 4 pages (with English translation).
Office Action in Russian Application No. 2006134254, dated Sep. 18, 2007, 9 pages (with English translation).
Office Action in Russian Application No. 2008110932, dated Dec. 3, 2008, 6 pages (with English translation).
Office Action in Russian Application No. 2012103471, dated May 20, 2014, 5 pages (with English translation).
Office Action in Russian Application No. 2012103471, dated Sep. 16, 2014, 5 pages (with English translation).

(56) References Cited

OTHER PUBLICATIONS

Office Action in Russian Application No. 2013139556, dated Dec. 2, 2013, 6 pages (with English translation).
Office Action in Russian Patent Application No. 2015115397, dated Oct. 26, 2017, 16 pages (English Translation).
Office Action in Russian Patent Application No. 2015148193, dated Dec. 25, 2017, 13 pages (English Translation).
Office Action in Russian Patent Application No. 2015148193, dated Jan. 27, 2016, 4 pages, (English Translation).
Office Action in Russian Patent Application No. 2015148193, dated May 10, 2016, 3 pages (English Translation).
Office Action in Singaporean Patent Application No. 11201706630U, dated Apr. 30, 2018, 8 pages (English Translation).
Office Action in Taiwanese Application No. 095130665, dated Mar. 2, 2012, 8 pages (with English translation).
Office Action in Taiwanese Application No. 100104281, dated Dec. 9, 2014, 13 pages (with English translation).
Office Action in U.S. Appl. No. 11/065,631, dated Feb. 28, 2008, 12 pages.
Office Action in U.S. Appl. No. 11/508,322, dated Dec. 18, 2008, 19 pages.
Office Action in U.S. Appl. No. 11/508,322, dated May 29, 2009, 8 pages.
Office Action in U.S. Appl. No. 11/662,425, dated Feb. 27, 2014, 152 pages.
Office Action in U.S. Appl. No. 11/662,425, dated Jun. 5, 2014, 30 pages.
Office Action in U.S. Appl. No. 11/662,425, dated Sep. 17, 2014, 3 pages.
Office Action in U.S. Appl. No. 11/997,543, dated Mar. 11, 2014, 20 pages.
Office Action in U.S. Appl. No. 12/031,568, dated Aug. 13, 2010, 15 pages.
Office Action in U.S. Appl. No. 12/031,568, dated Feb. 5, 2010, 16 pages.
Office Action in U.S. Appl. No. 12/031,568, dated May 12, 2011, 26 pages.
Office Action in U.S. Appl. No. 12/039,381, dated Jan. 9, 2014, 16 pages.
Office Action in U.S. Appl. No. 12/039,381, dated May 29, 2014, 78 pages.
Office Action in U.S. Appl. No. 12/039,381, dated Sep. 12, 2013, 15 pages.
Office Action in U.S. Appl. No. 12/315,291, dated Jun. 7, 2010, 20 pages.
Office Action in U.S. Appl. No. 12/439,339, dated May 23, 2013, 15 pages.
Rowe, R.C. et al. (ed.), Handbook of Pharmaceutical Excipients, 5th ed. Pharmaceutical Press, London, 2006, pp. 336-343.
Submission Document in Algerian Patent Application No. 120036, dated Feb. 22, 2018, 16 pages (English Translation).
Submission Document in European Patent Application No. 16837150.8, dated Sep. 19, 2018, 2 pages.
Sun et al., "Discovery of 5-[5-Fluoro-2-oxo-1,2- dihydroindol-(3Z)-ylidenemethyl]-2,4- dimethyl-1H-pyrrole-3-carboxylic Acid (2-Diethylaminoethyl)amide, a Novel Tyrosine Kinase Inhibitor Targeting Vascular Endothelial and Platelet-Derived Growth Factor Receptor Tyrosine Kinase," J. Med. Chem. 46, 7, 1116-1119 (2003).
Supplementary European Search Report for Application No. 01976786.2, dated Jul. 6, 2004.
U.S. Office Action for U.S. Appl. No. 12/524,754, issued on Dec. 19, 2011.
Wang, "Drugs of Today, Everolimus in renal cell carcinoma," Journals on the Web, vol. 46, issue 8, (2010), 1 page (abstract only).
Anderson et al., "Preparation of Water-soluble Compounds through Salt Formation." in C.G. Wermuth (Ed.) The Practice of Medicinal Chemistry, Academic Press, 1996.
Herbst and Khuri et al., "Mode of action of docetaxel—a basis for combination with novel anticancer agents," Cancer Treat Rev, 29:407-415, 2003.
Office Action in New Zealand Application No. 566793, dated Dec. 4, 2009, 1 page.
Byers, "What Can Randomized Controlled Trials Tell Us About Nutrition and Cancer Prevention?," CA Cancer Journal Clin., 49(6): 353-361, Nov./Dec. 1999.
Byrn et al., "Pharmaceutical Solids: A Strategic Approach to Regulatory Considerations," Pharmaceutical Research, 1995, 12 (7): 945-954.
Dong et al., "Tumor-associated B7-H1 promotes T-cell apoptosis: A potential mechanism of immune evasion," Nat Med. Aug. 2002; 8 (8): 793-800.
El-Abaseri et al., "Chemoprevention of UV Light-Induced Skin Tumorigenesis by Inhibition of the Epidermal Growth Factor Receptor," Cancer Research, 64, 3958-3965 (2004).
Gao et al., "Overexpression of PD-L1 significantly associates with tumor aggressiveness and postoperative recurrence in human hepatocellular carcinoma", Clinical Cancer Research (2009): 15: 971-979.
Ghebeh et al., "The B7-H1 (PD-L1) T Lymphocyte-Inhibitory Molecule Is Expressed in Breast Cancer Patients with Infiltrating Ductal Carcinoma: Correlation with Important High-Risk Propgnostic Factors," Neoplasia (2006) 8: 190-198.
Ghebeh, "Foxp3+ Tregs and B7-H1+/PD-1+ T lymphocytes co-infiltrate the tumor tissues of high-risk breast cancer patients: Implication for immunotherapy," BMC Cancer (2008) 8:57.
Granziero et al., "Adoptive immunotherapy prevents prostate cancer in transgenic animal model," Eur. J. Immunol., 29: 1127-1138 (Apr. 1999).
Haluska et al., "Genetic alterations in signaling pathways in melanoma," Clin. Cancer Res., 12(7 Suppl): 2301s-2307s (2006).
Hamanishi et al., "Programmed cell death 1 ligand 1 and tumor-infiltrating CD8+ T lymphocytes are prognostic factors of human ovarian cancer," Proceeding of the National Academy of Sciences (2007): 104: 3360-3365.
Hino et al., "Tumor Cell Expression of Programmed Cell Death-1 is a Prognostic Factor for Malignant Melanoma," Cancer (2010): 116: 1757-1766.
Hogaboam et al., "Novel Role of Transmembrane SCF for Mast Cell Activation and Eotaxin Production in Mast Cell-Fibroblast Interactions," J. Immunol., 160: 6166-6171 (1998).
International Search Report in International Patent Application No. PCT/JP2016/074090, dated Nov. 8, 2016, 2 pages (English Translation).
Kim et al., "RET oligonucleotide Microarray for the detection of RET mutations in multiple endocrine neoplasia type 2 syndromes," Clinical Cancer Research 8 (2):457-63 (2002).
Matsui et al., "E7080, a novel multi-targeted tyrosine kinase inhibitor, exhibits anti-angiogenic activity via inhibition of KIT signaling in a small cell lung cancer xenograft model," Eur. J. Cancer, 2(8): 47 (2004).
Motzer et al., "Investigation of novel circulating proteins, germ line single nucleotide polymorphisms, and molecular tumor markers as potential efficacy biomarkers of first-line sunitinib therapy for advanced renal cell carcinoma," Cancer Chemotherapy and Pharmacology, vol. 74 No.4, 739-750 (2014).
Watson et al., "Inhibition of c-Met as a therapeutic strategy for esophageal adenocarcinoma," Neoplasia, 2006, 8 (11): 949-955.
Inman et al., "PD-L1 (B7-H1) expression by urothelial carcinoma of the bladder and BCG-induced granulomata: associations with localized stage progression," Cancer (2007): 109: 1499-1505.
Official Notification in Indian Patent Application No. 201747004829, dated Mar. 20, 2018, including Annexures I-II, 87 pages (English Translation).
Mutschler E et al., "Arzneimittelwirkungen Lehrbuch der Pharmakologie und Toxikologie, "Wissenschaftliche Verlagsgesellschaft, Stuttgart, Germany, 1996, p. 1-p. 5, XP007919509 (English translation).
Notification of the Third Office Action isssued Oct. 30, 2020 in Chinese Patent Application No. 201580042365.3 with an English translation.
Notice of Allowance issued Oct. 21, 2020 in Korean Patent Application No. 10-2015-7032202.
Response to Office Action filed Oct. 7, 2020 in Argentinian Patent Appliction No. P20150102731.

(56) References Cited

OTHER PUBLICATIONS

Request for Continued Examination submitted together with an Information Disclosure Statement on Oct. 20, 2020 in U.S. Appl. No. 15/750,712.
Reply to Office Action filed Oct. 28, 2020 in U.S. Appl. No. 15/748,980.
Response to Second Office Action filed Oct. 13, 2020 in Chinese Patent Application No. 201680046598.5 with English translation.
Reply to Office Action filed Nov. 4, 2020 in U.S. Appl. No. 13/923,858.
Response to Office Action filed Oct. 8, 2020 in Mexican Patent Appliction No. MX/a/2017/010474.
Response to Unfavorable Opinion filed Oct. 20, 2020 in Brazilian Patent Application No. PI0418200-6 with English translation.
Preliminary Amendment filed Oct. 20, 2020 in U.S. Appl. No. 17/022,675.
Emami K H et al, "A small molecule inhibitor of beta-catenin/cyclic AMP response element-binding protein transcription", Proceedings of the National Academy of Sciences, National Academy of Sciences, Aug. 24, 2004 (vol. 101 No. 34), p. 12682-p. 12687, XP002317529.
Extended European Search Report issued Nov. 11, 2020 in European Patent Application No. 18751614.1.
Technical report issued Oct. 28, 2020 in Brazilian Patent Application No. PI0906576-08.
Response to Communication pursuant to Article 94(3) EPC filed Nov. 17, 2020 in European Patent Application No. 19151846.3.
Response filed Nov. 20, 2020 in Chinese Patent Application No. 201680009824.2 with English translation.
Office Action issued Nov. 23, 2020, in Russian Patent Application No. 2018134943.
Notice of Eligibility for Grant issued Nov. 26, 2020, in Singaporean Patent Application No. 11201700855X.
Response to Office Action submitted Oct. 23, 2020, in Mexican Patent Application No. MX/a/2019/006504.
Notice of Allowance issued Nov. 13, 2020, in Mexican Patent Application No. MX/a/2018/001439.
Response to Office Action submitted Dec. 7, 2020, in Chinese Patent Application No. 201680027234.2.
Examination Decision No. 180651 dated Jun. 10, 2019, in Chinese Patent Application No. 201380034056.2.
Response to Office Action submitted Dec. 7, 2020, in Chinese Patent Application No. 201680044979.X.
Notice of Allowance issued Dec. 1, 2020, in Israeli Patent Application No. 255564.
Examination Delay Approval issued Dec. 13, 2020, in Israeli Patent Application No. 253946.
Response submitted Dec. 18, 2020, in European Patent Application No. 18751614.1.
Reply to Office Action filed Dec. 9, 2020, in U.S. Appl. No. 15/934,242.
Response and Request for Delay of Examination submitted Dec. 16, 2020, in Israeli Patent Application No. 270317.
Office Action dispatched Dec. 9, 2020, in Korean Patent Application No. 10-2017-7003226.
Response submitted Dec. 3, 2020, in Mexican Patent Application No. MX/a/2018/012193.
Leonetti, A., et al., "Clinical use of lenvatinib in combination with everolimus for the treatment of advanced renal cell carcinoma," *Therapeutics and Clinical Risk Management*, 2017, 13: 799-806.
Office Action dispatched Dec. 31, 2020, in Indian Patent Application No. 201747040368.
Office Action dispatched Nov. 27, 2020, in Mexican Patent Application No. MX/a/2017/010474.
Office Action dispatched Dec. 14, 2020, in U.S. Appl. No. 13/923,858.
Appeal dated Dec. 16, 2020, in Indian Patent Application No. 7026/CHENP/2013 [Part 1 of 2].
Appeal dated Dec. 16, 2020, in Indian Patent Application No. 7026/CHENP/2013 [Part 2 of 2].
Request for Continued Examination filed Sep. 29, 2020, in U.S. Appl. No. 16/038,710.
Filing of Voluntary Amendments submitted Dec. 16, 2020, in Brazilian Patent Application No. BR112019014127-8.
Response submitted Dec. 25, 2020, in Chinese Patent Application No. 201680027234.2.
Response submitted Dec. 25, 2020, in Russian Patent Application No. 2017139090.
Pre-Grant Opposition Notice dated Dec. 31, 2020, in Indian Patent Application No. 201747040368.
Notification to Grant Patent Right for Invention issued Dec. 31, 2020, in Chinese Patent Application No. 201680046598.5.
Office Action issued Dec. 28, 2020, in Russian Patent Application No. 2019120680.
Office Action issued Dec. 28, 2020, in Jordanian Patent Application No. 203/2015.
Hearing Notice dated Jan. 4, 2021, in Indian Patent Application No. 2371/CHENP/2012.
Office Action issued Jan. 5, 2021, in Jordanian Patent Application No. 225/2020.
Extended European Search Report dated Jan. 20, 2021, in European Patent Application No. 18801285.0.
Examination Report dispatched Jan. 19, 2021, in Indian Patent Application No. 201947022655.
Notice of Allowance dated Jan. 13, 2021, in U.S. Appl. No. 15/750,712.
Notice of Allowance dated Jan. 6, 2021, in U.S. Appl. No. 16/038,710.
Specification submitted Jan. 10, 2021, in Jordanian Patent Application No. 225/2020.
Response submitted Jan. 27, 2021, in Indian Patent Application No. 1511/CHENP/2009.
Response submitted Jan. 25, 2021, in Mexican Patent Application No. MX/a/2017/010474.
Office Action dispatched Jan. 19, 2021, in Brazilian Patent Application No. BR112012032462- 4.
Office Action dated Jan. 26, 2021, in U.S. Appl. No. 15/934,242.
Notice of Allowance dispatched Jan. 28, 2021, in Chinese Patent Application No. 201680027234.2.
Response submitted Jan. 20, 2021, in European Patent Application No. 16837135.9.
Ueno, M., et al., "Phase 2 study of lenvatinib monotherapy as second-line treatment in unresectable biliary tract cancer: primary analysis results," *BMC Cancer*, 2020, 20: 1105.
Rejection Decision dispatched Jan. 12, 2021, in Chinese Patent Application No. 201680009824.2.
Specification submitted Jan. 11, 2021, in Singaporean Patent Application No. 10202100272R.
Notice of Allowance dispatched Jan. 26, 2021, in Taiwanese Patent Application No. 104127982.
Response submitted Jan. 28, 2021, in Indian Patent Application No. 2371/CHENP/2012.
Notice of Intention to Refuse Patent Application dispatched Feb. 8, 2021, in Singaporean Patent Application No. 11201706630U.
Response to Official Action submitted Feb. 8, 2021, in Canadian Patent Application No. 2,957,005.
Hearing Notice dispatched Feb. 1, 2021, in Indian Patent Application No. 1511/CHENP/2009.
Notice of Allowance dispatched Jan. 13, 2021, in Mexican Patent Application No. MX/a/2019/006504.
Notice of Allowance dispatched Feb. 11, 2021, in European Patent Application No. 16837150.8.
Decision to Grant dispatched Jan. 25, 2021, in Russian Patent Application No. 2017139090.
Office Action dispatched Dec. 15, 2020, in Thailand Patent Application No. 0401005163.
Notice of Reasons for Rejection dispatched Dec. 15, 2020, in Japanese Patent Application No. 2017-535551.
Takahashi, H., et al., "Axitinib (AG-013736), an Oral Specific VEGFR TKI, Shows Potential Therapeutic Utility Against Cholangiocarcinoma," *Jpn. J. Clin. Oncol.*, 2014, 44(6): 570-578.
Sugiyama, H., et al., "Potent in vitro and in vivo antitumor activity of sorafenib against human intrahepatic cholangiocarcinoma cells," *J. Gastroenterol.*, 2011, 46(6): 779-789.

(56) References Cited

OTHER PUBLICATIONS

Kondo, T., "Molecular Target Drugs for Renal Cell Carcinoma—Angiogenesis Inhibitor: The role of VEGFR-TKIs in the treatment of renal cell carcinoma," *Jpn. J. Nephrol.*, 2012, 54(5): 574-580.
Notice of Reasons for Rejection dispatched Feb. 2, 2021, in Japanese Patent Application No. 2018-552092.
Supportive Data to the Technical Examination dispatched Jan. 26, 2021, in Brazilian Patent Application No. PI0418200-6.
Examination Report dated Feb. 3, 2021, in Australian Patent Application No. 2016309356.
Response submitted Mar. 2, 2021, in Australian Patent Application No. 2016224583.
Extended European Search Report dated Mar. 10, 2021, in European Patent Application No. 20207489.4.
Office Action dated Jan. 27, 2021, in Israeli Patent Application No. 257292.
Office Action dated Feb. 22, 2021, in U.S. Appl. No. 16/609,895.
Examination Report dispatched Jan. 26, 2021, in GCC Patent Application No. GC2015-40053.
Search Report and Opinion dated Jan. 21, 2021, in Brazilian Patent Application No. BR112012032462-4.
Examination Report dated Feb. 2, 2021, in Australian Patent Application No. 2016308390.
Office Action dispatched Feb. 8, 2021, in Mexican Patent Application No. MX/a/2017/014540.
Office Action dated Mar. 16, 2021, in European Patent Application No. 17782552.8.
Response submitted Mar. 12, 2021, in Chinese Patent Application No. 201580042365.3.
Amendment submitted Mar. 17, 2021, in Australian Patent Application No. 2017249459.
Safety Data Sheet of Phenyl Chloroformate manufactured by Kanto Chemical Co., Inc., issued Oct. 9, 2003 (revised Jun. 11, 2014).
Safety Data Sheet of Phenyl Chloroformate manufactured by TCI America, revised Aug. 18, 2015.
Jacquemard, U., et al., "Mild and selective deprotection of carbamates with Bu4NF," *Tetrahedron*, 2004, 60(44): 10039-10047.
Luo, W., et al., "Synthesis and evaluation in vitro of 1-[2-(10-dihydroartemisininoxy) ethyl]-3-phenylurea derivatives as potential agents against cancer," *Med. Chem. Res.*, 2013, 22: 3170-3176.
Office Action dated Mar. 22, 2021, in U.S. Appl. No. 16/809,301.
Office Action dated Feb. 23, 2021, in Mexican Patent Application No. MX/a/2018/012193.
International Search Report and Written Opinion dispatched Feb. 12, 2021, in International Patent Application No. PCT/US2020/057650.
Written Submission dated Mar. 18, 2021, in Indian Patent Application No. 1511/CHENP/2009.
Reply Statement dated Apr. 1, 2021, in Indian Patent Application No. 201747040368.
Finn, R., et al., "Phase I study investigating everolimus combined with sorafenib in patients with advanced hepatocellular carcinoma," *J. Hepatol.*, 2013, 59: 1271-1277.
Notice of Reasons for Rejection dispatched Mar. 23, 2021, in Japanese Patent Application No. 2017-546075.
Reply to Office Action filed Mar. 31, 2021, in U.S. Appl. No. 16/092,245.
Office Action dispatched Mar. 25, 2021, in Chinese Patent Application No. 201680044979.X.
Request for Continued Examination filed Apr. 1, 2021, in U.S. Appl. No. 16/038,710.
Office Action dated Apr. 2, 2021, in U.S. Appl. No. 15/748,980.
Response submitted Mar. 17, 2021, in Russian Patent Application No. 2019120680.
Response submitted Apr. 16, 2021, in Indian Patent Application No. 201947022655.
Office Action dispatched Apr. 9, 2021, in Canadian Patent Application No. 2,957,005.
Notice of Allowance dated Mar. 2, 2021, in Mexican Patent Application No. MX/a/2018/001658.
Examination Report dated Mar. 30, 2021, in Australian Patent Application No. 2016224583.
Response submitted Apr. 22, 2021, in GCC Patent Application No. GC2015-40053.
Response submitted Apr. 27, 2021, in Australian Patent Application No. 2016309356.
Request for Continued Examination filed Apr. 9, 2021, in U.S. Appl. No. 15/750,712.
Response submitted Apr. 15, 2021, in Mexican Patent Application No. MX/a/2017/014540.
Finn, R., et al., "Phase Ib Study of Lenvatinib Plus Pembrolizumab in Patients With Unresectable Hepatocellular Carcinoma," *J. Clin. Oncol.*, 2020, 38(26): 2960-2970.
Dierks, C., et al., "Combination of Lenvatinib and Pembrolizumab Is an Effective Treatment Option for Anaplastic and Poorly Differentiated Thyroid Carcinoma," *Thyroid*, 2021. doi:10.1089/thy.2020.0322.
Motzer, R., et al., "Lenvatinib plus Pembrolizumab or Everolimus for Advanced Renal Cell Carcinoma," *N. Engl. J. Med.*, 2021, 384(14): 1289-1300.
Chen, T.-H., et al., "Combination of pembrolizumab and lenvatinib is a potential treatment option for heavily pretreated recurrent and metastatic head and neck cancer," *J. Chin. Med. Assoc.*, 2021, 84(4): 361-367.
Mo, D.-C., et al., "Safety and efficacy of pembrolizumab plus lenvatinib versus pembrolizumab and lenvatinib monotherapies in cancers: A systematic review," *Int. Immunopharmacol.*, 2021, 91: 107281. doi:10.1016/j.intimp.2020.107281.
Taylor, M., et al., "The LEAP program: lenvatinib plus pembrolizumab for the treatment of advanced solid tumors," *Future Oncol.*, 2021, 17(6): 637-647.
Official Letter issued Apr. 13, 2021 in Egyptian Patent Application No. PCT 283/2012 with an English translation (10 pages).
Official Letter issued Apr. 28, 2021 in Mexican Patent Application No. MX/a/2017/014540 with an English translation, 4 pages.
Official Letter issued Jun. 16, 2021 in Singapore Patent Application No. 11201801083U with an English Translation, 6 pages.
Official Letter issued Jun. 2, 2021 in Chinese Patent Application No. 201580042365 with an English translation, 4 pages.
Official Letter issued Jun. 8, 2021 in Indian Patent Application No. 201947044328 with an English translation, 7 pages.
Official Letter issued May 18, 2021 in Brazilian Patent Application No. BR112012032462 with an English translation, 11 pages.
Official Letter issued May 20, 2021 in Australian Patent Application No. 2016224583, 3 pages.
Official Letter mailed Aug. 16, 2021 in Singapore Patent Application No. 11201801083U.
Official Letter mailed Aug. 18, 2021 in Korean Patent Application No. 10-2017-7003226 with English translation.
Official Letter mailed Aug. 18, 2021 in Mexican Patent Application No. MX/a/2018/012193 (w/ English translation).
Official Letter mailed Aug. 18, 2021 in U.S. Appl. No. 17/228,025.
Official Letter mailed Aug. 20, 2021 in Russian Patent Application No. 2019134940 with an English translation.
Official Letter mailed Aug. 20, 2021 in U.S. Appl. No. 17/022,675.
Official Letter mailed Aug. 26, 2021 in U.S. Appl. No. 15/750,712.
Official Letter mailed Aug. 3, 2021 in Canadian Patent Application No. 2957005.
Official Letter mailed Aug. 3, 2021 in Japanese Patent Application No. P2017-535551 with an English translation.
Official Letter mailed Aug. 31, 2021 in Japanese Patent Application No. P2017-546075 with an English translation.
Official Letter mailed Aug. 6, 2021 in European Patent Application No. 19151846.3.
Official Letter mailed Aug. 8, 2021 in Egyptian Patent Application No. PCT 283/2012 (w/English translation).
Official Letter mailed Dec. 17, 2020 in Australian Patent Application No. 2015384801.
Official Letter mailed Jul. 1, 2021 in U.S. Appl. No. 16/038,710.
Official Letter mailed Jul. 29, 2021 in Chinese Patent Application No. 201880005026.1 with English translation.
Official Letter mailed Jul. 6, 2021 in Mexican Patent Application No. MX/a/2019/013014 with an English translation.

(56) References Cited

OTHER PUBLICATIONS

Official Letter mailed Jun. 10, 2021 in Australian Patent Application No. 2016309356.
Official Letter mailed Jun. 14, 2021 in Mexican Patent Application No. MX/a/2017/010474 with an English translation.
Official Letter mailed Jun. 2, 2021 in Australian Patent Application No. 2016308390, 3 pages.
Official Letter mailed Jun. 20, 2021 in Gulf Cooperation Council Patent Application No. GC2015-40053 with an English translation.
Official Letter mailed Jun. 21, 2021 in Australian Patent Application No. 2016273230, 4 pages.
Official Letter mailed Jun. 24, 2021 in Korean Patent Application No. 10-2017-7003226 with English translation, 12 pages.
Official Letter mailed Jun. 24, 2021 in U.S. Appl. No. 17/228,025, 3 pages.
Official Letter mailed Jun. 25, 2021 in U.S. Appl. No. 16/092,245, 30 pages.
Official Letter mailed Jun. 28, 2021 in Singapore Patent Application No. 11201709335X, 7 pages.
Official Letter mailed Jun. 8, 2021 in U.S. Appl. No. 15/554,577.
Official Letter mailed May 27, 2021 in Mexican Patent Application No. MX/a/2017/001980 with English translation, 7 pages.
Official Letter mailed Sep. 1, 2021 in U.S. Appl. No. 17/407,742.
Official Letter mailed Sep. 13, 2021 in U.S. Appl. No. 16/809,301.
Official Letter mailed Sep. 16, 2021 in U.S. Appl. No. 16/465,277.
Official Letter mailed Sep. 22, 2021 in U.S. Appl. No. 17/022,675.
Official Letter mailed Sep. 29, 2021 in Indian Patent Application No. 201747040368.
Official Letter mailed Sep. 30, 2021 in Singapore Patent Application No. 11201904020S.
Positive topline results of large phase 3 trial show Eisai's lenvatinib meets primary endpoint in unresectable hepatocellular carcinoma. Press Release [online]. Eisai Inc., Jan. 25, 2017. Retrieved from the internet: <URL: eisai.mediaroom.com/2017-01-25-Positive-Topline-Results-of-Large-Phase-3-Trial-Show-Eisais-Lenvatinib-Meets-Primary-Endpoint-in-Unresectable-Hepatocellular-Carcinoma>.
Submission Documents filed Aug. 12, 2021 in Brazilian Patent Application No. BR112012032462-4.
Submission Documents filed Aug. 20, 2021 in U.S. Appl. No. 16/609,895.
Submission Documents filed Aug. 3, 2021 in Singapore Patent Application No. 11201801083U.
Submission Documents filed Aug. 4, 2021 in Thai Patent Application No. 0401005163 with an English translation.
Submission documents filed Jul. 1, 2021 in Mexican Patent Application No. MX/a/2018/012193 with an English translation.
Submission documents filed Jul. 1, 2021 in Singapore Patent Application No. 11201904020S with English translation, 13 pages.
Submission documents filed Jul. 20, 2021 in U.S. Appl. No. 15/934,242.
Submission Documents filed Jul. 26, 2021 in Korean Patent Application No. 10-2017-7003226 with English translation.
Submission Documents filed Jul. 26, 2021 in U.S. Appl. No. 15/750,712.
Submission Documents filed Jul. 30, 2021 in Mexican Patent Application No. MX/a/2017/001980 with English translation.
Submission documents filed Jul. 9, 2021 in U.S. Appl. No. 16/038,710.
Submission documents filed Jun. 11, 2021 in Mexican Patent Application No. MX/a/2017/010474 with an English translation, 25 pages.
Submission documents filed Jun. 14, 2021 in Brazilian Patent Application No. PI0418200-6 with an English translation.
Submission documents filed Jun. 14, 2021 in U.S. Appl. No. 13/923,858, 7 pages.
Submission documents filed Jun. 15, 2021 in U.S. Appl. No. 17/228,025, 10 pages.
Submission documents filed Jun. 22, 2021 in U.S. Appl. No. 16/809,301.
Submission documents filed Jun. 28, 2021 in Egyptian Patent Application No. PCT 283/2012 with English translation, 3 pages.
Submission Documents filed May 24, 2021 in U.S. Appl. No. 15/554,577, 15 pages.
Submission Documents filed Sep. 23, 2021 in Singapore Patent Application No. 11201709335X.
Submission documents filed Sep. 3, 2021 in U.S. Appl. No. 17/022,675.
Submission Documents filed Sep. 6, 2021 in European Patent Application No. 16755489.8.
Communication pursuant to Article 94(3) EPC issued May 10, 2021 in European Patent Application No. 16 837 135.9.
Notice of Allowance issued Apr. 26, 2021 in U.S. Appl. No. 16/465,277.
Decision on Request to Participate in the Patent Prosecution Highway Program and Petiton to Make Special Under 37 C.F.R. 1.102(a) issued Jun. 4, 2021 in U.S. Appl. No. 17/228,025.
Request for Examination submitted May 6, 2021 in Korean Patent Application No. 10-2019-7032983.
Final Rejection issued May 11, 2021 in Japanese Patent Application No. 2018-552092 (5 pages) with an English translation (5 pages).
Official Letter dated May 18, 2021 in Canadian Patent Application No. 2,912,219.
Notice of Allowance mailed Apr. 30, 2021 in U.S. Appl. No. 15/750,712.
Communication pursuant to Article 94(3) EPC dated May 14, 2021 is European Patent Application No. 16 755 489.8.
Office Action issued May 13, 2021 in U.S. Appl. No. 15/573,197.
Response to Official Action dated May 12, 2021 in Canadian Patent Application No. 2,957,005.
Technical Examination Report and Opinion issued Apr. 27, 2021 in Brazilian Patent Application No. PI 0418200-6 (13 pages) with an English translation (16 pages).
Response to Examiner's Report dated May 11, 2021 in Australian Patent Application No. 2016308390.
Decision to Grant issued May 12, 2021 in Russian Patent Application No. 2019120680 (7 pages) with an English translation (6 pages).
Response and Supplementary Amendment after Third Office Action dated Apr. 27, 2021 in Chinese Patent Application No. 201580042 1365.3 (11 pages) with a English translation (11 pages).
Reply to Preliminary Office Action dated Apr. 16, 2021 in Brazilian Patent Application No. 112012032462-4 (16 pages) with an English translation (13 pages).
Response to an Examiner's Report dated May 11, 2021 in Australian Patent Application No. 2016224583.
Applicant's Observations dated Apr. 29, 2021 in Israeli Patent Application No., 257292 (1 page) with an English translation (5 pages).
Invitation to Response to Written Opinion (Supplementary Examination) dated May 19, 2021 in Singapore Patent Application No. 11201904020S.
Result of Substantive Examination dated Apr. 16, 2021 in Mexican Patent Application No. MX/a/2017/010474 (5 pages) with an English translation (5 pages).
Form 13 submitted May 10, 2021 in Indian Patent Application No. 201947044328.
Voluntary Amendments filed Apr. 28, 2021 in Brazilian Patent Application No. 11 2019 023064 5 (90 pages) with an English translation (58 pages).
"A Phase 1 Study of BMS-936558 Plus Sunitinib or Pazopanib in Subjects With Metastatic Renal Cell Carcinoma," ClinicalTrials.gov archive, Nov. 15, 2011, 4 pages.
"A Phase I/II Study to Assess the Safety and Efficacy of Pazopanib and MK 3475 in Subjects With Advanced Renal Cell Carcinoma," ClinicalTrials.gov archive, 8 pages, (Dec. 17, 2013).
"In 2572/CHENP/2006", Jun. 8, 2007, 74 pages (English Translation).
"Patent Term Extension document filed before the USPTO for the U.S. Pat. No. 7,253,286," Apr. 8, 2015, 89 pages.
[No Author Listed], "Contents of GTIs (Genotoxic impurities): Compound (A-1) and Compound (I) in the methane sulfonate of Compound (IV) using synthetic methods disclosed in PTL 2-4," Eisai, Nov. 1, 2018, 2 pages.
Amended Claims in Brazilian Application No. BR112012003592-4, dated Oct. 23, 2014, 12 pages, with English translation.

(56) References Cited

OTHER PUBLICATIONS

Amendment and RCE submission documents filed in U.S. Appl. No. 12/039,381, dated Oct. 23, 2013, 13 pages.
Amendment dated Jun. 22, 2010 in Chinese Application No. 200710007097.9, with English translation.
Amendment dated Nov. 19, 2009 in Chinese Application No. 200710007097.9, with English translation.
Amendment dated Sep. 23, 2009 in Chinese Application No. 200580026468.7, with English translation.
Amendment in Australian Application No. 2007289787, dated Apr. 7, 2009, 16 pages.
Amendment in Bangladesh Application No. 184/2006, dated May 6, 2008, 3 pages.
Amendment in European Application No. 05719973.9, dated Oct. 30, 2006, 2 pages.
Amendment in Japanese Application No. P2009-510543, dated Nov. 9, 2009, 25 pages, with English translation.
Amendment submitted Jan. 31, 2020, in Singaporean Patent Application No. 11201904020S.
Antibodies: A Laboratory Manual, E. Harlow and D. Lane, ed. Cold Spring Harbor Laboratory (Cold Spring Harbour, NY, 1988), 190 pages.
Argument Brief filed on Mar. 6, 2006 for KR Application No. 10-2003-7005506 (with English translation).
Argument Brief in KR Application No. 10-2007-7026886, dated Oct. 27, 2009, 7 pages (with English translation).
Argument filed on Apr. 19, 2005 for JP Application No. 2002-536056 (with English translation).
Argument filed on Aug. 13, 2013 in JP Application No. 2009-540099, 10 pages (with English translation).
Argument filed on May 21, 2009 for JP Application No. 2005-124034 (with English translation).
Australian Office Action for Application No. 2006309551 issued on Feb. 2, 2012.
Australian Second Statement of Proposed Amendments in Application No. 2011270165, dated Dec. 4, 2015, 5 pages.
Australian Voluntary Amendment Submitted in Application No. 2010285740, dated Nov. 20, 2015, 11 pages.
Bankston et al., "A Scaleable synthesis of BAY 43-9006: A Potent Raf Kinase Inhibitor for the Treatment of Cancer", Organic Process Res Dev., 6:777-81 (2002).
Canadian Office Action in Application No. 2828496, dated Nov. 30, 2015, 4 pages.
Decision of Final Rejection issued in CN Application No. 200780017371.9, dated Jul. 3, 2013, 16 pages (with English translation).
Eisai Public Relations Department: "Eisai and Merck Enter Collaboration to Explore Novel Combination Regimens of Anti-PD-1 Therapy with Multi-targeting RTK Inhibitor and Microtubule Dynamics in Multiple Types of Cancer," Mar. 4, 2015 URL:http//www.eisai.com/news/news201518.html.
Formality Requirement dated Jun. 18, 2003 for PH Application No. 1-2003-500266.
Glen et al., "Correlative Analyses of Serum Biomarkers and Clinical Outcomes in the Phase 2 Study of Lenvatinib, Everolimus, and the Combination, in Patients With a Metastatic Renal Cell Carcinoma Following 1 VEGF-Targeted Therapy", Poster presentation at 18th ECCO—40th ESMO European Cancer Congress, Vienna, Sep. 25-29, 2015.
Gould, "Salt Selection for Basic Drugs," International Journal of Pharmaceutics, 33:201-217, (1986) (XP025813036).
International Preliminary Report on Patentability for Application No. PCT/JP2012/057949, dated Oct. 10, 2013, 7 pages.
International Preliminary Report on Patentability in International Application No. PCT/JP2017/015461, dated Oct. 25, 2018, 8 pages [English Translation].
International Preliminary Report on Patentability in International Patent Application No. PCT/JP2015/073946, dated Mar. 9, 2017, 8 pages (English Translation).
International Preliminary Report on Patentability in International Patent Application No. PCT/JP2016/074090, dated Mar. 1, 2018, 6 pages (English Translation).
International Preliminary Report on Patentability in PCT Application No. PCT/US2012/040183, dated Apr. 3, 2014, 9 pages.
International Search Report and International Preliminary Report on Patentability for PCT Application No. PCT/JP2011/064430, Sep. 13, 2011, 8 pages.
International Search Report and Written Opinion mailed Apr. 28, 2016 in PCT/US2016/020734.
International Search Report for Application No. PCT/JP2004/003087, issued on Jul. 13, 2004.
International Search Report in International Application No. PCT/JP2013/084052, dated Mar. 4, 2014, 2 pages.
International Search Report in International Patent Application No. PCT/JP2015/073946, dated Dec. 1, 2015, 3 pages.
International Search Report in International Patent Application No. PCT/JP2016/002562, dated Aug. 9, 2016, 2 pages (English Translation).
International Search Report mailed May 18, 2016 for PCT/US2016/020747.
Israel Appl. No. 195282 IDS List filed on Jul. 1, 2010, 3 pages.
Israel Office Action directed at Appl. No. 205512 issued on Nov. 13, 2011, 4 pages with English translation.
Israeli Response to Office Action in Application No. 217197, dated Dec. 24, 2015, 6 pages.
Japanese Allowance for Application No. P2005-515330, issued on Apr. 21, 2009.
Japanese Office Action dated Jun. 19, 2018 for Application No. P2016-214593, 7 pages (with English translation).
Kato et al., "Effects of lenvatinib on tumor-associated macrophages enhance antitumor activity of PD-1 signal Inhibitors," Molecular Targets and Cancer Therapeutics, Abstract A92, Nov. 6, 2015, 1 page.
Korean Office Action for Application No. 10-2009-7005657, issued on Sep. 30, 2013, 27 pages (with English translation).
Leukemias, Hematology, and Oncology, http://www.merkmanuals.com/professional/print/sec11/ch142a.html Mar. 16, 2011, 5 pages.
Mexican Office Action in Application No. MX/a/2012/014776, dated Mar. 18, 2015, 3 pages, with English translation.
Motzer et al., "Randomized phase 2 three-arm trial of lenvatinib (LEN), everolimus (EVE), and LEN+EVE in patients (pts) with metastatic renal cell carcinoma (mRCC)," Oral presentation at ASCO Annual Meeting, Chicago, May 29-Jun. 2, 2015.
Motzer et al., "Randomized phase II, three-arm trial of lenvatinib (LEN), everolimus (EVE), and LEN+EVE in patients pts) with metastatic renal cell carcinoma (mRCC)," Journal of Clinical Oncology, May 20, 2015, vol. 33, Issue 15S, p. 248.
Norwegian Office Action in Application No. 20063383, dated Apr. 15, 2015, 2 pages, with English translation.
Norwegian Submission Documents in Application No. 20063383, dated Jun. 19, 2015, 8 pages, with English translation.
Notice of Allowance for Japanese Application No. P2008-532141, dated Sep. 10, 2013, 5 pages (with English translation).
Notice of Allowance for U.S. Appl. No. 12/524,754 dated Oct. 9, 2012, 8 pages.
Notice of Allowance for U.S. Appl. No. 13/083,338, dated Jun. 4, 2013, 57 pages.
Notice of Allowance for U.S. Appl. No. 13/205,328, dated Jun. 10, 2013, 58 pages.
Notice of Allowance in U.S. Appl. No. 11/892,785, dated Apr. 5, 2010, 23 pages.
Notice of Allowance in U.S. Appl. No. 11/065,631, dated Jan. 2, 2009, 6 pages.
Notice of Allowance in U.S. Appl. No. 11/065,631, dated Sep. 9, 2008, 10 pages.
Notice of Allowance in U.S. Appl. No. 11/508,322, dated Sep. 15, 2009, 6 pages.
Notice of Allowance in U.S. Appl. No. 11/662,425, dated Oct. 21, 2014, 49 pages.
Notice of Allowance in U.S. Appl. No. 14/890,207, dated Nov. 21, 2018, 12 pages.

(56) References Cited

OTHER PUBLICATIONS

Notice of Allowance in U.S. Appl. No. 15/503,108, dated Apr. 11, 2018, 7 pages.
Notice of Allowance in U.S. Appl. No. 15/503,108, dated Dec. 12, 2018, 8 pages.
Notice of Allowance issued in Chinese Application No. 200880115011.7, dated Aug. 5, 2013, 4 pages (with English translation).
Notice of Allowance issued in U.S. Appl. No. 12/524,754, dated Jul. 19, 2013, 11 pages.
Notice of decision for patent dated Apr. 17, 2006 for Korean Application No. 10-2005-7020292, (with English translation).
Office Action in Bangladeshis Application No. 184/2006, dated May 11, 2007, 2 pages.
Office Action in Canadian Application No. 2704000, dated Nov. 4, 2014, 3 pages.
Office Action in Chinese Application No. 200680020317.5, dated Nov. 28, 2013, 8 pages (with English translation).
Office Action in Chinese Application No. 200680021939.X, dated Mar. 30, 2011, 7 pages (with English translation).
Office Action in Chinese Patent Application No. 201510031628.2, dated Apr. 5, 2017, 8 pages (English Translation).
Office Action in Chilean Application No. 2012-00412, dated Sep. 3, 2014, 22 pages (with English translation).
Office Action in European Patent Application No. 12774278.1, dated Mar. 9, 2015, 6 pages.
Office Action in Indonesian App. Ser No. W-00 2008 00601, dated Jan. 13, 2012, 4 pages (with English translation).
Office Action in Indian Application No. 1424/CHENP/2008, dated Sep. 19, 2011, 18 pages, with an English translation.
Office Action in Indian Application No. 1908/DELNP/2008, dated Feb. 2, 2012, with an English translation.
Office Action in Israeli Patent Application No. 250454, dated Feb. 11, 2018, 4 pages (English Translation).
Office Action in Japanese Application No. P2009-551518, dated Jun. 18, 2013, 5 pages (with English translation).
Office Action in Mexican Application No. MX/a/2012/014776, dated Apr. 4, 2014, 22 pages (with English Translation).
Office Action in Mexican Application No. MX/a/2012/014776, dated Oct. 15, 2014, 15 pages (with English translation).
Office Action in Mexican Application No. MX/a/2013/009931, dated Sep. 5, 2014, 15 pages (with English translation).
Office Action in Pakistan Patent Application No. 548/2015, dated Oct. 18, 2017, 2 pages (English Abstract).
Office Action in U.S. Appl. No. 12/315,291, dated Jan. 12, 2011, 9 pages.
Office Action in U.S. Appl. No. 14/890,207, dated Jun. 30, 2017, 9 pages.
Office Action in U.S. Appl. No. 15/503,108, dated May 11, 2018, 115 pages.
Office Action in U.S. Appl. No. 15/550,124, dated Jan. 26, 2018, 12 pages.
Office Action in Vietnamese Application No. 1-2008-00723, dated Mar. 11, 2010, 4 pages (with English translation).
Official Letter re Granting Patent in European Application No. 06796594.7, dated Sep. 25, 2012, 270 pages.
Official Letter re invitation to declare maintenance in European Application No. 07805959.9, dated Dec. 3, 2010, 1 page.
Official Letter re invitation to declare maintenance in European Application No. 08711837.8, dated Apr. 14, 2011, 1 page.
Official Letter re invitation to declare maintenance in European Application No. 09713617.0, dated May 17, 2011, 5 pages.
Official Notification in Indian Patent Application No. 1511/CHENP/2009, dated Nov. 26, 2018, with Exhibits, 921 pages.
Official Notification in Indian Patent Application No. 2793/CHENP/2013, dated Mar. 19, 2018, 2 pages (English Translation).
Official Notification in Jordan Patent Application No. 55/2011, dated Feb. 12, 2018, 2 pages (English Translation).
Official Notification re Interview Summary in U.S. Appl. No. 13/805,826, dated Dec. 1, 2014, 3 pages.
Oya, "mTOR inhibitors," Nippon Rinsho, 68 (6): 1067-1072 (2010).
Peruvian Submission Documents in Application No. 2081-2011, dated May 27, 2016, 20 pages.
Preliminary Amendment filed on Dec. 2, 2005 for U.S. Appl. No. 11/293,785.
Registry's Letter in Malta Application No. 3723, dated Oct. 29, 2007, 1 page.
Reply to Non-Final Office Action mailed Nov. 20, 2018, filed Feb. 8, 2019 in U.S. Appl. No. 16/038,710.
Reply to Non-Final Office Action mailed Oct. 4, 2018, filed Jan. 2, 2019 in U.S. Appl. No. 13/923,858.
Reply to Notice of Allowance in U.S. Appl. No. 11/662,425, dated Jan. 20, 2015, 5 pages.
Response filed on Dec. 4, 2007 for IL Application No. 155447 (with English translation).
Response filed on Jan. 26, 2010 for CN Application No. 200710007097.9 (with English translation).
Response filed on Jul. 2, 2009 for CN Application No. 200710007097.9 (with English translation).
Response filed on Sep. 10, 2007 for Norwegian Application No. 20031731 (with English translation).
Response in U.S. Appl. No. 13/923,858 dated Oct. 3, 2017, 29 pages.
Response to Canadian Office Action filed on Apr. 12, 2011 for corresponding CA Application No. 2,620,594, 4 pages.
Response to Canadian Office Action filed on Apr. 26, 2011 for corresponding CA Application No. 2,620,594.
Response to Chinese Office Action for CN 200680020317.5 dated Sep. 11, 2012, 7 pages with English translation.
Response to Examiner's Substantive Report in CL Application No. 2012-00412, dated Nov. 28, 2014, 39 pages (with English translation).
Response to IL OA for IL 195282 filed on May 28, 2012, 5 pages.
Response to Israeli Office Action filed on Sep. 7, 2010 for the corresponding Israeli Application No. 189589.
Response to Japanese Office Action filed on Jan. 9, 2013 for corresponding Japanese Application JP-2007-533350.
Response to Office Action for CA Application No. 2661702, filed Jul. 16, 2013, 13 pages.
Response to Office Action for EP Application No. 0870437.6, dated Jan. 2, 2013, 22 pages.
Response to Office Action in IL Application No. 197002, dated Feb. 29, 2012, 7 pages (with English translation).
Response to Office Action in MX Application No. MX/a/2010/008187, dated Feb. 17, 2014, 7 pages (with English translation).
Response to Office Action in MX Application No. MX/a/2010/008187, dated Jun. 25, 2014, 5 pages (with English translation).
Response to Restriction Requirement in U.S. Appl. No. 11/892,785, dated Oct. 30, 2009, 19 pages.
Restriction Requirement mailed Jan. 11, 2019, filed Feb. 25, 2019 in U.S. Appl. No. 15/750,712.
Russian Office Action in Application No. 2012158142, dated Feb. 12, 2015, 21 pages, with English translation.
Russian Office Action in Application No. 2013140169, dated Nov. 6, 2015, 10 pages, with English translation.
Russian Response to Office Action directed at Appl. No. 2008149948115(065561) filed on Jul. 27, 2011, 14 pages with English translation.
Russian Response to Office Action in Application No. 2012158142, dated Apr. 13, 2015, with English translation.
Sonpavde G., et al., "Fibroblast growth factor receptors as therapeutic targets in clear-cell renal cell carcinoma," Expert Opinion on Investigational Drugs, vol. 23, No. 3, 305-315 (2014).
Stahl et al., "Handbook of Pharmaceutical Salts, Properties, Selection and Use," Publisher—Wiley-VCH-2002, Chapters 5, 6, 7 and 8, 2002, 110 pages.
Stahl, "Preparation of water-soluble compounds through salt formation," edited by Camille G. Wermuth, The Practice of Medicinal Chemistry Second Edition, 2003, 601-605.
Submission Document in Chinese Patent Application No. 201510031628.2, dated Feb. 27, 2018, 7 pages (English Translation).

(56) References Cited

OTHER PUBLICATIONS

Submission Document in Chinese Patent Application No. 201510031628.2, dated Oct. 10, 2018, 8 pages (English Translation).
Submission Document in Indian Patent Application No. 2371/CHENP/2012, dated Nov. 7, 2018, 10 pages.
Submission Document in Indian Patent Application No. 2793/CHENP/2013, dated Mar. 8, 2018, 1 page (English Translation).
Submission Document in Israeli Patent Application No. 255564, dated Dec. 10, 2018, 4 pages.
Submission Document in MY Application No. PI2011700172, dated Nov. 4, 2014, 3 pages.
Submission Document in U.S. Appl. No. 14/890,207, dated Sep. 21, 2018, 41 pages.
Submission Document in U.S. Appl. No. 15/503,108, dated Apr. 17, 2018, 5 pages.
Submission Document in U.S. Appl. No. 15/503,108, dated Nov. 28, 2018, 25 pages.
Submission Document re figures in AR Application No. P110100513, dated Oct. 22, 2014, 3 pages.
Submission Document re Petition on Oct. 2, 2013 in CL Application No. 2012-00412, 22 pages (with English translation).
Submission Documents Before the Patent Office for GC Patent Application No. GC2011-17812, dated Oct. 24, 2018, 16 pages (with an English Translation).
Submission Documents Before the Patent Office for U.S. Appl. No. 12/741,682, dated May 17, 2013, 16 pages.
Submission documents re RCE filed in U.S. Appl. No. 11/997,719, dated Dec. 11, 2013, 18 pages.
Submission of Document Before the Patent Office re Request for Voluntary Amendments dated Jan. 30, 2013 for NZ Application No. 598291, 8 pages.
Submission of Documents before the Patent Office for CN Application No. 200880115011.7, dated Apr. 11, 2013, 10 pages (with English translation).
Suzuki et al., "MP-412, a dual EGFR/HER2 tyrosine kinase inhibitor: 1. In vivo kinase inhibition profiled," Am. Assoc. Cancer Research, A3405, 2005, 2 pages.
Tahara et al., "Lenvatinib in Radioactive Iodine-refractory Differentiated Thyroid Cancer: Results of the Phase 3 trial (SELECT trial),"01-18-1, Abstract and Presentation Document, 12th Annual Meeting of Japanese Society of Medical Oncology, Jul. 17, 2014, 24 pages.
Tahara et al., "Presentation slides at European Society for Medical Oncology (ESMO) 2014 Congress (held in Madrid, Spain on Sep. 26-30, 2014)," Sep. 27, 2014, 24 pages.
Taiwanese Submission Documents in Application No. 100104281, dated Mar. 9, 2015, 21 pages, with English translation.
U.S. Notice of Allowance in U.S. Appl. No. 14/438,366, dated Feb. 12, 2016, 7 pages.
U.S. Notice of Appeal and Pre-Appeal Brief in U.S. Appl. No. 13/923,858, dated Nov. 25, 2015, 8 pages.
U.S. Office Action in U.S. Appl. No. 12/039,381, dated Oct. 7, 2015, 34 pages.
U.S. Office Action in U.S. Appl. No. 12/092,539, dated May 9, 2011, 14 pages.
U.S. Office Action in U.S. Appl. No. 13/923,858, dated Jul. 29, 2015, 16 pages.
U.S. Office Action in U.S. Appl. No. 14/438,366, dated Sep. 28, 2015, 11 pages.
U.S. Office Action in U.S. Appl. No. 14/862,349, dated Mar. 10, 2016, 13 pages.
U.S. Preliminary Amendment in U.S. Appl. No. 14/122,339, dated Aug. 27, 2015, 8 pages.
U.S. Reply to Office Action in U.S. Appl. No. 13/923,858, filed Apr. 1, 2015, 15 pages.
U.S. Response to Notice of Non-Compliant Amendment dated Jan. 18, 2005 for U.S. Appl. No. 10/420,466, 16 pages.
Voluntary Amendment filed on Feb. 21, 2007 for Australian Application No. 2006203099, 3 pages.
Voluntary Amendment for Australian Application No. 2010285740, filed on Nov. 21, 2011.
Voluntary Amendment in MX Application No. MX/a/2014/010594, dated Oct. 23, 2014, 6 pages (with English translation).
Written Opinion mailed May 18, 2016 for PCT/US2016/020747, 5 pages.
Cell Technology, Supplementary Volume, "Bio-Experiment Illustrated vol. 5,?No Fear of Proteins", Visual Laboratory Notebook Series, Section 6, Immunostaining, pp. 127-163, Shujunsha, Co., Ltd., 1997 (Japanese), 37 pages.
European Office Action in Application No. 4025700.8, dated Apr. 10, 2006, 3 pages.
Filipino Submission Documents in Application No. 1-2011-502441, dated May 22, 2015, 25 pages.
Folkman, "What is the evidence that tumors are angiogenesis dependent," J Nat Can Inst 82 (1), 1990, 3 pages.
Formality Requirement dated Jun. 18, 2003 for PH Application No. 1-2003-500266, 3 pages.
Indian Office Action for U.S. Application No. 383/CHENP/2008, issued on May 3, 2012, 2 pages.
International Preliminary Report on Patentability for Application No. PCT/JP2006/312487, issued on Jan. 10, 2008, 7 pages.
U.S. Office Action in U.S. Appl. No. 12/039,381, dated Oct. 7, 2015, 32 pages.
U.S. Office Action in U.S. Appl. No. 12/092,539, dated May 9, 2011, 19 pages.
U.S. Office Action in U.S. Appl. No. 13/923,858, dated Jul. 29, 2015, 18 pages.
U.S. Office Action in U.S. Appl. No. 14/862,349, dated Mar. 10, 2016, 17 pages.
"Impurities in New Drug Substances Q3A (R2)," ICH Harmonized—Tripartite Guideline, Oct. 25, 2006, 14 pages.
Amended Claims in Malaysian Application No. PI2011700172, dated in Jul. 3, 2014, 15 pages.
Amendment in Japanese Application No. 2009-554285, dated Aug. 19, 2010, 7 pages, with English translation.
Argument Brief filed on Oct. 25, 2005 for KR Application No. 10-2003-7005506 (with English translation), 73 pages.
Australian ("AU") Notice of Allowance dated Nov. 22, 2010 for corresponding AU Application No. 2006285673, 3 pages.
Australian ("AU") Office Action issued on May 19, 2010 for corresponding AU Application No. 2006285673, 2 pages.
Australian ("AU") Office Action issued on May 7, 2009 for corresponding AU Application No. 2006285673, 2 pages.
Canadian ("CA") Office Action issued on Jan. 14, 2010 for corresponding CA Application No. 2,620,594, 3 pages.
Chinese Voluntary Amendment in Application No. 201510031628.2, dated Oct. 10, 2015, 6 pages, with English translation.
FGBU, "Research Institute of Influenza of the Ministry of Health of the Russian Federation, Federal Center for Influenza and ARD, National Center for Influenza, WHO Guidelines for the Treatment and Prevention of Influenza in Adults," 2014 found in the Internet, http://gkb12.mznso.ru/media/cms_page_media/2149/rekomendaciipo-diagnostike-i-iecheniyu-grippa-u-vzroslyh_2.pdf, 2014, 42 pages.
Indian Patent Application No. 2572/CHENP/2006 filed Jul. 13, 2006, 101 pages.
Mexican Office Action in Application No. MX/a/2014/010594, dated Oct. 13, 2015, 10 pages, with English translation.
Petition in Japanese Application No. 2009-554285, dated Aug. 19, 2010, 7 pages (with English translation).
Reply to communication from the Examining Division for European Application No. 04025700.8, dated Feb. 15, 2007, 2 pages.
Response filed in KR Application No. 10-2009-7005657, dated Nov. 21, 2013, 49 pages (with English translation).
Submission Document re RCE and Information Disclosure Statement in U.S. Appl. No. 11/065,631, dated Oct. 8, 2008, 8 pages.
Submission Document re RCE in U.S. Appl. No. 12/558,982, dated Nov. 29, 2011, 17 pages.
Submission Document re RCE in U.S. Appl. No. 12/741,682, dated Aug. 14, 2014, 6 page.
Submission documents re RCE filed in U.S. Appl. No. 12/741,682, dated Jan. 17, 2014, 5 page.

(56) References Cited

OTHER PUBLICATIONS

U.S. Office Action for U.S. Appl. No. 12/092,539, issued on Jan. 7, 2011, 16 pages.
U.S. Office Action for U.S. Appl. No. 12/094,492, issued on Mar. 24, 2011, 22 pages.
Voluntary Amendment filed on Feb. 16, 2012 for BR Patent App. No. BR112012003592-4 (with partial English translation), 12 pages.
Official Letter mailed Mar. 15, 2022 in U.S. Appl. No. 15/750,712.
Official Letter mailed Apr. 1, 2022 in Canadian Patent Application No. 2976325.
Official Letter mailed Apr. 6, 2022 in U.S. Appl. No. 15/934,242.
Submission Documents filed Apr. 14, 2022 in Canadian Patent Application No. 3019682.
Official Letter mailed Apr. 12, 2022 in European Patent Application No. 16755489.8.
Official Letter mailed Mar. 2, 2022 in Mexican Patent Application No. MX/a/2019/013014 (w.English translation).
Submission Document filed Apr. 24, 2022 in Israeli Patent Application No. 253946 (w.English translation).
Official Letter mailed Mar. 16, 2022 in Australian Patent Application No. 2017249459.
Official Letter mailed Mar. 28, 2022 in Mexican Patent Application No. MX/a/2017/001980 (w.English translation).
Submission Documents filed Apr. 11, 2022 in U.S. Appl. No. 16/465,277.
Official Letter mailed May 3, 2022 in U.S. Appl. No. 15/573,197.
Official Letter mailed Apr. 6, 2022 in Israeli Patent Application No. 250454 (w.English translation).
Official Letter mailed Jan. 31, 2022 is U.S. Appl. No. 15/554,577.
Official Letter mailed Jan. 12, 2022 in Mexican Patent Application No. MX/a/2018/012193 (w.English translation).
Official Letter mailed Mar. 2, 2022 in Singapore Patent Application No. 10202010137Y.
Official Letter mailed Mar. 7, 2022 in Canadian Patent Application No. 2985596.
Official Letter mailed Feb. 25, 2022 in European Patent Application No. 19151846.3.
Official Letter mailed Feb. 25, 2022 in Chinese Patent Application No. 201880005026.1 (w.English translation).
Official Letter mailed Mar. 2, 2022 in Israeli Patent Application No. 267159 (w.English translation).
Submission Documents filed Feb. 18, 2022 in U.S. Appl. No. 15/934,242.
Submission Documents filed Jan. 21, 2022 in Mexican Patent Application No. MX/a/2019/013014 (w.English translation).
Official Letter mailed Feb. 1, 2022 in Egyptian Patent Application No., PCT 283/2012 (w.English translation).
Submission Documents filed Feb. 18, 2022 in U.S. Appl. No. 17/228,025.
Official Letter mailed Feb. 9, 2022 in Thailand Patent Application No. 0401005163 (w.English translation).
Submission Document filed Feb. 1, 2022 in U.S. Appl. No. 13/923,858.
Submission Documents filed Mar. 4, 2022 in U.S. Appl. No. 15/750,712.
Official Letter mailed Jan. 24, 2022 in U.S. Appl. No. 13/923,858.
Official Letter mailed Mar. 25, 2022 in U.S. Appl. No. 17/228,025.
Submission Documents filed Mar. 27, 2022 in Israeli Patent Application No. 250454 (w.English translation).
Official Letter mailed Mar. 11, 2022 in Russian Patent Application No. 2017104496 (w.English translation).
Official Letter mailed Feb. 22, 2022 in Russian Patent Application No. 2018134943 (w.English translation).
Submission Documents dated Jan. 12, 2022 in Russian Patent Application No. 2017104496 with English translation.
Submission Documents dated Jan. 3, 2022 in Indian Patent Application No. 201947044328.
Official Letter mailed Dec. 22, 2021 in U.S. Appl. No. 16/092,245.
Official Letter mailed Jan. 12, 2022 in U.S. Appl. No. 16/465,277.
Official Letter mailed Dec. 27, 2021 in Israeli Patent Application No. 253946 wtih English translation.
Official Letter mailed Jan. 24, 2022 in U.S. Appl. No. 16/092,245.
Official Letter mailed Jan. 14, 2022 in Australian Patent Application No. 2016273230.
Official Letter mailed Feb. 4, 2022 in Indian Patent Application No. 202148057534.
Submission Documents dated Feb. 14, 2022 in Chinese Patent Application No. 201880005026.1 with English translation.
Submission Documents dated Jan. 14, 2022 in U.S. Appl. No. 13/923,858.
Official Letter mailed May 20, 2022 in U.S. Appl. No. 13/923,858.
Submission Document filed May 11, 2022 in Korean Patent Application No. 10-2018-7028053 (w.English translation).
Official Letter mailed Apr. 11, 2022 in Egyptian Patent Application No. PCT 283/2012 (w.English translation).
Official Letter mailed Jun. 7, 2022 in Japanese Patent Application No. P2020-182679 (w.English translation).
Official Letter mailed May 30, 2022 in Mexican Patent Application No. MX/a/2017/001980 (w.English translation).
Official Letter mailed May 11, 2022 in Korean Patent Application No. 10-2017-7027616 (w.English translation).
Official Letter mailed Nov. 12, 2021 in KR Patent Application No. 10-2018-7028053.
Submission Documents dated Nov. 22, 2021 in U.S. Appl. No. 15/750,712.
Official Letter mailed Dec. 8, 2021 in U.S. Appl. No. 15/750,712.
Submission Documents dated Dec. 10, 2021 in Indian Patent Application No. 201947022655.
Official Letter mailed Dec. 21, 2021 in Australian Patent Application No. 2016273230.
Official Letter mailed Dec. 21, 2021 in European Patent Application No. 17782552.8.
Official Letter mailed Dec. 9, 2021 in Chinese Patent Application No. 201880005026.1 (w.English translation).
Submission Documents dated Dec. 10, 2021 in U.S. Appl. No. 16/465,277.
Submission Documents dated Dec. 16, 2021 in Brazilian Patent Application No. BR1120180027324 (w.English translation).
Official Letter issued Dec. 21, 2021 in Chinese Patent Application No. 201880005026.1 (w.English translation).
Submission Documents dated Dec. 10, 2021 in Indian Patent Application No. 202148057534.
Submission Documents dated Dec. 29, 2021 in European Patent Application No. 19151846.3.
Official Letter issued Dec. 16, 2021 in Australian Patent Application No. 2015384801.
Submission Documents dated Dec. 14, 2021 in Brazilian Patent Application No. BR1120170174286 (w.English translation).
Official Letter issued Jan. 5, 2022 in European Patent Application No. 17782552.8.
Submission Documents dated Dec. 20, 2021 in Brazilian Patent Application No. BR1120170241960 (w.English translation).
Submission Documents dated Dec. 17, 2021 in Mexican Patent Application No. MX/a/2018/012193 (w.English translation).
Official Letter issued Dec. 17, 2021 in European Patent Application No. 19151846.3.
Submission Documents dated Jan. 10, 2022 in European Patent Application No. 19151486.3.
Official Letter issued Dec. 23, 2021 in Russian Patent Application No. 2018134943.
BR Patent Application No. PI0418200-6, Official Notification dated May 31, 2022.
BR Patent Application No. BR112013021941-6, Office Action dated Jun. 7, 2022.
CA Patent Application No. 2976325, Response to Office Action dated Jul. 21, 2022.
EP Patent Application No. 19733190.3, Office Action dated Jul. 5, 2022.
IL Patent Application No. 250454, Response to PK 26 mailed Jul. 31, 2022.
IL Patent Application No. 253946, Office Action dated Jun. 19, 2022.
SG Application No. 11201709335X, Office Action dated Jul. 15, 2022.

(56) References Cited

OTHER PUBLICATIONS

SG Patent Application No. 10202010137Y, Response to Written Opinion dated Aug. 2, 2022.
U.S. Appl. No. 13/923,858, Reply Brief dated Jul. 20, 2022.
U.S. Appl. No. 15/750,712, Notice of Allowance dated Jun. 23, 2022.
Request for Continued Examination and Information Disclosure Statement filed on Feb. 17, 2023 for U.S. Appl. No. 16/465,277.
Amendment filed on Mar. 7, 2013 for KR Application No. 10-2019-7016853.
Examination Report mailed Mar. 14, 2023 for AU Application No. 2018219637.
Response to Final Office Action and Request for Continued Examination filed Feb. 14, 2023 for U.S. Appl. No. 16/092,245.
Technical Exam Report mailed Feb. 28, 2023 for BR Application No. 112018002732-4.
Request for Continued Examination filed on Jan. 6, 2023 for U.S. Appl. No. 15/750,712.
Rule 115(1) EPC mailed Jan. 19, 2023 for EP Application No. 16837150.8.
Phase 1/2 study of lenvatinib in children and adolescents with refractory or relapsed solid malignancies, U.S. National Library of Medicine Clin. Trials, (Dec. 2022).
Committee for Medicinal Products for Human Use. Assessment report: Lenvima, European Medicine Agency, (Mar. 2015).
European Sarcoma Network Working Group. Bone sarcomas: ESMO clinical practice guidelines for diagnosis, treatment and follow-up, Annals of Oncology, 25 (Supplement), iii113-iii123, (Sep. 2014).
Mutschler et al., Mutschler drug reactions, Pharmacological and toxicological textbook, 882-892, (2001).
Mutschler et al., Mutschler drug reactions, Pharmacological and toxicological textbook, 123-124 (2001).
Botter et al., Recent advances in osteosarcoma, Current Opinion in Pharmacology, 16: 15-23, (2014).
Lund, Pharmaceutical aspects of clinical trials, The Pharmaceutical Codex: Principles and Practice of Pharmaceutics, 12, (1994).
Pre-Grant Hearing Notice in Reference of Application No. 201847003846 mailed Jan. 19, 2023 for IN Application No. 201847003846.
Notice of Allowance for U.S. Appl. No. 15/750,712 mailed Jan. 25, 2023.
Reply to the unfavorable technical opinion (7.1) for BR Application No. BR112017002827-1.
Rule 115(1) EPC mailed Jan. 30, 2023 for EP Application No. 16837150.8. (2023).
Reply to Rule 71(3) EPC filed Feb. 17, 2023 for EP Application No. 16755489.8.
Order granting request for video hearing mailed Jan. 19, 2023 for U.S. Appl. No. 13/923,858.
Notice of Allowance mailed Jan. 31, 2023 for KR Application No. 10-2017-7003226.
Reply to Communication under Article 94(3) EPC filed Jan. 13, 2023 for EP Application No. 19733190.3.
Response to an Examiner's Report filed Feb. 22, 2023 for AU Application No. 2017249459.
Examination report mailed Mar. 16, 2023 for AU Application No. 2017249459.
Conditional Notice of Allowance mailed Feb. 16, 2023 for CA Application No. 2976325.
Hearing Notice in Reference of Application No. 202148057534 mailed Mar. 14, 2023 for IN Application No. 202148057534.
Notice before acceptance for patent application 250454 mailed Feb. 27, 2023 for IL Application No. 250454.
Decision on appeal mailed Mar. 1, 2023 for U.S. Appl. No. 13/923,858.
Technical examination report mailed Mar. 7, 2023 for BR Application No. BR112017002827-1.
Reply to non-final office action filed Mar. 3, 2023 for U.S. Appl. No. 17/511,773.
Notice of Allowance mailed Mar. 15, 2023 for U.S. Appl. No. 17/511,773.
Office Action issued Dec. 17, 2020 in Australian Patent Application No. 2015384801.
Notice of Reasons for Rejection dispatched Oct. 12, 2021, in Japanese Patent Application No. 2020-546133 with English translation (11 pages).
Office Action issued Nov. 1, 2021 in Canadian Patent Application No. 2,978,226.
Protest Against the Grant of Patent for Application No. CA2978226 filed Sep. 28, 2021 in Canadian Patent Application No. 2,978,226.
Emma Thornton, "Part 2 Nivolumab, a Novel Anti PD 1 Monoclonal Antibody for the Treatment of Solid and Hematologic Malignancies Personalized medicine in oncology", Published online Jun. 2014 by Personalised Medicine in Oncology. Retrieved from the internet: http://www.personalizedmedonc.com/publications/ito/june-2014-part-2/nivo | umab-a-novel-anti- pd-1-monoclonal-antibody-for-the-treatment-of-so lid-and-hematologic-malignancies/ (13 pages).
Pfizer; "Study NCT02133742: A Phase lb, Open Label, Dose Finding Study to Evaluate Safety, Pharmacokinetics and Pharmacodynamics of Axitinib (Ag-013736) in Combination with MK-3475 in Patients with Advanced Renal Cell Cancer", Published: Feb. 10, 2015 (8 pages).
GlaxoSmithKline; "Study NCT02014636-A Phase 1/11 Study to Assess the Safety and Efficacy of Pazopanib and MK 3475 in Subjects With Advanced Renal Cell Carcinoma", Published: Nov. 13, 2014 (11 pages).
News-Pfizer, "Pfizer and Merck to Collaborate on Innovative Anti-Cancer Combination Studies", Published: Feb. 5, 2014. Retrieved from the internet: https://www.pfizer.com/news/press-release/press-release-detail/pfizer and merck to collaborate on innovative anti cancer combination studies (5 pages).
Official Letter mailed Aug. 31, 2021 in Brazilian Patent Application No. BR112012032462-4 with English translation.
Submission Document filed Oct. 5, 2021 in U.S. Appl. No. 17/228,025.
Official Letter mailed Oct. 6, 2021 in Israeli Patent Application No. 267159.
Official Letter mailed Oct. 15, 2021 in European Patent Application No. 17782552.8.
Official Letter mailed Oct. 12, 2021 in Japanese Patent Application No. P2020-182679 with English translation.
Official Letter mailed Oct. 25, 2021 in European Patent Application No. 16755489.8.
Masha S. H. Lam, "Extemporaneous Compounding of Oral Liquid Dosage Formulations and Alternative Drug Delivery Methods for Anticancer Drugs ", Reviews of Therapeutics, Pharmacotherapy, 2011, vol. 31(2) , p. 164-p. 192.
Jennifer Walsh et al., "Playing hide and seek with poorly tasting paediatric medicines: Do not forget the excipients", Advanced Drug Delivery Reviews, 73(2014), p14-p33.
Official Letter mailed Oct. 12, 2021 in Japanese Patent Application No. P2020-182679.
Official Letter mailed Oct. 5, 2021 in Mexican Patent Application No. MX/a/2017/001980.
Submission Documents filed Oct. 22, 2021 in Indian Patent Application No. 201947044328.
Nathalie Gaspar et al., "Lenvatinib with etoposide plus ifosfamide in patients with refractory or relapsed osteosarcoma (ITCC-050): a multicentre, open-label, multicohort, phase 1/2 study", Lancet Oncol , vol. 22, Sep. 2021, p. 1312-p. 1321.
Official Letter mailed Oct. 25, 2021 in Indian Patent Application No. 201947022655 with English translation.
Submission Documents filed Sep. 16, 2021 in GC Patent Application No. GC2015-40053 with English translation.
Submission Document filed Oct. 22, 2021 in U.S. Appl. No. 17/407,742.
Submission Documents filed Oct. 29, 2021 in European Patent Application No. 20207489.4.
"Report on the Deliberation Results of the Evaluation and Licensing Division; Pharmaceutical and Food Safety Bureau", Ministry of Health, Labour and Welfare , Jan. 26, 2015.
Notice of Allowance mailed Jul. 28, 2022 for U.S. Appl. No. 15/554,577.

(56) References Cited

OTHER PUBLICATIONS

A phase I/II study to asses the safety and efficacy of pazopanib and MK 3475 in subjects, view of NCT02014636, (Dec. 2013).
A phase 1 study of BMS-936558 plus subitinib or pazopanib in subjects with metastatic renal, view of NCT01472081, (Nov. 2011).
Amin et al., Nivolumab (anti-PD-1; BMS-936558, ONO-4538) in combination with sunitinib or pazopanib in patients (pts) with metastatic renal cell carcinoma (mRCC), J. Clin. Oncol., 32(15): P1-4, (May 2014).
Notice of Reasons for Rejection for JP Application No. P2022-161848 mailed Oct. 31, 2023.
Notice of Allowance mailed Mar. 24, 2023 for KR Application No. 10-2019-7016853.
Supplemental Notice of Allowability mailed Apr. 4, 2023 for U.S. Appl. No. 16/465,277.
Amendment After Conditional Notice of Allowance and Payment of Final Fee filed Apr. 18, 2023 for CA Application No. 2,976,325.
Commissioner's Notice mailed Apr. 24, 2023 for CA Application No. 2,994,925.
Official order for IN Application No. 202148057534 mailed May 1, 2023.
Request for continued examination and reply to action for U.S. Appl. No. 17/228,025 submitted Apr. 20, 2023.
Request for continued examiation for U.S. Appl. No. 15/750,712 submitted Apr. 24, 2023.
Submission in opposition proceedings for EP Application No. 19151846.3 submitted May 17, 2023.
Response to Communication for EP Application No. 22180987.4 submitted May 15, 2023.
Notice of Preliminary Rejection for KR Application No. 10-2018-7003723 mailed May 8, 2023.
Response to Communication for EP Application No. 17782552.8 submitted May 19, 2023.
Notice of Allowance for U.S. Appl. No. 15/750,712 mailed May 9, 2023.
Notice of Reasons for Rejection for JP Application No. P2020-560740 mailed May 16, 2023.
Statement of Opposition for EP Application No. 19151846.3 submitted May 4, 2023.
Notice of Opposition for EP Application No. 19151846.3 submitted May 10, 2023.
Notice of Opposition for EP Application No. 19151846.3 submitted May 9, 2023.
2nd Notice of Opposition for EP Application No. 19151846.3 submitted May 10, 2023.
2nd Notice of Opposition for EP Application No. 19151846.3 submitted May 9, 2023.
3rd Notice of Opposition for EP Application No. 19151846.3 submitted May 10, 2023.
4th Notice of Opposition for EP Application No. 19151846.3 submitted May 10, 2023.
5th Notice of Opposition for EP Application No. 19151846.3 submitted May 10, 2023.
6th Notice of Opposition for EP Application No. 19151846.3 submitted May 10, 2023.
Communication under Rule 71(3) EPC for EP Application No. 16755489.8 mailed May 24, 2023.
Communication for CA Application No. 3019682 mailed May 31, 2023.
Notice of Preliminary Rejection for KR Application No. 10-2017-7022544 mailed Apr. 14, 2023.
Adachi et al., "E7386, a selective inhibitor of the interaction between ?-catenin and CREB-binding protein (CBP), enhances antitumor activity in combination with lenvatinib(LEN), and LEN + anti-PD-1antibody in a preclinical tumor model ", ASCO2023_102, Jun. 2-6, 2023.
Ikeda et al., "A Phase 1b Study of E7386, a CREB-Binding Protein/β-Catenin Interaction Inhibitor, in Combination With Lenvatinib in Patients With Advanced Hepatocellular Carcinoma", AACR 2023 Poster_1830 Presented at the American Society for Clinical Oncology Symposium, Jun. 2-6, 2023.
Kawano et al., "E7386, a selective inhibitor of the interaction between ?-catenin and CREB-binding protein (CBP), in combination with lenvatinib (LEN), exerts antitumor activity in preclinical tumor models with prior immune checkpoint inhibitor (ICI)-based combination treatment", AACR 2023 poster_1837 , Jun. 2-6, 2023.
"X-Bridge HPLC Colums Brochure", available from https://waters.com/webassets/cms/library/docs/720001255en.pdf, Feb. 2015.
L.R. Snyder, J.J. Kirkland and J.L. Glajch, "Practical HPLC Method Development—Second Edition", John Wiley & Sons Inc., New York, 1998.
"U.S. FDA Approves Anticancer Agent Lenvima (Lenvatinib Mesylate) as Treatment for Radioactive Iodine-Refractory Differentiated Thyroid Cancer", Eisai News Release, available from: https://www.eisai.com/news/pdf/enews201510pdf.pdf, Feb. 16, 2015.
"Drugs@FDA: FDA-Approved Drugs Lenvima", D12—Drugs@FDA_ FDA-Approved Drugs, unknown.
Shumaker et al., "Effect of Rifampicin on the Pharmacokinetics of Lenvatinib in Healthy Adults", Clin. Drug Investig. vol. 34, 2014 (D10), 2014, p. 651-p. 659.
"Experimental data", original file name: D11_Experimental Data., Other-evidence-4(D11).
"Translation of JP 2014-174062(first priority)", Aug. 28, 2014.
"Translation of JP 2015-034729(second priority)", Feb. 25, 2015.
"ICH guideline M7 on assesment and control of DNA reactive (mutagenic) impurities in pharmaceuticals to limit potential carcinogenic risk" issued by EMA, May 2013.
"Newly notified chemical substances (36 substances) confirmed to have mutagenicity from website https://anzeninfo.mhlw.go.jp/user/anzen/kag/20121211_heni.html;", Dec. 11, 2012.
"AMES/QSAR International Collaborative Study/Class A list; from website: http://www.nihs.go.jp/dgm/amesqsar.html;", 1.
"Summary of Manufacturing Changes", Feb. 13, 2018.
"Experimental Report".
S. Ahuja and M.W.Dong, "Handbook of Pharmaceutical Analysis by HPLC", 1st Edition, Elsevier, pp. 19-22, 43, 44, 123-127, 133, 134, 200-203, 212, 262, 274, 275, 370-377, Feb. 9, 2005.
"Patentee's brief ", Dec. 9, 2021.
"Vogel's Textbook of Quantitiative Chemical Analysis", 5th Edition, Longman Scientific & Technical, 216, 220-229, 232-233, (1989).
"Lenvatinib mesylate polymorphs; Title of invention: Crystal of salt of 4-(3-chloro-4-(cyclopropylaminocarbonyl)amino-phenoxy)-7-methoxy-6- quinolinecarboxamide or of solvate thereof and processes for producing these", Jun. 18, 2014.
EMEA, "Guideline on the limits of genotoxic impurities", Jun. 28, 2006.
Lutz Muller et al., "A rationale for determining, testing, and controlling specific impurities in pharmaceuticals that possess potential for genotoxicity", Regulatory Toxicology and Pharmacology , 2006, vol. 44.
European Medicines Agency, "Assessment Report Lenvima(lenvatinib)", Mar. 26, 2015.
Response to the first Examination Report for AU Application No. 2018219637 submitted Jun. 7, 2023.
Response to the Notice of Preliminalry Rejection for KR Application No. 2017-7022544 submitted Jun. 9, 2023.
Response to Technical Report for BR Application No. 112018002732-4 submitted May 29, 2023.
Non-final office action for U.S. Appl. No. 17/228,025 mailed May 23, 2023.
Relevant parts of an unfavorable opinion for BR Application No. 122023002744-2 mailed May 23, 2023.
Relevant parts of an unfavorable opinion for BR Application No. 122023002748-5 mailed May 23, 2023.
Notification before Examination of Israeli Application No. 302218 mailed Apr. 19, 2023.
Pre-grant hearing notice for IN Application No. 201747040368 mailed Jul. 6, 2023.

(56) References Cited

OTHER PUBLICATIONS

Reed et al., beta-catenin/CBPactivationofmTORC1signalingpromotespartialepithelial-mesenchymalstatesinheadandneckcancer, Translational Research, 1-15, (2023).
Non-final office action for U.S. Appl. No. 16/092,245 mailed Jun. 8, 2023.
Record of oral hearing for U.S. Appl. No. 13/923,858 mailed Jun. 13, 2023.
Notice of Abandonment for U.S. Appl. No. 13/923,858 mailed May 23, 2023.
Communication under Rule 71(3) EPC for EP Application No. 18751614.1 mailed Jun. 26, 2023.
Response to the Notice of Preliminary Rejection for KR Application No. 10-2018-7003723 submitted Jun. 29, 2023.
Request for continued examination for U.S. Appl. No. 16/465,277 submitted Jun. 8, 2023.
Notice of Appeal for U.S. Appl. No. 17/407,742 submitted Jun. 7, 2023.
Submission in opposition proceedings for EP Application No. 16837150.8 submitted Jul. 5, 2023.
Gasper et al., Lenvatinib with etoposide plus ifosfamide in patients with refractory or relapsed osteosarcoma (ITCC-050): a multicentre, open-label, multicohort, phase 1/2 study, Supplementary appendix, Lancet Oncol., (Aug. 17, 2021).
Van Winkle et al., Ifosfamide, Carboplatin, and Etoposide (ICE) Reintroduction Chemotherapy, Pediatr. Blood Cancer, 44: 338-347, (2005).
Invitation to Respond to Written Opinion for SG Application No. 10202010137Y mailed Jul. 28, 2023.
Notice of Allowance for U.S. Appl. No. 16/465,277 mailed Jul. 20, 2023.
Notice of acceptance of patent application for AU Application No. 2018219637 mailed Jun. 30, 2023.
Brief communication for EP Application No. 16837150.8 mailed Jul. 12, 2023.
Bruheim, et al., Antitumor activity of oral E7080, a novel inhibitor of multiple tyrosine kinases, in human sarcoma xenografts, Intl. J. Cancer, 129: 742-750, (2011).
Mutschler et al., Mutschler Drug Effects, Textbook of Pharmacology and Toxicology, ch. 10:120-122, (2001).
Fleuren, et al., Targeting receptor tyrosine kinases in osteocarcoma and Ewing sarcoma: Current hurdles and future perspectives, Biochimica et Biophysica Acta, 1845: 260-276, (2014).
Notification of deficiencies for IL Application No. 253946 mailed Jul. 17, 2023.
Brief communication for EP Application No. 16837150.8 mailed Jul. 21, 2023.
Registration and grant of patent for TH Application No. 1201000221 mailed Jul. 25, 2023.
Manifestation of technical opinion for BR Application No. 122023002748.5 mailed Aug. 25, 2023.
Notice of Allowance for U.S. Appl. No. 15/750,712 mailed Aug. 17, 2023.
Notice of Allowance for JO Application No. P/2020/225 mailed Sep. 4, 2023.
Manifestation of technical opinion for BR Application No. 122023002744.2 mailed Aug. 24, 2023.
Request for Continued Examination for U.S. Appl. No. 15/750,712 submitted Aug. 8, 2023.
Notice of Allowance for U.S. Appl. No. 17/511,773 mailed Jul. 20, 2023.
Final Office Action for U.S. Appl. No. 17/228,025 mailed Sep. 11, 2023.
Supplemental Notice of Allowabililty for U.S. Appl. No. 16/465,277 mailed Sep. 19, 2023.
Notice of preliminary rejection for KR Application No. 10-2023-7009398 mailed Jul. 31, 2023.
Reply to action for U.S. Appl. No. 17/228,025 submitted Jul. 31, 2023.
Notice of Allowance for KR application No. 10-2018-7003723 mailed Sep. 7, 2023.
Response to official action for CA application No. 3019682 submitted Sep. 28, 2023.
Notice of Appeal for U.S. Appl. No. 17/288,025 submitted Sep. 22, 2023.
Pre-grant hearing notice for IN application No. 201747004829 mailed Sep. 10, 2023.
Interlocutory decision in Opposition proceedings for EP application No. 16837150.8 mailed Sep. 29, 2023.
Notice of preliminary rejection for KR application No. 10-2017-7022544 mailed Oct. 10, 2023.
Notice of deficiencies for IL application No. 302218 mailed Oct. 18, 2023.
Response to office action for IL Application No. 253946 submitted Nov. 6, 2023.
Request for Continued Examination for U.S. Appl. No. 16/465,277 submitted Oct. 19, 2023.
Notice of Allowance for U.S. Appl. No. 16/465,277 mailed Nov. 2, 2023.
Decision to grant a patent for JP Application No. 2020-560740 mailed Nov. 7, 2023.
Brief on appeal for U.S. Appl. No. 17/228,025 submitted Nov. 14, 2023.
Technical examination report for BR Application No. 112018002732-4 mailed Nov. 21, 2023.
Response to Notice of Preliminary Rejection for KR Application No. 10-2017-7022544 submitted Nov. 30, 2023.
Request for continued examination for U.S. Appl. No. 15/750,712 submitted Nov. 16, 2023.
Reply to office action for U.S. Appl. No. 16/092,245 submitted Nov. 30, 2023.
Response to oppositions filed for EP Patent No. 3524595 submitted Dec. 4, 2023.
"Eisai Launches Anticancer Agent Lenvima in the United States", Eisai News Release, Mar. 2, 2015.
"Specifications: Test Procedures and Acceptance Criteria for New Drug Substances and New Drug Products: Chemical Substances", Guideline ICH Q6A, May 2000.
"ICH guideline S9 on nonclinical evaluation for anticancer pharmaceuticals Step 5", May 2010.
"Impurities in New Drug Products", ICH Topic Q3B(R2), Jun. 2006.
Blacker et al., Pharmaceutical Process Development: Current Chemical and Engineering Challenges, RSC Publishing, 283-316, (2011).
Tung et al., Crystallization of Organic Compounds, an Industrial Perspective, Wiley, 101-116, (2009).
"Impurities: Guideline for Reidual Solvents Q3C(R5)", ICH Harmonised Tripartite Guideline, Feb. 4, 2011.
"Except Study Report HOPE(HE130)", Feb. 12, 2013-Feb. 21, 2013.
"Excerpt NDA 2.3.S.2 Manufacture" Dec. 4, 2023.
Reply to the oppositions for EP Application No. 3338779 submitted Dec. 5, 2023.
Corrected Notice of Allowability for U.S. Appl. No. 16/465,277 mailed Dec. 6, 2023.
Reply to notice of allowance for U.S. Appl. No. 16/465,277 submitted Dec. 6, 2023.
Summons to attend oral proceedings pursuant to Rule 115(1) EPC for EP Application 17782552.8 mailed Dec. 18, 2023.
Notice of deficiencies for IL Application No. 262076 mailed Dec. 18, 2023.
Examination report for PK Application No. 807/2021 mailed Dec. 14, 2023.
Final office action for U.S. Appl. No. 16/092,245 mailed Dec. 22, 2023.
Examination report for PK Application No. 548/2015 mailed Dec. 14, 2023.
Response to opposition for EP Patent No. 3524595 submitted Dec. 4, 2023.
Non-final office action for U.S. Appl. No. 17/052,133 mailed Jan. 8, 2024.

(56) References Cited

OTHER PUBLICATIONS

Liu, Merck, Eisai's 007 goes down as Keytruda-Lenvima combo fails in newly diagnosed lung cancer, Fierce Pharma, retrieved from Internet: <https://www.fiercepharma.com/pharma/merck-eisai-s-007-goes-down-as-keytruda-lenvima-combo-fails-newly-diagnosed-lung-cancer>, (Dec. 2021).
Eisai Co., Ltd. and Merck & Co., Eisai and Merck & Co., Inc., Rahway, NJ, USA Provide Update on Phase 3 LEAP-002 Trial Evaluating LENVIMA® (lenvatinib) Plus KEYTRUDA® (pembrolizumab) Versus LENVIMA Monotherapy in Patients With Unresectable Hepatocellular Carcinoma, Eisai Global, retrieved from Internet: <https://www.eisai.com/news/2022/news202259.html>, (Aug. 2022).
Eisai Co. Ltd. and Merck & Co., Eisai and Merck & Co., Inc., Rahway, NJ, USA Provide Update on Phase 3 Trials of LENVIMA® (lenvatinib) Plus KEYTRUDA® (pembrolizumab) in Certain Patients With Advanced Melanoma (LEAP-003) and Metastatic Colorectal Cancer (LEAP-017), Eisai Global, retrieved from Internet: <https://www.eisai.com/news/2023/news202329.html>, (Apr. 2023).
Eisai Co. Ltd. and Merck & Co., Eisai and Merck & Co., Inc., Rahway, NJ, USA Provide Update on Phase 3 LEAP-010 Trial Evaluating LENVIMA® (lenvatinib) Plus KEYTRUDA® (pembrolizumab) in Patients With Certain Types of Recurrent or Metastatic Head and Neck Squamous Cell Carcinoma, Eisai Global, retrieved from Internet: <https://www.eisai.com/news/2023/news202355.html>, (Aug. 2023).
Eisai Co. Ltd. and Merck & Co., Eisai and Merck & Co., Inc., Rahway, NJ, USA Provide Update on Two Phase 3 Trials Evaluating LENVIMA® (lenvatinib) Plus KEYTRUDA® (pembrolizumab) in Patients With Certain Types of Metastatic Non-Small Cell Lung Cancer, Eisai Global, retrieved from Internet: <https://www.eisai.com/news/2023/news202358.html>, (Sep. 2023).
Merck Sharp & Dohme LLC, Safety and Efficacy of Lenvatinib (E7080/MK-7902) With Pembrolizumab (MK-3475) in Combination With Transarterial Chemoembolization (TACE) in Participants With Incurable/Non-metastatic Hepatocellular Carcinoma (MK-7902-012/E7080-G000-318/LEAP-012), Clinical Trials, (Sep. 2023).
Merck Sharp & Dohme LLC, Efficacy and Safety of Lenvatinib (E7080/MK-7902) Plus Pembrolizumab (MK-3475) for Advanced Melanoma in Anti-Programmed Death-1/Programmed Death-Ligand 1 (PD-1/L1)-Exposed Participants (MK-7902-004/E7080-G000-225/LEAP-004), Clincal Trials, (Oct. 2023).
Merck Sharpe & Dohme LLC, Lenvatinib (E7080/MK-7902) in Combination With Pembrolizumab (MK-3475) vs. Standard Chemotherapy and Lenvatinib Monotherapy in Participants With Recurrent/Metastatic Head and Neck Squamous Cell Carcinoma That Progressed After Platinum Therapy and Immunotherapy (MK-7902-009/E7080-G000-228/LEAP-009), Clincal Trials, (Mar. 2024).
Appeal against rejection decision for BR Application No. 112018002732-4 submitted Jan. 22, 2024.
Office action for CA Application No. 3044658 mailed Feb. 20, 2024.
Non-final office action for U.S. Appl. No. 17/407,742 mailed Feb. 14, 2024.
Response to office action for IL Application No. 302218 submitted Feb. 15, 2024.
Hearing notice for IN Application No. 6971/CHENP/2015 mailed Feb. 22, 2024.
Notice under Rule 55(3) of the patents rules for IN Application No. 201947022655 mailed Feb. 13, 2024.
English translation of original complete specification of PCT Application No. PCT/JP2018/004007 submitted Jun. 7, 2019.
Notice before acceptance for IL Application No. 302218 mailed Feb. 20, 2024.
Examiner's answer for U.S. Appl. No. 17/228,025 mailed Mar. 6, 2024.
Reply to observations made by the patent proprietor(s) for EP Application No. 19151846.3 submitted Mar. 12, 2024.
Heretsch, Experimental report, synthesis of lenvatinib mesylate following prior art patent US 2007/0078159 A1, (Mar. 2024).
Notice of allowance for U.S. Appl. No. 16/465,277 mailed Mar. 26, 2024.
Submission in opposition proceedings for EP Application No. 19151846.3 submitted Mar. 13, 2024.
Report on the Regulatory Uses and Applications in OECD Member Countries of (Quantitative) Structure-Activity Relationship [(Q)SAR] Models in the Assessment of New and Existing Chemicals, ENV/JM/MONO(2006)25, (Feb. 2007).
Eisai Inc., NCT01321554: A Multicenter, Randomized, Double-Blind, Placebo-Controlled, Trial of Lenvatinib(E7080) in 131I-Refractory Differentiated Thyroid Cancer(DTC)(Select), ClinicalTrials, (Dec. 2014).
Eisai Co., Ltd., NCT01268293: A Study of E7080 in Subjects With Solid Tumor, ClinicalTrials, (Feb. 2015).
Eisai Inc., NCT02199379: A Phase 1, Open-Label, Single-Dose, Pharmacokinetic and Safety Study of E7080(24mg) Administered to Subjects With Mild, Moderate, and Severa Renal Impairment and to Healthy Subject, ClinicalTrials, (Feb. 2015).
Chromatographic purification of lenvatinib, Aug. 2023.
Purified lenvatinib analysis report, Mar. 2024.
Waters Corporation, Waters Chromatography cols. and Supplies, retrieved from Internet: <https://www.waters.com/webassets/cms/library/docs/720002784en>, (2009).
Section 15 for IN Application No. 6971/CHENP/2015 mailed Mar. 22, 2024.
Brief communication for EP Application No. 19151846.3 mailed Apr. 2, 2024.
Written Opinion for JP Application No. 2022-161848 mailed Mar. 27, 2024.
Applicant's observations for IL Application No. 262076 submitted Apr. 11, 2024.
Petition to withdraw an application from issue after payment of hte issue fee, Request for Continued Examination, and information disclosure statement for U.S. Appl. No. 16/465,277 submitted Mar. 8, 2024.
Examination report for CA Application No. 3019682 mailed Apr. 4, 2024.
Motzer et al., Lenvatinib, everolimus, and the combination in patients with metastatic renal cell carcinoma : a randomised, phase 2, open-label, multicentre trial, Lancet Oncol., 16(15): 1473-1482, (Nov. 2015).
Lenvatinib Mesylate, National Library of Medicine, (Mar. 2012).
"Experimental data provided by the cancellation petitioner", unknown.
"Information of compound (I) on the NITE website", Dec. 11, 2012.
Reply brief for U.S. Appl. No. 17/228,025 submitted Apr. 18, 2024.
Notification of first office action for CN Application No. 202110939882.8 mailed Apr. 11, 2024.
Author/Publisher: Pfizer, Title: Study NCT02133742: A Phase 1b, Open Label, Dose Finding Study to Evaluate Safety, Pharmacokinetics and Pharmacodynamics of Axitinib (Ag-013736) in Combination with MK-3475 in Patients with Advanced Renal Cell Cancer, pages being submitted: 1-8, Publication date: Feb. 10, 2015; Journal/Publication: NIH U.S. National Library of Medicine, ClinicalTrials.gov, and place of publication: retrieved from internet URL: https://clinicaltrials.gov/ct2/show/NCT02133742, accessed on Jun. 1, 2022.†
Author/Publisher: GlaxoSmithKline, Title: Study NCT02014636-A Phase I/II Study to Assess the Safety and Efficacy of Pazopanib and MK 3475 in Subjects with Advanced Renal Cell Carcinoma, pages being submitted: 1-11, Publication date: Nov. 13, 2014, Journal/Publication: NIH U.S. National Library of Medicine, ClinicalTrials.gov, and place of publication: retrieved from internet URL: https://clinicaltrials.gov/ct2/show/NCT02014636, accessed on Jun. 1, 2022.†
Author names: DS Boss, H Glen, JH Beijnen, M Keesen, R Morrison, B Tait, W Copalu, A Mazur, J Wanders, JP O'Brien, JHM Schellens, and TRJ Evans, Title: A phase I study of E7080, a multitargeted tyrosine kinase inhibitor, in patients with advanced solid tumours, pages being submitted: 1598-1604, Publication date: Apr. 19, 2012, Journal: British Journal of Cancer, vol. 106, and place of publication: retrieved from internet URL: https://www.nature.com/articles/bjc2012154, accessed on Jun. 1, 2022.†
Author names: Eisai Inc., Title/product name: LENVIMA (lenvatinib) capsules, pages being submitted: 1-25, date of publication: Feb. 2015, publisher: USFDA drug online database, and place of publi-

(56) References Cited

OTHER PUBLICATIONS cation: retrieved from internet URL: https://www.accessdata.fda.gov/drugsatfda_docs/label/2015/206947s000lbl.pdf , accessed on Jun. 1, 2022.†

Author name: Emma Thornton, Title: Part 2 Nivolumab, a Novel Anti PD 1 Monoclonal Antibody for the Treatment of Solid and Hematologic Malignancies Personalized medicine in oncology, pages being submitted: 1-13, publication date: Jun. 2014, Journal: Personalised Medicine in Oncology, and place of publication—retrieved from the internet—URL: http://www.personalizedmedonc.com/publications/ito/june-2014-part-2/nivolumab-anovel-anti-pd-1-monoclonal-antibody-for-the-treatment-of-solid-and-hematologicmalignancies/ accessed on Jun. 1, 2022.†

\* cited by examiner
† cited by third party

FIGURE 1 hPD-1.08A light chain CDR1 (SEQ ID NO: 1)
Arg Ala Ser Lys Ser Val Ser Thr Ser Gly Phe Ser Tyr Leu His hPD-1.08A light chain CDR2 (SEQ ID NO: 2)
Leu Ala Ser Asn Leu Glu Ser hPD-1.08A light chain CDR3 (SEQ ID NO: 3)
Gln His Ser Trp Glu Leu Pro Leu Thr hPD-1.08A heavy chain CDR1 (SEQ ID NO: 4)
Ser Tyr Tyr Leu Tyr hPD-1.08A heavy chain CDR2 (SEQ ID NO: 5)
Gly Val Asn Pro Ser Asn Gly Gly Thr Asn Phe Ser Glu Lys Phe Lys Ser hPD-1.08A heavy chain CDR3 (SEQ ID NO: 6)
Arg Asp Ser Asn Tyr Asp Gly Gly Phe Asp Tyr

FIGURE 2 hPD-1.09A light chain CDR1 (SEQ ID NO: 7)
Arg Ala Ser Lys Gly Val Ser Thr Ser Gly Tyr Ser Tyr Leu His hPD-1.09A light chain CDR2 (SEQ ID NO: 8)
Leu Ala Ser Tyr Leu Glu Ser hPD-1.09A light chain CDR3 (SEQ ID NO: 9)
Gln His Ser Arg Asp Leu Pro Leu Thr hPD-1.09A heavy chain CDR1 (SEQ ID NO: 10)
Asn Tyr Tyr Met Tyr hPD-1.09A heavy chain CDR2 (SEQ ID NO: 11)
Gly Ile Asn Pro Ser Asn Gly Gly Thr Asn Phe Asn Glu Lys Phe Lys Asn hPD-1.09A heavy chain CDR3 (SEQ ID NO: 12)
Arg Asp Tyr Arg Phe Asp Met Gly Phe Asp Tyr

FIGURE 3A

109A-H heavy chain variable region (SEQ ID NO: 13)

```
Gln Val Gln Leu Val Gln Ser Gly Val Glu Val Lys Lys Pro Gly Ala Ser Val Lys
Val Ser Cys Lys Ala Ser Gly Tyr Thr Phe Thr Asn Tyr Tyr Met Tyr Trp Val Arg
Gln Ala Pro Gly Gln Gly Leu Glu Trp Met Gly Gly Ile Asn Pro Ser Asn Gly Gly
Thr Asn Phe Asn Glu Lys Phe Lys Asn Arg Val Thr Leu Thr Thr Asp Ser Ser Thr
Thr Thr Ala Tyr Met Glu Leu Lys Ser Leu Gln Phe Asp Asp Thr Ala Val Tyr Tyr
Cys Ala Arg Arg Asp Tyr Arg Phe Asp Met Gly Phe Asp Tyr Trp Gly Gln Gly Thr
Thr Val Thr Val Ser Ser
```

FIGURE 3B

409A-H heavy chain full length (SEQ ID NO: 14)

```
Gln Val Gln Leu Val Gln Ser Gly Val Glu Val Lys Lys Pro Gly Ala Ser Val Lys
Val Ser Cys Lys Ala Ser Gly Tyr Thr Phe Thr Asn Tyr Tyr Met Tyr Trp Val Arg
Gln Ala Pro Gly Gln Gly Leu Glu Trp Met Gly Gly Ile Asn Pro Ser Asn Gly Gly
Thr Asn Phe Asn Glu Lys Phe Lys Asn Arg Val Thr Leu Thr Thr Asp Ser Ser Thr
Thr Thr Ala Tyr Met Glu Leu Lys Ser Leu Gln Phe Asp Asp Thr Ala Val Tyr Tyr
Cys Ala Arg Arg Asp Tyr Arg Phe Asp Met Gly Phe Asp Tyr Trp Gly Gln Gly Thr
Thr Val Thr Val Ser Ser Ala Ser Thr Lys Gly Pro Ser Val Phe Pro Leu Ala Pro
Cys Ser Arg Ser Thr Ser Glu Ser Thr Ala Ala Leu Gly Cys Leu Val Lys Asp Tyr
Phe Pro Glu Pro Val Thr Val Ser Trp Asn Ser Gly Ala Leu Thr Ser Gly Val His
Thr Phe Pro Ala Val Leu Gln Ser Ser Gly Leu Tyr Ser Leu Ser Ser Val Val Thr
Val Pro Ser Ser Ser Leu Gly Thr Lys Thr Tyr Thr Cys Asn Val Asp His Lys Pro
Ser Asn Thr Lys Val Asp Lys Arg Val Glu Ser Lys Tyr Gly Pro Pro Cys Pro Pro
Cys Pro Ala Pro Glu Phe Leu Gly Gly Pro Ser Val Phe Leu Phe Pro Pro Lys Pro
Lys Asp Thr Leu Met Ile Ser Arg Thr Pro Glu Val Thr Cys Val Val Val Asp Val
Ser Gln Glu Asp Pro Glu Val Gln Phe Asn Trp Tyr Val Asp Gly Val Glu Val His
Asn Ala Lys Thr Lys Pro Arg Glu Glu Gln Phe Asn Ser Thr Tyr Arg Val Val Ser
Val Leu Thr Val Leu His Gln Asp Trp Leu Asn Gly Lys Glu Tyr Lys Cys Lys Val
Ser Asn Lys Gly Leu Pro Ser Ser Ile Glu Lys Thr Ile Ser Lys Ala Lys Gly Gln
Pro Arg Glu Pro Gln Val Tyr Thr Leu Pro Pro Ser Gln Glu Glu Met Thr Lys Asn
Gln Val Ser Leu Thr Cys Leu Val Lys Gly Phe Tyr Pro Ser Asp Ile Ala Val Glu
Trp Glu Ser Asn Gly Gln Pro Glu Asn Asn Tyr Lys Thr Thr Pro Pro Val Leu Asp
Ser Asp Gly Ser Phe Phe Leu Tyr Ser Arg Leu Thr Val Asp Lys Ser Arg Trp Gln
Glu Gly Asn Val Phe Ser Cys Ser Val Met His Glu Ala Leu His Asn His Tyr Thr
Gln Lys Ser Leu Ser Leu Ser Leu Gly Lys
```

FIGURE 4

K09A-L-11 light chain variable region (SEQ ID NO: 15)

Glu Ile Val Leu Thr Gln Ser Pro Ala Thr Leu Ser Leu Ser Pro Gly Glu Arg Ala
Thr Leu Ser Cys Arg Ala Ser Lys Gly Val Ser Thr Ser Gly Tyr Ser Tyr Leu His
Trp Tyr Gln Gln Lys Pro Gly Gln Ala Pro Arg Leu Leu Ile Tyr Leu Ala Ser Tyr
Leu Glu Ser Gly Val Pro Ala Arg Phe Ser Gly Ser Gly Ser Gly Thr Asp Phe Thr
Leu Thr Ile Ser Ser Leu Glu Pro Glu Asp Phe Ala Val Tyr Tyr Cys Gln His Ser
Arg Asp Leu Pro Leu Thr Phe Gly Gly Gly Thr Lys Val Glu Ile Lys

K09A-L-16 light chain variable region (SEQ ID NO: 16)

Glu Ile Val Leu Thr Gln Ser Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Asp Phe Thr
Leu Lys Ile Ser Arg Val Glu Ala Glu Asp Val Gly Val Tyr Tyr Cys Gln His Ser
Arg Asp Leu Pro Leu Thr Phe Gly Gln Gly Thr Lys Leu Glu Ile Lys

K09A-L-17 light chain variable region (SEQ ID NO: 17)

Asp Ile Val Met Thr Gln Thr Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Ala Phe Thr
Leu Lys Ile Ser Arg Val Glu Ala Glu Asp Val Gly Leu Tyr Tyr Cys Gln His Ser
Arg Asp Leu Pro Leu Thr Phe Gly Gln Gly Thr Lys Leu Glu Ile Lys

FIGURE 5A

K09A-L-11 light chain full length (SEQ ID NO: 18)

```
Glu Ile Val Leu Thr Gln Ser Pro Ala Thr Leu Ser Leu Ser Pro Gly Glu Arg Ala
Thr Leu Ser Cys Arg Ala Ser Lys Gly Val Ser Thr Ser Gly Tyr Ser Tyr Leu His
Trp Tyr Gln Gln Lys Pro Gly Gln Ala Pro Arg Leu Leu Ile Tyr Leu Ala Ser Tyr
Leu Glu Ser Gly Val Pro Ala Arg Phe Ser Gly Ser Gly Ser Gly Thr Asp Phe Thr
Leu Thr Ile Ser Ser Leu Glu Pro Glu Asp Phe Ala Val Tyr Tyr Cys Gln His Ser
Arg Asp Leu Pro Leu Thr Phe Gly Gly Gly Thr Lys Val Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys
```

K09A-L-16 light chain full length (SEQ ID NO: 19)

```
Glu Ile Val Leu Thr Gln Ser Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Asp Phe Thr
Leu Lys Ile Ser Arg Val Glu Ala Glu Asp Val Gly Val Tyr Tyr Cys Gln His Ser
Arg Asp Leu Pro Leu Thr Phe Gly Gln Gly Thr Lys Leu Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys
```

FIGURE 5B

K09A-L-17 light chain full length (SEQ ID NO: 20)

Asp Ile Val Met Thr Gln Thr Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Ala Phe Thr
Leu Lys Ile Ser Arg Val Glu Ala Glu Asp Val Gly Leu Tyr Tyr Cys Gln His Ser
Arg Asp Leu Pro Leu Thr Phe Gly Gln Gly Thr Lys Leu Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys

FIGURE 6

Prembrolizumab

Heavy chain ( SEQ ID NO: 21)

| | | | | | |
|---|---|---|---|---|---|
| QVQLVQSGVE | VKKPGASVKV | SCKASGYTFT | NYYMYWVRQA | PGQGLEWMGG | 50 |
| INPSNGGTNF | NEKFKNRVTL | TTDSSTTTAY | MELKSLQFDD | TAVYYCARRD | 100 |
| YRFDMGFDYW | GQGTTVTVSS | ASTKGPSVFP | LAPCSRSTSE | STAALGCLVK | 150 |
| DYFPEPVTVS | WNSGALTSGV | HTFPAVLQSS | GLYSLSSVVT | VPSSSLGTKT | 200 |
| YTCNVDHKPS | NTKVDKRVES | KYGPPCPPCP | APEFLGGPSV | FLFPPKPKDT | 250 |
| LMISRTPEVT | CVVVDVSQED | PEVQFNWYVD | GVEVHNAKTK | PREEQFNSTY | 300 |
| RVVSVLTVLH | QDWLNGKEYK | CKVSNKGLPS | SIEKTISKAK | GQPREPQVYT | 350 |
| LPPSQEEMTK | NQVSLTCLVK | GFYPSDIAVE | WESNGQPENN | YKTTPPVLDS | 400 |
| DGSFFLYSRL | TVDKSRWQEG | NVFSCSVMHE | ALHNHYTQKS | LSLSLGK | 447 |

Light chain (SEQ ID NO: 22)

| | | | | | |
|---|---|---|---|---|---|
| EIVLTQSPAT | LSLSPGERAT | LSCRASKGVS | TSGYSYLHWY | QQKPGQAPRL | 50 |
| LIYLASYLES | GVPARFSGSG | SGTDFTLTIS | SLEPEDFAVY | YCQHSRDLPL | 100 |
| TFGGGTKVEI | KRTVAAPSVF | IFPPSDEQLK | SGTASVVCLL | NNFYPREAKV | 150 |
| QWKVDNALQS | GNSQESVTEQ | DSKDSTYSLS | STLTLSKADY | EKHKVYACEV | 200 |
| THQGLSSPVT | KSFNRGEC | | | | 219 |

FIGURE 7

Nivolumab

Heavy chain (SEQ ID NO: 23)

```
QVQLVESGGG VVQPGRSLRL DCKASGITFS NSGMHWVRQA PGKGLEWVAV  50
IWYDGSKRYY ADSVKGRFTI SRDNSKNTLF LQMNSLRAED TAVYYCATND 100
DYWGQGTLVT VSSASTKGPS VFPLAPCSRS TSESTAALGC LVKDYFPEPV 150
TVSWNSGALT SGVHTFPAVL QSSGLYSLSS VVTVPSSSLG TKTYTCNVDH 200
KPSNTKVDKR VESKYGPPCP PCPAPEFLGG PSVFLFPPKP KDTLMISRTP 250
EVTCVVVDVS QEDPEVQFNW YVDGVEVHNA KTKPREEQFN STYRVVSVLT 300
VLHQDWLNGK EYKCKVSNKG LPSSIEKTIS KAKGQPREPQ VYTLPPSQEE 350
MTKNQVSLTC LVKGFYPSDI AVEWESNGQP ENNYKTTPPV LDSDGSFFLY 400
SRLTVDKSRW QEGNVFSCSV MHEALHNHYT QKSLSLSLGK            440
```

Light chain (SEQ ID NO: 24)

```
EIVLTQSPAT LSLSPGERAT LSCRASQSVS SYLAWYQQKP GQAPRLLIYD  50
ASNRATGIPA RFSGSGSGTD FTLTISSLEP EDFAVYYCQQ SSNWPRTFGQ 100
GTKVEIKRTV AAPSVFIFPP SDEQLKSGTA SVVCLLNNFY PREAKVQWKV 150
DNALQSGNSQ ESVTEQDSKD STYSLSSTLT LSKADYEKHK VYACEVTHQG 200
LSSPVTKSFN RGEC                                       214
```

COMBINATION OF A PD-1 ANTAGONIST AND A VEGFR/FGFR/RET TYROSINE KINASE INHIBITOR FOR TREATING CANCER

CROSS REFERENCE TO RELATED APPLICATIONS

This application is a continuation of U.S. application Ser. No. 15/554,577, filed on Aug. 30, 2017, pending, which is the National Stage of International Application No. PCT/US2016/020747, filed on Mar. 3, 2016, and which claims benefit to Japan Application JP 2015-042683 filed on Mar. 4, 2015, Japan Application JP 2015-114890 filed on Jun. 5, 2015, U.S. Provisional Application No. 62/128,232 filed Mar. 4, 2015, and U.S. Provisional Application 62/171,615 filed on Jun. 5, 2015, the contents of which are hereby incorporated by reference in their entirety.

SEQUENCE LISTING

This application contains a sequence listing that has been submitted in ASCII format via EFS-Web and incorporated herein by reference in its entirety. Said ASCII copy, created on Oct. 7, 2021, is named 213597_599495_SL.txt and is 31,622 bytes in size.

TECHNICAL FIELD

Combination therapies useful for the treatment of cancer are disclosed. In particular, a combination therapy which comprises an antagonist of a Programmed Death 1 protein (PD-1) and a multiple receptor tyrosine kinase (multi-RTK) inhibitor is disclosed. Even more particularly, disclosed is a tumor therapeutic agent containing a combination of a quinoline derivative that exhibits a multi-tyrosine kinase inhibitory action and an anti-PD-1 antibody.

BACKGROUND

PD-1 is recognized as an important player in immune regulation and the maintenance of peripheral tolerance. PD-1 is moderately expressed on naive T–, B– and Natural killer T (NKT)-cells and up-regulated by T/B– cell receptor signaling on lymphocytes, monocytes and myeloid cells (1).

Two known ligands for PD-1, PD-L1 (B7-H1) and PD-L2 (B7-DC), are expressed in human cancers arising in various tissues. In large sample sets of e.g. ovarian, renal, colorectal, pancreatic, liver cancers and melanoma, it was shown that PD-L1 expression correlated with poor prognosis and reduced overall survival irrespective of subsequent treatment (2-13). Similarly, PD-1 expression on tumor infiltrating lymphocytes was found to mark dysfunctional T cells in breast cancer and melanoma (14-15) and to correlate with poor prognosis in renal cancer (16). It has been proposed that PD-L1 expressing tumor cells interact with PD-1 expressing T cells to attenuate T cell activation and evasion of immune surveillance, thereby contributing to an impaired immune response against the tumor. Therefore, an antibody directed against either the PD-1 receptor or the PD-L1 ligand can inhibit the binding therebetween, resulting in an increased immune action on the tumor cells (23).

Several monoclonal antibodies that inhibit the interaction between PD-1 and one or both of its ligands PD-L1 and PD-L2 are in clinical development for treating cancer. It has been proposed that the efficacy of such antibodies might be enhanced if administered in combination with other approved or experimental cancer therapies, e.g., radiation, surgery, chemotherapeutic agents, targeted therapies, agents that inhibit other signaling pathways that are disregulated in tumors, and other immune enhancing agents.

Tyrosine kinases are involved in the modulation of growth factor signaling and thus are an important target for cancer therapies. Lenvatinib mesilate, discovered and developed by Eisai Co., Ltd., is an oral receptor tyrosine kinase (RTK) inhibitor that selectively inhibits the kinase activities of vascular endothelial growth factor (VEGF) receptors (VEGFR1 (FLT1), VEGFR2 (KDR) and VEGFR3 (FLT4)), and fibroblast growth factor (FGF) receptors FGFR1, 2, 3 and 4 in addition to other proangiogenic and oncogenic pathway-related RTKs (including the platelet-derived growth factor (PDGF) receptor PDGFRα; KIT; and the RET proto-oncogene (RET)) involved in tumor proliferation. In particular, lenvatinib possesses a new binding mode (Type V) to VEGFR2, as confirmed through X-ray crystal structural analysis, and exhibits rapid and potent inhibition of kinase activity, according to kinetic analysis.

Lenvatinib mesilate was recently approved in the United States for the treatment of patients with locally recurrent or metastatic, progressive, radioactive iodine-refractory differentiated thyroid cancer. Its chemical name is 4-[3-chloro-4-(cyclopropylaminocarbonyl) aminophenoxy]-7-methoxy-6-quinolinecarboxamide methanesulfonate. Eisai was granted Orphan Drug Designation (ODD) for lenvatinib mesilate in various types of thyroid cancer in the United States, Japan, and Europe. Lenvatinib mesilate is under investigation in thyroid, hepatocellular, endometrial, non-small cell lung cancer, renal cell carcinoma (RCC), melanoma, glioblastoma, and other solid tumor types. The compound represented by Formula (I) below has anti-angiogenic actions (17), inhibitory effects (18-21) against tyrosine kinases which are reported to be involved in malignant alteration of tumors and the like.

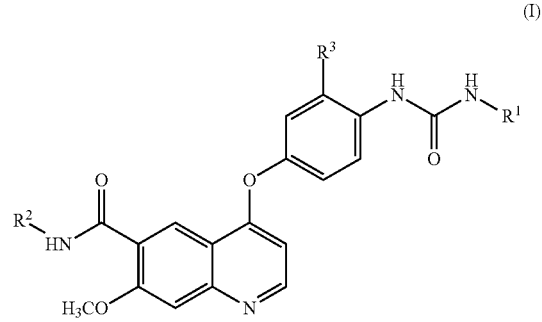

(I)

$R^1$ is $C_{1-6}$ alkyl or $C_{3-8}$ cycloalkyl. $R^2$ is a hydrogen atom or $C_{1-6}$ alkoxy. $R^3$ is a hydrogen atom or a halogen atom.

In general, tumor therapeutic agents are often not effective for all of the patients when administered individually. Thus, attempts have been made to increase the cure rate of such therapeutic agents by combining them (22).

SUMMARY

As disclosed herein, administration of a combination of a compound represented by Formula (I) and a PD-1 receptor antibody attains an unexpectedly excellent anti-tumor effect.

A method is provided for treating a cancer in an individual that includes administering to the individual a combination therapy which comprises a PD-1 antagonist, which is not MPDL3280A, and a multi-RTK inhibitor. In some instances, the individual is a human. The cancer may be a solid tumor, a non-small cell lung cancer (NSCLC), RCC, endometrial cancer, urothelial cancer, squamous cell carcinoma of head and neck or melanoma.

The PD-1 antagonist of the method may be a monoclonal antibody or an antigen binding fragment thereof. In some instances, the antagonist is an anti-PD-1 antibody. The antagonist may be pembrolizumab or nivolumab.

The multi-RTK inhibitor of the method may be a compound or pharmaceutically acceptable salt thereof represented by Formula (I):

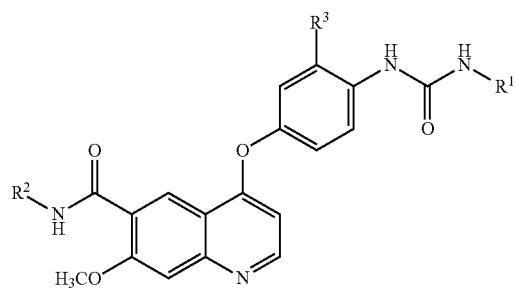

(I)

in which $R^1$ is $C_{1-6}$ alkyl or $C_{3-8}$ cycloalkyl, $R^2$ is a hydrogen atom or $C_{1-6}$ alkoxy, and $R^3$ is a hydrogen atom or a halogen atom. The compound represented by Formula (I) may be one or more of the following compounds:

4-[3-chloro-4-(cyclopropylaminocarbonyl)aminophenoxy]-7-methoxy-6-quinolinecarboxamide:

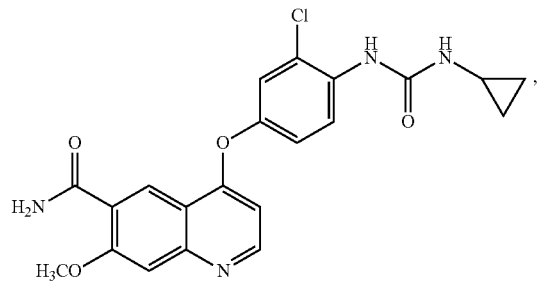 [SMILES: COc1cc2nccc(Oc3ccc(NC(=O)NC4CC4)c(Cl)c3)c2cc1C(N)=O]

4-[3-chloro-4-(methylaminocarbonyl)aminophenoxy]-7-methoxy-6-quinolinecarboxamide:

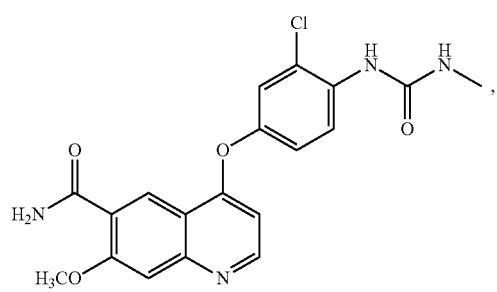 [SMILES: CNC(=O)Nc1ccc(Oc2ccnc3cc(OC)c(C(N)=O)cc23)cc1Cl]

4-[3-chloro-4-(ethylaminocarbonyl)aminophenoxy]-7-methoxy-6-quinolinecarboxamide:

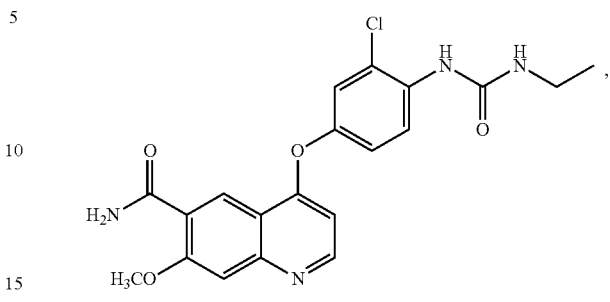

N6-methoxy-4-(3-chloro-4-{[(cyclopropylamino)carbonyl)amino]phenoxy}-7-methoxy-6-quinolinecarboxamide:

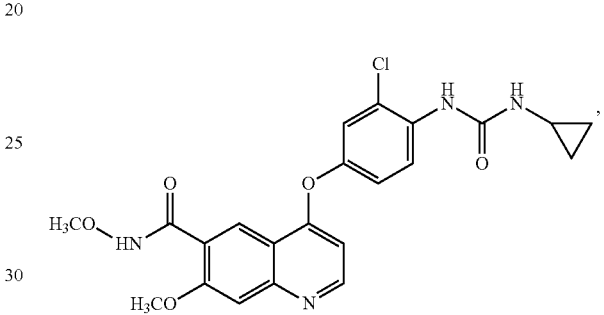

and N6-methoxy-4-(3-chloro-4-{[(ethylamino)carbonyl]amino}phenoxy)-7-methoxy-6-quinolinecarboxamide:

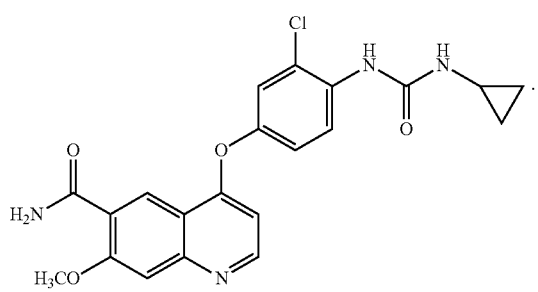 [SMILES: COc1cc2nccc(Oc3ccc(NC(=O)NC4CC4)c(Cl)c3)c2cc1C(N)=O]

More specifically, the compound represented by Formula (I) is 4-[3-chloro-4-(cyclopropylaminocarbonyl)aminophenoxy]-7-methoxy-6-quinolinecarboxamide:

In some instances, the PD-1 antagonist of the method is pembrolizumab and the multi-RTK inhibitor is lenvatinib or a pharmaceutically acceptable salt thereof. Administration of pembrolizumab may occur after the administration of lenvatinib in some treatment regimens. In some instances, the lenvatinib is administered after the pembrolizumab.

A kit is provided that includes a first container, a second container and a package insert. The first container of the kit includes at least one dose of a medicament comprising a PD-1 antagonist, which is not MPDL3280A, and the second container includes at least one dose of a medicament comprising a multi-RTK inhibitor. The package insert includes instructions for treating an individual for cancer using the medicaments. The instructions of the kit may state that the medicaments are intended for use in treating an individual having a cancer that tests positive for PD-L1 expression by an immunohistochemical (IHC) assay. In some instances, the individual may be a human.

The multi-RTK inhibitor of the kit may be is a compound or pharmaceutically acceptable salt thereof represented by Formula (I):

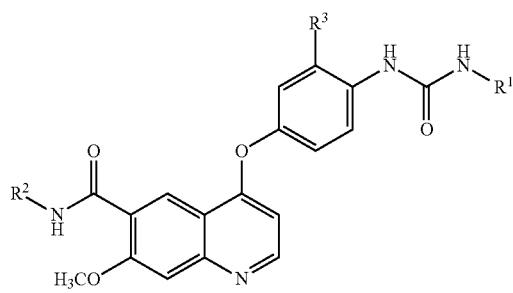
(I)

in which $R^1$ is $C_{1-6}$ alkyl or $C_{3-8}$ cycloalkyl, $R^2$ is a hydrogen atom or $C_{1-6}$ alkoxy, and $R^3$ is a hydrogen atom or a halogen atom. The compound represented by Formula (I) may be one or more of the following compounds:

4-[3-chloro-4-(cyclopropylaminocarbonyl)aminophenoxy]-7-methoxy-6-quinolinecarboxamide:

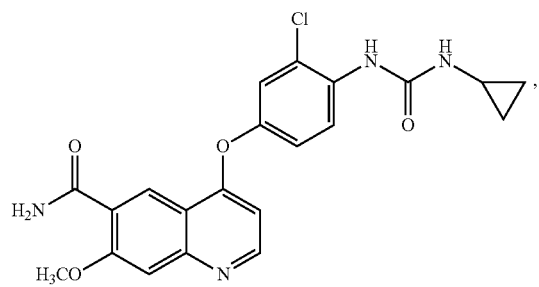 [SMILES: COc1cc2nccc(Oc3ccc(NC(=O)NC4CC4)c(Cl)c3)c2cc1C(N)=O]

4-[3-chloro-4-(methylaminocarbonyl)aminophenoxy]-7-methoxy-6-quinolinecarboxamide:

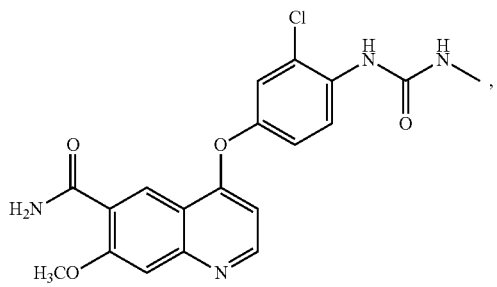 [SMILES: CNC(=O)Nc1ccc(Oc2ccnc3cc(OC)c(C(N)=O)cc23)cc1Cl]

4-[3-chloro-4-(ethylaminocarbonyl)aminophenoxy]-7-methoxy-6-quinolinecarboxamide:

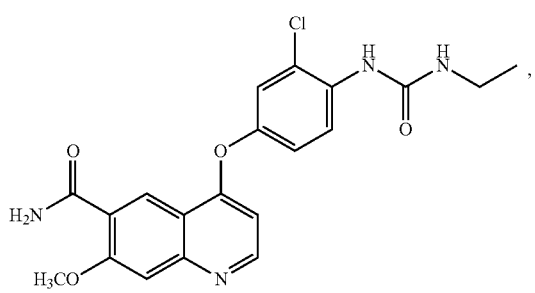 [SMILES: CCNC(=O)Nc1ccc(Oc2ccnc3cc(OC)c(C(N)=O)cc23)cc1Cl]

N6-methoxy-4-(3-chloro-4-{[(cyclopropylamino)carbonyl]amino]phenoxy}-7-methoxy-6-quinolinecarboxamide:

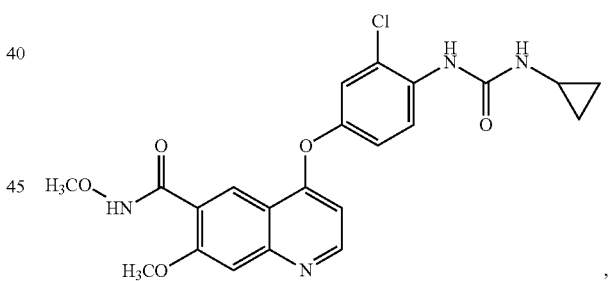

and N6-methoxy-4-(3-chloro-4-{[(ethylamino)carbonyl]amino}phenoxy)-7-methoxy-6-quinolinecarboxamide:

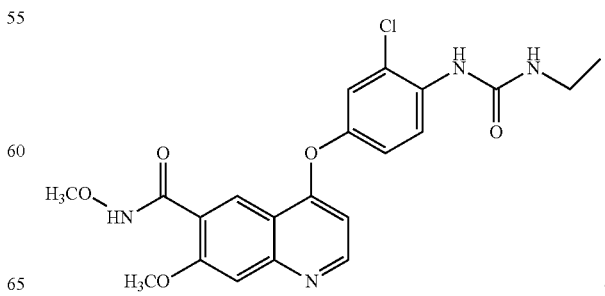

More specifically, the compound represented by Formula (I) may be 4-[3-chloro-4-(cyclopropylaminocarbonyl)aminophenoxy]-7-methoxy-6-quinolinecarboxamide:

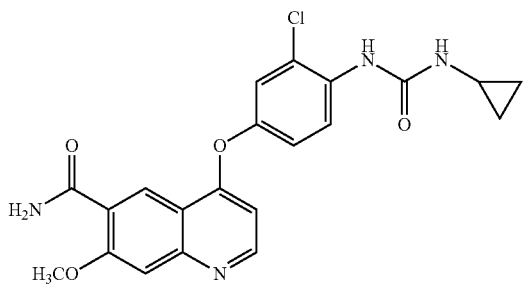

The PD-1 antagonist provided by the kit may be pembrolizumab formulated as a liquid medicament which comprises 25 mg/ml pembrolizumab, 7% (w/v) sucrose, 0.02% (w/v) polysorbate 80 in 10 mM histidine buffer pH 5.5, and the multi-RTK inhibitor may be lenvatinib or a pharmaceutically acceptable salt thereof formulated as a 4 mg or 10 mg lenvatinib capsule comprising calcium carbonate, mannitol, microcrystalline cellulose, hydroxypropylcellulose, low-substituted hydroxypropylcellulose, and talc.

The medicaments included with the kit may be applied to treat NSCLC, RCC, endometrial cancer, urothelial cancer, squamous cell carcinoma of head and neck or melanoma.

A method is provided for treating a human individual diagnosed with a cancer, comprising administering to the individual a combination therapy for at least 24 weeks. The combination therapy includes pembrolizumab and lenvatinib or a pharmaceutically acceptable salt thereof. Lenvatinib or a pharmaceutically acceptable salt thereof may be administered at a daily dose of 24 mg, 20 mg or 14 mg, each as lenvatinib, and pembrolizumab may be administered at a dose of 200 mg Q3W.

A medicament is provided comprising a PD-1 antagonist for use in combination with a multi-RTK inhibitor for treating a cancer.

A medicament is also provided comprising a multi-RTK inhibitor for use in combination with a PD-1 antagonist for treating a cancer.

A use is also provided of a PD-1 antagonist in the manufacture of medicament for treating a cancer in an individual when administered in combination with a multi-RTK inhibitor and use of a multi-RTK inhibitor in the manufacture of a medicament for treating a cancer in an individual when administered in combination with a PD-1 antagonist.

Also provided is an use of a PD-1 antagonist and a multi-RTK inhibitor in the manufacture of medicaments for treating a cancer in an individual. Said medicaments can comprise a kit, and the kit can also comprises a package insert comprising instructions for using the PD-1 antagonist in combination with a multi-RTK inhibitor to treat a cancer in an individual. The kit may include a pharmaceutical composition comprising a compound or pharmaceutically acceptable salt thereof represented by the above Formula (I) and a vehicle. The kit may include a pharmaceutical composition comprising an anti-PD-1 antibody and a vehicle.

In all of the above treatment methods, medicaments and uses, the PD-1 antagonist inhibits the binding of PD-L1 to PD-1, and preferably also inhibits the binding of PD-L2 to PD-1. In some of the above treatment methods, medicaments and uses, the PD-1 antagonist is a monoclonal antibody, or an antigen binding fragment thereof, which specifically binds to PD-1 or to PD-L1 and blocks the binding of PD-L1 to PD-1. For example, the PD-1 antagonist can be an anti-PD-1 antibody which comprises a heavy chain and a light chain, and wherein the heavy and light chains comprise the amino acid sequences shown in FIG. 6 (SEQ ID NO:21 and SEQ ID NO:22). The anti-PD-1 antibody may be combined with a compound or pharmaceutically acceptable salt thereof represented by the above Formula (I) for therapy of a tumor. The anti-PD-1 antibody may be combined with a compound or pharmaceutically acceptable salt thereof represented by the above Formula (I). Also provided is a method of treating a tumor is disclosed that can include the combined use of a compound or pharmaceutically acceptable salt thereof represented by the above Formula (I) and an anti-PD-1 antibody.

In all of the above treatment methods, medicaments and uses herein, the multi-RTK inhibitor inhibits the kinase activities of at least each of the following RTKs: (i) VEGFR2, (ii) at least one FGFR selected from the group consisting of FGFR1, 2, 3 and 4; and (iii) RET. In some instances, the multi-RTK inhibitor also inhibits the kinase activities of VEGFR1, VEGFR3, fibroblast growth factor (FGF) receptors FGFR1, 2, 3 and 4, platelet-derived growth factor (PDGF) receptor alpha (PDGFRα); and KIT.

In some of the above treatment methods, medicaments and uses, the multi-RTK inhibitor is lenvatinib or a pharmaceutically acceptable salt thereof, such as lenvatinib mesilate.

In the above treatment methods, medicaments and uses, the individual is a human and the cancer is a solid tumor and in some instances, the solid tumor is bladder cancer, breast cancer, clear cell kidney cancer, squamous cell carcinoma of head and neck, lung squamous cell carcinoma, malignant melanoma, NSCLC, ovarian cancer, pancreatic cancer, prostate cancer, RCC, small-cell lung cancer (SCLC) or triple negative breast cancer. The cancer may be NSCLC, endometrial cancer, urothelial cancer, squamous cell carcinoma of head and neck or melanoma.

In the above treatment methods, medicaments and uses, the individual can be a human and the cancer is a heme malignancy and in some instances, the heme malignancy is acute lymphoblastic leukemia (ALL), acute myeloid leukemia (AML), chronic lymphocytic leukemia (CLL), chronic myeloid leukemia (CML), diffuse large B-cell lymphoma (DLBCL), EBV-positive DLBCL, primary mediastinal large B-cell lymphoma, T-cell/histiocyte-rich large B-cell lymphoma, follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL).

Also, any of the above treatment methods, medicaments and uses can be utilized if the cancer tests positive for the expression of one or both of PD-L1 and PD-L2. In still other instances, the cancer has elevated PD-L1 expression.

In some of the above treatment methods, medicaments and uses, the individual is a human, the cancer tests positive for human PD-L1 and is selected from the group consisting of NSCLC, endometrial cancer, urothelial cancer, squamous cell carcinoma of head and neck, or melanoma.

In some of the above treatment methods, medicaments and uses, the multi-RTK inhibitor is a compound or pharmaceutically acceptable salt thereof represented by Formula (I):

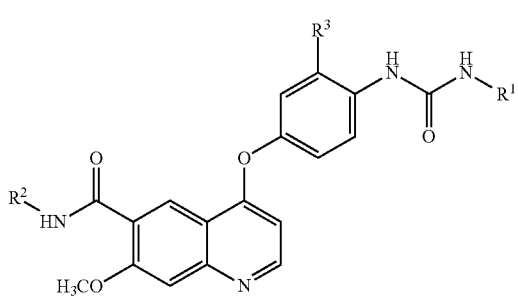

wherein $R^1$ is $C_{1-6}$ alkyl or $C_{3-8}$ cycloalkyl, $R^2$ is a hydrogen atom or $C_{1-6}$ alkoxy, and $R^3$ is a hydrogen atom or a halogen atom. The tumor therapeutic agent may administer simultaneously or separately a compound or pharmaceutically acceptable salt thereof represented by the above Formula (I) and an anti-PD-1 antibody. The tumor therapeutic agent may be administered simultaneously or separately. For example, a composition can comprise a compound or pharmaceutically acceptable salt thereof represented by the above Formula (I), and a composition comprising an anti-PD-1 antibody. The tumor therapeutic agent may include a compound or pharmaceutically acceptable salt thereof represented by the above Formula (I), and an anti-PD-1 antibody.

A compound or pharmaceutically acceptable salt thereof is disclosed that is represented by the Formula (I) for combined use with an anti-PD-1 antibody. The compound or pharmaceutically acceptable salt thereof represented by the Formula (I) may be used for therapy of a tumor by combined use with an anti-PD-1 antibody.

A pharmaceutical composition is disclosed that may include a compound or pharmaceutically acceptable salt thereof represented by the above Formula (I), an anti-PD-1 antibody, and a vehicle.

The compound represented by the above Formula (I) is preferably one or more of the following compounds:

4-[3-chloro-4-(cyclopropylaminocarbonyl)aminophenoxy]-7-methoxy-6-quinolinecarboxamide:

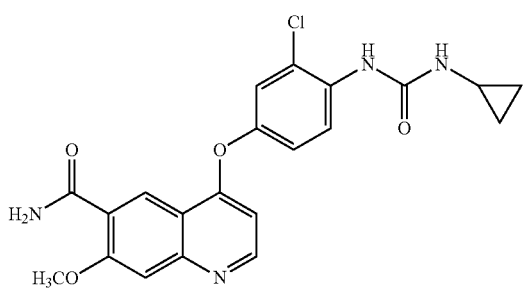

4-[3-chloro-4-(methylaminocarbonyl)aminophenoxy]-7-methoxy-6-quinolinecarboxamide:

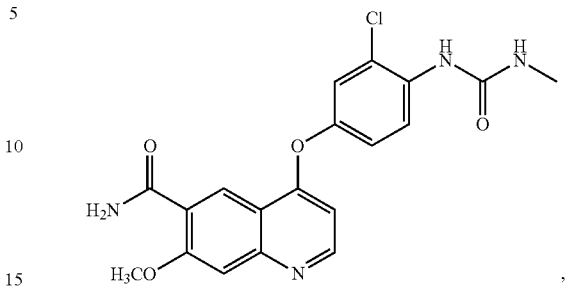

4-[3-chloro-4-(ethylaminocarbonyl)aminophenoxy]-7-methoxy-6-quinolinecarboxamide:

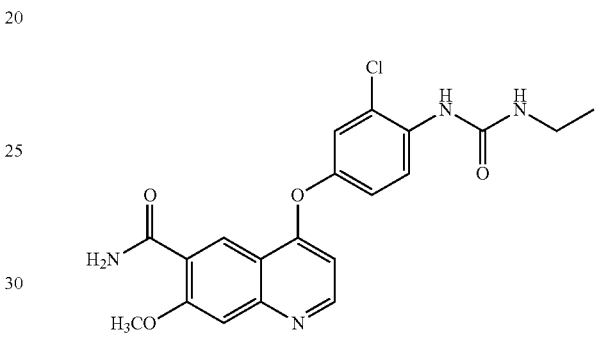

N6-methoxy-4-(3-chloro-4-{[(cyclopropylamino)carbonyl)amino]phenoxy}-7-methoxy-6-quinolinecarboxamide:

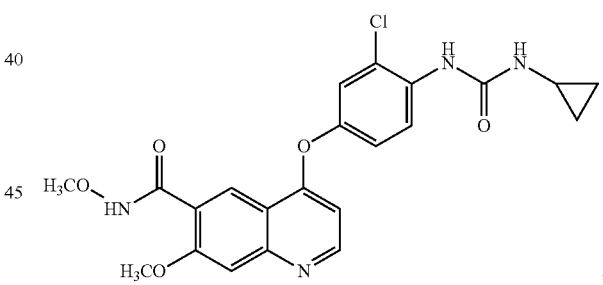

And N6-methoxy-4-(3-chloro-4-{[(ethylamino)carbonyl]amino}phenoxy)-7-methoxy-6-quinolinecarboxamide:

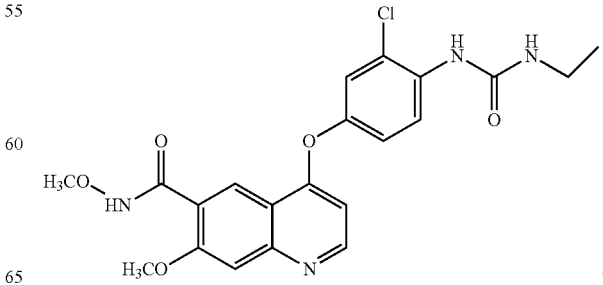

The compound represented by the above Formula (I) is more preferably 4-[3-chloro-4-(cyclopropylaminocarbonyl)aminophenoxy]-7-methoxy-6-quinolinecarboxamide:

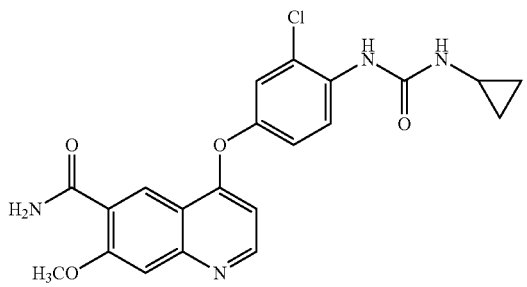 [SMILES: COc1cc2nccc(Oc3ccc(NC(=O)NC4CC4)c(Cl)c3)c2cc1C(N)=O]

(hereinafter, also sometimes indicated as lenvatinib).

A tumor therapeutic agent is provided for combined use of a compound having a multi-tyrosine kinase inhibitory action and an anti-PD-1 antibody. Such a tumor therapeutic agent exhibits an excellent anti-tumor effect compared to cases where these are individually used, and may exhibit anti-tumor effects against various cancer types.

BRIEF DESCRIPTION OF THE DRAWINGS

FIG. 1 shows amino acid sequences of the light chain and heavy chain CDRs for an exemplary anti-PD-1 monoclonal antibody (SEQ ID NOs:1-6).

FIG. 2 shows amino acid sequence of the light chain and heavy chain CDRs for another exemplary anti-PD-1 monoclonal antibody (SEQ ID NOs:7-12).

FIGS. 3A and 3B shows amino acid sequences of the heavy chain variable region (FIG. 3A) and full length heavy chain (FIG. 3B) for an exemplary anti-PD-1 monoclonal antibody (SEQ ID NO:13 and SEQ ID NO:14).

FIG. 4 shows amino acid sequences of alternative light chain variable regions for an exemplary anti-PD-1 monoclonal antibody (SEQ ID NOs:15-17).

FIGS. 5A and 5B show amino acid sequences of alternative light chains for an exemplary anti-PD-1 monoclonal antibody, with FIG. 5A showing the amino acid sequences for the K09A-L-11 and K09A-L-16 light chains (SEQ ID NOs:18 and 19, respectively) and FIG. 5B showing the amino acid sequence for the K09A-L-17 light chain (SEQ ID NO:20).

FIG. 6 shows amino acid sequences of the heavy and light chains for pembrolizumab (SEQ ID NOs. 21 and 22, respectively).

FIG. 7 shows amino acid sequences of the heavy and light chains for nivolumab (SEQ ID NOS: 23 and 24, respectively).

DETAILED DESCRIPTION

Figure 8:
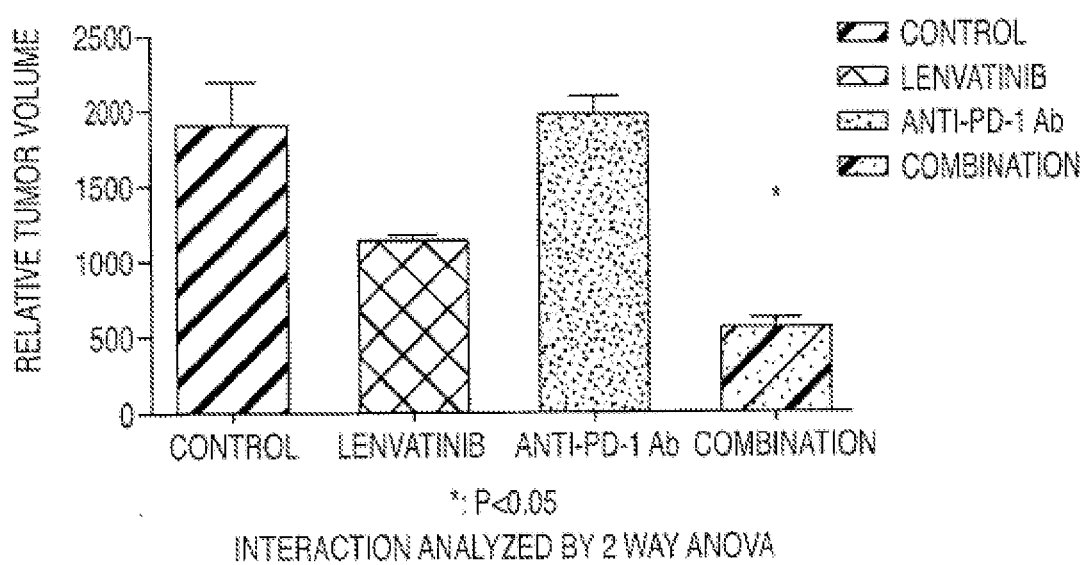
FIG. 8 is a diagram illustrating anti-tumor effects of lenvatinib, an anti-PD-1 antibody (RMP 1-14), and a combination of both in a subcutaneous LL/2 (LLc1) transplantation model.

Abbreviations. Throughout the detailed description and examples the following abbreviations will be used:
BOR Best overall response
BID One dose twice daily
CBR Clinical Benefit Rate
CDR Complementarity determining region
CHO Chinese hamster ovary
CR Complete Response
DCR Disease Control Rate
DFS Disease free survival
DLT Dose limiting toxicity
DOR Duration of Response
DSDR Durable Stable Disease Rate
FFPE Formalin-fixed, paraffin-embedded
FR Framework region
IgG Immunoglobulin G
IHC Immunohistochemistry or immunohistochemical
irRC Immune related response criteria
IV Intravenous
MTD Maximum tolerated dose
NCBI National Center for Biotechnology Information
NCI National Cancer Institute
ORR Objective response rate
OS Overall survival
PD Progressive disease
PD-1 Programmed Death 1
PD-L1 Programmed Cell Death 1 Ligand 1
PD-L2 Programmed Cell Death 1 Ligand 2
PFS Progression free survival
PR Partial response
Q2W One dose every two weeks
Q3W One dose every three weeks
QD One dose per day
RECIST Response Evaluation Criteria in Solid Tumors
SD Stable disease
VH Immunoglobulin heavy chain variable region
VK Immunoglobulin kappa light chain variable region

I. DEFINITIONS

So that the methods, compositions, and uses may be more readily understood, certain technical and scientific terms are specifically defined below. Unless specifically defined elsewhere in this document, all other technical and scientific terms used herein have the meaning commonly understood by one of ordinary skill in the art.

"About" when used to modify a numerically defined parameter (e.g., the dose of a PD-1 antagonist or a multi-RTK inhibitor, or the length of treatment time with a combination therapy described herein) means that the parameter may vary by as much as 10% below or above the stated numerical value for that parameter. For example, a dose of about 20 mg may vary between 18 mg and 22 mg.

"Preferably" means a more desirable choice. For example, when used to modify a numerically defined parameter it indicates that the preferred parameter provides an improved result over another value for the parameter. This meaning of "preferably" only applies outside of the United States.

As used herein, including the appended claims, the singular forms of words such as "a," "an," and "the," include their corresponding plural references unless the context clearly dictates otherwise.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human.

As used herein, the term "antibody" refers to any form of antibody that exhibits the desired biological or binding activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies, and camelized single domain antibodies. "Parental antibodies" are antibodies obtained by exposure of an immune system to an antigen prior to modification of the antibodies for an intended use, such as humanization of an antibody for use as a human therapeutic.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, FUNDAMENTAL IMMUNOLOGY Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of SEQUENCES OF PROTEINS OF IMMUNOLOGICAL INTEREST, Kabat, et al.; National Institutes of Health, Bethesda, Md.; 5$^{th}$ ed.; NIH Publ. No. 91-3242 (1991); Kabat (1978) Adv. Prot. Chem. 32: 1-75; Kabat, et al., (1977) J. Biol. Chem. 252: 6609-6616; Chothia, et al., (1987) J Mol. Biol. 196: 901-917 or Chothia, et al., (1989) Nature 342: 878-883.

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) SEQUENCES OF PROTEINS OF IMMUNOLOGICAL INTEREST, 5th Ed. Public Health Service, National Institutes of Health, Bethesda, Md. (defining the CDR regions of an antibody by sequence); see also Chothia and Lesk (1987) J. Mol. Biol. 196: 901-917 (defining the CDR regions of an antibody by structure). As used herein, the term "framework" or "FR" residues refers to those variable domain residues other than the hypervariable region residues defined herein as CDR residues.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies, or binding fragments thereof, will bind to the target protein with an affinity that is at least two fold greater, preferably at least ten times greater, more preferably at least 20-times greater, and most preferably at least 100-times greater than the affinity with non-target proteins. As used herein, an antibody is said to bind specifically to a polypeptide comprising a given amino acid sequence, e.g. the amino acid sequence of a mature human PD-1 or human PD-L1 molecule, if it binds to polypeptides comprising that sequence but does not bind to proteins lacking that sequence.

"Chimeric antibody" refers to an antibody in which a portion of the heavy and/or light chain is identical with or homologous to corresponding sequences in an antibody derived from a particular species (e.g., human) or belonging to a particular antibody class or subclass, while the remainder of the chain(s) is identical with or homologous to corresponding sequences in an antibody derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

"Anti-tumor response" when referring to a cancer patient treated with a therapeutic regimen, such as a combination therapy described herein, means at least one positive therapeutic effect, such as for example, reduced number of cancer cells, reduced tumor size, reduced rate of cancer cell infiltration into peripheral organs, reduced rate of tumor metastasis or tumor growth, or progression free survival. Positive therapeutic effects in cancer can be measured in a number of ways (See, W. A. Weber, *J. Null. Med.* 50: 1S-10S (2009); Eisenhauer et al., supra). In some instances, an anti-tumor response to a combination therapy described herein is assessed using RECIST 1.1 criteria (response evaluation criteria in solid tumors), bidimentional irRC (immune related response criteria), or unidimensional irRC. In some instances, an anti-tumor response is any of SD, PR, CR, PFS, or DFS.

"Bidimensional irRC" refers to the set of criteria described in Wolchok J D, et al. "Guidelines for the evaluation of immune therapy activity in solid tumors: immune-related response criteria," *Clin Cancer Res.* 2009; 15(23): 7412-7420. These criteria utilize bidimensional tumor measurements of target lesions, which are obtained by multiplying the longest diameter and the longest perpendicular diameter ($cm^2$) of each lesion.

"Biotherapeutic agent" means a biological molecule, such as an antibody or fusion protein, that blocks ligand/receptor signaling in any biological pathway that supports tumor maintenance and/or growth or suppresses the anti-tumor immune response. Classes of biotherapeutic agents include, but are not limited to, antibodies to VEGF, epidermal growth factor receptor (EGFR), Her2/neu, other growth factor receptors, CD20, CD40, CD-40L, CTLA-4, OX-40, 4-1BB, and ICOS.

The terms "cancer," "cancerous," "tumor," or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, hodgkin's lymphoma, non-hodgkin's lymphoma, acute myeloid leukemia (AML), multiple myeloma, adenoma, neurilemmoma, gastrointestinal (tract) cancer, gastric cancer, renal cancer, gallbladder cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, endometrial cancer, uterine body cancer, uterine cervical cancer, and head and neck cancer. Another particular example of cancer includes renal cell carcinoma. A further particular example of cancer includes clear cell kidney cancer. Cancers that may be treated in accordance with the disclosed treatment methods, medicaments, and disclosed uses include those characterized by elevated expression of one or both of PD-L1 and PD-L2 in tested tissue samples.

"CBR" or "Clinical Benefit Rate" means CR+PR+durable SD.

"CDR" or "CDRs" as used herein means complementarity determining region(s) in a immunoglobulin variable region, defined using the Kabat numbering system, unless otherwise indicated.

"Chemotherapeutic agent" is a chemical compound useful in the treatment of cancer. Classes of chemotherapeutic agents include, but are not limited to: alkylating agents, antimetabolites, kinase inhibitors, spindle poison plant alkaloids, cytoxic/antitumor antibiotics, topisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, EGFR inhibitors, VEGF inhibitors, and anti-sense oligonucleotides that inhibit expression of genes implicated in abnormal cell proliferation or tumor growth. Chemotherapeutic agents useful in the treatment methods disclosed herein include cytostatic and/or cytotoxic agents.

"Chothia" as used herein means an antibody numbering system described in Al-Lazikani et al., *JMB* 273: 927-948 (1997).

"Comprising" or variations such as "comprise", "comprises" or "comprised of" are used throughout the specification and claims in an inclusive sense, i.e., to specify the presence of the stated features but not to preclude the presence or addition of further features that may materially enhance the operation or utility of any of the disclosed treatment methods, medicaments, and disclosed uses, unless the context requires otherwise due to express language or necessary implication.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity or other desired property of the protein, such as antigen affinity and/or specificity. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 1 below.

TABLE 1

Exemplary Conservative Amino Acid Substitutions

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |

TABLE 1-continued

Exemplary Conservative Amino Acid Substitutions

| Original residue | Conservative substitution |
|---|---|
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a PD-1 antagonist that consists essentially of a recited amino acid sequence may also include one or more amino acids, including substitutions of one or more amino acid residues, which do not materially affect the properties of the binding compound.

"DCR" or "Disease Control Rate" means CR+PR+SD.

"Diagnostic anti-PD-L monoclonal antibody" means a mAb which specifically binds to the mature form of the designated PD-L (PD-L1 or PDL2) that is expressed on the surface of certain mammalian cells. A mature PD-L lacks the presecretory leader sequence, also referred to as leader peptide The terms "PD-L" and "mature PD-L" are used interchangeably herein, and will be understood to mean the same molecule unless otherwise indicated or readily apparent from the context.

As used herein, a diagnostic anti-human PD-L1 mAb or an anti-hPD-L1 mAb refers to a monoclonal antibody that specifically binds to mature human PD-L1. A mature human PD-L1 molecule consists of amino acids 19-290 of the following sequence:

(SEQ ID NO: 25)
MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET.

Specific examples of diagnostic anti-human PD-L1 mAbs useful as diagnostic mAbs for IHC detection of PD-L1 expression in FFPE tumor tissue sections are antibody 20C3 and antibody 22C3, which are described in the copending international patent application PCT/US13/075932, filed 18 Dec. 2013 and published as WO2014/100079 on 26 Jun. 2014. Another anti-human PD-L1 mAb that has been reported to be useful for IHC detection of PD-L1 expression in FFPE tissue sections (Chen, B. J. et al., Clin Cancer Res 19: 3462-3473 (2013)) is a rabbit anti-human PD-L1 mAb publicly available from Sino Biological, Inc. (Beijing, P. R. China; Catalog number 10084-R015).

"DSDR" or "Durable Stable Disease Rate" means SD for ≥23 weeks.

"Framework region" or "FR" as used herein means the immunoglobulin variable regions excluding the CDR regions.

"Homology" refers to sequence similarity between two polypeptide sequences when they are optimally aligned. When a position in both of the two compared sequences is occupied by the same amino acid monomer subunit, e.g., if a position in a light chain CDR of two different Abs is occupied by alanine, then the two Abs are homologous at that position. The percent of homology is the number of homologous positions shared by the two sequences divided by the total number of positions compared×100. For example, if 8 of 10 of the positions in two sequences are matched or homologous when the sequences are optimally aligned then the two sequences are 80% homologous. Generally, the comparison is made when two sequences are aligned to give maximum percent homology. For example, the comparison can be performed by a Basic Local Alignment Search Tool (BLAST®) algorithm, which is a registered mark of the National Library of Medicine, wherein the parameters of the algorithm are selected to give the largest match between the respective sequences over the entire length of the respective reference sequences.

The following representative references relate to BLAST® algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." IN ATLAS OF PROTEIN SEQUENCE AND STRUCTURE, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." IN ATLAS OF PROTEIN SEQUENCE AND STRUCTURE, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." IN THEORETICAL AND COMPUTATIONAL METHODS IN GENOME RESEARCH (S. Suhai, ed.), (1997) pp. 1-14, Plenum, New York.

"Isolated antibody" and "isolated antibody fragment" refers to the purification status and in such context means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Kabat" as used herein means an immunoglobulin alignment and numbering system pioneered by Elvin A. Kabat ((1991) SEQUENCES OF PROTEINS OF IMMUNOLOGICAL INTEREST, 5th Ed. Public Health Service, National Institutes of Health, Bethesda, Md.).

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the treatment methods, medicaments, and disclosed uses may be made by the hybridoma method first described by Kohler et al. (1975) Nature 256: 495, or may be made by recombinant deoxyribonucleic acid (DNA) methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

"Non-responsder patient", when referring to a specific anti-tumor response to treatment with a combination therapy described herein, means the patient did not exhibit the anti-tumor response.

"ORR" or "objective response rate" refers in some instances to CR+PR, and $ORR_{(week\ 24)}$ refers to CR and PR measured using irRECIST in each patient in a cohort after 24 weeks of treatment with lenvatinib mesilate in combination with pembrolizumab.

"Patient" or "subject" refers to any single subject for which therapy is desired or that is participating in a clinical trial, epidemiological study or used as a control, including humans and mammalian veterinary patients such as cattle, horses, dogs, and cats.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment methods, medicaments and disclosed uses in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively. The PD-1 antagonist is not anti-PD-L1 monoclonal antibody MPDL3280A.

PD-1 antagonists useful in the any of the treatment methods, medicaments and disclosed uses include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. The human constant region is selected from the group consisting of IgG1, IgG2, IgG3 and IgG4 constant regions, and preferably the human constant region is an IgG1 or IgG4 constant region. In some instances, the antigen binding fragment is selected from the group consisting of Fab, Fab'-SH, F(ab')$_2$, scFv and Fv fragments.

Examples of mAbs that bind to human PD-1, and useful in the treatment methods, medicaments and disclosed uses, are described in U.S. Pat. Nos. 7,488,802, 7,521,051, 8,008,449, 8,354,509, 8,168,757, WO2004/004771, WO2004/072286, WO2004/056875, and US2011/0271358. Specific anti-human PD-1 mAbs useful as the PD-1 antagonist in the treatment methods, medicaments and disclosed uses include: pembrolizumab (also known as MK-3475), a humanized IgG4 mAb with the structure described in WHO Drug Information, Vol. 27, No. 2, pages 161-162 (2013) and which comprises the heavy and light chain amino acid sequences shown in FIG. 6, nivolumab (BMS-936558), a human IgG4 mAb with the structure described in WHO Drug Information, Vol. 27, No. 1, pages 68-69 (2013) and which comprises the heavy and light chain amino acid sequences shown in FIG. 7, pidilizumab, a humanized monoclonal antibody, AMP-224, and AMP-514; the humanized antibodies h409A1, h409A16 and h409A17, which are described in WO2008/156712, and AMP-514, which is being developed by MedImmune.

Examples of mAbs that bind to human PD-L1, and useful in the treatment methods, medicaments and disclosed uses, are described in WO2013/019906, WO2010/077634 A1 and U.S. Pat. No. 8,383,796. Specific anti-human PD-L1 mAbs useful as the PD-1 antagonist in the treatment methods, medicaments and disclosed uses include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in the any of the treatment methods, medicaments and disclosed uses include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as a PD-1 antagonist in the treatment methods, medicaments and uses described herein include AMP-224 (also known as B7-DCIg), which is a PD-L2-FC fusion protein and binds to human PD-1.

The treatment methods, medicaments and disclosed uses provide for the PD-1 antagonist to be a monoclonal antibody, or antigen binding fragment thereof, which comprises: (a) light chain CDRs SEQ ID NOs: 1, 2 and 3 and heavy chain CDRs SEQ ID NOs: 4, 5 and 6; or (b) light chain CDRs SEQ ID NOs: 7, 8 and 9 and heavy chain CDRs SEQ ID NOs: 10, 11 and 12.

The treatment methods, medicaments and disclosed uses provide for the PD-1 antagonist to be a monoclonal antibody, or antigen binding fragment thereof, which specifically binds to human PD-1 and comprises (a) a heavy chain variable region comprising SEQ ID NO:13 or a variant thereof, and (b) a light chain variable region comprising an amino acid sequence selected from the group consisting of SEQ ID NO:15 or a variant thereof; SEQ ID NO:16 or a variant thereof; and SEQ ID NO: 17 or a variant thereof. A variant of a heavy chain variable region sequence is identical to the reference sequence except having up to 17 conservative amino acid substitutions in the framework region (i.e., outside of the CDRs), and preferably has less than ten, nine, eight, seven, six or five conservative amino acid substitutions in the framework region. A variant of a light chain variable region sequence is identical to the reference sequence except having up to five conservative amino acid substitutions in the framework region (i.e., outside of the CDRs), and preferably has less than four, three or two conservative amino acid substitution in the framework region.

The PD-1 antagonist for any of the treatment methods, medicaments and disclosed uses, can be a monoclonal antibody which specifically binds to human PD-1 and comprises (a) a heavy chain comprising SEQ ID NO: 14 and (b) a light chain comprising SEQ ID NO:18, SEQ ID NO:19 or SEQ ID NO:20.

The treatment methods, medicaments and disclosed uses provide for the PD-1 antagonist to be a monoclonal antibody which specifically binds to human PD-1 and comprises (a) a heavy chain comprising SEQ ID NO: 14 and (b) a light chain comprising SEQ ID NO:18.

Table 2 below provides a list of the amino acid sequences of exemplary anti-PD-1 mAbs for use in the treatment methods, medicaments and disclosed uses, and the sequences are shown in FIGS. 1-5B.

TABLE 2

EXEMPLARY ANTI-HUMAN PD-1 MONOCLONAL ANTIBODIES

A. Comprises light and heavy chain CDRs of hPD-1.08A in WO2008/156712

| | |
|---|---|
| CDRL1 | SEQ ID NO: 1 |
| CDRL2 | SEQ ID NO: 2 |
| CDRL3 | SEQ ID NO: 3 |
| CDRH1 | SEQ ID NO: 4 |
| CDRH2 | SEQ ID NO: 5 |
| CDRH3 | SEQ ID NO: 6 |

B. Comprises light and heavy chain CDRs of hPD-1.09A in WO2008/156712

| | |
|---|---|
| CDRL1 | SEQ ID NO: 7 |
| CDRL2 | SEQ ID NO: 8 |
| CDRL3 | SEQ ID NO: 9 |
| CDRH1 | SEQ ID NO: 10 |
| CDRH2 | SEQ ID NO: 11 |
| CDRH3 | SEQ ID NO: 12 |

C. Comprises the mature h109A heavy chain variable region and one of the mature K09A light chain variable regions in WO2008/156712

| | |
|---|---|
| Heavy chain VR | SEQ ID NO: 13 |
| Light chain VR | SEQ ID NO: 15 or SEQ ID NO: 16 or SEQ ID NO: 17 |

D. Comprises the mature 409 heavy chain and one of the mature K09A light chains in WO2008/156712

| | |
|---|---|
| Heavy chain | SEQ ID NO: 14 |
| Light chain | SEQ ID NO: 18 or SEQ ID NO: 19 or SEQ ID NO: 20 |

"PD-L1" or "PD-L2" expression as used herein means any detectable level of expression of the designated PD-L protein on the cell surface or of the designated PD-L mRNA within a cell or tissue. PD-L protein expression may be detected with a diagnostic PD-L antibody in an IHC assay of a tumor tissue section or by flow cytometry. Alternatively, PD-L protein expression by tumor cells may be detected by positron emission tomography (PET) imaging, using a binding agent (e.g., antibody fragment, affibody and the like) that specifically binds to the desired PD-L target, e.g., PD-L1 or PD-L2. Techniques for detecting and measuring PD-L mRNA expression include RT-PCR and realtime quantitative RT-PCR.

Several approaches have been described for quantifying PD-L1 protein expression in IHC assays of tumor tissue sections. See, e.g., Thompson, R. H., et al., *PNAS* 101 (49); 17174-17179 (2004); Thompson, R. H. et al., *Cancer Res.* 66:3381-3385 (2006); Gadiot, J., et al., *Cancer* 117:2192-2201 (2011); Taube, J. M. et al., *Sci Transl Med* 4, 127ra37 (2012); and Toplian, S. L. et al., *New Eng. J Med.* 366 (26): 2443-2454 (2012).

One approach employs a simple binary end-point of positive or negative for PD-L1 expression, with a positive result defined in terms of the percentage of tumor cells that exhibit histologic evidence of cell-surface membrane staining. A tumor tissue section is counted as positive for PD-L1 expression is at least 1%, and preferably 5% of total tumor cells.

In another approach, PD-L1 expression in the tumor tissue section is quantified in the tumor cells as well as in infiltrating immune cells, which predominantly comprise lymphocytes. The percentage of tumor cells and infiltrating immune cells that exhibit membrane staining are separately quantified as <5%, 5 to 9%, and then in 10% increments up to 100%. For tumor cells, PD-L1 expression is counted as negative if the score is <5% score and positive if the score is ≥5%. PD-L1 expression in the immune infiltrate is reported as a semi-quantitative measurement called the adjusted inflammation score (AIS), which is determined by multiplying the percent of membrane staining cells by the intensity of the infiltrate, which is graded as none (0), mild (score of 1, rare lymphocytes), moderate (score of 2, focal infiltration of tumor by lymphohistiocytic aggregates), or severe (score of 3, diffuse infiltration). A tumor tissue section is counted as positive for PD-L1 expression by immune infiltrates if the AIS is ≥5.

The level of PD-L mRNA expression may be compared to the mRNA expression levels of one or more reference genes that are frequently used in quantitative RT-PCR, such as ubiquitin C.

In some instances, a level of PD-L1 expression (protein and/or mRNA) by malignant cells and/or by infiltrating immune cells within a tumor is determined to be "overexpressed" or "elevated" based on comparison with the level of PD-L1 expression (protein and/or mRNA) by an appropriate control. For example, a control PD-L1 protein or mRNA expression level may be the level quantified in nonmalignant cells of the same type or in a section from a matched normal tissue (i.e. non-malignant tissue). PD-L1 expression in a tumor sample is preferably determined to be elevated if PD-L1 protein (and/or PD-L1 mRNA) in the sample is at least 10%, 20%, or 30% greater than in the control.

A "pembrolizumab biosimilar" means a biological product manufactured by an entity other than Merck & Co., Inc. d.b.a. Merck Sharp and Dohme (MSD) and which is approved by a regulatory agency in any country for marketing as a pembrolizumab biosimilar. A pembrolizumab biosimilar may include as the drug substance a pembrolizumab variant or an antibody with the same amino acid sequence as pembrolizumab.

As used herein, a "pembrolizumab variant" means a monoclonal antibody which comprises heavy chain and light chain sequences that are identical to those in pembrolizumab, except for having three, two or one conservative amino acid substitutions at positions that are located outside of the light chain CDRs and six, five, four, three, two or one conservative amino acid substitutions that are located outside of the heavy chain CDRs, e.g, the variant positions are located in the FR regions and/or the constant region. In other words, pembrolizumab and a pembrolizumab variant comprise identical CDR sequences, but differ from each other due to having a conservative amino acid substitution at no more than three or six other positions in their full length light and heavy chain sequences, respectively. A pembrolizumab variant is substantially the same as pembrolizumab with respect to the following properties: binding affinity to PD-1 and ability to block the binding of each of PD-L1 and PD-L2 to PD-1.

"RECIST 1.1 Response Criteria" as used herein means the definitions set forth in Eisenhauer et al., E. A. et al., *Eur. J Cancer* 45:228-247 (2009) for target lesions or nontarget lesions, as appropriate based on the context in which response is being measured.

"Responsder patient" when referring to a specific anti-tumor response to treatment with a combination therapy described herein, means the patient exhibited the anti-tumor response.

"Sustained response" means a sustained therapeutic effect after cessation of treatment with a therapeutic agent, or a combination therapy described herein. In some instances, the sustained response has a duration that is at least the same as the treatment duration, or at least 1.5, 2.0, 2.5 or 3 times longer than the treatment duration.

"Tissue Section" refers to a single part or piece of a tissue sample, e.g., a thin slice of tissue cut from a sample of a normal tissue or of a tumor.

"Treat" or "treating" a cancer as used herein means to administer a combination therapy of a PD-1 antagonist and a multi-RTK inhibitor to a subject having a cancer, or diagnosed with a cancer, to achieve at least one positive therapeutic effect, such as for example, reduced number of cancer cells, reduced tumor size, reduced rate of cancer cell infiltration into peripheral organs, or reduced rate of tumor metastasis or tumor growth. Positive therapeutic effects in cancer can be measured in a number of ways (See, W. A. Weber, *J. Nucl. Med.* 50:15-10S (2009)). For example, with respect to tumor growth inhibition, according to NCI standards, a T/C≤42% is the minimum level of anti-tumor activity. A T/C<10% is considered a high anti-tumor activity level, with T/C (%)=Median tumor volume of the treated/Median tumor volume of the control×100. In some instances, response to a combination therapy described herein is assessed using RECIST 1.1 criteria or irRC (bidimensional or unidimensional) and the treatment achieved by a combination of a multi-RTK inhibitor and a PD-1 antagonist is any of PR, CR, OR, PFS, DFS and OS. PFS, also referred to as "Time to Tumor Progression" indicates the length of time during and after treatment that the cancer does not grow, and includes the amount of time patients have experienced a CR or PR, as well as the amount of time patients have experienced SD. DFS refers to the length of time during and after treatment that the patient remains free of disease. OS refers to a prolongation in life expectancy as compared to naive or untreated individuals or patients. In some instances, response to a combination of a multi-RTK inhibitor and a PD-1 antagonist is any of PR, CR, PFS, DFS, OR and OS that is assessed using RECIST 1.1 response criteria. The treatment regimen for the disclosed combination that is effective to treat a cancer patient may vary according to factors such as the disease state, age, and weight of the patient, and the ability of the therapy to elicit an anti-cancer response in the subject. The treatment methods, medicaments, and disclosed uses may not be effective in achieving a positive therapeutic effect in every subject, they should do so in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

The terms "treatment regimen", "dosing protocol" and "dosing regimen" are used interchangeably to refer to the dose and timing of administration of each therapeutic agent in a combination of a multi-RTK inhibitor and a PD-1 antagonist.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood or heme cancers) generally do not form solid tumors (National Cancer Institute, Dictionary of Cancer Terms).

"Tumor burden" also referred to as "tumor load", refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g. by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

"Unidimensional irRC refers to the set of criteria described in Nishino M, Giobbie-Hurder A, Gargano M, Suda M, Ramaiya N H, Hodi F S. "Developing a Common Language for Tumor Response to Immunotherapy: Immune-related Response Criteria using Unidimensional measurements," *Clin Cancer Res.* 2013, 19(14): 3936-3943). These criteria utilize the longest diameter (cm) of each lesion.

"Variable regions" or "V region" as used herein means the segment of IgG chains which is variable in sequence between different antibodies. It extends to Kabat residue 109 in the light chain and 113 in the heavy chain.

"Multi-RTK Inhibitor" means a small molecule compound that inhibits the kinase activities of at least each of the following RTKs: (i) VEGFR2, (ii) at least one FGFR selected from the group consisting of FGFR1, 2, 3 and 4; and (iii) RET. The multi-RTK inhibitor may also inhibit the kinase activities of VEGFR1, VEGFR3, fibroblast growth factor (FGF) receptors FGFR1, 2, 3 and 4, platelet-derived growth factor (PDGF) receptor alpha (PDGFRα); and KIT. The multi-RTK inhibitor may have the structure represented by Formula (I):

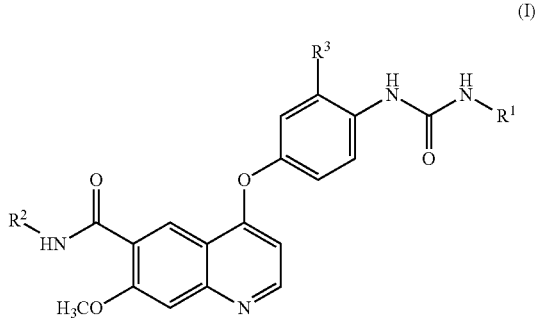

(I)

wherein $R^1$ is $C_{1-6}$ alkyl or $C_{3-8}$ cycloalkyl, $R^2$ is a hydrogen atom or $C_{1-6}$ alkoxy, and $R^3$ is a hydrogen atom or a halogen atom.

The treatment methods, medicaments and disclosed uses provide for the multi-RTK inhibitor as the compound, of the following structure:

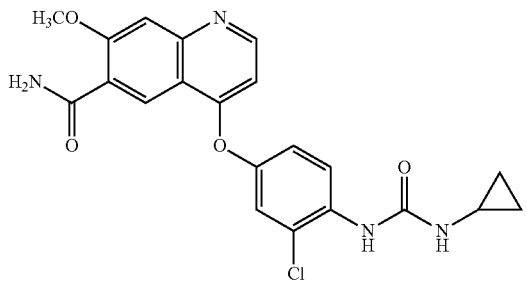 [SMILES: COc1cc2nccc(Oc3ccc(NC(=O)NC4CC4)c(Cl)c3)c2cc1C(N)=O]

which is known as lenvatinib, or a pharmaceutically acceptable salt thereof (e.g. lenvatinib mesilate).

II. METHODS, USES AND MEDICAMENTS

In one aspect, a method for treating a cancer in an individual is provided that comprises administering to the individual a combination therapy which comprises a PD-1 antagonist and a multi-RTK inhibitor.

The combination therapy may also comprise one or more additional therapeutic agents. The additional therapeutic agent may be, e.g., a chemotherapeutic other than a multi-RTK inhibitor, a biotherapeutic agent, an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF).

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (such as bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, preferably calicheamicin gamma1I and calicheamicin phiI1, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2, 2',2"-trichlorotriethylamine; trichothecenes (such as T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

Each therapeutic agent in a combination therapy disclosed herein may be administered either alone or in a medicament (also referred to herein as a pharmaceutical composition) which comprises the therapeutic agent and one or more pharmaceutically acceptable carriers, excipients and diluents, according to standard pharmaceutical practice. Each therapeutic agent may be prepared by formulating a compound or pharmaceutically acceptable salt thereof represented by Formula (I), and an anti-PD-1 antibody separately, and the both may be administered either at the same time or separately. Further, the two formulations may be placed in a single package, to provide the so called kit formulation. In some configurations, both compounds may be contained in a single formulation.

The compound or pharmaceutically acceptable salt thereof represented by Formula (I) can be produced by the method described in Reference 17. Examples of the pharmaceutically acceptable salt include salts with inorganic acids, salts with organic acids, salts with inorganic bases, salts with organic bases, and salts with acidic or basic amino acids. Preferred examples of the salts with inorganic acids include salts with hydrochloric acid, hydrobromic acid, sulfuric acid, nitric acid, phosphoric acid and the like. Preferred examples of the salts with organic acids include salts with acetic acid, succinic acid, fumaric acid, maleic acid, tartaric acid, citric acid, lactic acid, stearic acid, benzoic acid, methanesulfonic acid, ethanesulfonic acid, p-toluenesulfonic acid and the like. Preferred examples of the salts with inorganic bases include alkaline metal salts such as a sodium salt and a potassium salt; alkaline earth metal salts such as a calcium salt and a magnesium salt; an aluminum salt; and an ammonium salt. Preferred examples of the salts with organic bases include salts with diethylamine, diethanolamine, meglumine, N,N-dibenzylethylenediamine and the like. Preferred examples of the salts with acidic amino acids include salts with aspartic acid, glutamic acid and the like. Preferred examples of the salts with basic amino acids include salts with arginine, lysine, ornithine and the like. More preferred pharmaceutically acceptable salts are salts with organic acids and especially preferred pharmaceutically acceptable salts are salts with methanesulfonic acid.

Each therapeutic agent in a combination therapy disclosed herein may be administered simultaneously (i.e., in the same medicament), concurrently (i.e., in separate medicaments administered one right after the other in any order) or sequentially in any order. Sequential administration is particularly useful when the therapeutic agents in the combination therapy are in different dosage forms (one agent is a tablet or capsule and another agent is a sterile liquid) and/or are administered on different dosing schedules, e.g., a chemotherapeutic that is administered at least daily and a biotherapeutic that is administered less frequently, such as once weekly, once every two weeks, or once every three weeks.

In some instances, the multi-RTK inhibitor is administered before administration of the PD-1 antagonist, while in other instances, the multi-RTK inhibitor is administered after administration of the PD-1 antagonist.

In some instances, at least one of the therapeutic agents in the combination therapy is administered using the same dosage regimen (dose, frequency and duration of treatment) that is typically employed when the agent is used as monotherapy for treating the same cancer. In other instances, the patient receives a lower total amount of at least one of the therapeutic agents in the combination therapy than when the agent is used as monotherapy, e.g., smaller doses, less frequent doses, and/or shorter treatment duration.

Each small molecule therapeutic agent in a combination therapy disclosed herein can be administered orally in the form of a solid formulation such as a tablet, granule, fine granule, powder or capsule, or in the form of a liquid, jelly, syrup, or the like. Each small molecule therapeutic agent in a combination therapy disclosed herein may be administered parenterally, including the intravenous, intramuscular, intraperitoneal, subcutaneous, rectal, topical, and transdermal routes of administration.

A combination therapy disclosed herein may be used prior to or following surgery to remove a tumor and may be used prior to, during or after radiation therapy.

In some instances, a combination therapy disclosed herein is administered to a patient who has not been previously treated with a biotherapeutic or chemotherapeutic agent, i.e., is treatment-naïve. In other instances, the combination therapy is administered to a patient who failed to achieve a sustained response after prior therapy with a biotherapeutic or chemotherapeutic agent, i.e., is treatment-experienced.

A combination therapy disclosed herein is typically used to treat a tumor that is large enough to be found by palpation or by imaging techniques well known in the art, such as magnetic resonance imaging (MRI), ultrasound, or computerized axial tomography (CAT) scan.

A combination therapy disclosed herein is preferably administered to a human patient who has a cancer that tests positive for PD-L1 expression. PD-L1 expression is detected preferably using a diagnostic anti-human PD-L1 antibody, or antigen binding fragment thereof, in an IHC assay on an FFPE or frozen tissue section of a tumor sample removed from the patient. Typically, the patient's physician would order a diagnostic test to determine PD-L1 expression in a tumor tissue sample removed from the patient prior to initiation of treatment with the PD-1 antagonist and the multi-RTK inhibitor, but it is envisioned that the physician could order the first or subsequent diagnostic tests at any time after initiation of treatment, such as for example after completion of a treatment cycle.

Selecting a dosage regimen (also referred to herein as an administration regimen) for a combination therapy disclosed herein depends on several factors, including the serum or tissue turnover rate of the entity, the level of symptoms, the immunogenicity of the entity, and the accessibility of the target cells, tissue or organ in the individual being treated. Preferably, a dosage regimen maximizes the amount of each therapeutic agent delivered to the patient consistent with an acceptable level of side effects. Accordingly, the dose amount and dosing frequency of each biotherapeutic and chemotherapeutic agent in the combination depends in part on the particular therapeutic agent, the severity of the cancer being treated, and patient characteristics. Guidance in selecting appropriate doses of antibodies, cytokines, and small molecules are available. See, e.g., Wawrzynczak (1996) ANTIBODY THERAPY, Bios Scientific Pub. Ltd, Oxfordshire, UK; Kresina (ed.) (1991) MONOCLONAL ANTIBODIES, CYTOKINES AND ARTHRITIS, Marcel Dekker, New York, NY; Bach (ed.) (1993) MONOCLONAL ANTIBODIES AND PEPTIDE THERAPY IN AUTOIMMUNE DISEASES, Marcel Dekker, New York, NY; Baert et al. (2003) *New Engl. J. Med.* 348: 601-608; Milgrom et al. (1999) *New Engl. J. Med.* 341: 1966-1973; Slamon et al. (2001) *New Engl. J. Med.* 344: 783-792; Beniaminovitz et al. (2000) *New Engl. J. Med.* 342: 613-619; Ghosh et al. (2003) *New Engl. J. Med.* 348: 24-32; Lipsky et al. (2000) *New Engl. J. Med.* 343: 1594-1602; PHYSICIANS' DESK REFERENCE 2003 (Physicians' Desk Reference, 57th Ed.); Medical Economics Company; ISBN: 1563634457; 57th edition (November 2002). Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy.

Biotherapeutic agents in a combination therapy disclosed herein may be administered by continuous infusion, or by doses at intervals of, e.g., daily, every other day, three times per week, or one time each week, two weeks, three weeks, monthly, bimonthly, etc. A total weekly dose is generally at least 0.05 μg/kg, 0.2 μg/kg, 0.5 μg/kg, 1 μg/kg, 10 μg/kg, 100 μg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med.* 349: 427-434; Herold et al. (2002) *New Engl. J. Med.* 346: 1692-1698; Liu et al. (1999) *J. Neurol. Neurosurg. Psych.* 67: 451-456; Portielji et al. (20003) *Cancer Immunol. Immunother.* 52: 133-144.

The dose of the compound or pharmaceutically acceptable salt thereof represented by Formula (I) may be appropriately selected depending on the degrees of symptoms, age, sex, and body weight of the patient, difference in sensitivity, route, time and interval of administration, type of pharmaceutical formulation, and/or the like. Typically, in cases where oral administration is carried out for an adult (60 kg body weight), the dose is 1 to 600 mg, preferably 5 to 400 mg, more preferably 5 to 200 mg per day. The dose may be administered at one time or divided into smaller doses provided 2 to 3 times per day.

In some instances that employ an anti-human PD-1 mAb as the PD-1 antagonist in the combination therapy, the dosing regimen will comprise administering the anti-human PD-1 mAb at a dose of 1, 2, 3, 5 or 10 mg/kg at intervals of about 14 days (±2 days) or about 21 days (±2 days) or about 30 days (±2 days) throughout the course of treatment. The dosage of an anti-PD-1 antibody can be appropriately selected in the same manner as above. Typically, in cases where intravenous administration is carried out for an adult (60 kg body weight), the dose is 2 mg/kg on a schedule of once every 3 weeks on a 6-week cycle (a total of 2 doses). The antibody is administered for 1 to 10 cycles at an appropriate interval.

In other instances that employ an anti-human PD-1 mAb as the PD-1 antagonist in the combination therapy, the dosing regimen will comprise administering the anti-human PD-1 mAb at a dose of from about 0.005 mg/kg to about 10 mg/kg, with intra-patient dose escalation. The interval between doses can be progressively shortened, e.g., about 30 days (±2 days) between the first and second dose, about 14 days (±2 days) between the second and third doses. In certain embodiments, the dosing interval will be about 14 days (±2 days), for doses subsequent to the second dose.

In specific instances, a subject will be administered an intravenous (IV) infusion of a medicament comprising any of the PD-1 antagonists described herein.

The PD-1 antagonist in the combination therapy is preferably nivolumab in some instances, which is administered intravenously at a dose selected from the group consisting of: 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, and 10 mg Q3W.

The PD-1 antagonist in the combination therapy preferably is pembrolizumab, a pembrolizumab variant or a pembrolizumab biosimilar in some instances, which is administered in a liquid medicament at a dose selected from the group consisting of 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, 10 mg Q3W and flat-dose equivalents of any of these doses, i.e., such as 200 mg Q3W. In some instances, pembrolizumab is provided as a liquid medicament which comprises 25 mg/ml pembrolizumab, 7% (w/v) sucrose, 0.02% (w/v) polysorbate 80 in 10 mM histidine buffer pH 5.5.

In some instances, the selected dose of pembrolizumab is administered by IV infusion over a time period of between 25 and 40 minutes, or about 30 minutes.

The optimal dose for pembrolizumab in combination with lenvatinib or a pharmaceutically acceptable salt thereof (e.g. lenvatinib mesilate) may be identified by dose escalation or dose de-escalation of one or both of these agents. In some instances, the combination therapy comprises a 21 day treatment cycle in which pembrolizumab is administered at 200 mg Q3W by IV and lenvatinib mesilate is administered at (a) 24 mg per day orally, (b) 20 mg per day orally or (c) 14 mg per day orally, each as lenvatinib. In an embodiment, a patient is treated first with 200 mg of pembrolizumab Q3W by IV and 24 mg (as lenvatinib) of lenvatinib mesilate per day orally until at least one DLT is observed and then the dosage of lenvatinib mesilate is reduced to 20 or 14 mg (each as lenvatinib) per day while the pembrolizumab dose is continued at 200 mg of pembrolizumab Q3W.

As an example dosing regimen, lenvatinib or a pharmaceutically acceptable salt thereof can be administered with water orally once a day, with or without food, in 21 day cycles at approximately the same time each day. Lenvatinib or a pharmaceutically acceptable salt thereof can be provided as 4 mg and 10 mg (each as lenvatinib) capsules. On Day one (D1) of each cycle, lenvatinib or a pharmaceutically acceptable salt thereof can be administered approximately within 1 hour after completion of pembrolizumab administration. Pembrolizumab may be provided as a sterile, preservative-free, white to off-white lyophilized powder in single-use vials. Each vial can be reconstituted and diluted for intravenous infusion. Each 2 mL of reconstituted solution may contain approximately 50 mg of prembrolizumab. In some instances, pembrolizumab may be provided as a sterile, preservative-free, clear to slightly opalescent, colorless to slightly yellow solution that requires dilution for intravenous infusion. Each vial may contain 100 mg of pembrolizumab in 4 mL of solution. Each 1 mL of solution may contain 25 mg of pembrolizumab. Pembrolizumab may be administered as a dose of 200 mg as a 30-minute intravenous infusion, Q3W (25 minutes to 40 minutes, for example).

In cases where an oral solid formulation is prepared, a pharmaceutically acceptable vehicle, and, as required, a binder, disintegrator, lubricant, coloring agent, flavoring agent and/or the like may be added to the principal component, that is, a compound or pharmaceutically acceptable salt thereof represented by Formula (I), and an anti-PD-1 antibody, to prepare, thereafter, a tablet, granule, fine granule, powder, capsule or the like according to a conventional method. Examples of the vehicle include lactose, corn starch, white soft sugar, glucose, sorbitol, crystalline cellulose and silicon dioxide. Examples of the binder include polyvinyl alcohol, ethylcellulose, methylcellulose, gum Arabic, hydroxypropylcellulose and hydroxypropylmethylcellulose. Examples of the lubricant include magnesium stearate, talc, and silica. Examples of the coloring agent include titanium oxide, iron sesquioxide, yellow iron sesquioxide, cochineal, carmine, and riboflavin. Examples of the flavoring agent include cocoa powder, ascorbic acid, tartaric acid, peppermint oil, borneol, and cinnamon powder. These tablets and granules may be coated as may be required.

In some instances, the patient is treated with the combination therapy for at least 24 weeks, e.g., eight 3-week cycles. In some instances, treatment with the combination therapy continues until the patient exhibits evidence of PD or a CR.

In some instances, the patient selected for treatment with the combination therapy disclosed herein if the patient has been diagnosed with NSCLC, RCC, endometrial cancer, urothelial cancer, squamous cell carcinoma of head and neck or melanoma.

A medicament is provided which comprises a PD-1 antagonist as described above and a pharmaceutically acceptable excipient. When the PD-1 antagonist is a biotherapeutic agent, e.g., a mAb, the antagonist may be produced in CHO cells using conventional cell culture and recovery/purification technologies.

In some instances, a medicament comprising an anti-PD-1 antibody as the PD-1 antagonist may be provided as a liquid formulation or prepared by reconstituting a lyophilized powder with sterile water for injection prior to use. For example, WO 2012/135408 describes the preparation of liquid and lyophilized medicaments comprising pembrolizumab that are suitable for any treatment methods, medicatments, and disclosed uses. In some instances, a medicament comprising pembrolizumab is provided in a glass vial which contains about 100 mg of pembrolizumab in 4 ml of solution. Each 1 mL of solution contains 25 mg of pembrolizumab and is formulated in: L-histidine (1.55 mg), polysorbate 80 (0.2 mg), sucrose (70 mg), and Water for Injection, United States Pharmacopeial (USP) Convention. The solution requires dilution for IV infusion.

In cases where an injection is prepared, a pH adjustor, buffering agent, suspending agent, solubilizer, stabilizer, isotonic agent, preservative and/or the like may be added as required to the principal component, to prepare an intravenous, subcutaneous or intramuscular injection, or an intravenous drip infusion. As required, these may be prepared into lyophilized products by conventional methods. Examples of the suspending agent include methylcellulose, polysorbate 80, hydroxyethylcellulose, gum Arabic, powdered tragacanth, sodium carboxymethylcellulose, and polyoxyethylene sorbitan monolaurate. Examples of the solubilizer include polyoxyethylene hydrogenated castor oil, polysorbate 80, nicotinamide, polyoxyethylene sorbitan monolaurate, macrogol, and glycerin fatty acid ester. Examples of the stabilizer include sodium sulfite and sodium metabisulfite. Examples of the preservative include methyl parahydroxybenzoate, ethyl parahydroxybenzoate, sorbic acid, phenol, cresol, and chlorocresol.

A medicament is provided which comprises lenvatinib or a pharmaceutically acceptable salt thereof (e.g. lenvatinib mesilate) and a pharmaceutically acceptable excipient. In some instances, lenvatinib or a pharmaceutically acceptable salt thereof (e.g. lenvatinib mesilate) is provided as a 4 mg or 10 mg (each as lenvatinib) capsule and formulated with calcium carbonate, mannitol, microcrystalline cellulose, hydroxypropylcellulose, low-substituted hydroxypropylcellulose, and talc.

The PD-1 antagonist and lenvatinib or a pharmaceutically acceptable salt thereof (e.g. lenvatinib mesilate) medicaments described herein may be provided as a kit which comprises a first container and a second container and a package insert. The first container contains at least one dose of a medicament comprising a PD-1 antagonist, the second container contains at least one dose of a medicament comprising a multi-RTK inhibitor, and the package insert, or label, which comprises instructions for treating a patient for cancer using the medicaments. The first and second containers may be comprised of the same or different shape (e.g., vials, syringes and bottles) and/or material (e.g., plastic or glass). The kit may further comprise other materials that may be useful in administering the medicaments, such as diluents, filters, IV bags and lines, needles and syringes. The kit may preferably provide for the PD-1 antagonist to be an anti-PD-1 antibody and the instructions may state that the medicaments are intended for use in treating a patient having a cancer that tests positive for PD-L1 expression by an IHC assay.

These and other aspects disclosed herein, including the exemplary specific treatment methods, medicaments, and uses listed below, will be apparent from the teachings contained herein.

Specific Treatment Methods, Medicaments, and Uses

1. A method for treating a cancer in an individual comprising administering to the individual a combination therapy which comprises a PD-1 antagonist and a multi-RTK inhibitor.
2. The method of embodiment 1, wherein the PD-1 antagonist is a monoclonal antibody, or an antigen binding fragment thereof.
3. The method of embodiment 1 or 2, wherein the multi-RTK inhibitor is lenvatinib or a pharmaceutically acceptable salt thereof, and the PD-1 antagonist is not MPDL3280A.
4. A medicament comprising a PD-1 antagonist, which is not MPDL3280A, for use in combination with a multi-RTK inhibitor for treating a cancer in an individual, wherein the PD-1 antagonist is a monoclonal antibody, or an antigen binding fragment thereof.
5. A medicament comprising a multi-RTK inhibitor for use in combination with a PD-1 antagonist, which is not MPDL3280A, for treating a cancer in an individual.
6. The medicament of embodiment 4 or 5, which further comprises a pharmaceutically acceptable excipient.
7. Use of a PD-1 antagonist, which is not MPDL3280A, in the manufacture of medicament for treating a cancer in an individual when administered in combination with a multi-RTK inhibitor.
6. Use of a multi-RTK inhibitor in the manufacture of a medicament for treating a cancer in an individual when administered in combination with a PD-1 antagonist, which is not MPDL3280A.
7. Use of a PD-1 antagonist, which is not MPDL3280A, and a multi-RTK inhibitor in the manufacture of medicaments for treating a cancer in an individual.
8. A kit which comprises a first container, a second container and a package insert, wherein the first container comprises at least one dose of a medicament comprising an anti-PD-1 antagonist, which is not MPDL3280A, the second container comprises at least one dose of a medicament comprising a multi-RTK inhibitor, and the package insert comprises instructions for treating an individual for cancer using the medicaments.
9. The kit of embodiment 8, wherein the instructions state that the medicaments are intended for use in treating an individual having a cancer that tests positive for PD-L1 expression by an immunohistochemical (IHC) assay.

10. The method, medicament, use or kit of any of embodiments 1 to 9, wherein the individual is a human and the PD-1 antagonist is a monoclonal antibody, or an antigen binding fragment thereof, which specifically binds to human PD-L1 and blocks the binding of human PD-L1 to human PD-1.

11. The method, medicament, use or kit of embodiment 9, wherein the PD-1 antagonist is BMS-936559, MED14736, or MSB0010718C.

12. The method, medicament, use or kit of any of embodiments 1 to 9, wherein the individual is a human, and the PD-1 antagonist is a monoclonal antibody, or an antigen binding fragment thereof, which specifically binds to human PD-1 and blocks the binding of human PD-L1 to human PD-1.

13. The method, medicament, use or kit of embodiment 12, wherein the PD-1 antagonist also blocks binding of human PD-L2 to human PD-1.

14. The method, medicament, use or kit of embodiment 13, wherein the monoclonal antibody, or antigen binding fragment thereof, comprises: (a) light chain CDRs of SEQ ID NOs: 1, 2 and 3 and heavy chain CDRs of SEQ ID NOs: 4, 5 and 6; or (b) light chain CDRs of SEQ ID NOs: 7, 8 and 9 and heavy chain CDRs of SEQ ID NOs: 10, 11 and 12.

15. The method, medicament, use or kit of embodiment 13, wherein the monoclonal antibody, or antigen binding fragment thereof, comprises light chain CDRs of SEQ ID NOs: 7, 8 and 9 and heavy chain CDRs of SEQ ID NOs: 10, 11 and 12.

16. The method, medicament, use or kit of embodiment 13, wherein the PD-1 antagonist is an anti-PD-1 monoclonal antibody which comprises a heavy chain and a light chain, and wherein the heavy chain comprises SEQ ID NO:21 and the light chain comprises SEQ ID NO:22.

17. The method, medicament, use or kit of embodiment 13, wherein the PD-1 antagonist is an anti-PD-1 monoclonal antibody which comprises a heavy chain and a light chain, and wherein the heavy chain comprises SEQ ID NO:23 and the light chain comprises SEQ ID NO:24.

18. The method, medicament, use or kit of any of embodiments 10-17, wherein the cancer is a solid tumor.

19. The method, medicament, use or kit of any of embodiments 10-17, wherein the cancer is bladder cancer, breast cancer, clear cell kidney cancer, head/neck squamous cell carcinoma, lung squamous cell carcinoma, malignant melanoma, non-small-cell lung cancer (NSCLC), ovarian cancer, pancreatic cancer, prostate cancer, renal cell carcinoma (RCC), small-cell lung cancer (SCLC) or triple negative breast cancer.

20. The method, medicament, use or kit of any of embodiments 10-17, wherein the cancer is NSCLC, RCC, endometrial cancer, urothelial cancer, squamous cell carcinoma of head and neck or melanoma.

21. The method, medicament, use or kit of any of embodiments 10-17, wherein the individual has not been previously treated for NSCLC, RCC, endometrial cancer, urothelial cancer, squamous cell carcinoma of head and neck or melanoma.

23. The method, medicament, use or kit of any of embodiments 10-17, wherein the cancer is acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL).

24. The method, medicament, use or kit of any of embodiments 10-23, the cancer tests positive for human PD-L1.

25. The method, medicament, use or kit of embodiment 24, wherein the human PD-L1 expression is elevated.

26. The method, medicament, use or kit of embodiment 13, wherein the PD-1 antagonist is pembrolizumab, a pembrolizumab variant, a pembrolizumab biosimilar or nivolumab.

27. The method, medicament, use or kit of embodiment 26, wherein pembrolizumab is formulated as a liquid medicament which comprises 25 mg/ml pembrolizumab, 7% (w/v) sucrose, 0.02% (w/v) polysorbate 80 in 10 mM histidine buffer pH 5.5.

28. The method, medicament, use or kit of any of embodiments 1 to 27, wherein the multi-RTK inhibitor is lenvatinib or a pharmaceutically acceptable salt thereof (e.g. lanvatinib mesilate).

29. The method, medicament, use or kit of any of embodiments 1 to 28, wherein the mutli-RTK inhibitor is lenvatinib mesilate and is formulated with calcium carbonate, mannitol, microcrystalline cellulose, hydroxypropylcellulose, low-substituted hydroxypropylcellulose, and talc.

30. A method for treating a human individual diagnosed with a cancer, comprising administering to the individual a combination therapy which comprises pembrolizumab and lenvatinib or a pharmaceutically acceptable salt thereof (e.g. lanvatinib mesilate), wherein lenvatinib or a pharmaceutically acceptable salt thereof (e.g. lanvatinib mesilate) is administered at a daily dose of 24 mg, 20 mg or 14 mg, each as lenvatinib, and pembrolizumab is administered at 200 mg Q3W.

31. A medicament comprising pembrolizumab for use in combination with lenvatinib or a pharmaceutically acceptable salt thereof (e.g. lanvatinib mesilate) for treating a cancer in a human individual by a method comprising administering to the individual lenvatinib or a pharmaceutically acceptable salt thereof (e.g. lanvatinib mesilate) at a daily dose of 24 mg, 20 mg or 14 mg, each as lenvatinib, and pembrolizumab at 200 mg Q3W.

32. A medicament comprising lenvatinib or a pharmaceutically acceptable salt thereof (e.g. lanvatinib mesilate) for use in combination with pembrolizumab for treating a cancer in a human individual by a method comprising administering to the individual lenvatinib or a pharmaceutically acceptable salt thereof (e.g. lanvatinib mesilate) at a daily dose of 24 mg, 20 mg or 14 mg, each as lenvatinib, and pembrolizumab at 200 mg Q3W.

33. The method or medicament of any of embodiments 30 to 32, wherein the cancer is NSCLC, RCC, endometrial cancer, urothelial cancer, squamous cell carcinoma of head and neck or melanoma.

34. The method or medicament of embodiment 33, wherein the individual has not been previously treated for NSCLC, RCC, endometrial cancer, urothelial cancer, squamous cell carcinoma of head and neck or melanoma.

35. The method or medicament of any of embodiments 31 to 34, wherein a tissue section of the cancer removed from the individual prior to administration of the combination therapy tested positive for PD-L1 expression.

36. The method or medicament of embodiment 35, wherein at least 50% of the tumor cells in the tissue section tested positive for PD-L1 expression by an immunohistochemical (IHC) assay.

37. The method or medicament of embodiment 36, wherein the IHC assay employed the antibody 22C3 to detect PD-L1 expression.

38. The method or medicament of any of embodiments 31 to 37, wherein pembrolizumab is administered by IV infusion for 25 to 40 minutes or about 30 minutes.

General Methods

Standard methods in molecular biology are described Sambrook, Fritsch and Maniatis (1982 & 1989 2$^{nd}$ Edition, 2001 3$^{rd}$ Edition) MOLECULAR CLONING, A LABORATORY MANUAL, Cold Spring Harbor Laboratory Press, Cold Spring Harbor, NY; Sambrook and Russell (2001) MOLECULAR CLONING, 3$^{rd}$ ed., Cold Spring Harbor Laboratory Press, Cold Spring Harbor, NY; Wu (1993) RECOMBINANT DNA, Vol. 217, Academic Press, San Diego, CA). Standard methods also appear in Ausbel, et al. (2001) Current Protocols in Molecular Biology, Vols. 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) CURRENT PROTOCOLS IN PROTEIN SCIENCE, Vol. 1, John Wiley and Sons, Inc., New York). Chemical analysis, chemical modification, post-translational modification, production of fusion proteins, glycosylation of proteins are described (see, e.g., Coligan, et al. (2000) Current PROTOCOLS IN PROTEIN SCIENCE, Vol. 2, John Wiley and Sons, Inc., New York; Ausubel, et al. (2001) CURRENT PROTOCOLS IN MOLECULAR BIOLOGY, Vol. 3, John Wiley and Sons, Inc., NY, NY, pp. 16.0.5-16.22.17; Sigma-Aldrich, Co. (2001) PRODUCTS FOR LIFE SCIENCE RESEARCH, St. Louis, MO; pp. 45-89; Amersham Pharmacia Biotech (2001) BioDirectory, Piscataway, N.J., pp. 384-391). Production, purification, and fragmentation of polyclonal and monoclonal antibodies are described (Coligan, et al. (2001) CURRENT PROTCOLS IN IMMUNOLOGY, Vol. 1, John Wiley and Sons, Inc., New York; Harlow and Lane (1999) USING ANTIBODIES, Cold Spring Harbor Laboratory Press, Cold Spring Harbor, NY; Harlow and Lane, supra). Standard techniques for characterizing ligand/receptor interactions are available (see, e.g., Coligan, et al. (2001) CURRENT PROTOCOLS IN IMMUNOLOGY, Vol. 4, John Wiley, Inc., New York).

Monoclonal, polyclonal, and humanized antibodies can be prepared (see, e.g., Sheperd and Dean (eds.) (2000) Monoclonal Antibodies, Oxford Univ. Press, New York, NY; Kontermann and Dubel (eds.) (2001) Antibody Engineering, Springer-Verlag, New York; Harlow and Lane (1988) Antibodies A Laboratory Manual, Cold Spring Harbor Laboratory Press, Cold Spring Harbor, NY, pp. 139-243; Carpenter, et al. (2000) J. Immunol. 165:6205; He, et al. (1998) J. Immunol. 160:1029; Tang et al. (1999) J. Biol. Chem. 274:27371-27378; Baca et al. (1997) J. Biol. Chem. 272: 10678-10684; Chothia et al. (1989) Nature 342:877-883; Foote and Winter (1992) J. Mol. Biol. 224:487-499; U.S. Pat. No. 6,329,511).

An alternative to humanization is to use human antibody libraries displayed on phage or human antibody libraries in transgenic mice (Vaughan et al. (1996) Nature Biotechnol. 14:309-314; Barbas (1995) Nature Medicine 1:837-839; Mendez et al. (1997) Nature Genetics 15:146-156; Hoogenboom and Chames (2000) Immunol. Today 21:371-377; Barbas et al. (2001) Phage Display: A Laboratory Manual, Cold Spring Harbor Laboratory Press, Cold Spring Harbor, New York; Kay et al. (1996) Phage Display of Peptides and Proteins: A Laboratory Manual, Academic Press, San Diego, CA; de Bruin et al. (1999) Nature Biotechnol. 17:397-399).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) Immunity 7:283-290; Wright et al. (2000) Immunity 13:233-242; Preston et al., supra; Kaithamana et al. (1999) J. Immunol. 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) J. Immunol. 146:169-175; Gibellini et al. (1998) J. Immunol. 160:3891-3898; Hsing and Bishop (1999) J. Immunol. 162:2804-2811; Everts et al. (2002) J. Immunol. 168:883-889).

Methods for flow cytometry, including fluorescence activated cell sorting (FACS), are available (see, e.g., Owens, et al. (1994) Flow Cytometry Principles for Clinical Laboratory Practice, John Wiley and Sons, Hoboken, NJ; Givan (2001) Flow Cytometry, 2$^{nd}$ ed.; Wiley-Liss, Hoboken, NJ; Shapiro (2003) Practical Flow Cytometry, John Wiley and Sons, Hoboken, NJ). Fluorescent reagents suitable for modifying nucleic acids, including nucleic acid primers and probes, polypeptides, and antibodies, for use, e.g., as diagnostic reagents, are available (Molecular Probesy (2003) Catalogue, Molecular Probes, Inc., Eugene, OR; Sigma-Aldrich (2003) Catalogue, St. Louis, MO).

Standard methods of histology of the immune system are described (see, e.g., Muller-Harmelink (ed.) (1986) Human Thymus: Histopathology and Pathology, Springer Verlag, New York, NY; Hiatt, et al. (2000) Color Atlas of Histology, Lippincott, Williams, and Wilkins, Phila, PA; Louis, et al. (2002) Basic Histology: Text and Atlas, McGraw-Hill, New York, NY).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, MD); GCG Wisconsin Package (Accelrys, Inc., San Diego, CA); DeCypher® (TimeLogic Corp., Crystal Bay, Nevada); Menne, et al. (2000) Bioinformatics 16: 741-742; Menne, et al. (2000) Bioinformatics Applications Note 16:741-742; Wren, et al. (2002) Comput. Methods Programs Biomed. 68:177-181; von Heijne (1983) Eur. J. Biochem. 133:17-21; von Heijne (1986) Nucleic Acids Res. 14:4683-4690).

Table 3 provides a brief description of the sequences in the sequence listing.

TABLE 3

| SEQ ID NO: | Description |
|---|---|
| 1 | hPD-1.08A light chain CDR1 |
| 2 | hPD-1.08A light chain CDR2 |
| 3 | hPD-1.08A light chain CDR3 |
| 4 | hPD-1.08A heavy chain CDR1 |
| 5 | hPD-1.08A heavy chain CDR2 |
| 6 | hPD-1.08A heavy chain CDR3 |
| 7 | hPD-1.09A light chain CDR1 |
| 8 | hPD-1.09A light chain CDR2 |
| 9 | hPD-1.09A light chain CDR3 |
| 10 | hPD-1.09A heavy chain CDR1 |

TABLE 3-continued

| SEQ ID NO: | Description |
|---|---|
| 11 | hPD-1.09A heavy chain CDR2 |
| 12 | hPD-1.09A heavy chain CDR3 |
| 13 | 109A-H heavy chain variable region |
| 14 | 409A-H heavy chain full length |
| 15 | K09A-L-11 light chain variable region |
| 16 | K09A-L-16 light chain variable region |
| 17 | K09A-L-17 light chain variable region |
| 18 | K09A-L-11 light chain full length |
| 19 | K09A-L-16 light chain full length |
| 20 | K09A-L-17 light chain full length |
| 21 | Pembrolizumab Heavy chain |
| 22 | Pembrolizumab Light chain |
| 23 | Nivolumab Heavy chain |
| 24 | Nivolumab light chain |
| 25 | Human PD-L1 |

III. EXAMPLES

Example 1: Anti-Tumor Effect by Administration of Lenvatinib and Anti-PD-1 Antibody A DMEM culture medium (high-glucose type) containing 10% fetal bovine serum (FBS) and penicillin/streptomycin was used to culture a mouse lung cancer cell line LL/2 (LLc1) (ATCC number: CRL-1642). Next, phosphate buffered saline (PBS) was used to prepare a cell suspension having a concentration of $2.0 \times 10^7$ cells/mL. The cell suspension was subcutaneously transplanted at a dose of 0.1 mL on the right lateral side of the body of each of 7-week-old mice (C57BL/6J, female, Charles River Laboratories Japan Inc.). Eight (8) days after the transplantation, an electronic digital caliper (Digimatic™ Caliper; Mitutoyo Corporation) was used to measure the short and long diameters of a tumor of interest. The following equation was used to calculate the tumor volume TV.

Tumor Volume TV (mm³)=Long Diameter (mm)× Short Diameter (mm)×Short Diameter (mm)/2.

Based on the tumor volumes on the first day of administration, grouping was carried out such that the average values of the tumor volumes were almost the same. A 1 mg/ml solution of lenvatinib was prepared using water for injection (Otsuka Pharmaceutical Co., Ltd.) and was orally administered at a dose of 0.2 mL/20 g mouse body weight once daily for 14 days. 0.2 mL of an administration sample containing 2.5 mg/mL of an anti-mouse-PD-1 antibody (Clone: RMP1-14, BioXCell, Catalog #: BE0146), which had been diluted with PBS, was intraperitoneally administered (at a dosage of 500 μg/head) once every 3 days a total of 5 times (day 1, day 4, day 7, day 10, and day 13, with the day of the grouping set to day 1). To the control group, Otsuka water for injection was orally administered at a dose of 0.2 mL/20 g mouse body weight once daily for 14 days. Each group including 5 mice was used to conduct the experiment. The day (day 15) after the final administration, the respective tumor volumes (TV) were determined for the control group, the lenvatinib administration group, the anti-mouse-PD-1 antibody administration group, and the combination administration group. The values obtained by logarithmically transforming the tumor volumes were used to carry out statistical analysis.

In the subcutaneous LL/2 (LLc1) transplantation model, the combination of lenvatinib and the anti-mouse-PD-1 antibody exhibited a significantly higher anti-tumor effect than either administered alone. For example, at day 15, the combination group had greater than two and half fold less tumor volume compared to the control group and the anti-PD-1 group and over one and a half fold less tumor volume compared to the lenvatinib group. The daily change in the tumor volume is shown in Table 4. In addition, the tumor volumes the day after the final administration are shown in FIG. 8.

TABLE 4

| | Day 1 | Day 4 | Day 8 | Day 10 | Day 13 | Day 15 |
|---|---|---|---|---|---|---|
| Control group | 101 | 273 | 564 | 852 | 1455 | 1910 |
| Lenvatinib group | 100 | 243 | 394 | 553 | 837 | 1143 |
| Anti-PD-1 antibody group | 100 | 207 | 442 | 682 | 1083 | 1984 |
| Combination group | 100 | 203 | 351 | 452 | 573 | 691 |

Figure 9:
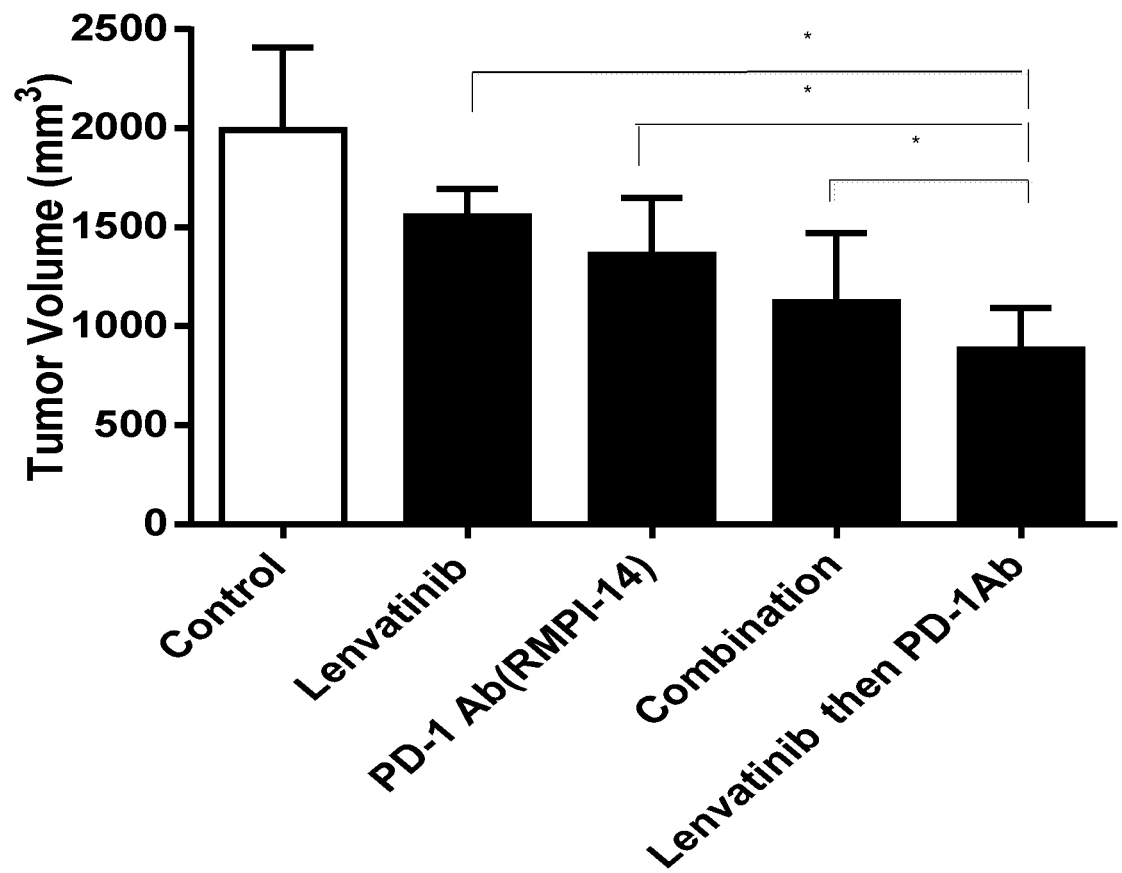
FIG. 9 shows the anti-cancer or -tumor effect on the eleventh day since commencing treatment in a mouse model with colon cancer as disclosed herein.

FIG. 9 shows the anti-cancer or -tumor effect on the eleventh day since commencing treatment in a mouse model with colon cancer. A RPMI1640 culture medium containing 10% FBS and penicillin/streptomycin was used to culture a mouse colon carcinoma cell line CT26.WT (ATCC number: CRL-2638). Hank's Balanced Salt Solution (HBSS) was used to prepare a cell suspension having a concentration of $3.0 \times 10^7$ cells/mL. The cell suspension was subcutaneously transplanted at a dose of 0.1 mL on the right lateral side of the body of each of 7-week-old mice (BALB/cAnNCrlCrlj, female, Charles River Laboratories Japan Inc.). 8 days after the transplantation, an electronic digital caliper (Digimatic™ Caliper; Mitutoyo Corporation) was used to measure the short and long diameters of a tumor of interest. The following equation was used to calculate the tumor volume TV.

Tumor Volume TV (mm³)=Long Diameter (mm)× Short Diameter (mm)×Short Diameter (mm)/2.

Based on the tumor volumes on the first day of administration, grouping was carried out such that the average values of the tumor volumes were almost the same. For each of lenvatinib only treatment group, simultaneous combination treatment group, and lenvatinib then PD-1 Ab group, 1 mg/ml solution of lenvatinib mesilate was prepared using water for injection (Otsuka Pharmaceutical Co., Ltd.) and was orally administered at a dose of 0.2 mL/20 g mouse body weight once daily for 14 days. For PD-1 Ab only treatment group and simultaneous combination treatment group, 0.2 mL of an administration sample containing 2.5 mg/mL of an anti-mouse-PD-1 antibody (Clone: RMP1-14, BioXCell, Catalog #: BE0146), which had been diluted with PBS, was intraperitoneally administered (at a dosage of 500 μg/head) once every 3 days a total of 5 times (day 1, day 4, day 7, day 10, and day 13, with the day of the grouping set to day 1). For lenvatinib then PD-1 Ab group, the same dose of an anti-mouse PD-1 antibody was intraperitoneally administrated once every 3 days a total of 3 times from day8 (day8, day1, day14).

To the control group, Otsuka water for injection was orally administered at a dose of 0.2 mL/20 g mouse body weight once daily for 14 days. Each group including 5 mice was used to conduct the experiment. The day (day 15) after the final administration, the respective tumor volumes TV were determined for the control group, the lenvatinib administration group, the anti-mouse-PD-1 antibody administration group, and the combination administration group. The values obtained by logarithmically transforming the tumor volumes were used to carry out statistical analysis.

Consistent with the above experiments, the combination of lenvatinib and anti-PD-1 demonstrates a synergistic effect between the two. Unexpectedly, the administration of lenvatinib only for 7 days followed by administration of lenvatinib and anti-PD-1 showed an even greater effect on reducing tumor volume than the combined administration of lenvatinib and anti-PD-1.

Example 2: Anti-Tumor Effect by Co-Administration of Lenvatinib Mesilate and Anti-PD-L1 Antibody A RPMI1640 culture medium containing 10% FBS and penicillin/streptomycin was used to culture a mouse colon carcinoma cell line CT26.WT (ATCC number: CRL-2638). Hank's Balanced Salt Solution (HBSS) was used to prepare a cell suspension having a concentration of $3.0 \times 10^7$ cells/mL. The cell suspension was subcutaneously transplanted at a dose of 0.1 mL on the right lateral side of the body of each of 7-week-old mice (BALB/cAnNCrlCrlj, female, Charles River Laboratories Japan Inc.). 8 days after the transplantation, an electronic digital caliper (Digimatic™ Caliper; Mitutoyo Corporation) was used to measure the short and long diameters of a tumor of interest. The following equation was used to calculate the tumor volume TV.

Tumor Volume TV (mm³)=Long Diameter (mm)× Short Diameter (mm)×Short Diameter (mm)/2.

Based on the tumor volumes on the first day of administration, grouping was carried out such that the average values of the tumor volumes were almost the same. A 1 mg/ml solution of lenvatinib mesilate was prepared using water for injection (Otsuka Pharmaceutical Co., Ltd.) and was orally administered at a dose of 0.2 mL/20 g mouse body weight once daily for 14 days. 0.2 mL of an administration sample containing 2.5 mg/mL of an anti-mouse-PD-L1 antibody, which had been diluted with PBS, was intraperitoneally administered (at a dosage of 500 µg/head) once every 3 days a total of 5 times (day 1, day 4, day 7, day 10, and day 13, with the day of the grouping set to day 1). To the control group, Otsuka water for injection was orally administered at a dose of 0.2 mL/20 g mouse body weight once daily for 14 days. Each group including 5 mice was used to conduct the experiment. The day (day 15) after the final administration, the respective tumor volumes TV were determined for the control group, the lenvatinib administration group, the anti-mouse-PD-L1 antibody administration group, and the combination administration group. The values obtained by logarithmically transforming the tumor volumes were used to carry out statistical analysis.

In the subcutaneous CT26.WT transplantation model, the combination of lenvatinib mesilate and the anti-mouse-PD-L1 antibody exhibited a significantly higher anti-tumor effect than either administered alone. For example, the combination group had a tumor volume that was at least two-fold less than the groups that received treatment with lenvatinib or anti-PD-L1. The daily change in the tumor volume is shown in Table 5. In addition, the tumor volumes the day after the final administration are shown in FIG. 8.

TABLE 5

|  | Day 1 | Day 4 | Day 8 | Day 11 |
|---|---|---|---|---|
| Control group | 153 | 456 | 1320 | 1990 |
| Lenvatinib group | 154 | 472 | 1172 | 1555 |
| Anti-PD-L1 antibody group | 153 | 380 | 962 | 1557 |
| Combination group | 154 | 358 | 635 | 720 |

Figure 10:
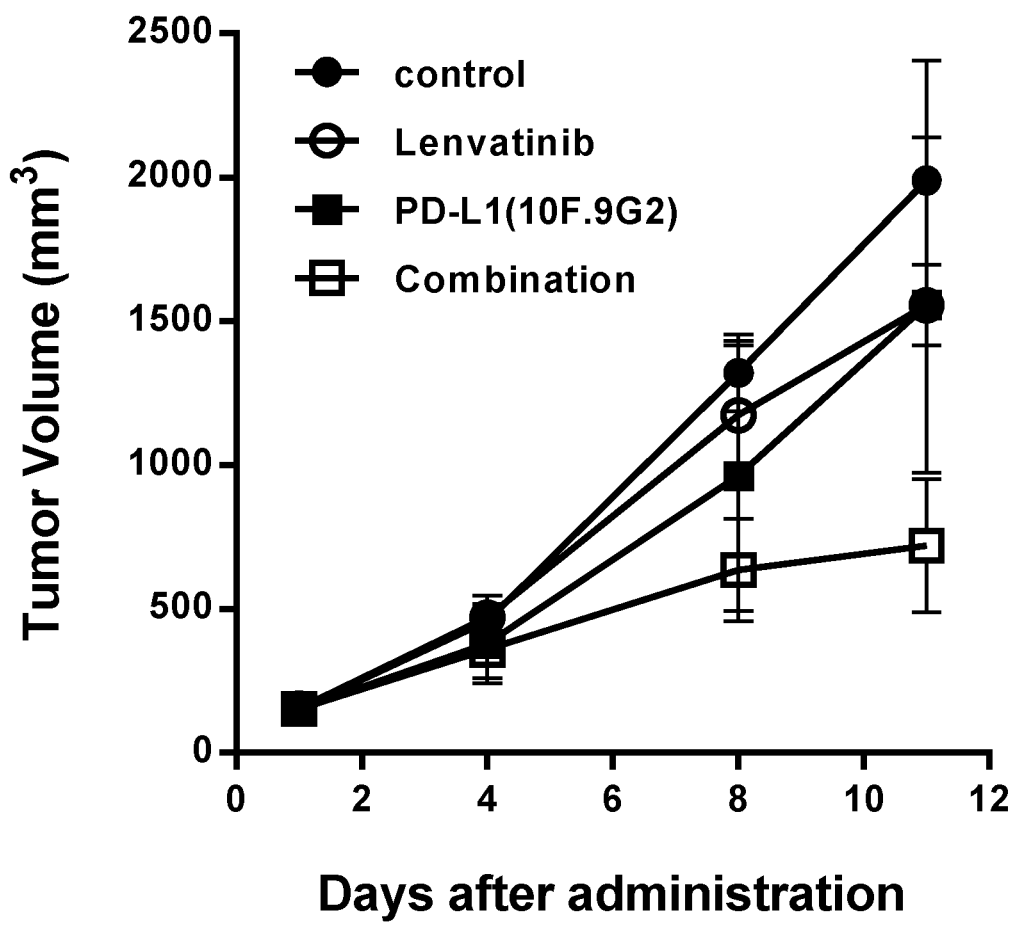
FIG. 10 is a graph of the tumor volume plotted by days subsequent to administration for the control group, lenvatinib or PD-L1 individually, and a combination of lenvatinib and PD-L1 as disclosed herein.

FIG. 10 shows a graph of the tumor volume plotted by days subsequent to administration for the control group, lenvatinib or PD-L1 individually, and a combination of lenvatinib and PD-L1. The combination of PD-L1 with lenvatinib exhibited a synergistic effect with respect to the tumor volume. The effect is noticeable at four days post commencement of treatment an very pronounced by days 8 and 11, with mice who received the combined lenvatinib and PD-L1 treatment showing a tumor volume nearly one third the size of the control group's tumor volume on day 11.

REFERENCES

1. Sharpe, A. H, Wherry, E. J., Ahmed R., and Freeman G. J. The function of programmed cell death 1 and its ligands in regulating autoimmunity and infection. *Nature Immunology* (2007); 8:239-245.
2. Dong H et al. Tumor-associated B7-H1 promotes T-cell apoptosis: a potential mechanism of immune evasion. Nat Med. 2002 August; 8(8):793-800.
3. Yang et al. PD-1 interaction contributes to the functional suppression of T-cell responses to human uveal melanoma cells in vitro. *Invest Ophthalmol Vis Sci.* 2008 June; 49(6 (2008): 49: 2518-2525.
4. Ghebeh et al. The B7-H1 (PD-L1) T lymphocyte-inhibitory molecule is expressed in breast cancer patients with infiltrating ductal carcinoma: correlation with important high-risk prognostic factors. *Neoplasia* (2006) 8: 190-198.
5. Hamanishi J et al. Programmed cell death 1 ligand 1 and tumor-infiltrating CD8+ T lymphocytes are prognostic factors of human ovarian cancer. *Proceeding of the National Academy of Sciences* (2007): 104: 3360-3365.
6. Thompson R H et al. Significance of B7-H1 overexpression in kidney cancer. Clinical genitourin *Cancer* (2006): 5: 206-211.
7. Nomi, T. Sho, M., Akahori, T., et al. Clinical significance and therapeutic potential of the programmed death-1 ligand/programmed death-1 pathway in human pancreatic cancer. *Clinical Cancer Research* (2007); 13:2151-2157.
8. Ohigashi Y et al. Clinical significance of programmed death-1 ligand-1 and programmed death-1 ligand 2 expression in human esophageal cancer. *Clin. Cancer Research* (2005): 11: 2947-2953.
9. Inman et al. PD-L1 (B7-H1) expression by urothelial carcinoma of the bladder and BCG-induced granulomata: associations with localized stage progression. *Cancer* (2007): 109: 1499-1505.
10. Shimauchi T et al. Augmented expression of programmed death-1 in both neoplasmatic and nonneoplastic CD4+ T-cells in adult T-cell Leukemia/Lymphoma. *Int. J. Cancer* (2007): 121:2585-2590.
11. Gao et al. Overexpression of PD-L1 significantly associates with tumor aggressiveness and postoperative recurrence in human hepatocellular carcinoma. *Clinical Cancer Research* (2009) 15: 971-979.
12. Nakanishi J. Overexpression of B7-H1 (PD-L1) significantly associates with tumor grade and postoperative prognosis in human urothelial cancers. *Cancer Immunol Immunother.* (2007) 56: 1173-1182.
13. Hino et al. Tumor cell expression of programmed cell death-1 is a prognostic factor for malignant melanoma. *Cancer* (2010): 00: 1-9.
14. Ghebeh H. Foxp3+ tregs and B7-H1+/PD-1+T lymphocytes co-infiltrate the tumor tissues of high-risk breast cancer patients: implication for immunotherapy. *BMC Cancer.* 2008 Feb. 23; 8:57.
15. Ahmadzadeh M et al. Tumor antigen-specific CD8 T cells infiltrating the tumor express high levels of PD-1 and are functionally impaired. *Blood* (2009) 114: 1537-1544.
16. Thompson R H et al. PD-1 is expressed by tumor infiltrating cells and is associated with poor outcome for patients with renal carcinoma. *Clinical Cancer Research* (2007) 15: 1757-1761.
17. US Patent Application Publication No. 2004-053908.
18. US Patent Application Publication No. 2004-253205.
19. US Patent Application Publication No. 2010-105031.
20. US Patent Application Publication No. 2009-209580.
21. US Patent Application Publication No. 2009-264464.
22. US Patent Application Publication No. 2004-259834.
23. Iwai et al., PNAS, 2002, 99 (19), 12293-7.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

What is claimed:

1. A method for treating a cancer in an individual comprising administering to the individual a combination therapy which comprises an antagonist of a Programmed Death 1 protein (PD-1) and a multiple receptor tyrosine kinase (multi-RTK) inhibitor, wherein the PD-1 antagonist is pembrolizumab, and wherein the multi-RTK inhibitor is lenvatinib or a pharmaceutically acceptable salt thereof, and wherein the cancer is thyroid cancer, hepatocellular carcinoma (HCC), renal cell carcinoma (RCC), endometrial cancer, squamous cell carcinoma of head and neck, glioblastoma, gastric cancer or melanoma.

2. The method of claim 1, wherein the individual is a human.

3. The method of claim 1, wherein the combination therapy which comprises pembrolizumab and lenvatinib or a pharmaceutically acceptable salt thereof is administered after an administration of lenvatinib or a pharmaceutically acceptable salt thereof.

4. The method of claim 3, wherein the combination therapy which comprises pembrolizumab and lenvatinib or a pharmaceutically acceptable salt thereof is administered after an administration of lenvatinib or a pharmaceutically acceptable salt thereof for at least 7 days.

5. The method of claim 1, wherein the combination therapy which comprises pembrolizumab and lenvatinib or a pharmaceutically acceptable salt thereof is administered after an administration of pembrolizumab.

6. A kit which comprises a first container, a second container and a package insert, wherein the first container comprises at least one dose of a medicament comprising an antagonist of a Programmed Death 1 protein (PD-1), the second container comprises at least one dose of a medicament comprising a multi-RTK inhibitor, and the package insert comprises instructions for treating an individual for cancer using the medicaments, wherein the PD-1 antagonist is pembrolizumab, and wherein the multi-RTK inhibitor is lenvatinib or a pharmaceutically acceptable salt thereof.

7. The kit of claim 6, wherein the instructions state that the medicaments are intended for use in treating an individual having a cancer that tests positive for PD-L1 expression by an immunohistochemical (IHC) assay.

8. The kit of claim 6, wherein the individual is a human.

9. The kit of claim 6, wherein the antagonist is pembrolizumab formulated as a liquid medicament which comprises 25 mg/ml pembrolizumab, 7% (w/v) sucrose, 0.02% (w/v) polysorbate 80 in 10 mM histidine buffer pH 5.5, and the multi-RTK inhibitor is lenvatinib or a pharmaceutically acceptable salt thereof formulated as a 4 mg or 10 mg lenvatinib capsule comprising calcium carbonate, mannitol, microcrystalline cellulose, hydroxypropylcellulose, low-substituted hydroxypropylcellulose, and talc.

10. The kit of claim 6, wherein the cancer is thyroid cancer, HCC, NSCLC, RCC, endometrial cancer, squamous cell carcinoma of head and neck, glioblastoma or melanoma.

11. A method for treating a human individual diagnosed with a cancer, comprising administering to the individual a combination therapy for at least 24 weeks, wherein the combination therapy comprises pembrolizumab and lenvatinib or a pharmaceutically acceptable salt thereof, wherein lenvatinib or a pharmaceutically acceptable salt thereof is administered at a daily dose of 24 mg, 20 mg or 14 mg, each as lenvatinib, and pembrolizumab is administered at a dose of 200 mg once every three weeks.

12. The method of claim 1, wherein the lenvatinib or a pharmaceutically acceptable salt thereof is administered at a daily dose of 24 mg, 20 mg or 14 mg, each as lenvatinib.

13. The method of claim 1, wherein pembrolizumab is administered at a dose of 200 mg once every three weeks.

14. The method of claim 1, wherein the cancer is thyroid cancer.

15. The method of claim 1, wherein the cancer is HCC.

16. The method of claim 1, wherein the cancer is RCC.

17. The method of claim 1, wherein the cancer is endometrial cancer.

18. The method of claim 1, wherein the cancer is squamous cell carcinoma of head and neck.

19. The method of claim 1, wherein the cancer is glioblastoma.

20. The method of claim 1, wherein the cancer is gastric cancer.

21. The method of claim 1, wherein the cancer is melanoma.

* * * * *

SEQUENCE LISTING

```
<160> NUMBER OF SEQ ID NOS: 25

<210> SEQ ID NO 1
<211> LENGTH: 15
<212> TYPE: PRT
<213> ORGANISM: Artificial Sequence
<220> FEATURE:
<223> OTHER INFORMATION: Antibody Light Chain CDR

<400> SEQUENCE: 1

Arg Ala Ser Lys Ser Val Ser Thr Ser Gly Phe Ser Tyr Leu His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Antibody Light Chain CDR

<400> SEQUENCE: 2

Leu Ala Ser Asn Leu Glu Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Antibody Light Chain CDR

<400> SEQUENCE: 3

Gln His Ser Trp Glu Leu Pro Leu Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Antibody Heavy Chain CDR

<400> SEQUENCE: 4

Ser Tyr Tyr Leu Tyr
```

```
1               5

<210> SEQ ID NO 5
<211> LENGTH: 17
<212> TYPE: PRT
<213> ORGANISM: Artificial Sequence
<220> FEATURE:
<223> OTHER INFORMATION: Antibody Heavy Chain CDR

<400> SEQUENCE: 5

Gly Val Asn Pro Ser Asn Gly Gly Thr Asn Phe Ser Glu Lys Phe Lys
1               5                   10                  15

Ser

<210> SEQ ID NO 6
<211> LENGTH: 11
<212> TYPE: PRT
<213> ORGANISM: Artificial Sequence
<220> FEATURE:
<223> OTHER INFORMATION: Antibody Heavy Chain CDR

<400> SEQUENCE: 6

Arg Asp Ser Asn Tyr Asp Gly Gly Phe Asp Tyr
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Antibody Light Chain CDR

<400> SEQUENCE: 7

Arg Ala Ser Lys Gly Val Ser Thr Ser Gly Tyr Ser Tyr Leu His
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Antibody Light Chain CDR

<400> SEQUENCE: 8

Leu Ala Ser Tyr Leu Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Antibody Light Chain CDR

<400> SEQUENCE: 9

Gln His Ser Arg Asp Leu Pro Leu Thr
1               5

<210> SEQ ID NO 10
<211> LENGTH: 5
<212> TYPE: PRT
<213> ORGANISM: Artificial Sequence
<220> FEATURE:
<223> OTHER INFORMATION: Antibody Heavy Chain CDR

<400> SEQUENCE: 10
```

```
Asn Tyr Tyr Met Tyr
 1               5
```

<210> SEQ ID NO 11
<211> LENGTH: 17
<212> TYPE: PRT
<213> ORGANISM: Artificial Sequence
<220> FEATURE:
<223> OTHER INFORMATION: Antibody Heavy Chain CDR

<400> SEQUENCE: 11

```
Gly Ile Asn Pro Ser Asn Gly Gly Thr Asn Phe Asn Glu Lys Phe Lys
 1               5                  10                  15

Asn
```

<210> SEQ ID NO 12
<211> LENGTH: 11
<212> TYPE: PRT
<213> ORGANISM: Artificial Sequence
<220> FEATURE:
<223> OTHER INFORMATION: Antibody Heavy Chain CDR

<400> SEQUENCE: 12

```
Arg Asp Tyr Arg Phe Asp Met Gly Phe Asp Tyr
 1               5                  10
```

<210> SEQ ID NO 13
<211> LENGTH: 120
<212> TYPE: PRT
<213> ORGANISM: Artificial Sequence
<220> FEATURE:
<223> OTHER INFORMATION: Humanized Antibody Heavy Chain Variable Region

<400> SEQUENCE: 13

```
Gln Val Gln Leu Val Gln Ser Gly Val Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120
```

<210> SEQ ID NO 14
<211> LENGTH: 447
<212> TYPE: PRT
<213> ORGANISM: Artificial Sequence
<220> FEATURE:
<223> OTHER INFORMATION: Humanized Antibody Heavy Chain

<400> SEQUENCE: 14

```
Gln Val Gln Leu Val Gln Ser Gly Val Glu Val Lys Lys Pro Gly Ala
 1               5                  10                  15

Ser Val Lys Val Ser Cys Lys Ala Ser Gly Tyr Thr Phe Thr Asn Tyr
```

```
                20                  25                  30
Tyr Met Tyr Trp Val Arg Gln Ala Pro Gly Gln Gly Leu Glu Trp Met
         35                  40                  45
Gly Gly Ile Asn Pro Ser Asn Gly Thr Asn Phe Asn Glu Lys Phe
     50                  55                  60
Lys Asn Arg Val Thr Leu Thr Thr Asp Ser Thr Thr Thr Ala Tyr
 65                  70                  75                  80
Met Glu Leu Lys Ser Leu Gln Phe Asp Asp Thr Ala Val Tyr Tyr Cys
                 85                  90                  95
Ala Arg Arg Asp Tyr Arg Phe Asp Met Gly Phe Asp Tyr Trp Gly Gln
                100                 105                 110
Gly Thr Thr Val Thr Val Ser Ser Ala Ser Thr Lys Gly Pro Ser Val
                115                 120                 125
Phe Pro Leu Ala Pro Cys Ser Arg Ser Thr Ser Glu Ser Thr Ala Ala
                130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Lys Thr Tyr Thr Cys Asn Val Asp His Lys
                195                 200                 205
Pro Ser Asn Thr Lys Val Asp Lys Arg Val Glu Ser Lys Tyr Gly Pro
210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Asp Val Ser Gln Glu Asp Pro Glu
                260                 265                 270
Val Gln Phe Asn Trp Tyr Val Asp Gly Val Glu Val His Asn Ala Lys
                275                 280                 285
Thr Lys Pro Arg Glu Glu Gln Phe Asn Ser Thr Tyr Arg Val Val Ser
                290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Gln Glu Glu Met Thr Lys Asn Gln Val Ser Leu Thr Cys Leu
                355                 360                 365
Val Lys Gly Phe Tyr Pro Ser Asp Ile Ala Val Glu Trp Glu Ser Asn
                370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
                420                 425                 430
His Asn His Tyr Thr Gln Lys Ser Leu Ser Leu Ser Leu Gly Lys
                435                 440                 445
```

<210> SEQ ID NO 15
<211> LENGTH: 111
<212> TYPE: PRT
<213> ORGANISM: Artificial Sequence
<220> FEATURE:
<223> OTHER INFORMATION: Humanized Antibody Light Chain Variable Region

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 16
<211> LENGTH: 111
<212> TYPE: PRT
<213> ORGANISM: Artificial Sequence
<220> FEATURE:
<223> OTHER INFORMATION: Humanized Antibody Light Chain Variable Region

<400> SEQUENCE: 16

Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys
            100                 105                 110

<210> SEQ ID NO 17
<211> LENGTH: 111
<212> TYPE: PRT
<213> ORGANISM: Artificial Sequence
<220> FEATURE:
<223> OTHER INFORMATION: Humanized Antibody Light Chain Variable Regon

<400> SEQUENCE: 17

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
            35                  40                  45

Gln Leu Leu Ile Tyr Leu Ala Ser Tyr Leu Glu Ser Gly Val Pro Asp
 50                  55                  60

Arg Phe Ser Gly Ser Gly Ser Gly Thr Ala Phe Thr Leu Lys Ile Ser
 65                  70                  75                  80

Arg Val Glu Ala Glu Asp Val Gly Leu Tyr Tyr Cys Gln His Ser Arg
                 85                  90                  95

Asp Leu Pro Leu Thr Phe Gly Gln Gly Thr Lys Leu Glu Ile Lys
            100                 105                 110

<210> SEQ ID NO 18
<211> LENGTH: 218
<212> TYPE: PRT
<213> ORGANISM: Artificial Sequence
<220> FEATURE:
<223> OTHER INFORMATION: Humanzed Antiboy LIght Chain

<400> SEQUENCE: 18

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Lys Gly Val Ser Thr Ser
             20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 19
<211> LENGTH: 218
<212> TYPE: PRT
<213> ORGANISM: Artificial Sequence
<220> FEATURE:
<223> OTHER INFORMATION: Humanized Antibody Light Chain

<400> SEQUENCE: 19

Glu Ile Val Leu Thr Gln Ser Pro Leu Ser Leu Pro Val Thr Pro Gly
 1               5                  10                  15

```
Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 20
<211> LENGTH: 218
<212> TYPE: PRT
<213> ORGANISM: Artificial Sequence
<220> FEATURE:
<223> OTHER INFORMATION: Humanized Antibody Light Chain

<400> SEQUENCE: 20

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Ala Phe Thr Leu Lys Ile Ser
65                  70                  75                  80

Arg Val Glu Ala Glu Asp Val Gly Leu Tyr Tyr Cys Gln His Ser Arg
                85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160
```

-continued

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 21
<211> LENGTH: 447
<212> TYPE: PRT
<213> ORGANISM: Artificial Sequence
<220> FEATURE:
<223> OTHER INFORMATION: Humanized Antibody Heavy Chain

<400> SEQUENCE: 21

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Thr Ala Val Tyr Tyr Cys
                85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 22
<211> LENGTH: 218
<212> TYPE: PRT
<213> ORGANISM: Artificial Sequence
<220> FEATURE:
<223> OTHER INFORMATION: Humanized Antibody Light Chain

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 23
<211> LENGTH: 440
<212> TYPE: PRT
<213> ORGANISM: Homo sapiens

<400> SEQUENCE: 23

```
Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
```

```
                        370                 375                 380
Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Lys
                435                 440

<210> SEQ ID NO 24
<211> LENGTH: 214
<212> TYPE: PRT
<213> ORGANISM: Homo sapiens

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 290
<212> TYPE: PRT
<213> ORGANISM: Homo sapiens
<220> FEATURE:
<221> NAME/KEY: mat_peptide
<222> LOCATION: (19)..(290)

<400> SEQUENCE: 25

Met Arg Ile Phe Ala Val Phe Ile Phe Met Thr Tyr Trp His Leu Leu
            -15                 -10                 -5

Asn Ala Phe Thr Val Thr Val Pro Lys Asp Leu Tyr Val Val Glu Tyr
```

-continued

```
        -1   1                    5                            10
        Gly Ser Asn Met Thr Ile Glu Cys Lys Phe Pro Val Glu Lys Gln Leu
        15                   20                  25                  30

Asp Leu Ala Ala Leu Ile Val Tyr Trp Glu Met Glu Asp Lys Asn Ile
                             35                  40                  45

Ile Gln Phe Val His Gly Glu Glu Asp Leu Lys Val Gln His Ser Ser
                        50                  55                  60

Tyr Arg Gln Arg Ala Arg Leu Leu Lys Asp Gln Leu Ser Leu Gly Asn
                    65                  70                  75

Ala Ala Leu Gln Ile Thr Asp Val Lys Leu Gln Asp Ala Gly Val Tyr
        80                  85                  90

Arg Cys Met Ile Ser Tyr Gly Gly Ala Asp Tyr Lys Arg Ile Thr Val
        95                  100                 105                 110

Lys Val Asn Ala Pro Tyr Asn Lys Ile Asn Gln Arg Ile Leu Val Val
                        115                 120                 125

Asp Pro Val Thr Ser Glu His Glu Leu Thr Cys Gln Ala Glu Gly Tyr
                    130                 135                 140

Pro Lys Ala Glu Val Ile Trp Thr Ser Ser Asp His Gln Val Leu Ser
                145                 150                 155

Gly Lys Thr Thr Thr Thr Asn Ser Lys Arg Glu Glu Lys Leu Phe Asn
        160                 165                 170

Val Thr Ser Thr Leu Arg Ile Asn Thr Thr Thr Asn Glu Ile Phe Tyr
        175                 180                 185                 190

Cys Thr Phe Arg Arg Leu Asp Pro Glu Glu Asn His Thr Ala Glu Leu
                    195                 200                 205

Val Ile Pro Glu Leu Pro Leu Ala His Pro Pro Asn Glu Arg Thr His
                    210                 215                 220

Leu Val Ile Leu Gly Ala Ile Leu Leu Cys Leu Gly Val Ala Leu Thr
                    225                 230                 235

Phe Ile Phe Arg Leu Arg Lys Gly Arg Met Met Asp Val Lys Lys Cys
                240                 245                 250

Gly Ile Gln Asp Thr Asn Ser Lys Lys Gln Ser Asp Thr His Leu Glu
        255                 260                 265                 270

Glu Thr
```